US009629877B2

(12) United States Patent
Cooper et al.

(10) Patent No.: US 9,629,877 B2
(45) Date of Patent: Apr. 25, 2017

(54) HUMAN APPLICATION OF ENGINEERED CHIMERIC ANTIGEN RECEPTOR (CAR) T-CELLS

(71) Applicant: BOARD OF REGENTS, THE UNIVERSITY OF TEXAS SYSTEM, Austin, TX (US)

(72) Inventors: Laurence JN Cooper, Houston, TX (US); Hiroki Torikai, Houston, TX (US); Ling Zhang, Houston, TX (US); Helen Huls, Houston, TX (US); Feng Wang-Johanning, Bastrop, TX (US); Lenka Hurton, Houston, TX (US); Simon Olivares, Houston, TX (US); Janani Krishnamurthy, Houston, TX (US)

(73) Assignee: BOARD OF REGENTS, THE UNIVERSITY OF TEXAS SYSTEM, Austin, TX (US)

(*) Notice: Subject to any disclaimer, the term of this patent is extended or adjusted under 35 U.S.C. 154(b) by 0 days.

(21) Appl. No.: 14/890,977

(22) PCT Filed: May 14, 2014

(86) PCT No.: PCT/US2014/038005
§ 371 (c)(1),
(2) Date: Nov. 13, 2015

(87) PCT Pub. No.: WO2014/186469
PCT Pub. Date: Nov. 20, 2014

(65) Prior Publication Data
US 2016/0158285 A1 Jun. 9, 2016

Related U.S. Application Data

(60) Provisional application No. 61/823,253, filed on May 14, 2013.

(51) Int. Cl.
| C12N 5/00 | (2006.01) |
| A61K 35/17 | (2015.01) |
| C07K 14/725 | (2006.01) |
| C07K 14/54 | (2006.01) |

(52) U.S. Cl.
CPC .......... *A61K 35/17* (2013.01); *C07K 14/5443* (2013.01); *C07K 14/7051* (2013.01)

(58) Field of Classification Search
None
See application file for complete search history.

(56) References Cited

U.S. PATENT DOCUMENTS

| 6,489,458 B2 | 12/2002 | Hackett et al. |
| 6,986,887 B2 | 1/2006 | Lawman |
| 7,435,596 B2 | 10/2008 | Campana |
| 7,833,706 B2 | 11/2010 | Begovich et al. |
| 7,888,121 B2 | 2/2011 | Urnov et al. |
| 8,026,097 B2 | 9/2011 | Campana |
| 8,507,222 B2 * | 8/2013 | Wong ............... C07K 14/5443 435/235.1 |
| 8,945,868 B2 | 2/2015 | Collingwood et al. |
| 8,956,828 B2 | 2/2015 | Bonini et al. |
| 2003/0194704 A1 | 10/2003 | Penn et al. |
| 2006/0286603 A1 | 12/2006 | Kolkman et al. |
| 2007/0032637 A1 | 2/2007 | Yokoyama et al. |
| 2007/0036773 A1 | 2/2007 | Cooper |
| 2007/0283453 A1 | 12/2007 | Cimadevilla |
| 2009/0197309 A1 | 8/2009 | Sycheva et al. |
| 2009/0258363 A1 | 10/2009 | Gregory |
| 2011/0158957 A1 | 6/2011 | Bonini et al. |
| 2011/0236363 A1 | 9/2011 | Chang et al. |
| 2013/0280220 A1 | 10/2013 | Ahmed et al. |

FOREIGN PATENT DOCUMENTS

| EP | 2173378 | 4/2010 |
| WO | WO 2016-073629 | 5/1916 |
| WO | WO 2016-073755 | 5/1916 |
| WO | WO 03-089618 | 10/2003 |
| WO | WO 2009-091826 | 7/2009 |
| WO | WO 2010-008564 | 1/2010 |
| WO | WO 2010-108127 | 9/2010 |
| WO | WO 2011-059836 | 5/2011 |
| WO | WO 2012-079000 | 6/2012 |
| WO | WO 2013-040557 | 3/2013 |
| WO | WO 2013-059593 | 4/2013 |
| WO | WO 2013-063419 | 5/2013 |
| WO | WO 2013-074916 | 5/2013 |

(Continued)

OTHER PUBLICATIONS

"Human leukocyte antigen", *Wikipedia*, downloaded on Jun. 3, 2016.
Aronovich et al., "The Sleeping Beauty transposon system: a non-viral vector for gene therapy", *Hum. Mol Genet.*, 20:R14-20, 2011.
Beerli and Barbas, "Engineering polydactyl zinc-finger transcription factors", *Nature Biotechnol.*, 20:135-141, 2002.
Beurdeley et al., "Compact designer TALENs for efficient genome engineering", *Nature Communications*, 4:1762 doi: 10.1038/ncomms2782, 2013.
Bhatnagar et al., "Turmor lysing genetically engineered T cless loaded with multi-modal imaging agents", *Sci Rep*, 4: 4502, 2014.
Boch et al., "Breaking the code of DNA binding specificity of TAL-type III effectors", *Science*, 326: 1509-1512, 2009.
Boissel et al., "megaTALs: a rare-cleaving nuclease architecture for therapeutic genome engineering", *Nucleic Acids Research*, 42(4): 2591-2601, 2014.

(Continued)

*Primary Examiner* — Michael Burkhart
(74) *Attorney, Agent, or Firm* — Parker Highlander PLLC

(57) ABSTRACT

The present invention concerns methods and compositions for immunotherapy employing a modified T cell comprising a chimeric antigen receptor (CAR). In particular aspects, CAR-expressing T-cells are producing using electroporation in conjunction with a transposon-based integration system to produce a population of CAR-expressing cells that require minimal ex vivo expansion or that can be directly administered to patients for disease (e.g., cancer) treatment.

31 Claims, 69 Drawing Sheets

(56) References Cited

FOREIGN PATENT DOCUMENTS

| WO | WO 2013-084147 | 6/2013 |
|---|---|---|
| WO | WO 2014-037807 | 3/2014 |
| WO | WO 2014-100385 | 6/2014 |
| WO | WO 2014-144622 | 9/2014 |
| WO | WO 2014-164554 | 10/2014 |
| WO | WO 2014-190273 | 11/2014 |
| WO | WO 2015-061694 | 4/2015 |
| WO | WO 2015-123642 | 8/2015 |
| WO | WO 2015-164594 | 10/2015 |
| WO | WO 2015-164740 | 10/2015 |

OTHER PUBLICATIONS

Bonas et al., "Genetic and structural characterization of the avirulence gene *avrBs3* from *Xanthomonas campestris* pv. *vesicatoria*", Mol Gen Genet., 218: 127-136, 1989.

Borrego et al., "Recognition of human histocompatibility leukocyte antigen (HLA)-E complexed with HLA class I signal sequence-derived peptides by CD94/NKG2 confers protection from natural killer cell-mediated lysis", *J Exp Med*., 187(5): 813-8, 1998.

Braud et al., "HLA-E binds to natural killer cell receptors CD94/NKG2A, B and C", *Nature*, 391: 795-799, 1998.

Brentjens et al., "CD19-targeted T cells rapidly induce molecular remissions in adults with chemotherapy-refractory acute lymphoblastic leukemia", *Sci. Transl. Med.*, 5:177ra38, 2013.

Bukur et al., "The role of classical and non-classical HLA class I antigens in human tumors", *Seminars in Cancer Biology*, 22: 350-358, 2012.

Bullain et al., "Genetically engineered T cells to target EGFRvIII expressing glioblastoma", *Journal of Neuro-Oncology*, 94(3): 373-382, 2009.

Caruso, "CAR-modified T cells capably of distinguishing normal cells from malignant cells", *UT GBS Dissertations and Theses*, dated May 1, 2014, retrieved from digitalcommons.library.tmc.edu/cgi/viewcontent.cgi?article=1497&context=utgsbs_dissertations on Jul. 15, 2015.

Chmielewski et al., "T cell activation by antibody-like immunorecepteros: increase in affinity of the single-chain fragment domain above threshold does not increase T cell activation against antigen-positive target cells but decrease selectivity", *Journal of Immunology*, 173(12): 7647-7653, 2004.

Choi et al., "A high throughput microelectroporation devise to introduce a chimeric antigen receptor to redirect the specificity of human T cells", *Biomed Microdevices*, 12(5): 855-63, 2010.

Choi et al., "Intercerebral delivery of a third generation EGFRvIII-specific chimeric antigen receptor is efficacious against human glioma", *Journal of Clinical Neuroscience*, 21(1): 189-190, 2014.

Choo and Isalan, "Advances in zinc finger engineering", *Curr Opin Struct Biol.*, 10(4): 411-6, 2000.

Cohen et al., "In vivo expression of MHC class I genes depends on the presence of a downstream barrier element", *PLoS ONE*, 4(8): e6748. Doi:10.1371/journal.pone.0006748, 2009. Figure 1.

Collin et al., "Concise review: putting a finger on stem cell biology: zinc finger nuclease-driven targeted genetic editing in human pluripotent stem cells", *Stem Cells* 19: 1021-1033, 2011.

Cooper et al., "Good T cells for bad B cells", *Blood*, 119: 2700-2702, 2012.

Cooper, "T-cell therapy for diffuse pontine glioma", *The Dana Foundation Grant Summary*, 2015.

Davies et al., "Combining CD19 redirection and alloanergization to generate tumor-specific human T cells for allogeneic cell therapy of B-cell malignancies", *Cancer Res.*, 70: 3915-3924, 2010.

Davies et al., "Flexible targeting of ErbB dimers that drive tumorigenesis by using genetically engineered T cells", *Molecular Medicine*, 18(1); 565-576, 2012.

De Oliveira et al., "A CD19/Fc fusion protein for detection of anti-CD19 chimeric antigen receptors", *Journal of Translational Medicine*, 11:23, 2013.

De Oliveira et al., "Modification of hematopoietic stem-progenitor cells with CD19-specific chimeric antigen receptors as a novel approach for cancer immunotherapy", *Hum Gene Ther.*, 24(10): 824-39, 2013.

Deniger et al. "Bispecific T-cells expressing polyclonal repertoire of endogenous gammadelta T-cell receptors and introduced CD19-specific chimeric antigen receptor", *Mol Ther.* Mar 2013;21(3):638-647.

Deniger, "T-Cell treatments for solid and hematological tumors", *UT GBS Dissertations and Theses*, dated Aug. 2013, retrieved from digitalcommons.library.tmc.edu/cgi/viewcontent.cgi?article=1421&context=utgsbs_dissertations on Dec. 14, 2014.

Ehlers et al., "Alphabeta T cell receptor-positive cells and interferon-gamma, but not inducible nitric oxide synthase, are critical for granuloma necrosis in a mouse model of mycobacteria-induced pulmonary immunopathy", *The Journal of Experimental Medicine*, 194(12):1847-1859, 2001.

Ertl et al., "Considerations for the clinical application of chimeric antigen receptor T cells: observations from a recombinant DNA Advisory Committee Symposium held Jun. 15, 2010", *Cancer Res.*, 71:3175-3181, 2011.

Fehling et al., "MHC class I expression in mice lacking the proteasome subunit LMP-7", *Science*, 265(5176): 1234-7, 1994.

Feng et al., "Scalable generation of universal platelets from human induced pluripotent stem cells", *Stem Cell Reports*, 3(5): 817-831, 2014.

Garbi et al., "Impaired immune responses and altered peptide repertoire in tapasin-deficient mice", *Nature Immunology*, 1(3): 234-8, 2000.

Gascoignet, "Transport and secretion of truncated T cell receptor and chamin occurs in the absence of association with CD3", *The Journal of Biological Chemistry*, 265(16):9296-9301, 1990.

Geurts et al., "Structure-based prediction of insertion-site preferences of transposons into chromosomes", *Nucleic Acids Res.*, 34:2803-2811, 2006.

Grandea et al., "Impaired assembly yet normal trafficking of MHC class I molecules in *Tapasin* mutant mice", *Immunity*, 13: 231-222, 2000.

Grupp et al., "Chimeric antigen receptor-modified T cells for acute lymphoid leukemia", *The New England Journal of Medicine*, 368(16): 1509-18, 2013.

Guerrero et al., "Th human application of gene therapy to re-program T-cell specificity using chimeric antigen receptors", *Chin J Cancer*, 33(9): 421-433, 2014.

Gupta et al., "Development of an EGFRvIII specific recombinant antibody", *BMC Biotechnology*, 10(1): 72, 2010.

Guschin et al., "A rapid and general assay for monitoring endogenous gene modification", in *Engineered Zinc Finger Proteins*, eds. Mackay and Segal, Ch. 15, pp. 247-256, 2010.

Hackett et al., "A transposon and transposase system for human application", *Mol. Ther.*, 18:674-683, 2010.

Hackett et al., "Efficacy and safety of *Sleeping Beauty* transposon-mediated gene transfer in preclinical animal studies", *Curr. Gene Ther.*, 11:341-349, 2011.

Haft et al., "A guild of 45 CRISPR-Associated (Cas) protein families and multiple CRISPR/Cas subtypes exist in prokaryotic genomes", *PLoS Comput Biol.*, 1(6): e60, 2005.

Heuer et al., "Repeat domain diversity of *avrBs3*-like genes in *Ralstonia solanacearum* strains and association with host preferences in the field", *Appl. Environ. Microbiol.*, 73(13): 4379-4384, 2007.

Hockemeyer et al., "A drug-inducible system for direct reprogramming of human somatic cells to pluripotency", *Cell Stem Cell*, 3: 346-353, 2008.

Holmes et al., "Disruption of HLA expression to enable allogeneic cells to escape immune recognition", *Human Gene Therapy*, 22(10): or 15, 2011.

Huang et al., "Genetically modified T cells targeting interleukin-11 receptor alpha-chain kill human osteosarcoma cells and induce the regression of established osteosarcoma lung metastases", *Cancer Res.*, 72:271-281, 2012.

(56) References Cited

OTHER PUBLICATIONS

Huls et al., "Clinical application of sleeping beauty and artificial antigen presenting cells to genetically modify T cells from peripheral and umbilical cord blood", *Journal of Visualized Experiments*, 72: e50070, 2013.
Isalan et al., "A rapid, generally applicable method to engineer zinc fingers illustrated by targeting the HIV-1 promoter", *Nat Biotechnol.*, 19(7): 656-660, 2001.
Ivics et al., "Molecular reconstruction of Sleeping Beauty, a Tcl-like transposon from fish, and its transposition in human cells", *Cell*, 91:501-510, 1997.
Izsvak and Ivics, "Sleeping beauty transposition: biology and applications for molecular therapy", *Mol. Ther.*, 9:147-156, 2004.
Izsvak et al., "Translating *Sleeping Beauty* transposition into cellular therapies: victories and challenges", *Bioessays*, 32:756-767, 2010.
Jamieson et al., "Drug discovery with engineered zinc-finger proteins", *Nature Reviews Drug Discovery*, 2(5): 361-368, 2003.
Jansen et al., "Identification of genes that are associated with DNA repeats in prokaryotes", *Molecular Microbiology*, 43(6): 1565-1575, 2002.
Jaramillo et al., "Abstract 1778: nimotuzumab, ahumanized antiepidermal growth factor receptor antibody, interacts with EGFRvIII", *Cancer Res.*, dated Apr. 15, 2010.
Jena et al., "Chimeric antigen receptor (CAR)—specific monoclonal antibody to detect CD19-specific T cells in clinical trials", PLoS One, 8(3): e57838, 2013.
Jena et al., "Redirecting T-cell specificity by introducing a tumor-specific chimeric antigen receptor", *Blood*, 116:1035-1044, 2010.
Jena et al., "Specifically targeting the interface between HER1-HER3 heterodimer on breast cancer to limit off-target effects using chimeric antigen receptor designs with improved T-cell energy balance", *Blood*, 124(21): 2151, 2014.
Jin et al., "The hyperactive *Sleeping Beauty* transposase SB100X improves the genetic modification of T cells to express a chimeric antigen receptor", *Gene Ther.*, 18:849-856, 2011.
Jutten et al., "Binding of cetuximab to the EGFRvIII deletion mutant and its biological consequences in malignant glioma cells", *Radiotherapy and Oncology*, 92(3): 393-398, 2009.
Kageshita et al., "Down-regulation of HLA class I antigen-processing molecules in malignant melanoma", *American Journal of Pathology*, 154(3): 745-754, 1999.
Kalos et al., "T cells with chimeric antigen receptors have potent antitumor effects and can establish memory in patients with advanced leukemia", *Sci Transl Med.*, 3: 95ra73, 2011.
Kay et al., "A bacterial effector acts as a plant transcription factor and induces a cell size regulator", *Science*, 318(5850): 648-51, 2007. Supporting Material.
Kebriaei et al., "Chimeric antibody receptors (CARs): driving T-cell specificity to enhance antitumor immunity", *Frontiers in Bioscience*, 4: 520-531, 2014.
Kebriaei et al., "Infusing CD19-directed T cells to augment disease control in patients undergoing autologous hematopoietic stem-cell transplantation for advanced B-lymphoid malignancies", *Hum. Gene Ther.*, 23:444-450, 2012.
Kochenderfer et al., "B-cell depletion and remissions of malignancy along with cytokine-associated toxicity in a clinical trial of anti-CD19 chimeric-antigen-receptor-transduced T cells", *Blood*, 119:2709-2720, 2012.
Kochenderfer et al., "Eradication of B-lineage cells and regression of lymphoma in a patient treated with autologous T cells genetically engineered to recognize CD19", *Blood*, 116:4099-4102, 2010.
Kohn et al., "CARs on track in the clinic", *Mol. Ther.*, 19:432-438, 2011.
Kowolik et al., "CD28 costimulation provided through a CD19-specific chimeric antigen receptor enhances in vino persistence and antitumor efficacy of adoptively transferred T cells", *Cancer Res.*, 66(22): 10995-11004, 2006.
Krishnamurthy et al., "Targeting an ancient retrovirus express in melanoma using adoptive T-cell therapy", *Oral presentation of Immunology Graduate Program, The University of Texas Graduate School of Biomedical Sciences*, dated Feb. 24, 2012.
L'Haridon et al., "Transcriptional regulation of the MHC class I HLA-A11 promoter by the zinc finger protein ZFX", *Nucleic Acids Research*, 24(10): 1928-1935, 1996.
LeibundGut-Landmann et al., "Specificity and expression of CIITA, the master regulator of MHC class II genes", *Eur. J. Immunol.*, 34: 1513-1525, 2004.
Lorimer et al., "Recombinant immunotoxins specific for a mutant epidermal growth factor receptor: targeting with a single chain antibody variable domain isolated by phage display", *Proceeding of the National Academy of Sciences U.S.A.*, 93: 14815-14820, 1996.
Maier et al., "High-resulution HLA alleles and haplotypes in the United States population", *Human Immunology*, 68: 779-788, 2007.
Maiti et al., "Sleeping beauty system to redirect T cell specific for human applications", *J Immunother.*, 36(2): 112-23, 2013.
Makarova et al., "A DNA repair system specific for thermophilic archaea and bacteria predicted by genomic context analysis", *Nucleic Acids Research*, 30(2): 482-496, 2002.
Makarova et al., "A putative RNA-interference-based immune system in prokaryotes: computational analysis of the predicted enzymatic machinery, functional analogies with eukaryotic RNAi, and hypothetical mechanisms of action", *Biology Direct*, 1:7, 2006.
Manuri et al., "*piggyback* transposon/transposase system to generate CD19-specific T cells for the treatment of B-lineage malignancies", *Human Gene Therapy*, 21: 427-437, 2010.
Mateo et al., "Humanization of a mouse monoclonal antibody that blocks the epidermal growth factor receptor: recovery of antagonistic activity", *Immunotechnology*, 3(1): 71-81, 1997.
Mates et al., "Molecular evolution of a novel hyperactive Sleeping Beauty transposase enables robust stable gene transfer in vertebrates", *Nat. Genetics.* 41(6):753-61, 2009.
Moscou and Bogdanove, "A simple cipher governs DNA recognition by TAL effectors", *Science*, 326: 1501, 2009.
Motmans et al., "Enhancing the tumor-specificity of human T cells by the expression of chimeric immunoglobulin/T cell receptor genes", *Immunotechnology* 2(4): 303-304, 1995.
Nakazawa et al., "Optimization of the piggyback transposon system for the sustained genetic modification of human T lymphocytes", *Journal of Immunotherapy*, 32(8): 826-836, 2009.
NCBI, Genbank accession No. AAT73716.1, dated Oct. 20, 2004.
NCBI, Genbank accession No. AAU14166.1, dated Mar. 16, 2005.
NCBI, Genbank accession No. ACC78293.1, dated Apr. 29, 2008.
NCBI, Genbank accession No. CAD61786.1, dated Jan. 24, 2003.
NCBI, Genbank accession No. CBK46760.1, dated May 13, 2010.
NCBI, NCBI reference sequence No. NP_002180.1, dated Apr. 21, 2013.
NCBI, PDB accession No. IUZ6_F, dated Oct. 18, 2012.
O'Conner et al., "Adoptive T-cell therapy improves treatment of canine non-Hodgkin lymphoma post chemotherapy", *Sci Rep.*, 2: 249, 2012.
Pabo et al., "Design and selection of novel $Cys_2His_2$ zinc finger proteins", *Annu. Rev. Biochem.*, 70: 313-40, 2001.
Parham, "MHC class I molecules and KIRS in human history, health and survival", Nature Reviews Immunology, 5: 201-214, 2005.
PCT International Preliminary Report on Patentability issued in International Application No. PCT/US2012/065506, mailed May 30, 2014.
PCT International Preliminary Report on Patentability issued in International Application No. PCT/US2014/039365, mailed Nov. 24, 2015.
PCT International Preliminary Report on Patentability issued in International Application No. PCT/US2014/038005, mailed Nov. 26, 2015.
PCT International Preliminary Report on Patentability issued in International Application No. PCT/US2014/062191, mailed Apr. 26, 2016.
PCT International Search Report and Written Opinion issued in International Application No. PCT/US2012/065506, mailed Mar. 4, 2013.
PCT International Search Report and Written Opinion issued in International Application No. PCT/US2014/039365, mailed Oct. 1, 2014.

(56) References Cited

OTHER PUBLICATIONS

PCT International Search Report and Written Opinion issued in International Application No. PCT/US2014/038005, mailed Feb. 13, 2015.
PCT International Search Report and Written Opinion issued in International Application No. PCT/US2014/062191, mailed Apr. 22, 2015.
PCT International Search Report and Written Opinion issued in International Application No. PCT/US2015/027511, mailed Jul. 29, 2015.
PCT International Search Report and Written Opinion issued in International Application No. PCT/US2015/027277, mailed Aug. 4, 2015.
PCT International Search Report and Written Opinion issued in International Application No. PCT/ US2015/059072, mailed Jan. 25, 2016.
PCT International Search Report and Written Opinion issued in International Application No. PCT/ US2015/059293, mailed May 3, 2016.
PCT Invitation to Pay Additional Fees issued in International Application No. PCT/US2016/021693, mailed May 19, 2016.
Porter et al., "Chimeric antigen receptor-modified T cells in chronic lymphoid leukemia", *The New England Journal of Medicine*, 365(8): 725-733, 2011.
Provasi et al., "Editing T cell specificity towards leukemia by zinc finger nucleases and lentiviral gene transfer", *Nature Medicine*, 18(5): 807-815, 2012.
Pule et al., "Virus-specific T cells engineered to coexpress tumor-specific receptors: persistence and antitumor activity in individuals with neuroblastoma", *Nat. Med.*, 14:1264-1270, 2008.
Ramos et al., "Chimeric antigen receptor (CAR)—engineered lymphocytes for cancer therapy", *Expert Opinion on Biological Therapy*,11(7): 855-873, 2011.
Riolobos et al., "HLA engineering of human pluripotent stem cells", *Molecular Therapy*, 21(6): 1232-1241, 2013.
Riteau et al., "HLA-G1 co-expression boosts the HLA class I-mediated NK lysis inhibition", *International Immunology*, 13(2): 193-201, 2001.
Rouas-Freiss et al., "The $\alpha_1$ domain of HLA-G1 and HLA-G2 inhibits cytotoxicity induced by natural killer cells: is HLA-G the public ligand for natural killer cell inhibitory receptors?", *Proc. Natl. Acad. Sci. USA*, 94: 5249-5254, 1997.
Rowley et al., "Expression of IL-15RA or an IL-15/IL-15RA fusion on CD8+ T cells modifies adoptively transferred T-cell function in cis", *European Journal of Immunology*, 39(2): 491-506, 2009.
Rushworth et al., "Universal artificial antigen presenting cells to selectively propagate T cells expressing chimeric antigen receptor independently of specifity", *J Immunother.*, 37(4): 204-13, 2014.
Sadelain et al., "The basic principles of chimeric antigen receptor design", *Cancer Discovery*, 3(4): 388-398, 2013.
Schornack et al., "Gene-for-gene-mediated recognition of nuclear-targeted AvrBs3-like bacterial effector proteins", *Journal of Plant Physiology*, 163: 256-272, 2006.
Segal and Barbas, "Customs DNA-binding proteins come of age: polydactyl zinc-finger proteins", *Current Opinion in Biotechnology*, 12: 632-637, 2001.
Shen et al., "Chimeric antigen receptor containing ICOS signaling domain mediates specific and efficient antitumor effect of T cells against EGFRvIII expressing glioma", *Journal of Hematology and Oncology*, 6(1): 33, 2013.
Singh et al., "Manufacture of clinical-grade CD19-specific T cells stably expressing chimeric antigen receptor using Sleeping Beauty system and artificial antigen presenting cells", *PLoS One.*, 8(5): e64138, 2013.
Singh et al., "Redirecting specificity of T-cell populations for CD19 using the *Sleeping Beauty* system", *Cancer Res.*, 68(8): 2961-2971, 2008.
Singh et al., "Reprogramming CD19-specific T cells with IL-21 signaling can improve adoptive immunotherapy of B-lineage malignancies", *Cancer Res.*, 71(10): 3516-3527, 2011.

Somanchi et al., "Engineering lymph node homing of ex vivo-expanded human natural killer cells via trogocytosis of the chemokine receptor CCR7", *Blood*, 119(22): 5164-5172, 2012.
Tamada et al., "Redirecting gene-modified T cells toward various cancer types using tagged antibodies", *Clinical Cancer Research*, 12(23): 6436-6445, 2012.
Till et al., "Adoptive immunotherapy for indolent non-Hodgkin lymphoma and mantle cell lymphoma using genetically modified autologous CD20-specific T cells", *Blood*, 112:2261-2271, 2008.
Torikai et al., "A foundation for universal T-cell based immunotherapy: T cells engineered to express a CD19-specific chimeric-antigen-receptor and eliminate expression of endogenous TCR", *Blood*, 119(24):5697-5705, 2012.
Torikai et al., "HLA and TCR knockout by zinc finger nucleases: toward "off-the-shelf" allogeneic t-cell therapy for CD19+ malignancies", *Blood* (*ASH Annual Meeting Abstracts*), 116: Abstract 3766, 2010.
Torikai et al., "Toward eliminating HLA class I expression to generate universal cells from allogeneic donors", *Blood*, 122(8): 1341-1349, 2013.
Villard et al., "A functionally essential domain of RFX5 mediates activation of major histocompatibility complex class Ii promoters by promoting cooperative binding between RFX and NF-Y", *Molecular and Cellular Biology*, 20(10): 3364-3376, 2000.
Williams, "*Sleeping beauty* vector system moves toward human trials in the United States", *Mol. Ther.*, 16:1515-1516, 2008.
Zheng et al., "Protein L: a novel reagent for the detection of chimeric antigen receptor (CAR) expression by flow cytometry", *Journal of Translational Medicine*, 10:29, 2012.
Zhu et al., "Overexpression of miR-152 leads to reduced expression of human leukocyte antigen-G and increased natural killer cell mediated cytolysis in JEG-3 cells", *Am J Obstet Gynecol.*, 202(6): 592. el-7, 2010.
Berger, C., M. C. Jensen, P. M. Lansdorp, M. Gough, C. Elliott, and S. R. Riddell. 2008. Adoptive transfer of effector CD8+ T cells derived from central memory cells establishes persistent T cell memory in primates. J Clin Invest 118:294-305.
Bessard, A., V. Sole, G. Bouchaud, A. Quemener, and Y. Jacques. 2009. High antitumor activity of RLI, an interleukin-15 (IL-15)-IL-15 receptor alpha fusion protein, in metastatic melanoma and colorectal cancer. Mol Cancer Ther 8:2736-2745.
Burkett, P. R., R. Koka, M. Chien, S. Chai, D. L. Boone, and A. Ma. 2004. Coordinate expression and trans presentation of interleukin (IL)-15Ralpha and IL-15 supports natural killer cell and memory CD8+ T cell homeostasis. J Exp Med 200:825-834.
Cheever MA (2008) Twelve immunotherapy drugs that could cure cancers. Immunol Rev 222:357-368.
Dadi Saïda, et al. "Cancer immunosurveillance by tissue-resident innate lymphoid cells and innate-like T cells." *Cell* 164.3 (2016): 365-377.
Denman, C J., V. V. Senyukov, S. S. Somanchi, P. V. Phatarpekar, L. M. Kopp, J. L. Johnson, H. Singh, L. Hurton, S. N. Maiti, M. H. Huls, R. E. Champlin, L. J. Cooper, and D. A. Lee. 2012. Membrane-bound IL-21 promotes sustained ex vivo proliferation of human natural killer cells. PLoS One 7:e30264.
Dubois, S., J. Mariner, T. A. Waldmann, and Y. Tagaya. 2002. IL-15Ralpha recycles and presents IL-15 in trans to neighboring cells. Immunity 17:537-547.
Epardaud, M., K. G. Elpek, M. P. Rubinstein, a. R. Yonekura, A. Bellemare- Pelletier, R. Bronson, J. A. Hamerman, A. W. Goldrath, and S. J. Turley. 2008. Interleukin-15/interleukin-15R alpha complexes promote destruction of established tumors by reviving tumor-resident CD8+ T cells. Cancer Res 68:2972-2983.
Guo, Y., Luan, L., Rabacal, W., Bohannon, J.K., Fensterheim, B.A., Hernandez, A. And Sherwood, E.R., 2015. IL-45 superagonist-mediated immunotoxicity: role of NK cells and IFN-γ. *The Journal of Immunology*,195(5), pp. 2353-2364.
Han, K. P., X. Zhu, B. Liu, E. Jeng, L. Kong, J. L. Yovandich, V. V. Vyas, W. D. Marcus, P. A. Chavaillaz, C. A. Romero, P. R. Rhode, and H. C. Wong. 2011. IL-15:IL-15 receptor alpha superagonist complex: high-level co-expression in recombinant mammalian cells, purification and characterization. Cytokine 56:804-810.

(56) References Cited

OTHER PUBLICATIONS

Hoyos V, et al. (2010) Engineering CD19-specific T lymphocytes with interleukin-15 and a suicide gene to enhance their anti-lymphoma/leukemia effects and safety. Leukemia 24(6):1160-1170.
Hsu C, Hughes MS, Zheng Z, Bray RB, Rosenberg SA, and Morgan RA. 2005. Primary human T lymphocytes engineered with a codon-optimized IL-15 gene resist cytokine withdrawal-induced apoptosis and persist long-term in the absence of exogenous cytokine. J Immunol 175(11):7226-34.
Hunter MR, et al. (2013) Chimeric gammac cytokine receptors confer cytokine independent engraftment of human T lymphocytes. Mol Immunol 56(1-2):1-11.
Huntington, N. D., N. Legrand, N. L. Alves, B. Jaron, K. Weijer, A. Plet, E. Corcuff, E. Mortier, Y. Jacques, H. Spits, and J. P. Di Santo. 2009. IL-15 trans-presentation promotes human NK cell development and differentiation in vivo. J Exp Med 206:25-34.
Hurton, Tethered IL-15 to Augment the Therapeutic Potential of T Cells Expressing Chimeric Antigen Receptor: Maintaining Memory Potential, Persistence, and Antitumor Activity, Thesis, Mar. 2014.
Imamura M, et al. (2014) Autonomous growth and increased cytotoxicity of natural killer cells expressing membrane-bound interleukin-15. Blood 124(7):1081-1088.
Kermer V, Baum V, Hornig N, Kontermann RE, & Muller D (2012) an antibody fusion protein for cancer immunotherapy mimicking IL-15 trans-presentation at the tumor site. Mol Cancer Ther 11(6):1279-1288.
Klebanoff CA, et al. (2004) IL-15 enhances the in vivo antitumor activity of tumor-reactive CD8+ T cells. Proc Natl Acad Sci U S A 101(7):1969-1974.
Kobayashi, H., S. Dubois, N. Sato, H. Sabzevari, Y. Sakai, T. A. Waldman, and Y. Tagaya. 2005. Role of trans-cellular IL-15 presentation in the activation of NK cellmediated killing, which leads to enhanced tumor immunosurveillance. Blood 105:721-727.
Markley JC and Sadelain M. 2010.IL-7 and IL-21 are superior to IL-2 and IL-15 in promoting human T cell-mediated rejection of systemic lymphoma in immunodeficient mice. Blood. 115(17):3508-19.
Marks-Konczalik J, et al. (2000) IL-2-induced activation-induced cell death is inhibited in IL-15 transgenic mice. Proc Natl Acad Sci U S A 97(21):11445-11450.
Mlecnik B, et al. (2014) Functional network pipeline reveals genetic determinants associated with in situ lymphocyte proliferation and survival of cancer patients. Sci Transl Med 6(228):228ra237.
Mortier E, et al. (2006) Soluble interleukin-15 receptor alpha (IL-15R alpha)-sushi as a selective and potent agonist of IL-15 action through IL-15R beta/gamma. Hyperagonist IL-15xIL-15R alpha fusion proteins. J Biol Chem 281(3):1612-1619
Olsen, S. K., N. Ota, S. Kishishita, M. Kukimoto-Niino, K. Murayama, H. Uchiyama, M. Toyama, T. Terada, M. Shirouzu, O. Kanagawa, and S. Yokoyama 2007. Crystal Structure of the interleukin-15.interleukin-15 receptor alpha complex: insights into trans and cis presentation. J Biol Chem 282:37191-37204.

Perdreau, H., E. Mortier, G. Bouchaud, V. Sole, Y. Boublik, A. Plet, and Y. Jacques. 2010. Different dynamics of IL-15R activation following IL-15 cis- or transpresentation. Eur Cytokine Netw 21:297-307.
Rhode PR, et al. (2015) Comparison of the Superagonist Complex, ALT-803, to IL15 as Cancer Immunotherapeutics in Animal Models. Cancer Immunol Res.
Sandau, M. M., K. S. Schluns, L. Lefrancois, and S. C. Jameson. 2004. Cutting edge: transpresentation of IL-15 by bone marrow-derived cells necessitates expression of IL-15 and IL-15R alpha by the same cells. J Immunol 173:6537-6541.
Sato N, Patel HJ, Waldman TA, & Tagaya Y (2007) The IL-15/IL-15Ralpha on cell surfaces enables sustained IL-15 activity and contributes to the long survival of CD8 memory T cells. Proc Natl Acad Sci U S A 104(2):588-593.
Steel, J. C., T. A. Waldmann, and J. C. Morris. 2012. Interleukin-15 biology and its therapeutic implications in cancer. Trends Pharmacol Sci 33:35-41.
Stoklasek TA, Schluns KS, & Lefrancois L (2006) Combined IL-15/IL-15Ralpha immunotherapy maximizes IL-15 activity in vivo. J Immunol 177(9):6072-6080.
Stone JD, Chervin AS, Schreiber H, and Kranz DM. 2012. Design and characterization of a protein superagonist of IL-15 fused with IL-15Ra and a high-affinity T cell receptor. Biotechnol. Prog. 28(6):1588-97.
Stonier SW, Ma LJ, Castillo EF, & Schluns KS (2008) Dendritic cells drive memory CD8 T-cell homeostasis via IL-15 transpresentation. Blood 112(12):4546-4554.
Teague RM, et al. (2006) Interleukin-15 rescues tolerant CD8+ T cells for use in adoptive immunotherapy of established tumors. Nat Med 12(3):335-341.
Vincent, M., A. Bessard, D. Cochonneau, G. Teppaz, V. Sole, M. Maillasson, S. Birkle, L. Garrigue-Antar, A. Quemener, and Y. Jacques. 2013. Tumor targeting of the IL-15 superagonist RLI by an anti-GD2 antibody strongly enhances its antitumor potency. Int J Cancer 133:757-765.
Waldmann, T. A. 2006. The biology of interleukin-2 and interleukin-15: implications for cancer therapy and vaccine design. Nat Rev Immunol 6:595-601.
Zakrzewski, J. L., D. Suh, J. C. Markley, O. M. Smith, C. King, G. L. Goldberg, R. Je nq, A. M. Holland, J. Gmbin, J. Cabrera-Perez, R. J. Brentjens, S. X. Lu, G. Rizzuto, D. B. Sant'Angelo, I. Riviere, M. Sadelain, G. Heller, J. C. Zuniga-Pflucker, C. Lu, and M. R. van den Brink. 2008. Tumor immunotherapy across MHC barriers using allogeneic T-cell precursors. Nat Biotechnol 26:453-461.
Zhang X, Sun S, Hwang I, Tough DF, & Sprent J (1998) Potent and selective stimulation of memory-phenotype CD8+ T cells in vivo by IL-15. Immunity 8(5):591-599.
Zhu, W.D. Marcus, W. Xu, H.-I. Lee, K. Han, J.O. Egan, et al., Novel human interleukin-15 . agonists, J. Immunol. 183 (2009) 3598.
Extended European Search Report issued in EP Application No. 14798046, dated Oct. 10, 2016.
Han et al., "IL-15: IL-15 receptor alpha superagonist complex: high-level co-expression in recombinant mammalian cells, purification and characterization." *Cytokine* 56.3 (2011): 804-810.

\* cited by examiner

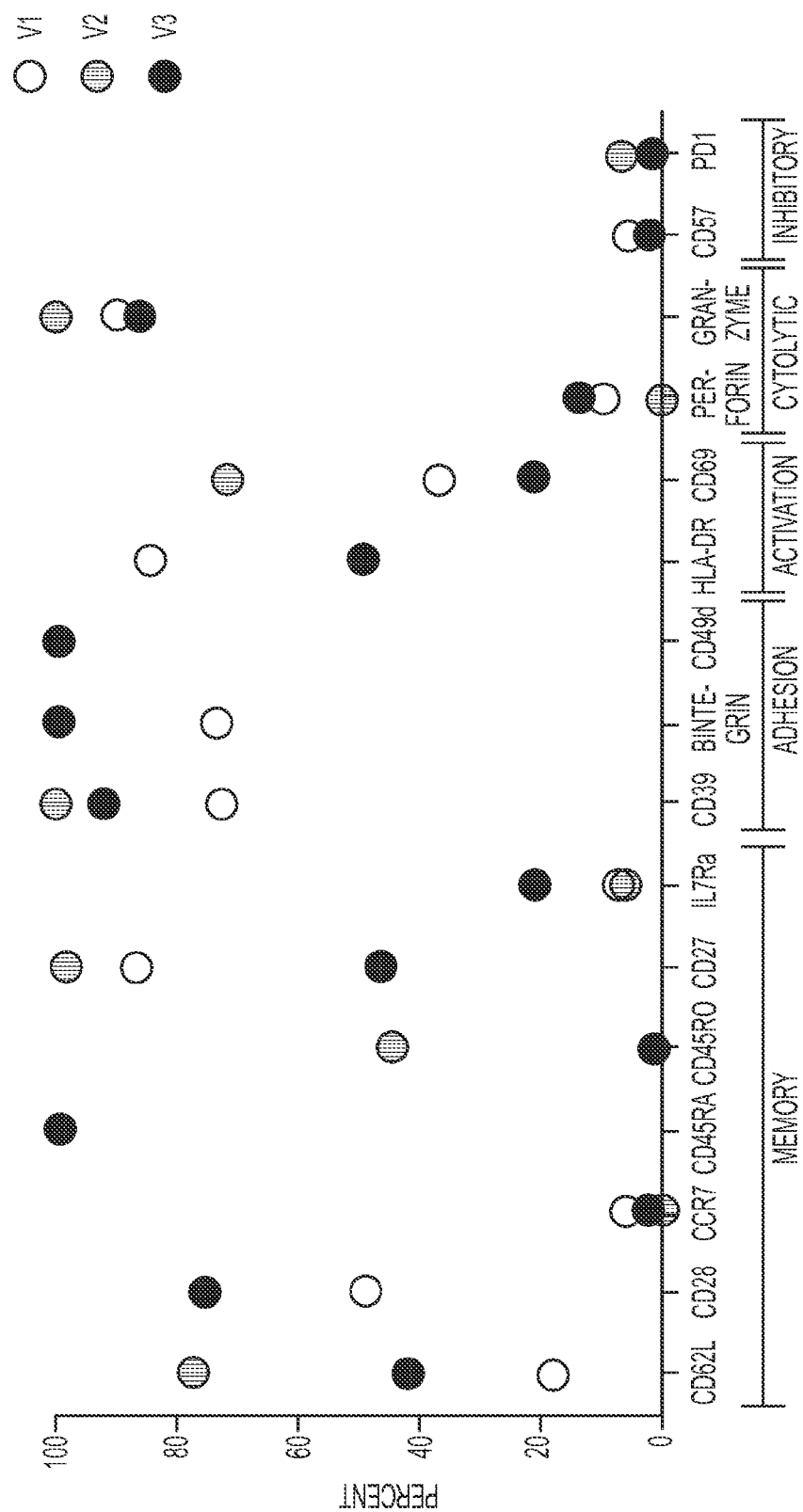

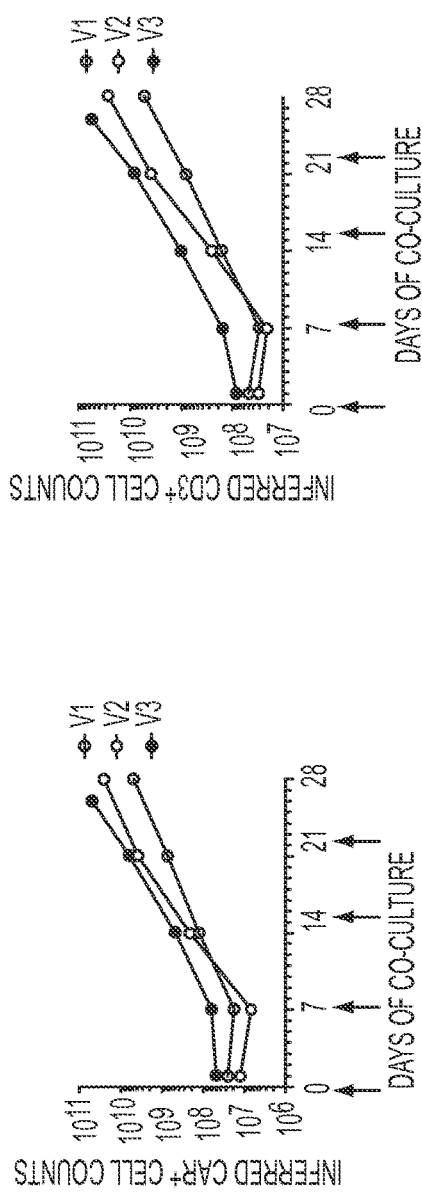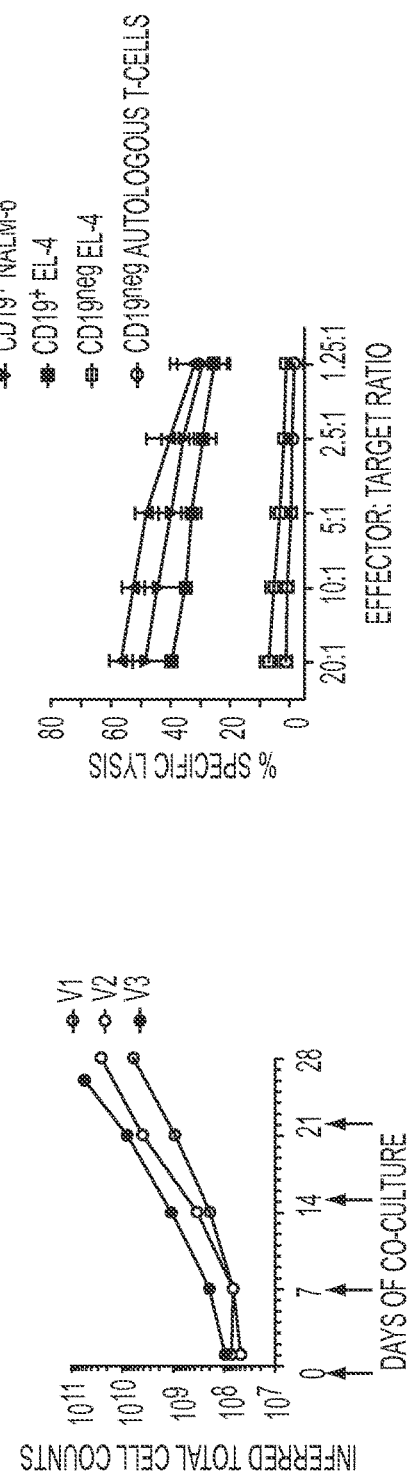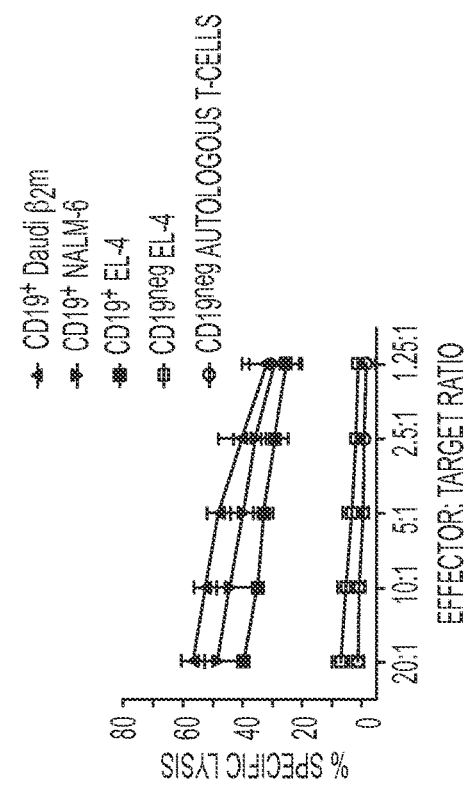
FIG. 8A
FIG. 8B
FIG. 8C
FIG. 8D

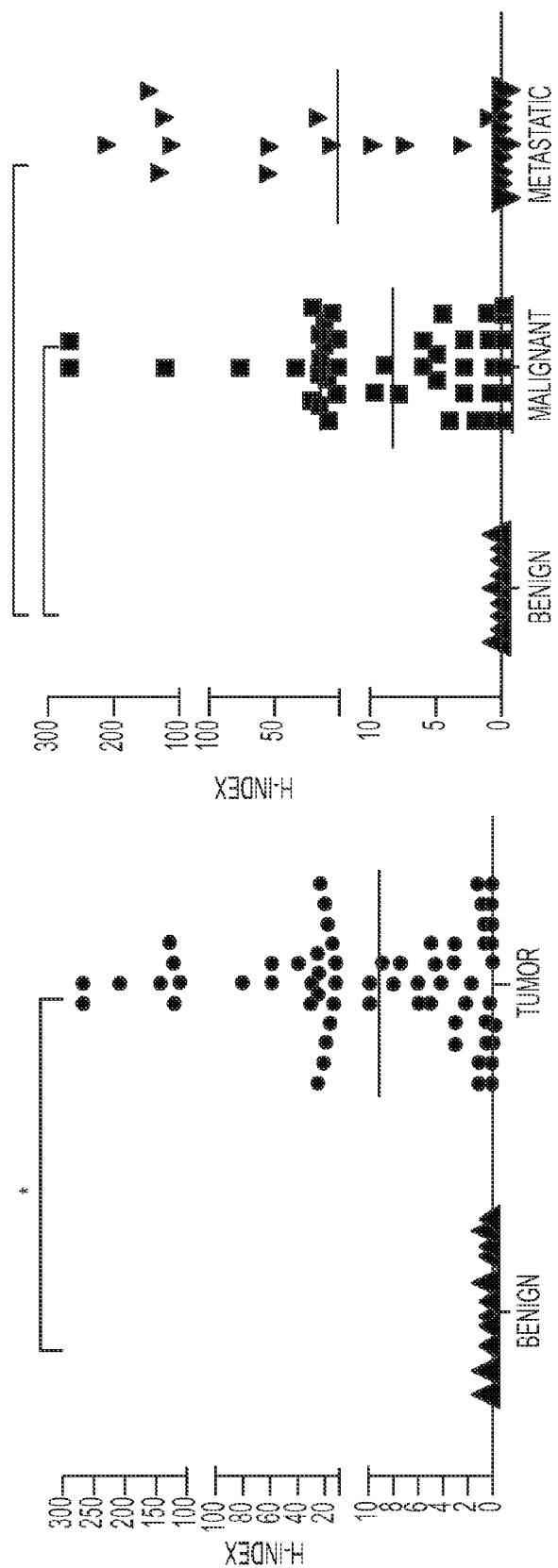

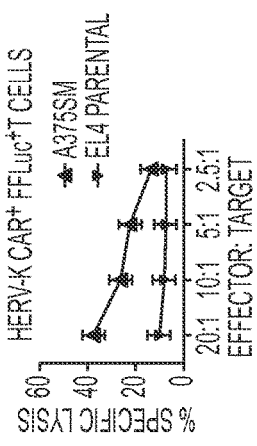
FIG. 27A
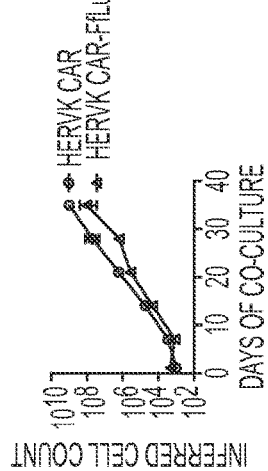
FIG. 27B
FIG. 27C
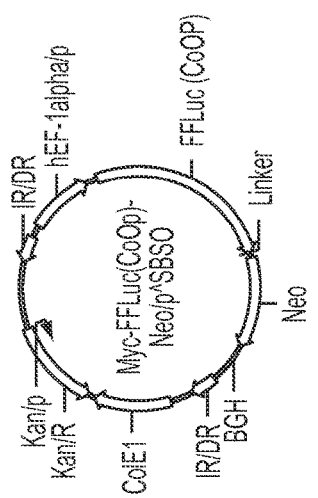
FIG. 27D
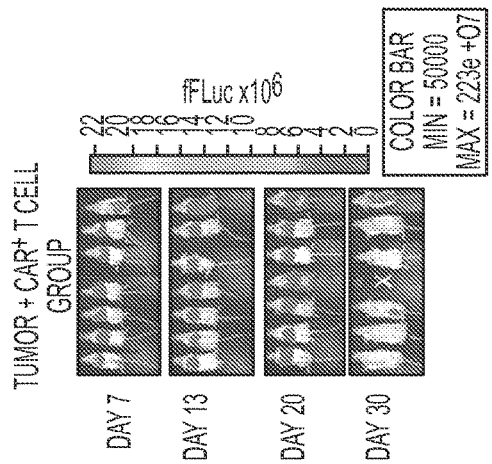
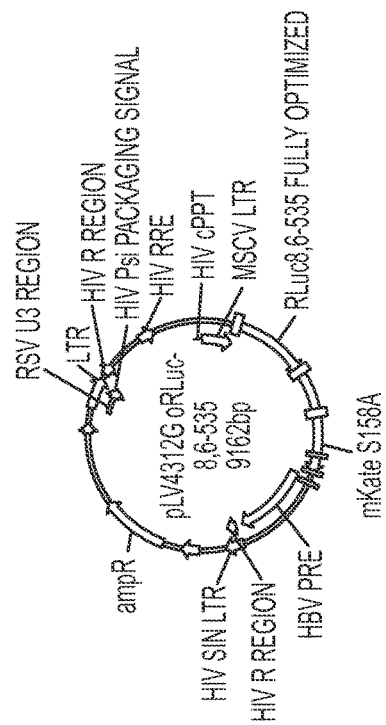
FIG. 27E

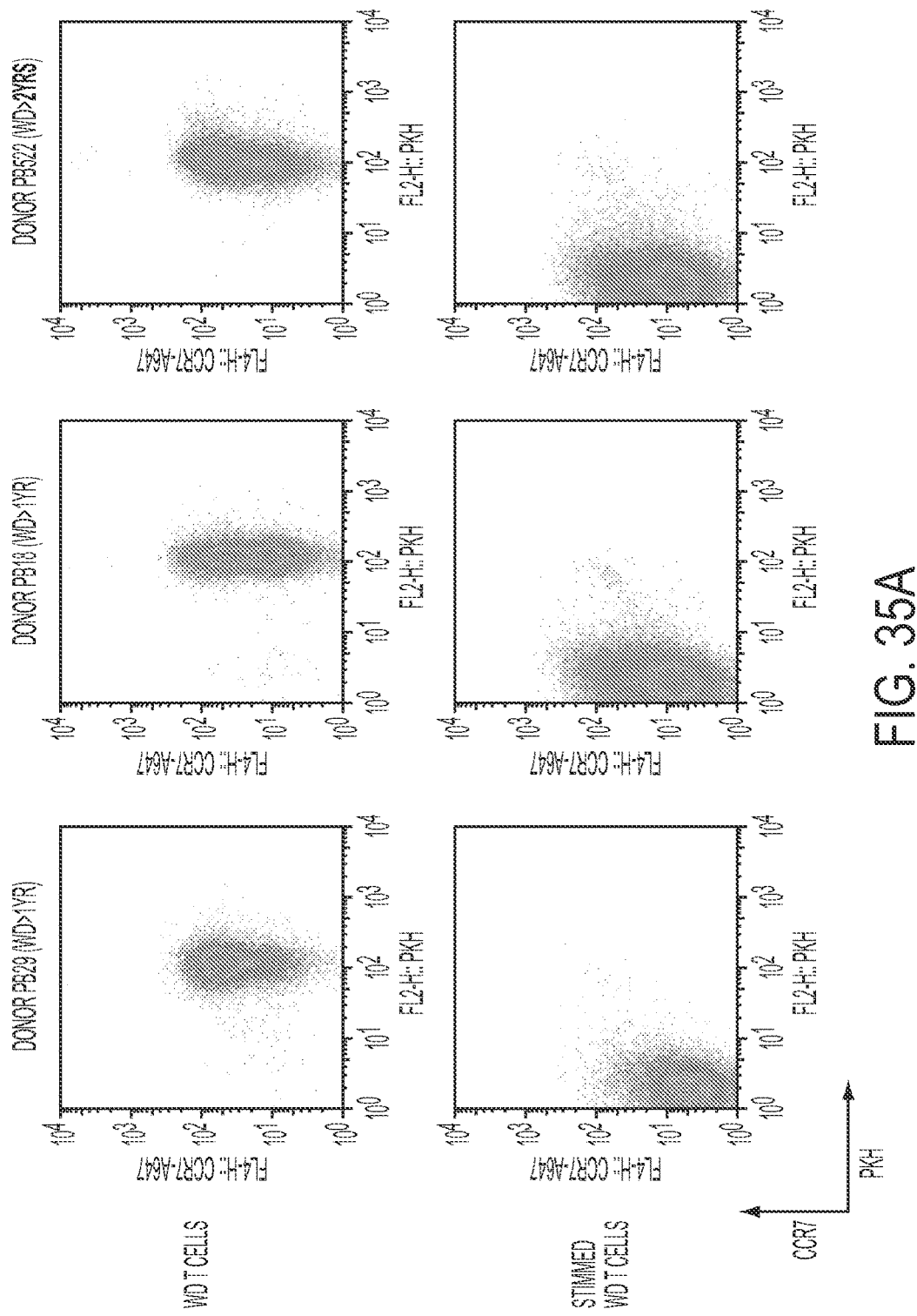

SEQUENCE LISTING

```
<160> NUMBER OF SEQ ID NOS: 17

<210> SEQ ID NO 1
<211> LENGTH: 711
<212> TYPE: PRT
<213> ORGANISM: Artificial Sequence
<220> FEATURE:
<223> OTHER INFORMATION: fusion protein

<400> SEQUENCE: 1

Met Leu Leu Leu Val Thr Ser Leu Leu Leu Cys Glu Leu Pro His
1               5                   10                  15

Pro Ala Phe Leu Leu Ile Pro Asp Ile Gln Met Thr Gln Thr Thr
            20                  25                  30

Ser Ser Leu Ser Ala Ser Leu Gly Asp Arg Val Thr Ile Ser Cys Arg
            35                  40                  45

Ala Ser Ser Gln Asp Ile Ser Lys Tyr Leu Asn Trp Tyr Gln Gln Lys
```

```
                50                  55                  60
Pro Asp Gly Thr Val Lys Leu Leu Ile Tyr His Thr Ser Arg Leu
 65                  70                  75                  80

His Ser Gly Val Pro Ser Arg Phe Ser Gly Ser Gly Ser Gly Thr
                 85                  90                  95

Asp Tyr Ser Leu Thr Ile Ser Asn Leu Glu Gln Glu Asp Ile Ala Thr
                100                 105                 110

Tyr Tyr Phe Cys Gln Gln Gly Asn Thr Leu Pro Tyr Thr Phe Gly Gly
                115                 120                 125

Gly Thr Lys Leu Glu Ile Ile Thr Gly Ser Thr Ser Gly Ser Gly Lys
                130                 135                 140

Pro Gly Ser Gly Glu Gly Ser Thr Lys Gly Glu Val Lys Leu Gln
145                 150                 155                 160

Glu Ser Gly Pro Gly Leu Val Ala Pro Ser Gln Ser Leu Ser Val Thr
                165                 170                 175

Thr Cys Thr Val Ser Gly Val Ser Leu Pro Asp Tyr Gly Val Ser Trp
                180                 185                 190

Ile Arg Gln Pro Pro Arg Lys Gly Leu Glu Trp Leu Gly Val Ile
                195                 200                 205

Trp Gly Ser Glu Thr Thr Tyr Tyr Asn Ser Ser Ala Leu Lys Ser Arg
210                 215                 220

Leu Thr Ile Ile Lys Asp Asn Ser Lys Ser Gln Val Phe Leu Lys Lys
225                 230                 235                 240

Met Asn Ser Leu Gln Thr Asp Asp Thr Ala Ile Tyr Tyr Cys Ala Lys
                245                 250                 255

His Tyr Tyr Tyr Gly Gly Ser Tyr Ala Met Asp Tyr Trp Gly Gln
                260                 265                 270

Gly Thr Ser Val Thr Val Ser Ser Glu Glu Ser Lys Tyr Gly Pro Pro
                275                 280                 285

Cys Pro Pro Cys Pro Ala Pro Glu Phe Leu Gly Gly Pro Ser Ser Val
                290                 295                 300

Phe Leu Phe Pro Pro Lys Pro Lys Asp Thr Leu Met Ile Ser Arg Thr
305                 310                 315                 320

Pro Glu Val Val Thr Cys Val Val Asp Val Ser Gln Glu Asp Pro
                325                 330                 335

Glu Val Gln Phe Asn Trp Tyr Val Asp Gly Val Glu Val His Asn
                340                 345                 350

Ala Lys Thr Lys Pro Arg Glu Glu Gln Phe Asn Ser Thr Thr Tyr Arg
                355                 360                 365

Val Val Ser Val Leu Thr Val Leu His Gln Asp Trp Leu Asn Gly Lys
                370                 375                 380

Glu Tyr Tyr Lys Cys Lys Val Ser Asn Lys Gly Leu Pro Ser Ser Ile
385                 390                 395                 400

Glu Lys Thr Ile Ser Lys Ala Ala Lys Gly Gln Pro Arg Glu Pro Gln
                405                 410                 415

Val Tyr Thr Leu Pro Pro Ser Gln Glu Glu Met Thr Thr Lys Asn Gln
                420                 425                 430

Val Ser Leu Thr Cys Leu Val Lys Gly Phe Tyr Pro Ser Asp Ile Ala
                435                 440                 445

Val Val Glu Trp Glu Ser Asn Gly Gln Pro Glu Asn Asn Tyr Lys Thr
                450                 455                 460

Thr Pro Pro Val Leu Asp Asp Ser Asp Gly Ser Phe Phe Leu Tyr Ser
465                 470                 475                 480
```

```
Arg Leu Thr Val Asp Lys Ser Arg Trp Gln Glu Gly Asn Val Phe
            485                 490                 495

Ser Cys Ser Val Met His Glu Ala Leu His Asn His Tyr Thr Gln Lys
        500                 505                 510

Lys Ser Leu Ser Leu Ser Leu Gly Lys Met Phe Trp Val Leu Val Val
        515                 520                 525

Val Gly Gly Val Leu Leu Ala Cys Tyr Ser Leu Leu Val Thr Val Ala
    530                 535                 540

Phe Ile Ile Phe Trp Val Arg Ser Lys Arg Arg Ser Arg Gly Gly His
545                 550                 555                 560

Ser Asp Tyr Met Asn Met Thr Pro Arg Arg Pro Gly Pro Thr Arg Arg
            565                 570                 575

Lys His Tyr Gln Pro Tyr Ala Pro Pro Arg Asp Phe Ala Ala Tyr Arg
        580                 585                 590

Ser Arg Val Lys Lys Phe Ser Arg Ser Ala Asp Ala Pro Ala Tyr Gln
        595                 600                 605

Gln Gly Gln Asn Gln Leu Tyr Asn Glu Leu Asn Leu Gly Arg Arg
    610                 615                 620

Glu Glu Tyr Asp Val Leu Asp Lys Arg Arg Gly Arg Asp Pro Pro Glu
625                 630                 635                 640

Met Gly Gly Lys Pro Arg Arg Lys Asn Pro Gln Glu Gly Leu Tyr Asn
            645                 650                 655

Glu Leu Gln Gln Lys Asp Lys Met Ala Glu Ala Tyr Ser Glu Ile Gly
        660                 665                 670

Met Lys Gly Glu Arg Arg Arg Gly Lys Gly His Asp Gly Leu Tyr
        675                 680                 685

Gln Gly Leu Ser Thr Ala Thr Lys Asp Thr Tyr Asp Ala Ala Leu His
    690                 695                 700

Met Gln Ala Leu Pro Pro Arg
705                 710

<210> SEQ ID NO 2
<211> LENGTH: 2034
<212> TYPE: DNA
<213> ORGANISM: Artificial Sequence
<220> FEATURE:
<223> OTHER INFORMATION: Synthetic polynucleotide sequence

<400> SEQUENCE: 2
atgctgctgc tggtgaccag cctgctgctg tgtgagctgc ccacccgc ctttctgctg      60 atccccgaca tccagatgac ccagaccacc tccagcctga gcgccagcct gggcgaccgg     120
gtgaccatca gctgccgggc cagccaggac atcagcaagt acctgaactg gtatcagcag     180
aagcccgacg gcaccgtcaa gctgctgatc taccacacca gccggctgca cagcggcgtg     240
cccagccggt ttagcggcag cggctccggc accgactaca gcctgaccat ctccaacctg     300
gagcaggagg acatcgccac ctactttgc cagcagggca cacactgcc ctacaccttt       360 ggcggcggaa caaagctgga gatcaccggc agcacctccg cagcggcaa gcctggcagc      420 ggcgagggca gcaccaaggg cgaggtgaag ctgcaggaga gcggccctgg cctggtggcc     480
cccagccaga gcctgagcgt gacctgtacc gtgtccggcg tgtccctgcc cgactacggc     540
gtgtcctgga tccggcagcc ccctaggaag ggcctggagt ggctgggcgt gatctggggc     600
agcgagacca cctactacaa cagcgccctg aagagccggc tgaccatcat caaggacaac     660
agcaagagcc aggtgttcct gaagatgaac agcctgcaga ccgacgacac cgccatctac     720
```

```
tactgtgcca agcactacta ctacggcggc agctacgcca tggactactg gggccagggc      780
accagcgtga ccgtgtccag cgagagcaag tacggccctc cctgcccccc ttgccctgcc      840
cccgagttcc tgggcggacc cagcgtgttc ctgttccccc ccaagcccaa ggacaccctg      900
atgatcagcc ggaccccga ggtgacctgt gtggtggtgg acgtgtccca ggaggacccc       960
gaggtccagt tcaactggta cgtggacggc gtggaggtgc acaacgccaa gaccaagccc     1020
cgggaggagc agttcaatag cacctaccgg gtggtgtccg tgctgaccgt gctgcaccag     1080
gactggctga acggcaagga atacaagtgt aaggtgtcca acaagggcct gcccagcagc     1140
atcgagaaaa ccatcagcaa ggccaagggc cagcctcggg agccccaggt gtacaccctg     1200
cccctagcc aagaggagat gaccaagaat caggtgtccc tgacctgcct ggtgaagggc      1260
ttctacccca gcgacatcgc cgtggagtgg gagagcaacg gccagcccga gaacaactac     1320
aagaccaccc cccctgtgct ggacagcgac ggcagcttct tcctgtacag caggctgacc     1380
gtggacaaga ccggtggca ggagggcaac gtctttagct gctccgtgat gcacgaggcc      1440
ctgcacaacc actacaccca agagagcctg tccctgagcc tgggcaagat gttctgggtg     1500
ctggtcgtgg tgggtggcgt gctggcctgc tacagcctgc tggtgacagt ggccttcatc     1560
atcttttggg tgaggagcaa gcggagcaga ggcggccaca gcgactacat gaacatgacc     1620
ccccggaggc ctggccccac ccggaagcac taccagccct acgcccctcc cagggacttc     1680
gccgcctacc ggagccgggt gaagttcagc cggagcgccg acgcccctgc ctaccagcag     1740
ggccagaacc agctgtacaa cgagctgaac ctgggccgga gggaggagta cgacgtgctg     1800
gacaagcgga gaggccggga ccctgagatg ggcggcaagc cccggagaaa gaaccctcag     1860
gagggcctgt ataacgaact gcagaaagac aagatggccg aggcctacag cgagatcggc     1920
atgaagggcg agcggcggag gggcaagggc cacgacggcc tgtaccaggg cctgagcacc     1980
gccaccaagg atacctacga cgccctgcac atgcaggccc tgccccccag atga           2034
```

<210> SEQ ID NO 3
<211> LENGTH: 4246
<212> TYPE: DNA
<213> ORGANISM: Artificial Sequence
<220> FEATURE:
<223> OTHER INFORMATION: Synthetic polynucleotide sequence

<400> SEQUENCE: 3

```
agttgaagtc ggaagtttac atacacttaa gttggagtca ttaaaactcg ttttcaact       60
actccacaaa tttcttgtta acaaacaata gttttggcaa gtcagttagg acatctactt     120
tgtgcatgac acaagtcatt tttccaacaa ttgtttacag acagattatt tcacttataa     180
ttcactgtat cacaattcca gtgggtcaga agtttacata cactaagttg actgtgcctt     240
taaacagctt ggaaaattcc agaaaatgat gtcatggctt tagaagcttc tgatagacta     300
attgacatca tttgagtcaa ttggaggtgt acctgtggat gtatttcaag gaattctgtg     360
gaatgtgtgt cagttagggt gtggaaagtc cccaggctcc ccagcaggca agtatgca      420
aagcatcgag cggccgcaat aaaatatctt tattttcatt acatctgtgt gttggttttt     480
tgtgtgaatc gtaactaaca tacgctctcc atcaaaacaa aacgaaacaa acaaactag     540
caaaataggc tgtccccagt gcaagtgcag gtgccagaac atttctctat cgaaggatct     600
gcgatcgctc cggtgcccgt cagtgggcag agcgcacatc gcccacagtc cccgagaagt     660
tgggggagg ggtcggcaat tgaaccggtg cctagagaag gtggcgcggg gtaaactggg     720
```

```
aaagtgatgt cgtgtactgg ctccgccttt ttcccgaggg tggggagaa  ccgtatataa    780
gtgcagtagt cgccgtgaac gttcttttc  gcaacgggtt tgccgccaga acacagctga    840
agcttcgagg ggctcgcatc tctccttcac gcgcccgccg ccctacctga ggccgccatc    900
cacgccggtt gagtcgcgtt ctgccgcctc ccgcctgtgg tgcctcctga actgcgtccg    960
ccgtctaggt aagtttaaag ctcaggtcga gaccgggcct ttgtccggcg ctcccttgga   1020
gcctacctag actcagccgg ctctccacgc tttgcctgac cctgcttgct caactctacg   1080
tctttgtttc gttttctgtt ctgcgccgtt acagatccaa gctgtgaccg gcgcctacct   1140
gagatcaccg gcgaaggagg cctatcatga agatctatcg attgtacagc tagccgccac   1200
catgctgctg ctggtgacca gcctgctgct gtgtgagctg ccccaccccg cctttctgct   1260
gatccccgac atccagatga cccagaccac ctccagcctg agcgccagcc tgggcgaccg   1320
ggtgaccatc agctgccggg ccagccagga catcagcaag tacctgaact ggtatcagca   1380
gaagcccgac ggcaccgtca agctgctgat ctaccacacc agccggctgc acagcggcgt   1440
gcccagccgg tttagcggca gcggctccgg caccgactac agcctgacca tctccaacct   1500
ggagcaggag gacatcgcca cctacttttg ccagcagggc aacacactgc cctacacctt   1560
tggcggcgga acaaagctgg agatcaccgg cagcacctcc ggcagcggca agcctggcag   1620
cggcgagggc agcaccaagg gcgaggtgaa gctgcaggag agcggccctg gcctggtggc   1680
ccccagccag agcctgagcg tgacctgtac cgtgtccggc gtgtccctgc ccgactacgg   1740
cgtgtcctgg atccggcagc cccctaggaa gggcctggag tggctgggcg tgatctgggg   1800
cagcgagacc acctactaca acagcgccct gaagagccgg ctgaccatca tcaaggacaa   1860
cagcaagagc caggtgttcc tgaagatgaa cagcctgcag accgacgaca ccgccatcta   1920
ctactgtgcc aagcactact actacggcgg cagctacgcc atggactact ggggccaggg   1980
caccagcgtg accgtgtcca gcgagagcaa gtacggccct ccctgccccc cttgccctgc   2040
ccccgagttc ctgggcggac ccagcgtgtt cctgttcccc cccaagccca aggacaccct   2100
gatgatcagc cggacccccg aggtgacctg tgtggtggtg gacgtgtccc aggaggaccc   2160
cgaggtccag ttcaactggt acgtggacgg cgtggaggtg cacaacgcca agaccaagcc   2220
ccgggaggag cagttcaata gcacctaccg ggtggtgtcc gtgctgaccg tgctgcacca   2280
ggactggctg aacggcaagg aatacaagtg taaggtgtcc aacaagggcc tgcccagcag   2340
catcgagaaa accatcagca aggccaaggg ccagcctcgg gagccccagg tgtacaccct   2400
gcccccctagc caagaggaga tgaccaagaa tcaggtgtcc ctgacctgcc tggtgaaggg   2460
cttctacccc agcgacatcg ccgtggagtg ggagagcaac ggccagcccg agaacaacta   2520
caagaccacc ccccctgtgc tggacagcga cggcagcttc ttcctgtaca gcaggctgac   2580
cgtggacaag agccggtggc aggagggcaa cgtctttagc tgctccgtga tgcacgaggc   2640
cctgcacaac cactacaccc agaagagcct gtccctgagc ctgggcaaga tgttctgggt   2700
gctggtcgtg gtgggtggcg tgctggcctg ctacagcctg ctggtgacag tggccttcat   2760
catcttttgg gtgaggagca agcggagcag aggcggccac agcgactaca tgaacatgac   2820
cccccggagg cctggcccca cccggaagca ctaccagccc tacgcccctc caagggactt   2880
cgccgcctac cggagccggg tgaagttcag ccggagcgcc gacgcccctg cctaccagca   2940
gggccagaac cagctgtaca acgagctgaa cctgggccgg agggaggagt acgacgtgct   3000
ggacaagcgg agaggccggg accctgagat gggcggcaag ccccgagaa  agaaccctca   3060
ggagggcctg tataacgaac tgcagaaaga caagatggcc gaggcctaca gcgagatcgg   3120
```

-continued

```
catgaagggc gagcggcgga ggggcaaggg ccacgacggc ctgtaccagg gcctgagcac   3180
cgccaccaag gatacctacg acgccctgca catgcaggcc ctgcccccca gatgactacg   3240
acccgggtga tcagcgggat ctgctgtgcc ttctagttgc cagccatctg ttgtttgccc   3300 ctccccgtg ccttccttga ccctggaagg tgccactccc actgtccttt cctaataaaa   3360
tgaggaaatt gcatcgcatt gtctgagtag gtgtcattct attctggggg gtggggtggg   3420
gcaggacagc aagggggagg attgggaaga caatagcagg catgctgggg atgcggtggg   3480
ctctatgggt acccaggtgc tgaagaattg acccggttcc tcctgggcca gaaagaagca   3540
ggcacatccc cttctctgtg acacaccctg tccacgcccc tggttcttag ttccagcccc   3600
actcatagga cactcatagc tcaggagggc tccgccttca atcccacccg ctaaagtact   3660
tggagcggtc tctccctccc tcatcagccc accaaaccaa acctagcctc caagagtggg   3720
aagaaattaa agcaagatag gctattaagt gcagagggag agaaaatgcc tccaacatgt   3780
gaggaagtaa tgagagaaat catagaatta tcgggccgct gcattctagt tgtggttgt    3840 ccaaactcat caatgtatct tatcatgtct ggatcccatc acaaagctct gacctcaatc   3900
ctatagaaag gaggaatgag ccaaaattca cccaacttat tgtgggaagc ttgtggaagg   3960
ctactcgaaa tgtttgaccc aagttaaaca atttaaaggc aatgctacca aatactaatt   4020
gagtgtatgt taacttctga cccactggga atgtgatgaa agaaataaaa gctgaaatga   4080
atcattctct ctactattat tctgatattt cacattctta aaataaagtg gtgatcctaa   4140
ctgaccttaa gacagggaat ctttactcgg attaaatgtc aggaattgtg aaaaagtgag   4200
tttaaatgta tttggctaag gtgtatgtaa acttccgact tcaact                   4246
```

<210> SEQ ID NO 4
<211> LENGTH: 680
<212> TYPE: PRT
<213> ORGANISM: Artificial Sequence
<220> FEATURE:
<223> OTHER INFORMATION: Fusion protein

<400> SEQUENCE: 4

```
Met Leu Leu Leu Val Thr Ser Leu Leu Cys Glu Leu Pro His Pro
1               5                   10                  15

Ala Phe Leu Leu Ile Pro Met Ala Gln Val Lys Leu Gln Gln Ser Gly
            20                  25                  30

Pro Asp Leu Val Lys Pro Gly Ala Ser Val Lys Ile Ser Cys Lys Ala
        35                  40                  45

Ser Gly Tyr Ser Phe Thr Gly Tyr Tyr Met His Trp Val Lys Gln Ser
    50                  55                  60

His Gly Lys Ser Leu Glu Trp Ile Gly Arg Val Asn Pro Asn Ser Gly
65                  70                  75                  80

Gly Thr Ser Tyr Asn Gln Lys Phe Lys Asp Lys Ala Ile Leu Thr Val
                85                  90                  95

Asp Lys Ser Ser Ser Thr Ala Tyr Met Glu Leu Arg Ser Leu Thr Ser
            100                 105                 110

Glu Asp Ser Ala Val Tyr Tyr Cys Ala Arg Ser Lys Gly Asn Tyr Phe
        115                 120                 125

Tyr Ala Met Asp Tyr Trp Gly Gln Gly Thr Thr Val Thr Val Ser Ser
    130                 135                 140

Ser Gly Gly Gly Ser Gly Gly Gly Gly Ser Gly Gly Gly Gly Ser Asp
145                 150                 155                 160
```

```
Ile Glu Leu Thr Gln Ser Pro Ser Ser Leu Ala Val Ser Leu Gly Gln
            165                 170                 175

Arg Ala Thr Ile Ser Cys Arg Ala Ser Glu Ser Val Asp Ser His Gly
        180                 185                 190

Thr Ser Leu Met His Trp Tyr Gln Gln Lys Pro Gly Gln Pro Pro Lys
    195                 200                 205

Phe Leu Ile Tyr Arg Ala Ser Asn Leu Glu Ser Gly Ile Pro Ala Arg
    210                 215                 220

Phe Ser Gly Ser Gly Ser Arg Thr Asp Phe Thr Leu Thr Ile Asn Pro
225                 230                 235                 240

Val Glu Thr Asp Asp Val Ala Ile Tyr Tyr Cys Gln Gln Ser Asn Glu
                245                 250                 255

Asp Pro Pro Thr Phe Gly Gly Gly Thr Lys Leu Glu Leu Lys Glu Ser
            260                 265                 270

Lys Tyr Gly Pro Pro Cys Pro Pro Cys Pro Ala Pro Glu Phe Leu Gly
        275                 280                 285

Gly Pro Ser Val Phe Leu Phe Pro Pro Lys Pro Lys Asp Thr Leu Met
    290                 295                 300

Ile Ser Arg Thr Pro Glu Val Thr Cys Val Val Val Asp Val Ser Gln
305                 310                 315                 320

Glu Asp Pro Glu Val Gln Phe Asn Trp Tyr Val Asp Gly Val Glu Val
                325                 330                 335

His Asn Ala Lys Thr Lys Pro Arg Glu Gln Phe Asn Ser Thr Tyr
            340                 345                 350

Arg Val Val Ser Val Leu Thr Val Leu His Gln Asp Trp Leu Asn Gly
        355                 360                 365

Lys Glu Tyr Lys Cys Lys Val Ser Asn Lys Gly Leu Pro Ser Ser Ile
    370                 375                 380

Glu Lys Thr Ile Ser Lys Ala Lys Gly Gln Pro Arg Glu Pro Gln Val
385                 390                 395                 400

Tyr Thr Leu Pro Pro Ser Gln Glu Glu Met Thr Lys Asn Gln Val Ser
                405                 410                 415

Leu Thr Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
        435                 440                 445

Val Leu Asp Ser Asp Gly Ser Phe Phe Leu Tyr Ser Arg Leu Thr Val
    450                 455                 460

Asp Lys Ser Arg Trp Gln Glu Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Leu Gly Lys Met Phe Trp Val Leu Val Val Val Gly Gly Val Leu Ala
            500                 505                 510

Cys Tyr Ser Leu Leu Val Thr Val Ala Phe Ile Ile Phe Trp Val Arg
        515                 520                 525

Ser Lys Arg Ser Arg Gly Gly His Ser Asp Tyr Met Asn Met Thr Pro
    530                 535                 540

Arg Arg Pro Gly Pro Thr Arg Lys His Tyr Gln Pro Tyr Ala Pro Pro
545                 550                 555                 560

Arg Asp Phe Ala Ala Tyr Arg Ser Arg Val Lys Phe Ser Arg Ser Ala
                565                 570                 575

Asp Ala Pro Ala Tyr Gln Gln Gly Gln Asn Gln Leu Tyr Asn Glu Leu
```

```
                580             585             590
Asn Leu Gly Arg Arg Glu Glu Tyr Asp Val Leu Asp Lys Arg Arg Gly
            595                 600                 605
Arg Asp Pro Glu Met Gly Gly Lys Pro Arg Arg Lys Asn Pro Gln Glu
        610                 615                 620
Gly Leu Tyr Asn Glu Leu Gln Lys Asp Lys Met Ala Glu Ala Tyr Ser
625                 630                 635                 640
Glu Ile Gly Met Lys Gly Glu Arg Arg Arg Gly Lys Gly His Asp Gly
                645                 650                 655
Leu Tyr Gln Gly Leu Ser Thr Ala Thr Lys Asp Thr Tyr Asp Ala Leu
            660                 665                 670
His Met Gln Ala Leu Pro Pro Arg
                675                 680

<210> SEQ ID NO 5
<211> LENGTH: 4255
<212> TYPE: DNA
<213> ORGANISM: Artificial Sequence
<220> FEATURE:
<223> OTHER INFORMATION: Synthetic polynucleotide sequence

<400> SEQUENCE: 5
```

| | | | | | |
|---|---|---|---|---|---|
| agttgaagtc | ggaagtttac | atacacttaa | gttggagtca | ttaaaactcg | ttttcaact | 60 |
| actccacaaa | tttcttgtta | acaaacaata | gttttggcaa | gtcagttagg | acatctactt | 120 |
| tgtgcatgac | acaagtcatt | tttccaacaa | ttgtttacag | acagattatt | tcacttataa | 180 |
| ttcactgtat | cacaattcca | gtgggtcaga | agtttacata | cactaagttg | actgtgcctt | 240 |
| taaacagctt | ggaaaattcc | agaaaatgat | gtcatggctt | agaagcttc | tgatagacta | 300 |
| attgacatca | tttgagtcaa | ttggaggtgt | acctgtggat | gtatttcaag | gaattctgtg | 360 |
| gaatgtgtgt | cagttagggt | gtggaaagtc | cccaggctcc | ccagcaggca | gaagtatgca | 420 |
| aagcatcgag | cggccgcaat | aaaatatctt | tattttcatt | acatctgtgt | gttggttttt | 480 |
| tgtgtgaatc | gtaactaaca | tacgctctcc | atcaaaacaa | aacgaaacaa | aacaaactag | 540 |
| caaaataggc | tgtccccagt | gcaagtgcag | gtgccagaac | atttctctat | cgaaggatct | 600 |
| gcgatcgctc | cggtgcccgt | cagtgggcag | agcgcacatc | gcccacagtc | cccgagaagt | 660 |
| tggggggagg | ggtcggcaat | tgaaccggtg | cctagaaag | gtggcgcggg | gtaaactggg | 720 |
| aaagtgatgt | cgtgtactgg | ctccgccttt | ttcccgaggg | tgggggagaa | ccgtatataa | 780 |
| gtgcagtagt | cgccgtgaac | gttctttttc | gcaacgggtt | tgccgccaga | acacagctga | 840 |
| agcttcgagg | ggctcgcatc | tctccttcac | gcgcccgccg | ccctacctga | ggccgccatc | 900 |
| cacgccggtt | gagtcgcgtt | ctgccgcctc | ccgcctgtgg | tgcctcctga | actgcgtccg | 960 |
| ccgtctaggt | aagtttaaag | ctcaggtcga | gaccgggcct | ttgtccggcg | ctcccttgga | 1020 |
| gcctacctag | actcagccgg | ctctccacgc | tttgcctgac | cctgcttgct | caactctacg | 1080 |
| tctttgtttc | gttttctgtt | ctgcgccgtt | acagatccaa | gctgtgaccg | gcgcctacct | 1140 |
| gagatcaccg | gcgaaggagg | cctatcatga | agatctatcg | attgtacagc | tagccgccac | 1200 |
| catgctgctg | ctggtgacca | gcctgctgct | gtgtgagctg | ccccacccgg | cctttctgct | 1260 |
| gatccccatg | gcccaggtga | agctgcagca | gagcggccct | gatctggtga | gcctggcgc | 1320 |
| cagcgtgaag | atcagctgca | aggccagcgg | ctacagcttc | accggctact | acatgcactg | 1380 |
| ggtgaaacag | agccacggca | agagcctgga | atggatcggc | agagtgaacc | ccaatagcgg | 1440 |
| cggcaccagc | tacaaccaga | agttcaagga | caaggccatc | ctgaccgtgg | acaagagcag | 1500 |

```
cagcaccgcc tacatggaac tgcggagcct gaccagcgag acagcgccg tgtactactg   1560 cgcccggtcc aagggcaact acttctacgc catggactac tggggccagg gcaccaccgt   1620
gaccgtgtct agcagcggcg gaggaagcgg agggggagga tctggcggag gcggcagcga   1680
tatcgagctg acccagagcc ctagcagcct ggccgtgtca ctgggccaga gagccaccat   1740
cagctgcaga gcctccgaga gcgtggatag ccacggcacc agcctgatgc actggtatca   1800
gcagaagccc ggccagcccc ccaagttcct gatctaccgg gccagcaacc tggaaagcgg   1860
catccccgcc agattttccg gcagcggcag cagaaccgac ttcaccctga ccatcaaccc   1920
cgtggagaca gacgacgtgg ccatctacta ctgccagcag agcaacgagg accctcccac   1980
ctttggcgga ggcaccaagc tggaactgaa ggagagcaag tacggccctc cctgcccccc   2040
ttgccctgcc cccgagttcc tgggcggacc cagcgtgttc ctgttccccc caagcccaa    2100 ggacaccctg atgatcagcc ggaccccga ggtgacctgt gtggtggtgg acgtgtccca    2160
ggaggacccc gaggtccagt tcaactggta cgtggacggc gtggaggtgc acaacgccaa   2220
gaccaagccc cgggaggagc agttcaatag cacctaccgg gtggtgtccg tgctgaccgt   2280
gctgcaccag gactggctga acggcaagga atacaagtgt aaggtgtcca acaagggcct   2340
gcccagcagc atcgagaaaa ccatcagcaa ggccaagggc cagcctcggg agccccaggt   2400
gtacaccctg cccctagcc aagaggagat gaccaagaat caggtgtccc tgacctgcct   2460
ggtgaagggc ttctacccca gcgacatcgc cgtggagtgg gagagcaacg ccagcccga    2520 gaacaactac aagaccaccc cccctgtgct ggacagcgac ggcagcttct tcctgtacag   2580
caggctgacc gtggacaaga gccggtggca ggagggcaac gtctttagct gctccgtgat   2640
gcacgaggcc ctgcacaacc actacaccca gaagagcctg tccctgagcc tgggcaagat   2700 gttctggtg ctggtcgtgg tgggtggcgt gctggcctgc tacagcctgc tggtgacagt    2760
ggccttcatc atcttttggg tgaggagcaa gcggagcaga ggcggccaca gcgactacat   2820
gaacatgacc ccccggaggc ctggccccac ccggaagcac taccagccct acgcccctcc   2880
cagggacttc gccgcctacc ggagccgggt gaagttcagc cggagcgccg acgcccctgc   2940
ctaccagcag ggccagaacc agctgtacaa cgagctgaac ctgggccgga gggaggagta   3000
cgacgtgctg gacaagcgga gaggccggga ccctgagatg ggcggcaagc cccggagaaa   3060
gaaccctcag gagggcctgt ataacgaact gcagaaagac aagatggccg aggcctacag   3120
cgagatcggc atgaagggcg agcggcggag gggcaagggc cacgacggcc tgtaccaggg   3180
cctgagcacc gccaccaagg atacctacga cgccctgcac atgcaggccc tgccccccag   3240
atgactacga cccgggtgat cagcgggatc tgctgtgcct tctagttgcc agccatctgt   3300
tgtttgcccc tcccccgtgc cttccttgac cctggaaggt gccactccca ctgtcctttc   3360
ctaataaaat gaggaaattg catcgcattg tctgagtagg tgtcattcta ttctgggggg   3420
tggggtgggg caggacagca aggggagga ttggaagac aatagcaggc atgctgggga    3480
tgcggtgggc tctatgggta cccaggtgct gaagaattga cccggttcct cctgggccag   3540
aaagaagcag gcacatcccc ttctctgtga cacaccctgt ccacgcccct ggttcttagt   3600
tccagcccca ctcataggac actcatagct caggagggct ccgccttcaa tcccaccgc    3660 taaagtactt ggagcggtct ctccctccct catcagccca ccaaaccaaa cctagcctcc   3720
aagagtggga agaaattaaa gcaagatagg ctattaagtg cagagggaga gaaaatgcct   3780
ccaacatgtg aggaagtaat gagagaaatc atagaattat cgggccgctg cattctagtt   3840
```

-continued

```
gtggtttgtc caaactcatc aatgtatctt atcatgtctg gatcccatca caaagctctg    3900
acctcaatcc tatagaaagg aggaatgagc caaaattcac ccaacttatt gtgggaagct    3960
tgtggaaggc tactcgaaat gtttgaccca agttaaacaa tttaaaggca atgctaccaa    4020
atactaattg agtgtatgtt aacttctgac ccactgggaa tgtgatgaaa gaaataaaag    4080
ctgaaatgaa tcattctctc tactattatt ctgatatttc acattcttaa aataaagtgg    4140
tgatcctaac tgaccttaag acagggaatc tttactcgga ttaaatgtca ggaattgtga    4200
aaaagtgagt ttaaatgtat ttggctaagg tgtatgtaaa cttccgactt caact         4255
```

```
<210> SEQ ID NO 6
<211> LENGTH: 422
<212> TYPE: PRT
<213> ORGANISM: Artificial Sequence
<220> FEATURE:
<223> OTHER INFORMATION: Fusion protein

<400> SEQUENCE: 6
```

Met Asp Trp Thr Trp Ile Leu Phe Leu Val Ala Ala Thr Arg Val
1               5                   10                  15

His Ser Asn Trp Val Asn Val Ile Ser Asp Leu Lys Lys Ile Glu Asp
            20                  25                  30

Leu Ile Gln Ser Met His Ile Asp Ala Thr Leu Tyr Thr Glu Ser Asp
        35                  40                  45

Val His Pro Ser Cys Lys Val Thr Ala Met Lys Cys Phe Leu Leu Glu
    50                  55                  60

Leu Gln Val Ile Ser Leu Glu Ser Gly Asp Ala Ser Ile His Asp Thr
65                  70                  75                  80

Val Glu Asn Leu Ile Ile Leu Ala Asn Asn Ser Leu Ser Ser Asn Gly
                85                  90                  95

Asn Val Thr Glu Ser Gly Cys Lys Glu Cys Glu Glu Leu Glu Glu Lys
            100                 105                 110

Asn Ile Lys Glu Phe Leu Gln Ser Phe Val His Ile Val Gln Met Phe
        115                 120                 125

Ile Asn Thr Ser Ser Gly Gly Gly Ser Gly Gly Gly Gly Ser Gly Gly
    130                 135                 140

Gly Gly Ser Gly Gly Gly Gly Ser Gly Gly Ser Leu Gln Ile Thr
145                 150                 155                 160

Cys Pro Pro Pro Met Ser Val Glu His Ala Asp Ile Trp Val Lys Ser
                165                 170                 175

Tyr Ser Leu Tyr Ser Arg Glu Arg Tyr Ile Cys Asn Ser Gly Phe Lys
            180                 185                 190

Arg Lys Ala Gly Thr Ser Ser Leu Thr Glu Cys Val Leu Asn Lys Ala
        195                 200                 205

Thr Asn Val Ala His Trp Thr Thr Pro Ser Leu Lys Cys Ile Arg Asp
    210                 215                 220

Pro Ala Leu Val His Gln Arg Pro Ala Pro Ser Thr Val Thr Thr
225                 230                 235                 240

Ala Gly Val Thr Pro Gln Pro Glu Ser Leu Ser Pro Ser Gly Lys Glu
                245                 250                 255

Pro Ala Ala Ser Ser Pro Ser Ser Asn Asn Thr Ala Ala Thr Thr Ala
            260                 265                 270

Ala Ile Val Pro Gly Ser Gln Leu Met Pro Ser Lys Ser Pro Ser Thr
        275                 280                 285

Gly Thr Thr Glu Ile Ser Ser His Glu Ser Ser His Gly Thr Pro Ser

```
                    290                 295                 300
Gln Thr Thr Ala Lys Asn Trp Glu Leu Thr Ala Ser Ala Ser His Gln
305                 310                 315                 320

Pro Pro Gly Val Tyr Pro Gln Gly His Ser Asp Thr Val Ala Ile
                325                 330                 335

Ser Thr Ser Thr Val Leu Leu Cys Gly Leu Ser Ala Val Ser Leu Leu
                340                 345                 350

Ala Cys Tyr Leu Lys Ser Arg Gln Thr Pro Pro Leu Ala Ser Val Glu
                355                 360                 365

Met Glu Ala Met Glu Ala Leu Pro Val Thr Trp Gly Thr Ser Ser Arg
            370                 375                 380

Asp Glu Asp Leu Glu Asn Cys Ser His His Leu Ser Arg Met Asp Tyr
385                 390                 395                 400

Lys Asp Asp Asp Asp Lys Asp Tyr Lys Asp Asp Asp Asp Lys Asp Tyr
                405                 410                 415

Lys Asp Asp Asp Asp Lys
            420

<210> SEQ ID NO 7
<211> LENGTH: 3499
<212> TYPE: DNA
<213> ORGANISM: Artificial Sequence
<220> FEATURE:
<223> OTHER INFORMATION: Synthetic polynucleotide sequence

<400> SEQUENCE: 7
agttgaagtc ggaagtttac atacacttaa gttggagtca ttaaaactcg ttttttcaact    60
actccacaaa tttcttgtta acaaacaata gttttggcaa gtcagttagg acatctactt   120
tgtgcatgac acaagtcatt tttccaacaa ttgtttacag acagattatt tcacttataa   180
ttcactgtat cacaattcca gtgggtcaga agtttacata cactaagttg actgtgcctt   240
taaacagctt ggaaaattcc agaaaatgat gtcatggctt tagaagcttc tgatagacta   300
attgacatca tttgagtcaa ttggaggtgt acctgtggat gtatttcaag gaattctgtg   360
gaatgtgtgt cagttagggt gtggaaagtc cccaggctcc ccagcaggca gaagtatgca   420
aagcatcgag cggccgcaat aaaatatctt tattttcatt acatctgtgt gttggttttt   480
tgtgtgaatc gtaactaaca tacgctctcc atcaaaacaa aacgaaacaa acaaaactag   540
caaaataggc tgtccccagt gcaagtgcag gtgccagaac atttctctat cgaaggatct   600
gcgatcgctc cggtgcccgt cagtgggcag agcgcacatc gcccacagtc ccgagaagt    660
tgggggagg ggtcggcaat tgaaccggtg cctagagaag gtggcgcggg gtaaactggg   720
aaagtgatgt cgtgtactgg ctccgccttt ttcccgaggg tgggggagaa ccgtatataa   780
gtgcagtagt cgccgtgaac gttctttttc gcaacgggtt tgccgccaga acacagctga   840
agcttcgagg ggctcgcatc tctccttcac gcgcccgccg ccctacctga ggccgccatc   900
cacgccggtt gagtcgcgtt ctgccgcctc cgcctgtgg tgcctcctga actgcgtccg    960
ccgtctaggt aagtttaaag ctcaggtcga gaccgggcct ttgtccggcg ctcccttgga  1020
gcctacctag actcagccgg ctctccacgc tttgcctgac cctgcttgct caactctacg  1080
tctttgtttc gttttctgtt ctgcgccgtt acagatccaa gctgtgaccg gcgcctacct  1140
gagatcaccg gcgaaggagg cctatcatga agatctatcg attgtacagc tagccgccac  1200
catggattgg acctggattc tgtttctggt ggccgctgcc acaagagtgc acagcaactg  1260
ggtgaatgtg atcagcgacc tgaagaagat cgaggatctg atccagagca tgcacattga  1320
```

```
tgccaccctg tacacagaat ctgatgtgca ccctagctgt aaagtgaccg ccatgaagtg    1380
ttttctgctg gagctgcagg tgatttctct ggaaagcgga gatgcctcta tccacgacac    1440
agtggagaat ctgatcatcc tggccaacaa tagcctgagc agcaatggca atgtgacaga    1500
gtctggctgt aaggagtgtg aggagctgga ggagaagaac atcaaggagt ttctgcagag    1560
ctttgtgcac atcgtgcaga tgttcatcaa tacaagctct ggcggaggat ctggaggagg    1620
cggatctgga ggaggaggca gtggaggcgg aggatctggc ggaggatctc tgcagattac    1680
atgccctcct ccaatgtctg tggagcacgc cgatatttgg gtgaagtcct acagcctgta    1740
cagcagagag agatacatct gcaacagcgg ctttaagaga aaggccggca cctcttctct    1800
gacagagtgc gtgctgaata aggccacaaa tgtggcccac tggacaacac ctagcctgaa    1860
gtgcattaga gatcctgccc tggtccacca gaggcctgcc cctccatcta cagtgacaac    1920
agccggagtg acacctcagc ctgaatctct gagcccttct ggaaaagaac ctgccgccag    1980
ctctcctagc tctaataata ccgccgccac aacagccgcc attgtgcctg gatctcagct    2040
gatgcctagc aagtctccta gcacaggcac aacagagatc agcagccacg aatcttctca    2100
cggaacacct tctcagacca ccgccaagaa ttgggagctg acagcctctg cctctcacca    2160
gcctccagga gtgtatcctc agggccactc tgatacaaca gtggccatca gcacatctac    2220
agtgctgctg tgtggactgt ctgccgtgtc tctgctggcc tgttacctga agtctagaca    2280
gacacctcct ctggcctctg tggagatgga ggccatggaa gccctgcctg tgacatgggg    2340
aacaagcagc agagatgagg acctggagaa ttgttctcac cacctgtcgc gaatggacta    2400
caaggacgat gacgacaagg attataaaga tgatgatgat aaagattata agacgacga    2460 tgataagtcg cgatgatgat gactcgagac tagtcccggg tgatcagcgg gatctgctgt    2520
gccttctagt tgccagccat ctgttgtttg cccctccccc gtgccttcct gaccctgga    2580 aggtgccact cccactgtcc tttcctaata aatgaggaa attgcatcgc attgtctgag    2640
taggtgtcat tctattctgg ggggtggggt ggggcaggac agcaagggg aggattggga    2700 agacaatagc aggcatgctg gggatgcggt gggctctatg ggtacccagg tgctgaagaa    2760
ttgacccggt tcctcctggg ccagaaagaa gcaggcacat ccccttctct gtgacacacc    2820
ctgtccacgc ccctggttct tagttccagc cccactcata ggacactcat agctcaggag    2880
ggctccgcct tcaatcccac ccgctaaagt acttggagcg tctctccct ccctcatcag    2940 cccaccaaac caaacctagc ctccaagagt gggaagaaat taaagcaaga taggctatta    3000
agtgcagagg gagagaaaat gcctccaaca tgtgaggaag taatgagaga aatcatagaa    3060
ttatcgggcc gctgcattct agttgtggtt tgtccaaact catcaatgta tcttatcatg    3120
tctggatccc atcacaaagc tctgacctca atcctataga aaggaggaat gagccaaaat    3180
tcacccaact tattgtggga agcttgtgga aggctactcg aaatgtttga cccaagttaa    3240
acaatttaaa ggcaatgcta ccaaatacta attgagtgta tgttaacttc tgacccactg    3300
ggaatgtgat gaaagaaata aaagctgaaa tgaatcattc tctctactat tattctgata    3360
tttcacattc ttaaaataaa gtggtgatcc taactgacct taagacaggg aatctttact    3420
cggattaaat gtcaggaatt gtgaaaaagt gagtttaaat gtatttggct aaggtgtatg    3480
taaacttccg acttcaact                                                 3499
```

<210> SEQ ID NO 8
<211> LENGTH: 18
<212> TYPE: DNA

```
<213> ORGANISM: Artificial Sequence
<220> FEATURE:
<223> OTHER INFORMATION: Synthetic primer

<400> SEQUENCE: 8
cagcgacggc agcttctt                                                   18

<210> SEQ ID NO 9
<211> LENGTH: 17
<212> TYPE: DNA
<213> ORGANISM: Artificial Sequence
<220> FEATURE:
<223> OTHER INFORMATION: Synthetic primer

<400> SEQUENCE: 9
tgcatcacgg agctaaa                                                    17

<210> SEQ ID NO 10
<211> LENGTH: 15
<212> TYPE: DNA
<213> ORGANISM: Artificial Sequence
<220> FEATURE:
<223> OTHER INFORMATION: Synthetic primer

<400> SEQUENCE: 10
agagccggtg gcagg                                                      15

<210> SEQ ID NO 11
<211> LENGTH: 21
<212> TYPE: DNA
<213> ORGANISM: Artificial Sequence
<220> FEATURE:
<223> OTHER INFORMATION: Synthetic primer

<400> SEQUENCE: 11
atgggaaaat caaagaaat c                                                21

<210> SEQ ID NO 12
<211> LENGTH: 20
<212> TYPE: DNA
<213> ORGANISM: Artificial Sequence
<220> FEATURE:
<223> OTHER INFORMATION: Synthetic primer

<400> SEQUENCE: 12
ctagtatttg gtagcattgc                                                 20

<210> SEQ ID NO 13
<211> LENGTH: 24
<212> TYPE: DNA
<213> ORGANISM: Artificial Sequence
<220> FEATURE:
<223> OTHER INFORMATION: Synthetic primer

<400> SEQUENCE: 13
tctccagaac atcatccctg ccac                                            24

<210> SEQ ID NO 14
<211> LENGTH: 24
<212> TYPE: DNA
<213> ORGANISM: Artificial Sequence
<220> FEATURE:
<223> OTHER INFORMATION: Synthetic primer

<400> SEQUENCE: 14
tgggccatga ggtccaccac cctg                                            24
```

```
<210> SEQ ID NO 15
<211> LENGTH: 20
<212> TYPE: DNA
<213> ORGANISM: Artificial Sequence
<220> FEATURE:
<223> OTHER INFORMATION: Synthetic primer

<400> SEQUENCE: 15
gagggcaacg tctttagctg                                               20

<210> SEQ ID NO 16
<211> LENGTH: 20
<212> TYPE: DNA
<213> ORGANISM: Artificial Sequence
<220> FEATURE:
<223> OTHER INFORMATION: Synthetic primer

<400> SEQUENCE: 16
gatgatgaag gccactgtca                                               20

<210> SEQ ID NO 17
<211> LENGTH: 20
<212> TYPE: DNA
<213> ORGANISM: Artificial Sequence
<220> FEATURE:
<223> OTHER INFORMATION: Synthetic primer

<400> SEQUENCE: 17
agatgttctg ggtgctggtc                                               20
```

HUMAN APPLICATION OF ENGINEERED CHIMERIC ANTIGEN RECEPTOR (CAR) T-CELLS

This application is a national phase application under 35 U.S.C. §371 of International Application No. PCT/US2014/038005, filed May 14, 2014, which claims the benefit of U.S. Provisional Patent Application No. 61/823,253 filed May 14, 2013. The entire text of each of the above referenced applications is incorporated herein by reference.

The invention was made with government support under Grant No. W81XWH-11-1-0002-01 awarded by the Department of Defense. The government has certain rights in the invention.

INCORPORATION OF SEQUENCE LISTING

The sequence listing that is contained in the file named "UTFC.P1222WO_ST25.txt", which is 37 KB (as measured in Microsoft Windows®) and was created on May 14, 2014, is filed herewith by electronic submission and is incorporated by reference herein.

BACKGROUND OF THE INVENTION

1. Field of the Invention

The present invention relates generally to the fields of medicine, immunology, cell biology, and molecular biology. In certain aspects, the field of the invention concerns immunotherapy. More particularly, it concerns the manufacture of clinical-grade chimeric antigen receptor (CAR) T cells and therapeutic methods using such cells.

2. Description of Related Art

The potency of clinical-grade T cells can be improved by combining gene therapy with immunotherapy to engineer a biologic product with the potential for superior (i) recognition of tumor-associated antigens (TAAs), (ii) persistence after infusion, (iii) potential for migration to tumor sites, and (iv) ability to recycle effector functions within the tumor microenvironment. Such a combination of gene therapy with immunotherapy can redirect the specificity of T cells for B-lineage antigens and patients with advanced B-cell malignancies benefit from infusion of such tumor-specific T cells (Jena et al., 2010; Till et al., 2008; Porter et al., 2011; Brentjens et al., 2011; Cooper and Bollard, 2012; Kalos et al., 2011; Kochenderfer et al., 2010; Kochenderfer et al., 2012; Brentjens et al., 2013). Most approaches to genetic manipulation of T cells engineered for human application have used retrovirus and lentivirus for the stable expression of chimeric antigen receptor (CAR) (Jena et al., 2010; Ertl et al., 2011; Kohn et al., 2011). This approach, although compliant with current good manufacturing practice (cGMP), can be expensive as it relies on the manufacture and release of clinical-grade recombinant virus from a limited number of production facilities. New methods are needed to generate genetically-modified clinical-grade T cell products with specificity for hematologic malignancies and solid tumors.

SUMMARY OF THE INVENTION

In a first embodiment there is provided a method of providing a T-cell response in a human subject having a disease comprising obtaining a sample of cells from the subject, (comprising T-cells or T-cell progenitors); transfecting the cells with a nucleic acid encoding chimeric T-cell receptor (CAR), capable of integration into the genome of the cells, and administering an effective amount of the transgenic cells to the subject to provide a T-cell response.

Thus, in some aspects, a method of the embodiments comprises: (a) obtaining a sample of cells from the subject, the sample comprising T-cells or T-cell progenitors; (b) transfecting the cells with a DNA encoding a transposon-flanked chimeric antigen receptor (CAR) and a transposase effective to integrate the DNA encoding the CAR into the genome of the cells, to provide a population of transgenic CAR-expressing cells; (c) optionally, culturing the population of transgenic CAR cells ex vivo in a medium that selectively enhances proliferation of CAR-expressing T-cells, wherein the transgenic CAR cells are cultured, if at all, no more than 21 days; and (d) administering an effective amount of the transgenic CAR cells to the subject to provide a T-cell response. Thus, in some aspects, the transgenic CAR cells are cultured ex vivo for less than 21 days, such as for less than 18, 17, 16, 15, 14, 13, 12, 11, 10, 9, 8, 7, 6, 5, 4, 3, 2 days or less. In certain aspects, the CAR cells are cultured ex vivo no more that 3 to 5 days. In still further aspects, steps (a)-(d) of the instant method (i.e., obtaining cell samples to administering CAR T cells) is completed in no more that 21, 20, 19, 18, 17, 16, 15, 14, 13, 12, 11, 10, 9, 8, 7, 6, or 5 days.

In further aspects, a method of providing a T-cell response in a human subject having a disease according to the embodiments comprises: (a) obtaining a sample of cells from the subject, the sample comprising T-cells or T-cell progenitors and having an initial volume of between about 20 and 200 mls when obtained from the subject; (b) transfecting the cells with a DNA encoding a transposon-flanked chimeric antigen receptor (CAR) and a transposase effective to integrate the DNA encoding the CAR into the genome of the cells, to provide a population of transgenic CAR-expressing T-cells; (c) optionally, culturing the population of transgenic CAR cells ex vivo in a medium that selectively enhances proliferation of CAR-expressing T-cells; and (d) administering an effective amount of the transgenic CAR T-cells to the subject to provide a T-cell response. For example, the sample of cells from the subject may be a sample of less than about 200 mls of a peripheral blood or umbilical cord blood. In some aspects, the sample may be collected by apheresis. However, in certain preferred aspects, the sample is collected by a method that does not involved apheresis (e.g., by venipuncture). In still further aspects, the sample of cells has an initial volume of less than about 175, 150, 125, 100, 75, 50 or 25 mls (e.g., the sample of cells has an initial volume of between about 50 and 200 mls, 50 and 100 mls, or 100 and 200 mls when obtained from the subject).

In a further embodiment there is provided an isolated transgenic cell comprising an expressed CAR targeted to the envelope protein of HERV-K. In certain aspects, the cells comprise DNA encoding the CAR integrated into the genome of the cell (e.g., CAR DNA flanked by transposon repeat sequences). For example, the CAR sequence can comprise the CDR sequences (e.g., CDRs 1-6) of monoclonal antibody 6H5 or the scFv sequence of monoclonal antibody 6H5. In some aspects, HERV-K-targeted CAR is at least 85% identical to the amino acid sequence of SEQ ID NO: 4 (e.g., a sequence at least about 90%, 91%, 92%, 93%, 94%, 95%, 96%, 97%, 98% or 99% identical to SEQ ID NO: 4). In certain aspects, a cell of the embodiments (e.g., a human HERV-K-targeted CAR cell) can be used to treat a subject (or provide an immune response in a subject) having a HERV-K-expressing cancer.

In still a further embodiment there is provided an isolated transgenic cell comprising an expressed CAR and an expressed membrane-bound IL-15. For example, in some aspects, the membrane-bound IL-15 comprises a fusion protein between IL-15 and IL-15Rα. In yet further aspects, the membrane-bound IL-15 comprises an amino acid sequence at least about 85%, 90%, 91%, 92%, 93%, 94%, 95%, 96%, 97%, 98% or 99% identical to SEQ ID NO: 6 (referred to herein as mIL15). As further detailed herein, in some cases, the membrane-bound IL-15 is encoded by a RNA or a DNA (e.g., an extra chromosomal or episomal vector). In certain aspects, the cell comprises DNA encoding the membrane-bound IL-15 integrated into the genome of the cell (e.g., coding DNA flanked by transposon repeat sequences). In certain aspects, a cell of the embodiments (e.g., human CAR cell, expressing a membrane-bound cytokine) can be used to treat a subject (or provide an immune response in a subject) having low levels of target antigen, such as a subject with minimal residual disease (as further detailed herein).

In some aspects, methods of the embodiments concern transfecting the cells with a DNA encoding a chimeric T-cell receptor (CAR) and, in some cases, a transposase. Methods of transfecting of cells are well known in the art, but in certain aspects, highly efficient transfections methods such as electroporation are employed. For example, nucleic acids may be introduced into cells using a nucleofection apparatus. Preferably, the transfection step does not involve infecting or transducing the cells with virus, which can cause genotoxicity and/or lead to an immune response to cells containing viral sequences in a treated subject.

Further aspects of the embodiments concern transfecting cells with an expression vector encoding a CAR. A wide range of CAR constructs and expression vectors for the same are known in the art and are further detailed herein. For example, in some aspects, the CAR expression vector is a DNA expression vector such as a plasmid, linear expression vector or an episome. In some aspects, the vector comprises additional sequences, such as sequence that facilitate expression of the CAR, such a promoter, enhancer, poly-A signal, and/or one or more introns. In preferred aspects, the CAR coding sequence is flanked by transposon sequences, such that the presence of a transposase allows the coding sequence to integrate into the genome of the transfected cell.

As detailed supra, in certain aspects, cells are further transfected with a transposase that facilitates integration of a CAR coding sequence into the genome of the transfected cells. In some aspects, the transposase is provided as DNA expression vector. However, in preferred aspects, the transposase is provided as an expressible RNA or a protein such that long-term expression of the transposase does not occur in the transgenic cells. For example, in some aspects, the transposase is provided as an mRNA (e.g., an mRNA comprising a cap and poly-A tail). Any transposase system may be used in accordance with the embodiments. However, in some aspects, the transposase is salmonid-type Tcl-like transposase (SB). For example, the transposase can be the so called "Sleeping beauty" transposase, see e.g., U.S. Pat. No. 6,489,458, incorporated herein by reference. In certain aspects, the transposase is an engineered enzyme with increased enzymatic activity. Some specific examples of transposases include, without limitation, SB10, SB11 or SB100× transposase (see, e.g., Mates et al., 2009, incorporated herein by reference). For example, a method can involve electroporation of cells with a mRNA encoding a SB10, SB11 or SB100× transposase.

In still further aspects, a transgenic CAR cell of the embodiments further comprises an expression vector for expression of a membrane-bound cytokine that stimulates proliferation and/or survival of T-cells. In particular, CAR cells comprising such cytokines can proliferate and/or persist with little or no ex vivo culture with activating and propagating cells (AaPCs) or artificial antigen presenting cells (aAPCs) due the simulation provided by the cytokine expression. Likewise, such CAR cells can proliferate in vivo even when large amounts of antigen recognized by the CAR is not present (e.g., as in the case of a cancer patient in remission or a patient with minimal residual disease). In some aspects, the CAR cells comprise a DNA or RNA expression vector for expression of a Cγ cytokine and elements (e.g., a transmembrane domain) to provide surface expression of the cytokine. For example, the CAR cells can comprise membrane-bound versions of IL-7, IL-15 or IL-21. In some aspects, the cytokine is tethered to the membrane by fusion of the cytokine coding sequence with the receptor for the cytokine. For example, a cell can comprise a vector for expression of a IL-15-IL-15Rα fusion protein (e.g., a protein comprising the sequence of SEQ ID NO: 6). In still further aspects, a vector encoding a membrane-bound Cγ cytokine is a DNA expression vector, such as vector integrated into the genome of the CAR cells or an extra-chromosomal vector (e.g., and episomal vector). In still further aspects, expression of the membrane-bound Cγ cytokine is under the control of an inducible promoter (e.g., a drug inducible promoter) such that the expression of the cytokine in the CAR cells (and thereby the proliferation of the CAR cells) can be controlled by inducing or suppressing promoter activity.

Aspects of the embodiments concern obtaining a sample from a patient comprising NK cells, NKT cells, T-cells or T-cell progenitor cells. For example, in some cases, the sample is an umbilical cord blood sample, a peripheral blood sample (e.g., a mononuclear cell fraction) or a sample from the subject comprising pluripotent cells. In some aspects, a sample from the subject can be cultured to generate induced pluripotent stem (iPS) cells and these cells used to produce NK cells, NKT cells or T-cells. Cell samples may be cultured directly from the subject or may be cryopreserved prior to use. In some aspects, obtaining a cell sample comprises collecting a cell sample. In other aspects, the sample is obtained by a third party. In still further aspects, a sample from a subject can be treated to purify or enrich the T-cells or T-cell progenitors in the sample. For example, the sample can be subjected to gradient purification, cell culture selection and/or cell sorting (e.g., via fluorescence-activated cell sorting (FACS)).

In some aspects, a method of the embodiments further comprises obtaining, producing or using antigen presenting cells. For example, the antigen presenting cells can be dendritic cells, activating and propagating cells (AaPCs), or inactivated (e.g., irradiated) artificial antigen presenting cells (aAPCs). Methods for producing such aAPCs are know in the art and further detailed herein. Thus, in some aspects, transgenic CAR cells are co-cultured with inactivated aAPCs ex vivo for a limited period of time in order to expand the CAR cell population. The step of co-culturing CAR cells with aAPCs can be done in a medium that comprises, for example, interleukin-21 (IL-21) and/or interleukin-2 (IL-2). In some aspects, the co-culturing is performed at a ratio of CAR cells to inactivated aAPCs of about 10:1 to about 1:10; about 3:1 to about 1:5; or about 1:1 to about 1:3. For example, the co-culture of CAR cells and aAPCs can be at a ratio of about 1:1, about 1:2 or about 1:3.

In some aspects, cells for culture of CAR cells such as AaPCs or aAPCs are engineered to express specific polypeptide to enhance growth of the CAR cells. For example, the cells can comprise (i) an antigen targeted by the CAR expressed on the transgenic CAR cells; (ii) CD64; (ii) CD86; (iii) CD137L; and/or (v) membrane-bound IL-15, expressed on the surface of the aAPCs. In some aspects, the AaPCs or aAPCS comprise a CAR-binding antibody or fragment thereof expressed on the surface of the AaPCs or aAPCs. Preferably, AaPCs or aAPCs for use in the instant methods are tested for, and confirmed to be free of, infectious material and/or are tested and confirmed to be inactivated and non-proliferating.

While expansion on AaPCs or aAPCs can increase the number or concentration of CAR cells in a culture, this proceed is labor intensive and expensive. Moreover, in some aspects, a subject in need of therapy should be re-infused with transgenic CAR cells in as short a time as possible. Thus, in some aspects, ex vivo culturing the transgenic CAR cells (c) is for no more than 14 days, no more than 7 days or no more than 3 days. For example, the ex vivo culture (e.g., culture in the presence of AaPCs or aAPCs) can be performed for less than one population doubling of the transgenic CAR cells. In still further aspects, the transgenic cells are not cultured ex vivo in the presence of AaPCs or aAPCs.

In still further aspects, a method of the embodiments comprises a step for enriching the cell population for CAR-expressing T-cells after transfection of the cells (step (b)) or after ex vivo expansion of the cells (step (c)). For example, the enrichment step can comprise sorting of the cell (e.g., via FACS), for example, by using an antigen bound by the CAR or a CAR-binding antibody. In still further aspects, the enrichment step comprises depletion of the non-T-cells or depletion of cells that lack CAR expression. For example, $CD56^+$ cells can be depleted from a culture population. In yet further aspects, a sample of CAR cells is preserved (or maintained in culture) when the cells are administered to the subject. For example, a sample may be cryopreserved for later expansion or analysis.

In certain aspects, transgenic CAR cells of the embodiments are inactivated for expression of an endogenous T-cell receptor and/or endogenous HLA. For example, T cells can be engineered to eliminate expression of endogenous alpha/beta T-cell receptor (TCR). In specific embodiments, $CAR^+$ T cells are genetically modified to eliminate expression of TCR. In some aspects, there is a disruption of the T-cell receptor $\alpha/\beta$ in CAR-expressing T cells using zinc finger nucleases (ZFNs). In certain aspects, the T-cell receptor $\alpha\beta$-chain in CAR-expressing T cells is knocked-out, for example, by using zinc finger nucleases.

As further detailed herein, CAR cells of the embodiments can be used to treat a wide range of diseases and conditions. Essentially any disease that involves the specific or enhanced expression of a particular antigen can be treated by targeting CAR cells to the antigen. For example, autoimmune diseases, infections, and cancers can be treated with methods and/or compositions of the invention. These include cancers, such as primary, metastatic, recurrent, sensitive-to-therapy, refractory-to-therapy cancers (e.g., chemo-refractory cancer). The cancer may be of the blood, lung, brain, colon, prostate, breast, liver, kidney, stomach, cervix, ovary, testes, pituitary gland, esophagus, spleen, skin, bone, and so forth (e.g., B-cell lymphomas or a melanomas). In the case of cancer treatment CAR cells typically target a cancer cell antigen (also known as a tumor-associated antigen (TAA)).

In still further aspects, transgenic CAR cells of the embodiments may be used to treat subject having minimal residual disease (e.g., a subject having very low amounts of CAR-targeted antigen present), such as cancer patients that are in apparent remission. Using new highly sensitive diagnostic techniques, cancer-associated antigens (or cancer cells) can be detected in patients that do not exhibit overt cancer symptoms. Such patients may be treated by the instant methods to eliminate residual disease by use of antigen-targeted CAR cells. In preferred embodiments, transgenic CAR cells for targeting of residual disease further comprise expression of a membrane-bound proliferative cytokine, as these cells will retain the ability to expand in vivo despite the low amount to target antigen.

The processes of the embodiments can be utilized to manufacture (e.g., for clinical trials) of $CAR^+$ T cells for various tumor antigens (e.g., CD19, ROR1, CD56, EGFR, CD123, c-met, GD2). $CAR^+$ T cells generated using this technology can be used to treat patients with leukemias (AML, ALL, CML), infections and/or solid tumors. For example, methods of the embodiments can be used to treat cell proliferative diseases, fungal, viral, bacterial or parasitic infections. Pathogens that may be targeted include, with limitation, *Plasmodium*, trypanosome, *Aspergillus, Candida*, HSV, RSV, EBV, CMV, JC virus, BK virus, or Ebola pathogens. Further examples of antigens that can be targeted by CAR cells of the embodiments include, without limitation, CD19, CD20, carcinoembryonic antigen, alphafetoprotein, CA-125, 5T4, MUC-1, epithelial tumor antigen, melanoma-associated antigen, mutated p53, mutated ras, HER2/Neu, ERBB2, folate binding protein, HIV-1 envelope glycoprotein gp120, HIV-1 envelope glycoprotein gp41, GD2, CD123, CD23, CD30, CD56, c-Met, meothelin, GD3, HERV-K, IL-11Ralpha, kappa chain, lambda chain, CSPG4, ERBB2, EGFRvIII, or VEGFR2. In certain aspects, method of the embodiments concern targeting of CD19 or HERV-K-expressing cells. For example, a HERV-K targeted CAR cell can comprise a CAR including the scFv sequence of monoclonal antibody 6H5. In still further aspects, a CAR of the embodiments can be conjugated or fused with a cytokine, such as IL-2, IL-7, IL-15, IL-21 or a combination thereof.

In some embodiments, methods are provided for treating an individual with a medical condition comprising the step of providing an effective amount of cells from the population of cells described herein, including more than once in some aspects, such as at least 1, 2, 3, 4, 5, 6, 7, 8, 9, 10, 11, 12, 13, 14, or more days apart. In specific embodiments, the cancer is lymphoma, leukemia, non-Hodgkin's lymphoma, acute lymphoblastic leukemia, chronic lymphoblastic leukemia, chronic lymphocytic leukemia, or B cell-associated autoimmune diseases.

In still yet a further embodiment there is a provided an isolated or recombinant polypeptide comprising the a CD19-targeted CAR comprising an amino acid sequence at least about 85%, 90%, 91%, 92%, 93%, 94%, 95%, 96%, 97%, 98% or 99% identical to SEQ ID NO: 1. In a related embodiment an isolated or recombinant polynucleotide sequence is provided encoding a CD19-targeted CAR (e.g., encoding an amino acid sequence 85%, 90%, 91%, 92%, 93%, 94%, 95%, 96%, 97%, 98% or 99% identical to SEQ ID NO: 1). For example, in some aspects, the polynucleotide sequence is 85%, 90%, 91%, 92%, 93%, 94%, 95%, 96%, 97%, 98% or 99% identical to SEQ ID NO: 3 (which encodes the CD-19-targeted CAR) or SEQ ID NO: 4 (which encodes the CD-19-targeted CAR, expression control sequences and flanking transposon repeats). In still a further embodiment a host cell is provided comprising polypeptide encoding a CD 19-targeted CAR and/or a polynucleotide encoding a CD19-targeted CAR of the embodiments. For example, the host cell can be a T-cell or T-cell precursor. Preferably the host cell is a human cell. A skilled artisan will recognize that any of the forgoing polypeptides, polynucleotides or host cells may be used in accordance with the methods detailed herein.

In still yet a further embodiment there is a provided an isolated or recombinant polypeptide comprising the a HERV-K-targeted CAR comprising an amino acid sequence at least about 85%, 90%, 91%, 92%, 93%, 94%, 95%, 96%, 97%, 98% or 99% identical to SEQ ID NO: 4. In a related embodiment an isolated or recombinant polynucleotide sequence is provided encoding a HERV-K-targeted CAR (e.g., encoding an amino acid sequence 85%, 90%, 91%, 92%, 93%, 94%, 95%, 96%, 97%, 98% or 99% identical to SEQ ID NO: 4). For example, in some aspects, the polynucleotide sequence is 85%, 90%, 91%, 92%, 93%, 94%, 95%, 96%, 97%, 98% or 99% identical to SEQ ID NO: 5 (which encodes the HERV-K-targeted CAR, expression control sequences and flanking transposon repeats). In still a further embodiment a host cell is provided comprising polypeptide encoding a HERV-K-targeted CAR and/or a polynucleotide encoding a HERV-K-targeted CAR of the embodiments. For example, the host cell can be a T-cell or T-cell precursor. Preferably the host cell is a human cell. A skilled artisan will recognize that any of the forgoing polypeptides, polynucleotides or host cells may be used in accordance with the methods detailed herein.

In still yet a further embodiment there is a provided an isolated or recombinant polypeptide comprising the a membrane-bound IL-15 comprising an amino acid sequence at least about 85%, 90%, 91%, 92%, 93%, 94%, 95%, 96%, 97%, 98% or 99% identical to SEQ ID NO: 6. In a related embodiment an isolated or recombinant polynucleotide sequence is provided encoding a membrane-bound IL-15 (e.g., encoding an amino acid sequence 85%, 90%, 91%, 92%, 93%, 94%, 95%, 96%, 97%, 98% or 99% identical to SEQ ID NO: 6). For example, in some aspects, the polynucleotide sequence is 85%, 90%, 91%, 92%, 93%, 94%, 95%, 96%, 97%, 98% or 99% identical to SEQ ID NO: 7 (a membrane-bound IL-15, expression control sequences and flanking transposon repeats). In still a further embodiment a host cell is provided comprising polypeptide encoding a membrane-bound IL-15 and/or a polynucleotide encoding a membrane-bound IL-15 of the embodiments. For example, the host cell can be a T-cell, T-cell precursor or aAPC. Preferably the host cell is a human cell. A skilled artisan will recognize that any of the forgoing polypeptides, polynucleotides or host cells may be used in accordance with the methods detailed herein.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 8: Expansion kinetics and redirected specificity of CAR$^+$ T cells. Genetically modified T cells were co-cultured with aAPC clone #4 for 28 days. At the end of each stimulation cycle (7 days), cells were counted and stained for expression of CAR and CD3. Three validation runs (V1, V2, and V3) were performed and the graphs represent inferred (A) CAR$^+$ T cells, (B) CD3$^+$ T cells, (C) Total viable cells over time. Arrows indicate addition of aAPC to the culture. (D) Lysis of CD19$^+$ targets (Daudiβ$_2$m, NALM-6, CD19$^+$ EL-4) as compared to background lysis of CD19$^{neg}$ EL-4 using 4-hr chromium release assay by CAR$^+$ T cells. Mean±SD of three validation runs is represented.

FIG. 27: (A) SB Plasmid encoding myc-ffLuc with Neomycin resistance gene. (B) Total cell growth of HERV-K-specific CAR+ T cells and HERV-K-specific CAR-ffLuc+ T cells. (C) Four-hour CRA of A375SM and EL4 parental cells with HERV-K-specific CAR-ffLuc+ T cells. (D) Mouse image representing ffLuc activity. (E) Lentiviral plasmid encoding RLuc and mKate for tumor cell imaging.

FIGS. 35A-E: Graphs show additional characterization of mIL15+CAR+ T cells by flow cytometry analysis. FIG. 35A, Homeostatic proliferation level of WD-mIL15+CAR+ T cells from three normal donors (PKH dilution at 10 days after staining) that have been in culture without antigen re-stimulation for 1-2 years (top panel) and proliferative capacity of these cells upon antigen re-stimulation with aAPC (bottom panel). FIG. 35B, Phenotype of long-term withdrawal mIL15+CAR+ T cells (CD3 and mIL15 surface expression) that were submitted for karyotyping. Withdrawal T cells were first re-stimulated with aAPC prior to phenotyping and submission for karyotyping. FIG. 35C, Normal karyotype (G-banding) result of mIL15+CAR+ T cells persisting long-term (1.5-2.46 years) in vitro in the absence of antigen re-stimulation and exogenous cytokines. A representative metaphase spread is shown from four normal donors. FIG. 35D, Memory kinetics after stimulation of cells using K562 aAPCs. FIG. 35E, Memory kinetics with 1 versus 2 stimulations of CAR and mIL15+CAR+ T cells.

FIG. 44A, graph (left panel) and flow cytometry histograms (right panel) show the percentage of T-cells stably expressing CAR is increasing significantly from day 9 (8.3%) to day 16 (66.2%). FIG. 44B, graph shows that T-cells grow quickly and amplify by 20-folds to day 16 after electroporation. FIG. 44C, graphs show results from chromium release assays using day 16 T-cells. The CAR T-cell produced provided CD-19-specific cytotoxicity against target cells (left panel). Essentially no cytotoxic activity was seen for unmodified T-cells (right panel). FIG. 44D, Flow cytometry histograms showing the number of central memory T-cells (Tcm) at day 9 (left panel) and day 17 (right panel) post electroporation. Cells for these studies were from a donor designated as #0 and SB11 mRNA was used in the electroporation.

FIG. 45A, graphs show results from chromium release assays using day 9 (upper panels) and day 15 (lower panels) T-cells. The CAR T-cell produced provided CD-19-specific cytotoxicity against target cells (left panels). Essentially no cytotoxic activity was seen for unmodified T-cells (right panels). The modified T-cells kill CD19-positive target cells on day 9 and day 15 with similar efficiency despite the different number of CAR-positive cells. FIG. 45B, Graphs show CAR copy number (left panel) and CAR expression (right panel) in electroporated cells. Results show that CAR DNA copy number decreases from 1.5 to 0.9 from day 15 to day 22 and stays stable after that time point. Cells for these studies were from a donor designated as #1 and SB100× mRNA was used in the electroporation.

DESCRIPTION OF ILLUSTRATIVE EMBODIMENTS

Figure 1:
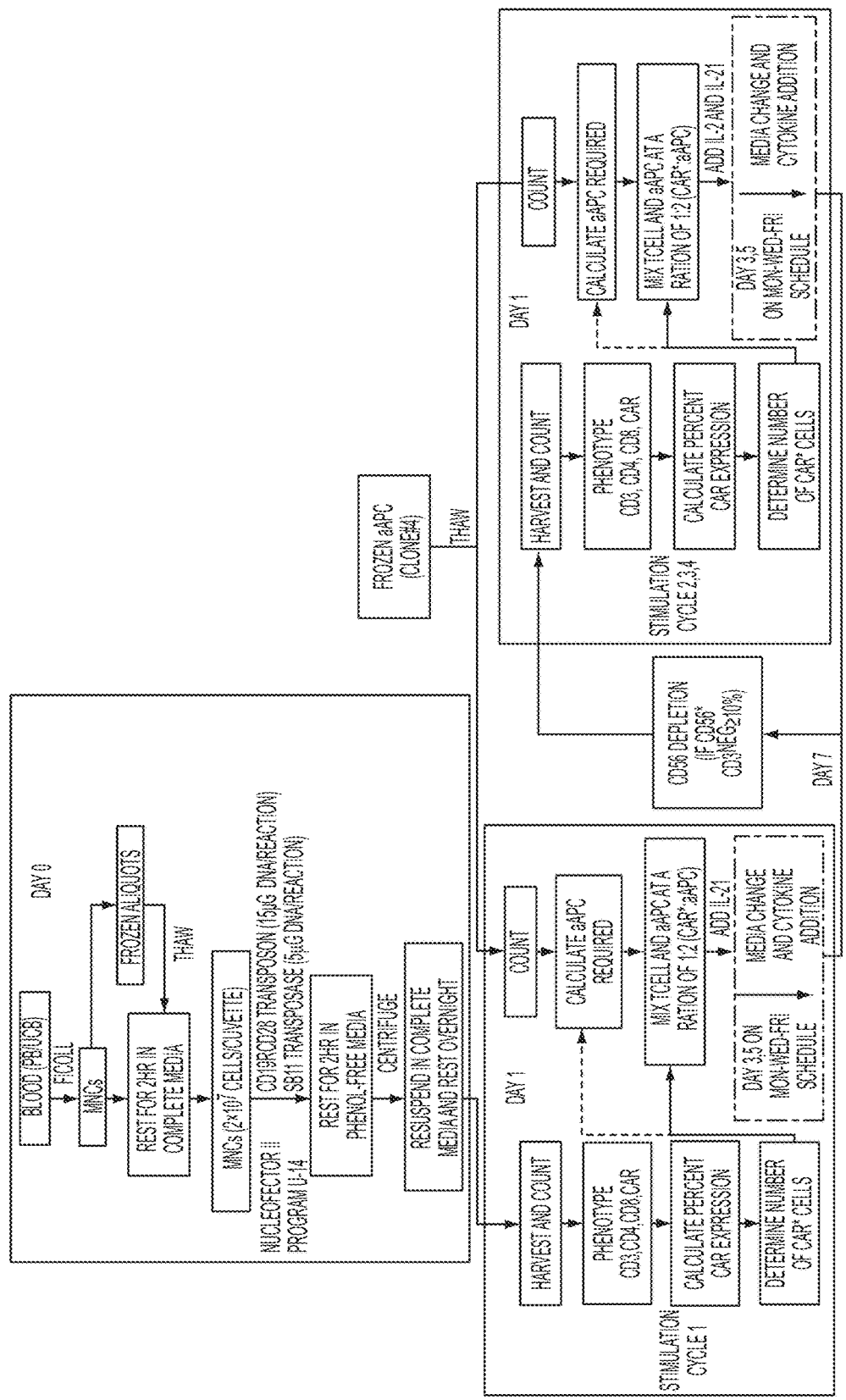
FIG. 1: Steps outlining the process to electroporate and propagate CAR$^+$ T cells from PB and UCB.

Clinical trials have demonstrated anti-tumor effects in patients that have received T cells genetically modified to have desired specificity. Herein, a new approach to manufacturing antigen-specific CAR+ T cells in compliance with cGMP is detailed. The system employs a highly efficient transfection system in conjunction with a transposon and transposase system CAR gene integration. These non-viral approaches have significant advantages as an alternative to viral-mediated transduction since clinical grade CAR+ T cells preferably should not include added viral sequences. High quality cGMP CAR T-cells were achieved by electro-transfer of DNA plasmids derived from a transposon system, such as from Sleeping Beauty or piggyBac, and propagation of the genetically modified T cells on aAPC. The approach resulted in outgrowth of clinically appealing numbers of CAR+ T cells that demonstrated specificity for their target antigen (e.g., CD19). Importantly, the cells met release criteria established by the FDA for use in clinical trials. These methods avoid genotoxicity due to virus-mediated transduction and immunogenicity due to use of virus.

A chimeric antigen receptor (CAR) recognizes cell-surface tumor-associated antigen independent of human leukocyte antigen (HLA) and employs one or more signaling molecules to activate genetically modified T cells for killing, proliferation, and cytokine production (Jena et al., 2010). Adoptive transfer of T cells expressing CAR has shown promise in multiple clinical trials. It is now possible to use a modular approach to manufacture clinical grade genetically modified T cells. In certain embodiments, the platform technologies disclosed herein comprise (i) non-viral gene transfer using an electroporation device (e.g., a nucleofector), (ii) transposition (e.g., an SB transposon, see, U.S. Pat. No. 6,489,458, incorporated herein by reference), (iii) CARs that signal through endodomains (e.g., CD28/CD3-ζ, CD137/CD3-ζ, or other combinations), (iv) CARs with variable lengths of extracellular domains connecting the antigen-recognition domain to the cell surface, and, in some cases, (v) artificial antigen presenting cells (aAPC) derived from K562 to be able to robustly and numerically expand CAR+ T cells (Singh et al., 2008; Singh et al., 2011; Huang et al., 2012).

In some embodiments, the presently disclosed process can be used to genetically modify T cells derived from peripheral blood and/or umbilical cord blood to express CAR(s) that can be numerically expanded in vitro using aAPC (Singh et al., 2008; Singh et al., 2011). The process has implications for cell and gene therapy, due to the relative ease of DNA plasmid production, electroporation, use of thawed γ-irradiated master-bank aAPC, and can be readily transferred to facilities operating in compliance with current good manufacturing practice (cGMP) for Phase I/II trials. The disclosed method of manufacturing T cells is unique at least in that it does not use (i) viral-transduction or (ii) naked DNA electroporation followed by rapid expansion on a PBMC/LCL feeder layer. As an example, methods are disclosed for targeting CD19 through the enforced expression of a CAR that recognizes CD19 independent of HLA. These T cells meet release criteria defined by sterility, phenotype, viability, and cell number. In-process testing revealed that the electroporated/propagated T cells express CAR in a memory/naïve population, have a normal karyotype, preserved TCR Vβ repertoire, and are able to recognize and lyse CD19+ tumor targets in a CAR-dependent manner.

The electro-transfer of non-viral plasmids is an appealing alternative to transduction since DNA species can be produced to clinical grade at approximately $\frac{1}{10}^{th}$ the cost of recombinant GMP-grade virus. To improve the efficiency of integration, the inventors adapted Sleeping Beauty (SB) transposon and transposase for human application (Aronovich et al., 2011; Hackett et al., 2010; Izsvak et al., 2010; Kebriaei et al., 2012; Williams, 2008). Additionally, they have used the piggyBac transposon/transposase system to enforce expression of CAR (Manuri et al., 2010). The inventor's SB system uses two DNA plasmids that comprise a transposon coding for a gene of interest (e.g., 2nd generation CD19-specific CAR transgene, such as designated CD19RCD28) and a transposase (e.g., SB11), which inserts the transgene into TA dinucleotide repeats in the target cell genome (Geurts et al., 2006; Ivics et al., 1997; Izsvak and Ivics, 1997). To improve therapeutic potential, the inventor's $2^{nd}$ generation CAR (Kowolik et al., 2006) signals through CD28 and CD3-ζ with the expectation that this will sustain T-cell proliferation and recycle effector functions in vivo. In addition, CARs with varying extracellular lengths and different endodomain signaling motifs can be expressed using the SB system.

To retrieve T-cell integrants stably expressing the CAR, K562 aAPC (clone #4) were developed, expressing the desired antigen (e.g., CD19) along with costimulatory molecules, such as CD86, CD137L, a membrane-bound version of interleukin (IL)-15 (peptide fused to modified IgG4 Fc region or cytokine peptide fused to IL-15 receptor alpha), and CD64 (Fc-γ receptor 1), to select for T cells in vitro that are capable of sustained CAR-mediated propagation. This powerful technology has allowed the manufacture of clinically relevant numbers (up to $10^{10}$) of CAR+ T cells suitable for human application. As needed, additional stimulation cycles can be undertaken to generate larger numbers of genetically modified T cells. Furthermore, if fewer CAR+ T cells are needed, the approach of electroporation and propagation can be scaled back employing fewer cuvettes and carrying forward just a sub-set of the numerically expanded T cells for 0, 1, or more rounds of proliferation on aAPC (added at the beginning of each stimulation cycle). Typically, at least 90% of the propagated T cells express CAR and are cryopreserved for infusion. Furthermore, this approach can be harnessed to generate T cells to diverse tumor types by pairing the specificity of the introduced CAR with expression of the tumor-associated antigen (TAA) recognized by the CAR on the aAPC. The ex vivo expansion platform has also been adapted to manufacture NK cells, NK T cells, and γδ T cells.

The outgrowth of CD4+ and CD8+ T cells expressing the $2^{nd}$ generation CAR include cells with a stem-cell/memory/naive phenotype and exhibit three hallmarks of re-directed specificity. First, the genetically modified T cells specifically lyse CD19+ targets. Second, they produce cytokine (e.g., IFN-γ) in response to CD19+ stimulator cells. Third, they proliferate in response to CD19+ stimulation, all in a CAR-dependent manner (Singh et al., 2011; Singh et al. 2008). The aAPC and tissue culture environment (e.g., the addition of IL-21) have been modified to generate patient- and donor-derived CD19-specific T cells for infusion after hematopoietic stem-cell transplantation (Singh et al., 2011; Singh et al. 2008). The inventors can produce CAR+ T cells from peripheral blood simply obtained by venipuncture, which avoids the cost, discomfort, and inconvenience of obtaining mononuclear cells by apheresis. The ability to derive large numbers of CAR+ T cells from small numbers of mononuclear cells is particularly appealing for infusing T cells after allogeneic umbilical cord blood transplantation. The small size and anonymity of the neonatal donor precludes re-accessing this individual at a later time point and only limited numbers of harvested mononuclear cells are available as starting material for T cell manufacture to avoid interfering with hematopoiesis. Further advances to the manufacturing process include a high throughput electroporation device coupled with a fully closed WAVE bioreactor to minimize handling.

The present approach to manufacturing includes the implementation of processing and culturing systems to reduce work load and safeguard against a breach in sterility. To this end, the inventors co-cultured T cells with γ-irradiated aAPC in bioreactors and/or bags rather than flasks. This transition typically occurs after day 14 following electroporation. In addition, the aAPC as source material are numerically expanded in bioreactors and/or bags, and the inventors adapted the Sepax device to process the aAPC for cryopreservation. The Sepax harvest procedure has additional advantages beyond automation when using large volumes of culture media (>900 mL) as it reduces additional centrifuging steps required by the manual process.

I. Definitions

The term "chimeric antigen receptors (CARs)," as used herein, may refer to artificial T-cell receptors, chimeric T-cell receptors, or chimeric immunoreceptors, for example, and encompass engineered receptors that graft an artificial specificity onto a particular immune effector cell. CARs may be employed to impart the specificity of a monoclonal antibody onto a T cell, thereby allowing a large number of specific T cells to be generated, for example, for use in adoptive cell therapy. In specific embodiments, CARs direct specificity of the cell to a tumor associated antigen, for example. In some embodiments, CARs comprise an intracellular activation domain, a transmembrane domain, and an extracellular domain comprising a tumor associated antigen binding region. In particular aspects, CARs comprise fusions of single-chain variable fragments (scFv) derived from monoclonal antibodies, fused to CD3-zeta a transmembrane domain and endodomain. The specificity of other CAR designs may be derived from ligands of receptors (e.g., peptides) or from pattern-recognition receptors, such as Dectins. In particular embodiments, one can target malignant B cells by redirecting the specificity of T cells by using a CAR specific for the B-lineage molecule, CD19. In certain cases, the spacing of the antigen-recognition domain can be modified to reduce activation-induced cell death. In certain cases, CARs comprise domains for additional co-stimulatory signaling, such as CD3-zeta, FcR, CD27, CD28, CD137, DAP10, and/or OX40. In some cases, molecules can be co-expressed with the CAR, including co-stimulatory molecules, reporter genes for imaging (e.g., for positron emission tomography), gene products that conditionally ablate the T cells upon addition of a pro-drug, homing receptors, chemokines, chemokine receptors, cytokines, and cytokine receptors.

The term "T-cell receptor (TCR)" as used herein refers to a protein receptor on T cells that is composed of a heterodimer of an alpha (α) and beta (β) chain, although in some cells the TCR consists of gamma and delta (γ/δ) chains. In embodiments of the invention, the TCR may be modified on any cell comprising a TCR, including a helper T cell, a cytotoxic T cell, a memory T cell, regulatory T cell, natural killer T cell, and gamma delta T cell, for example.

The terms "tumor-associated antigen" and "cancer cell antigen" are used interchangeably herein. In each case, the terms refer to proteins, glycoproteins or carbohydrates that are specifically or preferentially expressed by cancer cells.

II. Chimeric Antigen Receptors

As used herein, the term "antigen" is a molecule capable of being bound by an antibody or T-cell receptor. An antigen is additionally capable of inducing a humoral immune response and/or cellular immune response leading to the production of B and/or T lymphocytes.

Embodiments of the present invention involve nucleic acids, including nucleic acids encoding an antigen-specific chimeric antigen receptor (CAR) polypeptide, including a CAR that has been humanized to reduce immunogenicity (hCAR), comprising an intracellular signaling domain, a transmembrane domain, and an extracellular domain comprising one or more signaling motifs. In certain embodiments, the CAR may recognize an epitope comprised of the shared space between one or more antigens. Pattern recognition receptors, such as Dectin-1, may be used to derive specificity to a carbohydrate antigen. In certain embodiments, the binding region can comprise complementary determining regions of a monoclonal antibody, variable regions of a monoclonal antibody, and/or antigen binding fragments thereof. In another embodiment, that specificity is derived from a peptide (e.g., cytokine) that binds to a receptor. A complementarity determining region (CDR) is a short amino acid sequence found in the variable domains of antigen receptor (e.g., immunoglobulin and T-cell receptor) proteins that complements an antigen and therefore provides the receptor with its specificity for that particular antigen. Each polypeptide chain of an antigen receptor contains three CDRs (CDR1, CDR2, and CDR3). Since the antigen receptors are typically composed of two polypeptide chains, there are six CDRs for each antigen receptor that can come into contact with the antigen—each heavy and light chain contains three CDRs. Because most sequence variation associated with immunoglobulins and T-cell receptors are found in the CDRs, these regions are sometimes referred to as hypervariable domains. Among these, CDR3 shows the greatest variability as it is encoded by a recombination of the VJ (VDJ in the case of heavy chain and TCR $\alpha\beta$ chain) regions.

It is contemplated that the human CAR nucleic acids are human genes to enhance cellular immunotherapy for human patients. In a specific embodiment, the invention includes a full length CAR cDNA or coding region. The antigen binding regions or domain can comprise a fragment of the $V_H$ and $V_L$ chains of a single-chain variable fragment (scFv) derived from a particular human monoclonal antibody, such as those described in U.S. Pat. No. 7,109,304, incorporated herein by reference. The fragment can also be any number of different antigen binding domains of a human antigen-specific antibody. In a more specific embodiment, the fragment is an antigen-specific scFv encoded by a sequence that is optimized for human codon usage for expression in human cells.

The arrangement could be multimeric, such as a diabody or multimers. The multimers are most likely formed by cross pairing of the variable portion of the light and heavy chains into what has been referred to by Winters as a diabody. The hinge portion of the construct can have multiple alternatives from being totally deleted, to having the first cysteine maintained, to a proline rather than a serine substitution, to being truncated up to the first cysteine. The Fc portion can be deleted. Any protein that is stable and/or dimerizes can serve this purpose. One could use just one of the Fc domains, e.g., either the CH2 or CH3 domain from human immunoglobulin. One could also use the hinge, CH2 and CH3 region of a human immunoglobulin that has been modified to improve dimerization. One could also use just the hinge portion of an immunoglobulin. One could also use portions of CD8alpha.

The intracellular signaling domain of the chimeric receptor of the invention is responsible for activation of at least one of the normal effector functions of the immune cell in which the chimeric receptor has been placed. The term "effector function" refers to a specialized function of a differentiated cell. Effector function of a T cell, for example, may be cytolytic activity or helper activity including the secretion of cytokines. Effector function in a naive, memory, or memory-type T cell includes antigen-dependent proliferation. Thus the term "intracellular signaling domain" refers to the portion of a protein that transduces the effector function signal and directs the cell to perform a specialized function. While usually the entire intracellular signaling domain will be employed, in many cases it will not be necessary to use the entire intracellular polypeptide. To the extent that a truncated portion of the intracellular signaling domain may find use, such truncated portion may be used in place of the intact chain as long as it still transduces the effector function signal. The term intracellular signaling domain is thus meant to include any truncated portion of the intracellular signaling domain sufficient to transduce the effector function signal. Examples include the zeta chain of the T-cell receptor or any of its homologs (e.g., eta, delta, gamma, or epsilon), MB 1 chain, B29, Fc RIII, Fc RI, and combinations of signaling molecules, such as CD3$\zeta$ and CD28, CD27, 4-1BB, DAP-10, OX40, and combinations thereof, as well as other similar molecules and fragments. Intracellular signaling portions of other members of the families of activating proteins can be used, such as Fc$\gamma$RIII and Fc$\epsilon$RI. See Gross et al. (1992), Stancovski et al. (1993), Moritz et al. (1994), Hwu et al. (1995), Weijtens et al. (1996), and Hekele et al. (1996) for disclosures of cTCR's using these alternative transmembrane and intracellular domains. In a preferred embodiment, the human CD3 $\zeta$ intracellular domain was taken for activation.

The antigen-specific extracellular domain and the intracellular signaling-domain may be linked by a transmembrane domain, such as the human IgG$_4$Fc hinge and Fc regions. Alternatives include the human CD4 transmembrane domain, the human CD28 transmembrane domain, the transmembrane human CD3$\zeta$ domain, or a cysteine mutated human CD3$\zeta$ domain, or other transmembrane domains from other human transmembrane signaling proteins, such as CD16 and CD8 and erythropoietin receptor.

In some embodiments, the CAR nucleic acid comprises a sequence encoding other costimulatory receptors, such as a transmembrane domain and a modified CD28 intracellular signaling domain. Other costimulatory receptors include, but are not limited to one or more of CD28, CD27, OX-40 (CD134), DAP10, and 4-1BB (CD137). In addition to a primary signal initiated by CD3 $\zeta$, an additional signal provided by a human costimulatory receptor inserted in a human CAR is important for full activation of T cells and could help improve in vivo persistence and the therapeutic success of the adoptive immunotherapy.

In particular embodiments, the invention concerns isolated nucleic acid segments and expression cassettes incorporating DNA sequences that encode the CAR. Vectors of the present invention are designed, primarily, to deliver desired genes to immune cells, preferably T cells under the control of regulated eukaryotic promoters, for example, MNDU3 promoter, CMV promoter, EF1alpha promoter, or Ubiquitin promoter. Also, the vectors may contain a selectable marker, if for no other reason, to facilitate their manipulation in vitro. In other embodiments, the CAR can be expressed from mRNA in vitro transcribed from a DNA template.

Chimeric antigen receptor molecules are recombinant and are distinguished by their ability to both bind antigen and transduce activation signals via immunoreceptor activation motifs (ITAM's) present in their cytoplasmic tails. Receptor constructs utilizing an antigen-binding moiety (for example, generated from single chain antibodies (scFv)) afford the additional advantage of being "universal" in that they bind native antigen on the target cell surface in an HLA-independent fashion. For example, several laboratories have reported on scFv constructs fused to sequences coding for the intracellular portion of the CD3 complex's zeta chain ($\zeta$), the Fc receptor gamma chain, and sky tyrosine kinase (Eshhar et al., 1993; Fitzer-Attas et al., 1998). Re-directed T cell effector mechanisms including tumor recognition and lysis by CTL have been documented in several murine and human antigen-scFv: ζ systems (Eshhar, 1997; Altenschmidt et al., 1997; Brocker et al., 1998).

To date non-human antigen binding regions are typically used in constructing a chimeric antigen receptor. A potential problem with using non-human antigen binding regions, such as murine monoclonal antibodies, is the lack of human effector functionality and inability to penetrate into tumor masses. In other words, such antibodies may be unable to mediate complement-dependent lysis or lyse human target cells through antibody-dependent cellular toxicity or Fc-receptor mediated phagocytosis to destroy cells expressing CAR. Furthermore, non-human monoclonal antibodies can be recognized by the human host as a foreign protein, and therefore, repeated injections of such foreign antibodies can lead to the induction of immune responses leading to harmful hypersensitivity reactions. For murine-based monoclonal antibodies, this is often referred to as a Human Anti-Mouse Antibody (HAMA) response. Therefore, the use of human antibodies is more preferred because they do not elicit as strong a HAMA response as murine antibodies. Similarly, the use of human sequences in the CAR can avoid immune-mediated recognition and therefore elimination by endogenous T cells that reside in the recipient and recognize processed antigen in the context of HLA.

In some embodiments, the chimeric antigen receptor comprises: a) an intracellular signaling domain, b) a transmembrane domain, and c) an extracellular domain comprising an antigen binding region.

In specific embodiments, intracellular receptor signaling domains in the CAR include those of the T cell antigen receptor complex, such as the zeta chain of CD3, also Fcγ RIII costimulatory signaling domains, CD28, CD27, DAP10, CD137, OX40, CD2, alone or in a series with CD3zeta, for example. In specific embodiments, the intracellular domain (which may be referred to as the cytoplasmic domain) comprises part or all of one or more of TCR zeta chain, CD28, CD27, OX40/CD134, 4-1BB/CD137, FcεRIγ, ICOS/CD278, IL-2Rbeta/CD122, IL-2Ralpha/CD132, DAP10, DAP12, and CD40. In some embodiments, one employs any part of the endogenous T cell receptor complex in the intracellular domain. One or multiple cytoplasmic domains may be employed, as so-called third generation CARs have at least two or three signaling domains fused together for additive or synergistic effect, for example.

In certain embodiments of the chimeric antigen receptor, the antigen-specific portion of the receptor (which may be referred to as an extracellular domain comprising an antigen binding region) comprises a tumor associated antigen or a pathogen-specific antigen binding domain including carbohydrate antigen recognized by pattern-recognition receptors, such as Dectin-1. A tumor associated antigen may be of any kind so long as it is expressed on the cell surface of tumor cells. Exemplary embodiments of tumor associated antigens include CD19, CD20, carcinoembryonic antigen, alphafetoprotein, CA-125, MUC-1, CD56, EGFR, c-Met, AKT, Her2, Her3, epithelial tumor antigen, melanoma-associated antigen, mutated p53, mutated ras, and so forth. In certain embodiments, the CAR can be co-expressed with a membrane-bound cytokine to improve persistence when there is a low amount of tumor-associated antigen. For example, CAR can be co-expressed with membrane-bound IL-15.

In certain embodiments intracellular tumor associated antigens may be targeted, such as HA-1, survivin, WT1, and p53. This can be achieved by a CAR expressed on a universal T cell that recognizes the processed peptide described from the intracellular tumor associated antigen in the context of HLA. In addition, the universal T cell may be genetically modified to express a T-cell receptor pairing that recognizes the intracellular processed tumor associated antigen in the context of HLA.

The pathogen may be of any kind, but in specific embodiments the pathogen is a fungus, bacteria, or virus, for example. Exemplary viral pathogens include those of the families of Adenoviridae, EpsteinBarr virus (EBV), Cytomegalovirus (CMV), Respiratory Syncytial Virus (RSV), JC virus, BK virus, HSV, HHV family of viruses, Picornaviridae, Herpesviridae, Hepadnaviridae, Flaviviridae, Retroviridae, Orthomyxoviridae, Paramyxoviridae, Papovaviridae, Polyomavirus, Rhabdoviridae, and Togaviridae. Exemplary pathogenic viruses cause smallpox, influenza, mumps, measles, chickenpox, ebola, and rubella. Exemplary pathogenic fungi include *Candida, Aspergillus, Cryptococcus, Histoplasma, Pneumocystis*, and *Stachybotrys*. Exemplary pathogenic bacteria include *Streptococcus, Pseudomonas, Shigella, Campylobacter, Staphylococcus, Helicobacter, E. coli, Rickettsia, Bacillus, Bordetella, Chlamydia, Spirochetes*, and *Salmonella*. In one embodiment the pathogen receptor Dectin-1 can be used to generate a CAR that recognizes the carbohydrate structure on the cell wall of fungi. T cells genetically modified to express the CAR based on the specificity of Dectin-1 can recognize *Aspergillus* and target hyphal growth. In another embodiment, CARs can be made based on an antibody recognizing viral determinants (e.g., the glycoproteins from CMV and Ebola) to interrupt viral infections and pathology.

In some embodiments, the pathogenic antigen is an *Aspergillus* carbohydrate antigen for which the extracellular domain in the CAR recognizes patterns of carbohydrates of the fungal cell wall, such as via Dectin-1.

A chimeric immunoreceptor according to the present invention can be produced by any means known in the art, though preferably it is produced using recombinant DNA techniques. A nucleic acid sequence encoding the several regions of the chimeric receptor can be prepared and assembled into a complete coding sequence by standard techniques of molecular cloning (genomic library screening, PCR, primer-assisted ligation, scFv libraries from yeast and bacteria, site-directed mutagenesis, etc.). The resulting coding region can be inserted into an expression vector and used to transform a suitable expression host allogeneic T-cell line.

As used herein, a nucleic acid construct or nucleic acid sequence or polynucleotide is intended to mean a DNA molecule that can be transformed or introduced into a T cell and be transcribed and translated to produce a product (e.g., a chimeric antigen receptor).

In an exemplary nucleic acid construct (polynucleotide) employed in the present invention, the promoter is operably linked to the nucleic acid sequence encoding the chimeric receptor of the present invention, i.e., they are positioned so as to promote transcription of the messenger RNA from the DNA encoding the chimeric receptor. The promoter can be of genomic origin or synthetically generated. A variety of promoters for use in T cells are well-known in the art (e.g., the CD4 promoter disclosed by Marodon et al. (2003)). The promoter can be constitutive or inducible, where induction is associated with the specific cell type or a specific level of maturation, for example. Alternatively, a number of well-known viral promoters are also suitable. Promoters of interest include the β-actin promoter, SV40 early and late promoters, immunoglobulin promoter, human cytomegalovirus promoter, retrovirus promoter, and the Friend spleen focus-forming virus promoter. The promoters may or may not be associated with enhancers, wherein the enhancers may be naturally associated with the particular promoter or associated with a different promoter.

The sequence of the open reading frame encoding the chimeric receptor can be obtained from a genomic DNA source, a cDNA source, or can be synthesized (e.g., via PCR), or combinations thereof. Depending upon the size of the genomic DNA and the number of introns, it may be desirable to use cDNA or a combination thereof as it is found that introns stabilize the mRNA or provide T cell-specific expression (Barthel and Goldfeld, 2003). Also, it may be further advantageous to use endogenous or exogenous non-coding regions to stabilize the mRNA.

For expression of a chimeric antigen receptor of the present invention, the naturally occurring or endogenous transcriptional initiation region of the nucleic acid sequence encoding N-terminal components of the chimeric receptor can be used to generate the chimeric receptor in the target host. Alternatively, an exogenous transcriptional initiation region can be used that allows for constitutive or inducible expression, wherein expression can be controlled depending upon the target host, the level of expression desired, the nature of the target host, and the like.

Likewise, a signal sequence directing the chimeric receptor to the surface membrane can be the endogenous signal sequence of N-terminal component of the chimeric receptor. Optionally, in some instances, it may be desirable to exchange this sequence for a different signal sequence. However, the signal sequence selected should be compatible with the secretory pathway of T cells so that the chimeric receptor is presented on the surface of the T cell.

Similarly, a termination region may be provided by the naturally occurring or endogenous transcriptional termination region of the nucleic acid sequence encoding the C-terminal component of the chimeric receptor. Alternatively, the termination region may be derived from a different source. For the most part, the source of the termination region is generally not considered to be critical to the expression of a recombinant protein and a wide variety of termination regions can be employed without adversely affecting expression.

As will be appreciated by one of skill in the art that, in some instances, a few amino acids at the ends of the antigen binding domain in the CAR can be deleted, usually not more than 10, more usually not more than 5 residues, for example. Also, it may be desirable to introduce a small number of amino acids at the borders, usually not more than 10, more usually not more than 5 residues. The deletion or insertion of amino acids may be as a result of the needs of the construction, providing for convenient restriction sites, ease of manipulation, improvement in levels of expression, or the like. In addition, the substitute of one or more amino acids with a different amino acid can occur for similar reasons, usually not substituting more than about five amino acids in any one domain.

The chimeric construct that encodes the chimeric receptor according to the invention can be prepared in conventional ways. Because, for the most part, natural sequences may be employed, the natural genes may be isolated and manipulated, as appropriate, so as to allow for the proper joining of the various components. Thus, the nucleic acid sequences encoding for the N-terminal and C-terminal proteins of the chimeric receptor can be isolated by employing the polymerase chain reaction (PCR), using appropriate primers that result in deletion of the undesired portions of the gene. Alternatively, restriction digests of cloned genes can be used to generate the chimeric construct. In either case, the sequences can be selected to provide for restriction sites that are blunt-ended, or have complementary overlaps.

The various manipulations for preparing the chimeric construct can be carried out in vitro and in particular embodiments the chimeric construct is introduced into vectors for cloning and expression in an appropriate host using standard transformation or transfection methods. Thus, after each manipulation, the resulting construct from joining of the DNA sequences is cloned, the vector isolated, and the sequence screened to ensure that the sequence encodes the desired chimeric receptor. The sequence can be screened by restriction analysis, sequencing, or the like.

The chimeric constructs of the present invention find application in subjects having or suspected of having cancer by reducing the size of a tumor or preventing the growth or re-growth of a tumor in these subjects. Accordingly, the present invention further relates to a method for reducing growth or preventing tumor formation in a subject by introducing a chimeric construct of the present invention into an isolated T cell of the subject and reintroducing into the subject the transformed T cell, thereby effecting anti-tumor responses to reduce or eliminate tumors in the subject. Suitable T cells that can be used include cytotoxic lymphocytes (CTL) or any cell having a T cell receptor in need of disruption. As is well-known to one of skill in the art, various methods are readily available for isolating these cells from a subject. For example, using cell surface marker expression or using commercially available kits (e.g., ISO-CELL™ from Pierce, Rockford, Ill.).

It is contemplated that the chimeric construct can be introduced into the subject's own T cells as naked DNA or in a suitable vector. Methods of stably transfecting T cells by electroporation using naked DNA are known in the art. See, e.g., U.S. Pat. No. 6,410,319. Naked DNA generally refers to the DNA encoding a chimeric receptor of the present invention contained in a plasmid expression vector in proper orientation for expression. Advantageously, the use of naked DNA reduces the time required to produce T cells expressing the chimeric receptor of the present invention.

Alternatively, a viral vector (e.g., a retroviral vector, adenoviral vector, adeno-associated viral vector, or lentiviral vector) can be used to introduce the chimeric construct into T cells. Suitable vectors for use in accordance with the method of the present invention are non-replicating in the subject's T cells. A large number of vectors are known that are based on viruses, where the copy number of the virus maintained in the cell is low enough to maintain the viability of the cell. Illustrative vectors include the pFB-neo vectors (STRATAGENE®) disclosed herein as well as vectors based on HIV, SV40, EBV, HSV, or BPV.

Once it is established that the transfected or transduced T cell is capable of expressing the chimeric receptor as a surface membrane protein with the desired regulation and at a desired level, it can be determined whether the chimeric receptor is functional in the host cell to provide for the desired signal induction. Subsequently, the transduced T cells are reintroduced or administered to the subject to activate anti-tumor responses in the subject. To facilitate administration, the transduced T cells according to the invention can be made into a pharmaceutical composition or made into an implant appropriate for administration in vivo, with appropriate carriers or diluents, which further can be pharmaceutically acceptable. The means of making such a composition or an implant have been described in the art (see, for instance, Remington's Pharmaceutical Sciences, 16th Ed., Mack, ed. (1980)). Where appropriate, the transduced T cells can be formulated into a preparation in semisolid or liquid form, such as a capsule, solution, injection, inhalant, or aerosol, in the usual ways for their respective route of administration. Means known in the art can be utilized to prevent or minimize release and absorption of the composition until it reaches the target tissue or organ, or to ensure timed-release of the composition. Desirably, however, a pharmaceutically acceptable form is employed that does not ineffectuate the cells expressing the chimeric receptor. Thus, desirably the transduced T cells can be made into a pharmaceutical composition containing a balanced salt solution, preferably Hanks' balanced salt solution, or normal saline.

III. Methods and Compositions Related to the Embodiments

In certain aspects, the invention includes a method of making and/or expanding the antigen-specific redirected T cells that comprises transfecting T cells with an expression vector containing a DNA construct encoding the hCAR, then, optionally, stimulating the cells with antigen positive cells, recombinant antigen, or an antibody to the receptor to cause the cells to proliferate.

In another aspect, a method is provided of stably transfecting and re-directing T cells by electroporation, or other non-viral gene transfer (such as, but not limited to sonoporation) using naked DNA. Most investigators have used viral vectors to carry heterologous genes into T cells. By using naked DNA, the time required to produce redirected T cells can be reduced. "Naked DNA" means DNA encoding a chimeric T-cell receptor (cTCR) contained in an expression cassette or vector in proper orientation for expression. The electroporation method of this invention produces stable transfectants that express and carry on their surfaces the chimeric TCR (cTCR).

"Chimeric TCR" means a receptor that is expressed by T cells and that comprises intracellular signaling, transmembrane, and extracellular domains, where the extracellular domain is capable of specifically binding in an MHC unrestricted manner an antigen that is not normally bound by a T-cell receptor in that manner. Stimulation of the T cells by the antigen under proper conditions results in proliferation (expansion) of the cells and/or production of IL-2. The exemplary CD19- and HERV-K specific chimeric receptors of the instant application are examples of a chimeric TCR. However, the method is applicable to transfection with chimeric TCRs that are specific for other target antigens, such as chimeric TCRs that are specific for HER2/Neu (Stancovski et al., 1993), ERBB2 (Moritz et al., 1994), folate binding protein (Hwu et al., 1995), renal cell carcinoma (Weitjens et al., 1996), and HIV-1 envelope glycoproteins gp120 and gp41 (Roberts et al., 1994). Other cell-surface target antigens include, but are not limited to, CD20, carcinoembryonic antigen, mesothelin, ROR1, c-Met, CD56, GD2, GD3, alphafetoprotein, CD23, CD30, CD123, IL-11Ralpha, kappa chain, lambda chain, CD70, CA-125, MUC-1, EGFR and variants, epithelial tumor antigen, and so forth.

In certain aspects, the T cells are primary human T cells, such as T cells derived from human peripheral blood mononuclear cells (PBMC), PBMC collected after stimulation with G-CSF, bone marrow, or umbilical cord blood. Conditions include the use of mRNA and DNA and electroporation. Following transfection the cells may be immediately infused or may be stored. In certain aspects, following transfection, the cells may be propagated for days, weeks, or months ex vivo as a bulk population within about 1, 2, 3, 4, 5 days or more following gene transfer into cells. In a further aspect, following transfection, the transfectants are cloned and a clone demonstrating presence of a single integrated or episomally maintained expression cassette or plasmid, and expression of the chimeric receptor is expanded ex vivo. The clone selected for expansion demonstrates the capacity to specifically recognize and lyse CD19 expressing target cells. The recombinant T cells may be expanded by stimulation with IL-2, or other cytokines that bind the common gamma-chain (e.g., IL-7, IL-12, IL-15, IL-21, and others). The recombinant T cells may be expanded by stimulation with artificial antigen presenting cells. The recombinant T cells may be expanded on artificial antigen presenting cell or with an antibody, such as OKT3, which cross links CD3 on the T cell surface. Subsets of the recombinant T cells may be deleted on artificial antigen presenting cell or with an antibody, such as Campath, which binds CD52 on the T cell surface. In a further aspect, the genetically modified cells may be cryopreserved.

T-cell propagation (survival) after infusion may be assessed by: (i) q-PCR using primers specific for the CAR; (ii) flow cytometry using an antibody specific for the CAR; and/or (iii) soluble TAA.

Embodiments of the invention also concern the targeting of a B-cell malignancy or disorder including B cells, with the cell-surface epitope being CD19-specific using a redirected immune T cell. Malignant B cells are an excellent target for redirected T cells, as B cells can serve as immunostimulatory antigen-presenting cells for T cells. Preclinical studies that support the anti-tumor activity of adoptive therapy with donor-derived CD19-specific T-cells bearing a human or humanized CAR include (i) redirected killing of $CD19^+$ targets, (ii) redirected secretion/expression of cytokines after incubation with $CD19^+$ targets/stimulator cells, and (iii) sustained proliferation after incubation with $CD19^+$ targets/stimulator cells.

In certain embodiments of the invention, the CAR cells are delivered to an individual in need thereof, such as an individual that has cancer or an infection. The cells then enhance the individual's immune system to attack the respective cancer or pathogenic cells. In some cases, the individual is provided with one or more doses of the antigen-specific CAR T-cells. In cases where the individual is provided with two or more doses of the antigen-specific CAR T-cells, the duration between the administrations should be sufficient to allow time for propagation in the individual, and in specific embodiments the duration between doses is 1, 2, 3, 4, 5, 6, 7, or more days.

The source of the allogeneic T cells that are modified to include both a chimeric antigen receptor and that lack functional TCR may be of any kind, but in specific embodiments the cells are obtained from a bank of umbilical cord blood, peripheral blood, human embryonic stem cells, or induced pluripotent stem cells, for example. Suitable doses for a therapeutic effect would be at least $10^5$ or between about $10^5$ and about $10^{10}$ cells per dose, for example, preferably in a series of dosing cycles. An exemplary dosing regimen consists of four one-week dosing cycles of escalating doses, starting at least at about $10^5$ cells on Day 0, for example increasing incrementally up to a target dose of about $10^{10}$ cells within several weeks of initiating an intra-patient dose escalation scheme. Suitable modes of administration include intravenous, subcutaneous, intracavitary (for example by reservoir-access device), intraperitoneal, and direct injection into a tumor mass.

A pharmaceutical composition of the present invention can be used alone or in combination with other well-established agents useful for treating cancer. Whether delivered alone or in combination with other agents, the pharmaceutical composition of the present invention can be delivered via various routes and to various sites in a mammalian, particularly human, body to achieve a particular effect. One skilled in the art will recognize that, although more than one route can be used for administration, a particular route can provide a more immediate and more effective reaction than another route. For example, intradermal delivery may be advantageously used over inhalation for the treatment of melanoma. Local or systemic delivery can be accomplished by administration comprising application or instillation of the formulation into body cavities, inhalation or insufflation of an aerosol, or by parenteral introduction, comprising intramuscular, intravenous, intraportal, intrahepatic, peritoneal, subcutaneous, or intradermal administration.

A composition of the present invention can be provided in unit dosage form wherein each dosage unit, e.g., an injection, contains a predetermined amount of the composition, alone or in appropriate combination with other active agents. The term unit dosage form as used herein refers to physically discrete units suitable as unitary dosages for human and animal subjects, each unit containing a predetermined quantity of the composition of the present invention, alone or in combination with other active agents, calculated in an amount sufficient to produce the desired effect, in association with a pharmaceutically acceptable diluent, carrier, or vehicle, where appropriate. The specifications for the novel unit dosage forms of the present invention depend on the particular pharmacodynamics associated with the pharmaceutical composition in the particular subject.

Desirably an effective amount or sufficient number of the isolated transduced T cells is present in the composition and introduced into the subject such that long-term, specific, anti-tumor responses are established to reduce the size of a tumor or eliminate tumor growth or regrowth than would otherwise result in the absence of such treatment. Desirably, the amount of transduced T cells reintroduced into the subject causes a 10%, 20%, 30%, 40%, 50%, 60%, 70%, 80%, 90%, 95%, 98%, or 100% decrease in tumor size when compared to otherwise same conditions wherein the transduced T cells are not present.

Accordingly, the amount of transduced T cells administered should take into account the route of administration and should be such that a sufficient number of the transduced T cells will be introduced so as to achieve the desired therapeutic response. Furthermore, the amounts of each active agent included in the compositions described herein (e.g., the amount per each cell to be contacted or the amount per certain body weight) can vary in different applications. In general, the concentration of transduced T cells desirably should be sufficient to provide in the subject being treated at least from about $1\times10^6$ to about $1\times10^9$ transduced T cells, even more desirably, from about $1\times10^7$ to about $5\times10^8$ transduced T cells, although any suitable amount can be utilized either above, e.g., greater than $5\times10^8$ cells, or below, e.g., less than $1\times10^7$ cells. The dosing schedule can be based on well-established cell-based therapies (see, e.g., Topalian and Rosenberg, 1987; U.S. Pat. No. 4,690,915), or an alternate continuous infusion strategy can be employed.

These values provide general guidance of the range of transduced T cells to be utilized by the practitioner upon optimizing the method of the present invention for practice of the invention. The recitation herein of such ranges by no means precludes the use of a higher or lower amount of a component, as might be warranted in a particular application. For example, the actual dose and schedule can vary depending on whether the compositions are administered in combination with other pharmaceutical compositions, or depending on interindividual differences in pharmacokinetics, drug disposition, and metabolism. One skilled in the art readily can make any necessary adjustments in accordance with the exigencies of the particular situation.

IV. Exemplary Human CD19-specific Chimeric Antigen Receptor T Cells

CD19, a cell surface glycoprotein of the immunoglobulin superfamily, is a potentially attractive target for antibody therapy of B cell-associated malignancies. This antigen is absent from hematopoietic stem cells, and in healthy individuals its presence is exclusively restricted to the B-lineage and possibly some follicular dendritic cells (Scheuermann et al., 1995). In fact, it is present on B cells from the earliest recognizable B-lineage cells during development to B-cell blasts but is lost on maturation to plasma cells. Furthermore, CD19 is not shed from the cell surface and rarely lost during neoplastic transformation (Scheuermann et al., 1995). The protein is expressed on most malignant B-lineage cells, including cells from patients with chronic lymphocytic leukemia (CLL), non-Hodgkin lymphoma (NHL), and acute lymphoblastic leukemia (ALL) (Uckun et al., 1988). CD19 primarily acts as a B cell co-receptor in conjunction with CD21 and CD81. Upon activation, the cytoplasmic tail of CD19 becomes phosphorylated, which leads to binding by Src-family kinases and recruitment of PI-3 kinase.

In one aspect compositions and methods of the embodiments concern human CD19-specific chimeric T cell receptor (or chimeric antigen receptor, CAR) polypeptide (designated hCD19CAR) comprising an intracellular signaling domain, a transmembrane domain, and an extracellular domain, the extracellular domain comprising a human CD19 binding region. In another aspect, the CD19 binding region is a F(ab')2, Fab', Fab, Fv, or scFv. The binding region may comprise an amino acid sequence that is at least, at most, or about 70%, 75%, 80%, 85%, 90%, 95%, 96%, 97%, 98%, 99%, or 100% identical to the wild-type amino acid sequence. The intracellular domain may comprise an intracellular signaling domain of human CD3ζ and may further comprise human CD28 intracellular segment. In certain aspects the transmembrane domain is a CD28 transmembrane domain.

In a further aspect compositions of the invention include a nucleic acid encoding the polypeptide described above. In certain aspects the nucleic acid sequence is optimized for human codon usage.

In still a further aspect compositions of the invention include cells expressing the polypeptide described herein. The T cell may comprise an expression cassette encoding hCD19CAR polypeptide. The expression cassette can be comprised in a non-viral vector, such as a transposon, or a human transposon, or recombinant variant thereof. The expression cassette can be comprised in a viral vector or recombinant variant thereof. The expression cassette can be genomically integrated or episomally maintained or expressed from mRNA.

In yet a further aspect the invention includes a method of making a T cell expressing a human CD19-specific CAR comprising introducing an expression cassette into the cell, wherein the expression cassette encodes a polypeptide comprising a human extracellular CD19 binding domain, a transmembrane domain, and one or more intracellular signaling domain(s). The method may further comprise stimulating the cells with CD19$^+$ cells, recombinant CD19, or an antibody to the receptor to cause the cells to proliferate, kill, and/or make cytokines; for example, the cells may be stimulated to proliferate or expand with CD19$^+$ artificial antigen presenting cells.

In certain aspects the invention includes methods of treating a human disease condition associated with a cell expressing endogenous CD19 comprising infusing a patient with an amount of a recombinant cell expressing a human CD19-specific CAR sufficient to treat the condition, wherein the human CD19-specific CAR comprises a human CD19 extracellular binding domain, a transmembrane domain, and an intracellular signaling domain. The condition can be lymphoma, leukemia, Non-Hodgkin's lymphoma, acute lymphoblastic leukemia, chronic lymphoblastic leukemia, chronic lymphocytic leukemia, or B cell-associated autoimmune diseases, for example.

The invention relates to the generation of a human CD19-specific chimeric antigen receptor (hCD19RCD28 or hCAR). In certain aspects recombinant cells expressing hCAR have improved in vivo persistence and anti-tumor efficacy. The human hCAR has a reduced immunogenicity compared to murine hCAR, which comprises a scFv segment derived from a murine CD19-specific monoclonal antibody (mAb). Anti-tumor effects can be augmented by genetically modified cells, rendered specific for CD19. Typically, T cell specificity is achieved by electrotransfer of an expression cassette encoding hCAR.

The hCAR may be a chimeric receptor comprising one or more activation endodomain(s), such as a CD3-ζ-derived activation domain. Additional T-cell activation motifs include, but are not limited to, CD28, CD27, OX-40, DAP10, and 4-1BB. In certain aspects the activation domain can also include a CD28 transmembrane and/or activation domain. In a further aspect the hCAR encoding region and/or expression cassette codon optimized for expression in human cells and subjects, e.g., in one embodiment the scFv region obtained from VH and VL sequences of a CD19-specific human antibodies are incorporated into the CD19 binding segment of the hCAR (for example see U.S. Pat. No. 7,109,304, which is incorporated herein by reference in its entirety). In another embodiment, the hCAR expression cassette is episomally maintained or integrated into the genome of the recombinant cell. In certain aspects the expression cassette is comprised in a nucleic acid capable of integration by using an integrase mechanism, a viral vector, such as a retroviral vector, or a nonviral vector, such as a transposon mechanism. In a further embodiment the expression cassette is included in a transposon based nucleic acid. In a particular embodiment, the expression cassette is part of a two component Sleeping Beauty (SB) or piggyBac system that utilizes a transposon and transposase for enhanced non-viral gene transfer.

Recombinant hCAR expressing cells can be numerically expanded to clinically-meaningful numbers. One example of such expansion uses artificial antigen presenting cells (aAPC). Recombinant hCAR expressing cells can be verified and identified by flow cytometry and western blot analyses. Recombinant hCAR expressing T cells, expressing a CD19-specific CAR can recognize and kill CD19 expressing target cells. In a further aspect, hCAR can be expressed into Universal cells that can be infused across transplantation barriers to help prevent immunogenicity. The hCAR can be used along with human genes for imaging (such as by positron emission tomography, PET) and conditional ablation of T cells, in the event of cytotoxicity. The recombinant cells of the invention can be used in CD19-specific cellular therapies.

V. Exemplary HERV-targeting Chimeric Antigen Receptor T Cells

During the human genome project, a set of ancient retrovirus named human endogenous retrovirus (HERVs) was discovered to be stably integrated into the human genome forming 8.5% of the total human genome. Among the HERVs, HERV-K was found as an oncogenic allelic variant involved in melanoma, breast cancer, ovarian cancer, teratocarcinoma and prostate cancer along with various autoimmune diseases like multiple sclerosis and rheumatoid arthritis (Buscher et al., 2005; Dreyfus, 2011; Seifarth et al., 1995). The oncogenic potential of HERV-K is contributed by the envelope (env) and GAG protein (Rec). Recent studies have shown that the expression of the HERV-K env protein exclusively on tumor cell surface and not on normal skin cells (Wang-Johanning et al., 2008; Li et al., 2010). The expression of HERV-K env protein was found to increase with more aggressive and metastatic type III and type IV melanoma than less aggressive and localized type I melanoma (Buscher et al., 2005; Hahn et al., 2008; Serafino et al., 2009). This selective expression of HERV-K env protein on melanoma cells can be harnessed as a treatment strategy for patients with refractory or metastatic melanoma. Patients with metastatic melanoma have a poor prognosis due to resistance to conventional therapies such as chemotherapy, radiation and surgery (Bhatia et al., 2009). Thus, new targeted treatment strategies are needed to improve therapeutic outcome.

To generate T-cell therapy for melanoma, the inventors targeted a TAA derived from HERV, whose genome stably integrated into humans millions of years ago. To target HERK-K, T cells were engineered to express a CAR specific for the env protein by replacing the antigen-binding exodomain of CD19-specific CAR with the single chain antibody (scFv) sequence of an anti-HERV-K env-specific monoclonal antibody. This new CAR was cloned as a transposon into the SB system. DNA plasmids coding for the HERV-K env-specific CAR and SB transposase were electro-transferred into primary human T cells and genetically modified CAR$^+$ T cells were selectively propagated on irradiated artificial antigen presenting cells (aAPC) expressing HERV-K env and desired T-cell co-stimulatory molecules. After co-culture on γ-irradiated aAPC, 95% of CD3$^+$ T cells expressed the CAR and these CAR$^+$ T cells were able to specifically kill HERV-K env$^+$, but not HERV-K env$^-$, tumor targets in vitro in contrast to CAR$^+$ T cells. Specificity of these CAR$^+$ T cells was proven by expressing the HERV-K env protein in antigen negative EL4 mouse cells which were preferentially killed compared to HERV-K env EL4 parental cells and HERV-K knockdown by shRNA (specific targeting for HERV-K env RNA) on A888-mel cells resulted in reduced killing compared to parental. The CAR$^+$ T cells were also successful in reducing tumor growth and metastasis of A375-super metastatic (SM) tumor cells from lungs to liver in vivo. The mice with tumor receiving the CAR$^+$ T cells lived longer and appeared healthier than the tumor alone mice group. Thus, T cells targeting an active retrovirus can be used as an immunotherapy for melanoma, using an approach that has translational appeal for clinical trials.

Clonal evolution of melanoma cells can render the TCR therapy ineffective due to its dependency on MHC complex for tumor recognition. A CAR can overcome this clonal evolution of melanoma cells by mediated cell death in a MHN independent manner, unlike TCR-based T-cell therapy. The HERV-K antigen is expressed only on the tumor cell surface and not on normal cells. Therefore, HERV-K-specific CAR$^+$ T cells can specifically target and abolish tumor cells without any adverse side effects. They may be infused to treat HERV-K$^+$ malignancies at many stages along the cancer spectrum, from minimal residual disease, to bulk tumors, to disease that is refractory to conventional therapies.

HERV-K is expressed on many tumor types, including, but not limited to, melanoma (Muster et al., 2003; Buscher et al., 2005; Li et al., 2010; Reiche et al., 2010; Serafino et al., 2009), breast cancer (Patience et al., 1996; Wang-Johanning et al., 2003; Seifarth et al., 1995), ovarian cancer (Wang-Johanning et al., 2007), lymphoma (Contreras-Galindo et al., 2008), and teratocarcinoma (Bieda et al., 2001; Lower et al., 1993). Furthermore, infected cells, including those infected by HIV (Jones et al., 2012), also express HERV-K. This provides an attractive opportunity that one CAR design targeting HERV-K may be used to treat a variety of cancers and infections.

VI. Exemplary Membrane-bound IL-15 Co-expressing Chimeric Antigen Receptor T Cells for Targeting Minimally Residual Disease Chemotherapeutic treatment of adult and pediatric B-lineage acute lymphoblastic leukemia (B-ALL) have disease relapse rates of 65% and 20%, respectively, due to drug-resistant residual disease. The high incidence of B-ALL relapse, especially in poor prognostic groups, has prompted the use of immune-based therapies using allogeneic hematopoietic stem cell transplantation (HSCT). This therapy is dependent on alloreactive cells present in the donor graft for the eradication of remaining leukemic cells, or minimal residual disease, to improve disease-free survival. Donor lymphocyte infusions have been used to enhance the ability of engrafted T cells to target residual B-ALL after allogeneic HSCT, but this treatment approach for such patients achieves less than a 10% remission rate and is associated with a high degree of morbidity and mortality from the frequency and severity of graft-versus-host disease (GVHD). With relapse a common and lethal problem in these refractory malignancies, adoptive therapy using peripheral blood mononuclear cells (PBMC)-derived T cells after HSCT may be used to increase the anti-tumor effect, or graft-versus-leukemia (GVL) effect, by retargeting the specificity of donor T cells to a tumor-associated antigen (TAA).

Numerous formulations of CARs specific for target antigens have been developed, with CD19-specific CAR targeting the CD19 antigen on the cell surface of B-ALL. Observing long-term persistence of CAR$^+$ cells and achieving durable responses in patients across different clinical protocols remains a critical issue hampering the therapeutic efficacy of CAR-based therapies.

Currently, CAR-modified T cells are reliant on obtaining survival signaling through the CAR which occurs only upon encounter with the tumor antigen. In clinical situations where these CAR-modified T cells are infused into patients with bulky disease, there is ample tumor antigen present to provide sufficient activation and survival signaling via the CAR. However, patients with relapsed B-ALL are often conditioned with myeloablative chemotherapy followed by HSCT and present with minimal residual disease (MRD). In this case, patients have a low tumor load and the minute level of TAA severely restricts the CAR-mediated signaling necessary for supporting the infused T cells consequently compromising therapeutic potential. An alternate CAR-independent means for improving T cell persistence would be anticipated to improve the engraftment of CAR-modified T cells.

Cytokines in the common gamma chain receptor family ($\gamma$C) are important costimulatory molecules for T cells that are critical to lymphoid function, survival, and proliferation. IL-15 possesses several attributes that are desirable for adoptive therapy. IL-15 is a homeostatic cytokine that supports the survival of long-lived memory cytotoxic T cells, promotes the eradication of established tumors via alleviating functional suppression of tumor-resident cells, and inhibits AICD.

IL-15 is tissue restricted and only under pathologic conditions is it observed at any level in the serum, or systemically. Unlike other $\gamma$C cytokines that are secreted into the surrounding milieu, IL-15 is trans-presented by the producing cell to T cells in the context of IL-15 receptor alpha (IL-15R$\alpha$). The unique delivery mechanism of this cytokine to T cells and other responding cells: (i) is highly targeted and localized, (ii) increases the stability and half-life of IL-15, and (iii) yields qualitatively different signaling than is achieved by soluble IL-15.

In one embodiment, the invention provides a method of generating chimeric antigen receptor (CAR)-modified T cells with long-lived in vivo potential for the purpose of treating, for example, leukemia patients exhibiting minimal residual disease (MRD). In aggregate, this method describes how soluble molecules such as cytokines can be fused to the cell surface to augment therapeutic potential. The core of this method relies on co-modifying CAR T cells with a human cytokine mutein of interleukin-15 (IL-15), henceforth referred to as mIL15. The mIL15 fusion protein is comprised of codon-optimized cDNA sequence of IL-15 fused to the full length IL15 receptor alpha via a flexible serine-glycine linker. This IL-15 mutein was designed in such a fashion so as to: (i) restrict the mIL15 expression to the surface of the CAR$^+$ T cells to limit diffusion of the cytokine to non-target in vivo environments, thereby potentially improving its safety profile as exogenous soluble cytokine administration has led to toxicities; and (ii) present IL-15 in the context of IL-15R$\alpha$ to mimic physiologically relevant and qualitative signaling as well as stabilization and recycling of the IL-15/IL-15Ra complex for a longer cytokine half-life. T cells expressing mIL15 are capable of continued supportive cytokine signaling, which is critical to their survival post-infusion. The mIL15$^+$CAR$^+$ T cells generated by non-viral Sleeping Beauty System genetic modification and subsequent ex vivo expansion on a clinically applicable platform yielded a T cell infusion product with enhanced persistence after infusion in murine models with high, low, or no tumor burden. Moreover, the mIL15$^+$CAR$^+$ T cells also demonstrated improved anti-tumor efficacy in both the high or low tumor burden models.

The improved persistence and anti-tumor activity of mIL15$^+$CAR$^+$ T cells over CAR$^+$ T cells in the high tumor burden model indicates that mIL15$^+$CAR$^+$ T cells may be more efficacious than CAR$^+$ T cells in treating leukemia patients with active disease where tumor burden is prevalent. Thus, mIL15$^+$CAR$^+$ T cells could supplant CAR$^+$ T cells in adoptive therapy in the broadest of applications. The capability of mIL15$^+$CAR$^+$ T cells to survive independent of survival signaling via the CAR enables these modified T cells to persist post-infusion despite the lack of tumor antigen. Consequently, this is anticipated to generate the greatest impact in therapeutic efficacy in a MRD treatment setting, especially in patients who have had myeloablative chemotherapy and hematopoietic stem cell transplantation. These patients would receive adoptive T cell transfer with mIL15$^+$CAR$^+$ T cells to treat their MRD and prevent relapse.

Membrane-bound cytokines, such as mIL15, have broad implications. In addition to membrane-bound IL-15, other membrane-bound cytokines are envisioned. The membrane-bound cytokines can also be extended to cell surface expression of other molecules associated with activating and propagating cells used for human application. These include, but are not limited to cytokines, chemokines, and other molecules that contribute to the activation and proliferation of cells used for human application.

Membrane-bound cytokine, such as mIL15 can be used ex vivo to prepare cells for human application(s) and can be on infused cells (e.g., T cells) used for human application. For example, membrane-bound IL-15 can be expressed on artificial antigen presenting cells (aAPC), such as derived from K562, to stimulate T cells and NK cells (as well as other cells) for activation and/or proliferation. The population of T cells activated/propagated by mIL15 on aAPC includes genetically modified lymphocytes, but also tumor-infiltrating lymphocytes, and other immune cells. These aAPC are not infused. In contrast, mIL15 (and other membrane-bound molecules) can be expressed on T cells, and other cells, that are infused.

Therapeutic efficacy of MRD treatment with CAR-modified T cells is hampered by a lack of persistence after adoptive transfer of the T cells. The capability of mIL15$^+$ CAR$^+$ T cells to survive long-term in vivo independently of tumor antigen indicates great potential for treating patients with MRD. In this case, mIL15 and the persisting T cells that it supports would address a need, as current approaches for MRD patients are insufficient. The persistence of T cells and other lymphocytes that are infused in patients with MRD applies beyond CAR$^+$ T cells. Any immune cell that is used to treat and prevent malignancy, infection or auto-immune disease must be able to persist over the long term if continued therapeutic impact is to be achieved. Thus, activating T cells for persistence beyond the signal derived from endogenous T-cell receptor or an introduced immunoreceptor is important to many aspects of adoptive immunotherapy. The expression of membrane-bound cytokine(s) thus can be used to augment the therapeutic potential and persistence of T cells and other immune cells infused for a variety of pathologic conditions.

The inventors have generated a mutein of IL-15 that is expressed as a membrane-bound fusion protein of IL-15 and IL-15Rα (mIL15) on CAR$^+$ T cells. The mIL15 construct was co-electro-transferred with a CD19-specific CAR (on Day 0) into primary human T cells as two Sleeping Beauty DNA transposon plasmids. Clinically relevant numbers of mIL15$^+$CAR$^+$ T cells were generated by co-culture on CD19$^+$ artificial antigen presenting cells and supplemented IL-21. Signaling through the IL-15 receptor complex in genetically modified T cells was validated by phosphorylation of STAT5 (pSTAT5) and these T cells demonstrated redirected specific lysis of CD19$^+$ tumor targets equivalent to CAR$^+$ T cells. Furthermore, after antigen withdrawal, signaling generated by mIL15 increased the prevalence of T cells with a less differentiated/younger phenotype that possessed memory-associated attributes including specific cell surface markers, transcription factors, and the capacity to secrete IL-2. These characteristics are desirable traits in T cells used in adoptive transfer as they are correlated with T cell subsets with demonstrated capability to persist long-term in vivo. In immunocompromised NSG mice bearing a disseminated CD19$^+$ leukemia, the mIL15$^+$CAR$^+$ T cells demonstrated both persistence and an anti-tumor effect whereas its CAR$^+$ T cell counterpart could not maintain significant persistence despite the presence of TAA. In a preventative mouse (NSG) model where mIL15$^{+/-}$CAR$^+$ T cells were first engrafted for six days followed by the introduction of a disseminated CD19$^+$ leukemia, only the mIL15$^+$CAR$^+$ T cells were found to persist as well as prevent tumor engraftment. To test whether mIL15$^+$CAR$^+$ T cells were capable of persistence independent of stimulation from TAA, mIL15$^{+/-}$CAR$^+$ T cells were adoptively transferred into NSG mice with no tumor. Only mIL15$^+$CAR$^+$ T cells were capable of persisting in this in vivo environment without exogenous cytokine support or the presence of CD19 TAA. These data demonstrate that mIL15 can be co-expressed on CAR$^+$ T cells resulting in enhanced in vivo persistence without the need for TAA or exogenous cytokine support. In summary, this cytokine fusion molecule: (i) provides stimulatory signals via pSTAT5 leading to augmented in vivo T-cell persistence while maintaining tumor-specific functionality, (ii) maintains T-cell subsets that promotes a memory-like phenotype, (iii) eliminates the need and cost for clinical-grade IL-2 for in vitro and in vivo T-cell expansion and persistence, and (iv) mitigates the need for clinical-grade soluble IL-15.

VII. Immune System and Immunotherapy

In some embodiments, a medical disorder is treated by transfer of a redirected T cell that elicits a specific immune response. In one embodiment of the present invention, B-cell lineage malignancy or disorder is treated by transfer of a redirected T cell that elicits a specific immune response. Thus, a basic understanding of the immunologic responses is necessary.

The cells of the adaptive immune system are a type of leukocyte, called a lymphocyte. B cells and T cells are the major types of lymphocytes. B cells and T cells are derived from the same pluripotent hematopoietic stem cells, and are indistinguishable from one another until after they are activated. B cells play a large role in the humoral immune response, whereas T cells are intimately involved in cell-mediated immune responses. They can be distinguished from other lymphocyte types, such as B cells and NK cells by the presence of a special receptor on their cell surface called the T-cell receptor (TCR). In nearly all other vertebrates, B cells and T cells are produced by stem cells in the bone marrow. T cells travel to and develop in the thymus, from which they derive their name. In humans, approximately 1%-2% of the lymphocyte pool recirculates each hour to optimize the opportunities for antigen-specific lymphocytes to find their specific antigen within the secondary lymphoid tissues.

T lymphocytes arise from hematopoietic stem cells in the bone marrow, and typically migrate to the thymus gland to mature. T cells express a unique antigen binding receptor on their membrane (T-cell receptor), which can only recognize antigen in association with major histocompatibility complex (MHC) molecules on the surface of other cells. There are at least two populations of T cells, known as T helper cells and T cytotoxic cells. T helper cells and T cytotoxic cells are primarily distinguished by their display of the membrane bound glycoproteins CD4 and CD8, respectively. T helper cells secret various lymphokines that are crucial for the activation of B cells, T cytotoxic cells, macrophages, and other cells of the immune system. In contrast, T cytotoxic cells that recognize an antigen-MHC complex proliferate and differentiate into effector cell called cytotoxic T lymphocytes (CTLs). CTLs eliminate cells of the body displaying antigen, such as virus infected cells and tumor cells, by producing substances that result in cell lysis. Natural killer cells (or NK cells) are a type of cytotoxic lymphocyte that constitutes a major component of the innate immune system.

NK cells play a major role in the rejection of tumors and cells infected by viruses. The cells kill by releasing small cytoplasmic granules of proteins called perforin and granzyme that cause the target cell to die by apoptosis.

Antigen-presenting cells, which include macrophages, B lymphocytes, and dendritic cells, are distinguished by their expression of a particular MHC molecule. APCs internalize antigen and re-express a part of that antigen, together with the MHC molecule on their outer cell membrane. The major histocompatibility complex (MHC) is a large genetic complex with multiple loci. The MHC loci encode two major classes of MHC membrane molecules, referred to as class I and class II MHCs. T helper lymphocytes generally recognize antigen associated with MHC class II molecules, and T cytotoxic lymphocytes recognize antigen associated with MHC class I molecules. In humans the MHC is referred to as the HLA complex and in mice the H-2 complex.

The T-cell receptor, or TCR, is a molecule found on the surface of T lymphocytes (or T cells) that is generally responsible for recognizing antigens bound to major histocompatibility complex (MHC) molecules. It is a heterodimer consisting of an alpha and beta chain in 95% of T cells, while 5% of T cells have TCRs consisting of gamma and delta chains. Engagement of the TCR with antigen and MHC results in activation of its T lymphocyte through a series of biochemical events mediated by associated enzymes, co-receptors, and specialized accessory molecules. In immunology, the CD3 antigen (CD stands for cluster of differentiation) is a protein complex composed of four distinct chains (CD3-γ, CD3δ, and two times CD3ε) in mammals, that associate with molecules known as the T-cell receptor (TCR) and the ζ-chain to generate an activation signal in T lymphocytes. The TCR, ζ-chain, and CD3 molecules together comprise the TCR complex. The CD3-γ, CD3δ, and CD3ε chains are highly related cell surface proteins of the immunoglobulin superfamily containing a single extracellular immunoglobulin domain. The transmembrane region of the CD3 chains is negatively charged, a characteristic that allows these chains to associate with the positively charged TCR chains (TCRα and TCRβ). The intracellular tails of the CD3 molecules contain a single conserved motif known as an immunoreceptor tyrosine-based activation motif or ITAM for short, which is essential for the signaling capacity of the TCR.

CD28 is one of the molecules expressed on T cells that provide co-stimulatory signals, which are required for T cell activation. CD28 is the receptor for B7.1 (CD80) and B7.2 (CD86). When activated by Toll-like receptor ligands, the B7.1 expression is upregulated in antigen presenting cells (APCs). The B7.2 expression on antigen presenting cells is constitutive. CD28 is the only B7 receptor constitutively expressed on naive T cells. Stimulation through CD28 in addition to the TCR can provide a potent co-stimulatory signal to T cells for the production of various interleukins (IL-2 and IL-6 in particular).

The strategy of isolating and expanding antigen-specific T cells as a therapeutic intervention for human disease has been validated in clinical trials (Riddell et al., 1992; Walter et al., 1995; Heslop et al., 1996).

Malignant B cells appear to be an excellent targets for redirected T cells, as B cells can serve as immunostimulatory antigen-presenting cells for T cells (Glimcher et al., 1982). Lymphoma, by virtue of its lymph node tropism, is anatomically ideally situated for T cell-mediated recognition and elimination. The localization of infused T cells to lymph node in large numbers has been documented in HIV patients receiving infusions of HIV-specific CD8$^+$ CTL clones. In these patients, evaluation of lymph node biopsy material revealed that infused clones constituted approximately 2%-8% of CD8$^+$ cells of lymph nodes. Lymph node homing might be further improved by co-transfecting T cells with a cDNA construct encoding the L-selection molecule under a constitutive promoter since this adhesion molecule directs circulating T cells back to lymph nodes and is down-regulated by in vitro expansion (Chao et al., 1997). The present invention may provide a method of treating a human disease condition associated with a cell expressing endogenous CD19 comprising infusing a patient with a therapeutically effective dose of the recombinant human CD19-specific CAR expressing cell as described above. The human disease condition associated with a cell expressing endogenous CD19 may be selected from the group consisting of lymphoma, leukemia, non-Hodgkin's lymphoma, acute lymphoblastic leukemia, chronic lymphoblastic leukemia, chronic lymphocytic leukemia, and B cell-associated autoimmune diseases.

Leukemia is a cancer of the blood or bone marrow and is characterized by an abnormal proliferation (production by multiplication) of blood cells, usually white blood cells (leukocytes). It is part of the broad group of diseases called hematological neoplasms. Leukemia is a broad term covering a spectrum of diseases. Leukemia is clinically and pathologically split into its acute and chronic forms.

Acute leukemia is characterized by the rapid proliferation of immature blood cells. This crowding makes the bone marrow unable to produce healthy blood cells. Acute forms of leukemia can occur in children and young adults. In fact, it is a more common cause of death for children in the U.S. than any other type of malignant disease. Immediate treatment is required in acute leukemia due to the rapid progression and accumulation of the malignant cells, which then spill over into the bloodstream and spread to other organs of the body. Central nervous system (CNS) involvement is uncommon, although the disease can occasionally cause cranial nerve palsies. Chronic leukemia is distinguished by the excessive build up of relatively mature, but still abnormal, blood cells. Typically taking months to years to progress, the cells are produced at a much higher rate than normal cells, resulting in many abnormal white blood cells in the blood. Chronic leukemia mostly occurs in older people, but can theoretically occur in any age group. Whereas acute leukemia must be treated immediately, chronic forms are sometimes monitored for some time before treatment to ensure maximum effectiveness of therapy.

Furthermore, the diseases are classified into lymphocytic or lymphoblastic, which indicate that the cancerous change took place in a type of marrow cell that normally goes on to form lymphocytes, and myelogenous or myeloid, which indicate that the cancerous change took place in a type of marrow cell that normally goes on to form red cells, some types of white cells, and platelets (see lymphoid cells vs. myeloid cells).

Acute lymphocytic leukemia (also known as acute lymphoblastic leukemia, or ALL) is the most common type of leukemia in young children. This disease also affects adults, especially those aged 65 and older. Chronic lymphocytic leukemia (CLL) most often affects adults over the age of 55. It sometimes occurs in younger adults, but it almost never affects children. Acute myelogenous leukemia (also known as acute myeloid leukemia, or AML) occurs more commonly in adults than in children. This type of leukemia was previously called "acute nonlymphocytic leukemia."

Chronic myelogenous leukemia (CML) occurs mainly in adults. A very small number of children also develop this disease.

Lymphoma is a type of cancer that originates in lymphocytes (a type of white blood cell in the vertebrate immune system). There are many types of lymphoma. According to the U.S. National Institutes of Health, lymphomas account for about five percent of all cases of cancer in the United States, and Hodgkin's lymphoma in particular accounts for less than one percent of all cases of cancer in the United States. Because the lymphatic system is part of the body's immune system, patients with a weakened immune system, such as from HIV infection or from certain drugs or medication, also have a higher incidence of lymphoma.

In the 19th and 20th centuries the affliction was called Hodgkin's Disease, as it was discovered by Thomas Hodgkin in 1832. Colloquially, lymphoma is broadly categorized as Hodgkin's lymphoma and non-Hodgkin lymphoma (all other types of lymphoma). Scientific classification of the types of lymphoma is more detailed. Although older classifications referred to histiocytic lymphomas, these are recognized in newer classifications as of B, T, or NK cell lineage.

Autoimmune disease, or autoimmunity, is the failure of an organism to recognize its own constituent parts (down to the sub-molecular levels) as "self," which results in an immune response against its own cells and tissues. Any disease that results from such an aberrant immune response is termed an autoimmune disease. Prominent examples include Coeliac disease, diabetes mellitus type 1 (IDDM), systemic lupus erythematosus (SLE), Sjögren's syndrome, multiple sclerosis (MS), Hashimoto's thyroiditis, Graves' disease, idiopathic thrombocytopenic purpura, and rheumatoid arthritis (RA).

Inflammatory diseases, including autoimmune diseases are also a class of diseases associated with B-cell disorders. Examples of autoimmune diseases include, but are not limited to, acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcalnephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitisubiterans, Sjogren's syndrome, primary biliary cirrhosis, Hashimoto's thyroiditis, thyrotoxicosis, scleroderma, chronic active hepatitis, polymyositis/dermatomyositis, polychondritis, pamphigus vulgaris, Wegener's granulomatosis, membranous nephropathy, amyotrophic lateral sclerosis, tabes dorsalis, giant cell arteritis/polymyalgia, perniciousanemia, rapidly progressive glomerulonephritis, psoriasis, and fibrosing alveolitis. The most common treatments are corticosteroids and cytotoxic drugs, which can be very toxic. These drugs also suppress the entire immune system, can result in serious infection, and have adverse affects on the bone marrow, liver, and kidneys. Other therapeutics that has been used to treat Class III autoimmune diseases to date have been directed against T cells and macrophages. There is a need for more effective methods of treating autoimmune diseases, particularly Class III autoimmune diseases.

VIII. Artificial Antigen Presenting Cells

In some cases, aAPCs are useful in preparing therapeutic compositions and cell therapy products of the embodiments. For general guidance regarding the preparation and use of antigen-presenting systems, see, e.g., U.S. Pat. Nos. 6,225,042, 6,355,479, 6,362,001 and 6,790,662; U.S. Patent Application Publication Nos. 2009/0017000 and 2009/0004142; and International Publication No. WO2007/103009).

aAPCs are typically incubated with a peptide of an optimal length that allows for direct binding of the peptide to the MHC molecule without additional processing. Alternatively, the cells can express and antigen of interest (i.e., in the case of MHC-independent antigen recognition). In addition to peptide-MHC molecules or antigens of interest, the aAPC systems may also comprise at least one exogenous assisting molecule. Any suitable number and combination of assisting molecules may be employed. The assisting molecule may be selected from assisting molecules such as co-stimulatory molecules and adhesion molecules. Exemplary co-stimulatory molecules include CD70 and B7.1 (B7.1 was previously known as B7 and also known as CD80), which among other things, bind to CD28 and/or CTLA-4 molecules on the surface of T cells, thereby affecting, for example, T-cell expansion, Th1 differentiation, short-term T-cell survival, and cytokine secretion such as interleukin (IL)-2 (see Kim et al., 2004, Nature, Vol. 22(4), pp. 403-410). Adhesion molecules may include carbohydrate-binding glycoproteins such as selectins, transmembrane binding glycoproteins such as integrins, calcium-dependent proteins such as cadherins, and single-pass transmembrane immunoglobulin (Ig) superfamily proteins, such as intercellular adhesion molecules (ICAMs), that promote, for example, cell-to-cell or cell-to-matrix contact. Exemplary adhesion molecules include LFA-3 and ICAMs, such as ICAM-1. Techniques, methods, and reagents useful for selection, cloning, preparation, and expression of exemplary assisting molecules, including co-stimulatory molecules and adhesion molecules, are exemplified in, e.g., U.S. Pat. Nos. 6,225,042, 6,355,479, and 6,362,001.

Cells selected to become aAPCs, preferably have deficiencies in intracellular antigen-processing, intracellular peptide trafficking, and/or intracellular MHC Class I or Class II molecule-peptide loading, or are poikilothermic (i.e., less sensitive to temperature challenge than mammalian cell lines), or possess both deficiencies and poikilothermic properties. Preferably, cells selected to become aAPCs also lack the ability to express at least one endogenous counterpart (e.g., endogenous MHC Class I or Class II molecule and/or endogenous assisting molecules as described above) to the exogenous MHC Class I or Class II molecule and assisting molecule components that are introduced into the cells. Furthermore, aAPCs preferably retain the deficiencies and poikilothermic properties that were possessed by the cells prior to their modification to generate the aAPCs. Exemplary aAPCs either constitute or are derived from a transporter associated with antigen processing (TAP)-deficient cell line, such as an insect cell line. An exemplary poikilothermic insect cells line is a *Drosophila* cell line, such as a Schneider 2 cell line (see, e.g. Schneider, J. Embryol. Exp. Morph. 1972 Vol 27, pp. 353-365). Illustrative methods for the preparation, growth, and culture of Schneider 2 cells, are provided in U.S. Pat. Nos. 6,225,042, 6,355,479, and 6,362,001.

In one embodiment, aAPCs are also subjected to a freeze-thaw cycle. In an exemplary freeze-thaw cycle, the aAPCs may be frozen by contacting a suitable receptacle containing the aAPCs with an appropriate amount of liquid nitrogen, solid carbon dioxide (i.e., dry ice), or similar low-temperature material, such that freezing occurs rapidly. The frozen aAPCs are then thawed, either by removal of the aAPCs from the low-temperature material and exposure to ambient room temperature conditions, or by a facilitated thawing process in which a lukewarm water bath or warm hand is employed to facilitate a shorter thawing time. Additionally, aAPCs may be frozen and stored for an extended period of time prior to thawing. Frozen aAPCs may also be thawed and then lyophilized before further use. Preferably, preservatives that might detrimentally impact the freeze-thaw procedures, such as dimethyl sulfoxide (DMSO), polyethylene glycols (PEGs), and other preservatives, are absent from media containing aAPCs that undergo the freeze-thaw cycle, or are essentially removed, such as by transfer of aAPCs to media that is essentially devoid of such preservatives.

In other preferred embodiments, xenogenic nucleic acid and nucleic acid endogenous to the aAPCs, may be inactivated by crosslinking, so that essentially no cell growth, replication or expression of nucleic acid occurs after the inactivation. In one embodiment, aAPCs are inactivated at a point subsequent to the expression of exogenous MHC and assisting molecules, presentation of such molecules on the surface of the aAPCs, and loading of presented MHC molecules with selected peptide or peptides. Accordingly, such inactivated and selected peptide loaded aAPCs, while rendered essentially incapable of proliferating or replicating, retain selected peptide presentation function. Preferably, the crosslinking also yields aAPCS that are essentially free of contaminating microorganisms, such as bacteria and viruses, without substantially decreasing the antigen-presenting cell function of the aAPCs. Thus crosslinking maintains the important APC functions of aAPCs while helping to alleviate concerns about safety of a cell therapy product developed using the aAPCs. For methods related to crosslinking and aAPCs, see for example, U.S. Patent Application Publication No. 20090017000, which is incorporated herein by reference.

IX. Kits of the Invention

Any of the compositions described herein may be comprised in a kit. In some embodiments, allogeneic CAR T-cells are provided in the kit, which also may include reagents suitable for expanding the cells, such as media, aAPCs, growth factors, antibodies (e.g., for sorting or characterizing CAR T-cells) and/or plasmids encoding CARs or transposase.

In a non-limiting example, a chimeric receptor expression construct, one or more reagents to generate a chimeric receptor expression construct, cells for transfection of the expression construct, and/or one or more instruments to obtain allogeneic cells for transfection of the expression construct (such an instrument may be a syringe, pipette, forceps, and/or any such medically approved apparatus).

In some embodiments, an expression construct for eliminating endogenous TCR α/β expression, one or more reagents to generate the construct, and/or CAR$^+$ T cells are provided in the kit. In some embodiments, there includes expression constructs that encode zinc finger nuclease(s).

In some aspects, the kit comprises reagents or apparatuses for electroporation of cells.

The kits may comprise one or more suitably aliquoted compositions of the present invention or reagents to generate compositions of the invention. The components of the kits may be packaged either in aqueous media or in lyophilized form. The container means of the kits may include at least one vial, test tube, flask, bottle, syringe, or other container means, into which a component may be placed, and preferably, suitably aliquoted. Where there is more than one component in the kit, the kit also will generally contain a second, third, or other additional container into which the additional components may be separately placed. However, various combinations of components may be comprised in a vial. The kits of the present invention also will typically include a means for containing the chimeric receptor construct and any other reagent containers in close confinement for commercial sale. Such containers may include injection or blow molded plastic containers into which the desired vials are retained, for example.

X. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Clinical Application of Sleeping Beauty and Artificial Antigen Presenting Cells to Genetically Modify T Cells From Peripheral and Umbilical Cord Blood Materials and Methods Isolation of Mononuclear Cells (MNC) from PB and UCB. On or before Day 0, dilute PB with an equal volume and UCB with four volumes of PBS-EDTA. Slowly layer diluted blood (25 mL) onto Ficoll (12 mL) in a 50 mL centrifuge tube(s) and centrifuge at 400×g for 30-40 min (no brake). Collect and transfer the mononuclear cell fraction (interface) using a transfer pipette to a fresh 50 mL centrifuge tube. Bring the volume up to 50 mL with PBS-EDTA and centrifuge at 450×g for 10 min. Aspirate the supernatant and gently re-suspend the cell pellet(s) in 50 mL of Complete Culture Media (CCM). Centrifuge at 400×g for 10 min. Gently re-suspend and pool the cell pellets in CCM and perform a cell count using Trypan blue exclusion (Cellometer, PBMC program). MNC can be used for electroporation (Nucleofection) or cryopreserved for future use.

Preparation of T Cells for Electroporation on Day 0. If using cryopreserved MNC, quickly thaw sufficient cells for a full scale electroporation ($2 \times 10^8$ adding ~20% to account for cell loss during centrifugation and 2 hr incubation) in a 37° C. water bath. Gently re-suspend and transfer cells to an appropriately sized centrifuge tube containing pre-warmed Complete Phenol-Free RPMI culture media (PF-RPMI), centrifuge at 200×g for 10 min (no brake), and aspirate the supernatant. Next, and if using freshly isolated MNC, re-suspend the MNC in PF-RPMI, perform a cell count (Cellometer) and transfer cells to an appropriately sized cell culture vessel at a concentration of $10^6$ cells/ml. Incubate the cells in a humidified 37° C./5% $CO_2$ incubator for 2 h±30 min. Transfer the MNC to a sterile centrifuge tube, spin at 200×g for 5 min (no brakes), aspirate the supernatant, and gently re-suspend and combine the cell pellets in PF-RPMI. Perform a cell count (Cellometer) and calculate the volume of the cell suspension required ($2 \times 10^8$ MNC). Transfer the calculated volume to a sterile 50 mL centrifuge tube and spin at 200×g for 10 min (no brake). Aspirate the supernatant so that no residual media remains and gently re-suspend by tapping side of tube.

Electroporation (Nucleofection) of MNC (Full Scale Process Using 10 Cuvettes) on Day 0. Pre-incubate a sterile 12-well plate with 10 wells containing 4 mL of warm PF-RPMI in a humidified 37° C./5% $CO_2$ incubator. Prepare and pre-warm the Lonza Nucleofector Solution Human T cell kit (reconstituted per manufacturer's instructions, www.lonza.com) to ambient temperature in a Biosafety Cabinet (BSC). Prepare Nucleofector solution/DNA master mix by adding 100 µL of supplemented Nucleofector solution, 15 µg of transposon (supercoiled DNA plasmid designated as CD19RCD28/pSBSO), and 5 µg of transposase (supercoiled DNA plasmid designated as pCMV-SB11) per reaction/cuvette. Disperse the MCN cell pellet by gently tapping the side of the centrifuge tube and re-suspend in Nucleofection solution/DNA master mix at a final cell concentration of $2 \times 10^7$ cells/100 µL. Carefully transfer 100 µL of the cell suspension to each of ten Lonza Nucleofection cuvettes, being careful to avoid bubbles. Tap the cuvette once, and electroporate using program U-014 (for unstimulated T cells). Transfer the cuvettes and the 12-well plate to the BSC. Harvest the electroporated cells from each cuvette using an Amaxa fine tip transfer pipette by adding ~500 µL of the pre-warmed culture medium from the corresponding well and return the plate to a humidified 37° C./5% $CO_2$ incubator for 2 h±30 min. Following the 2-hr incubation, harvest and transfer the cells from all wells to a sterile centrifuge tube. Wash cells by centrifugation at 140×g for 8 min, ambient temperature, no brake and aspirate and discard the supernatant so that no residual medium covers the cell pellet. Disperse the cell pellet by gently tapping the side of the centrifuge tube and gently re-suspend in CCM to achieve a single cell suspension. Perform cell count and adjust cell concentration to $10^6$ cells/mL in CCM. Transfer the cell suspension to cell culture flask(s) and place in the incubator overnight. The same process may be used for control EGFP-transfected cells ($5 \times 10^6$ cells/cuvette with 5 µg Amaxa control EGFP supercoiled plasmid, pmaxGFP).

Analysis of CAR Expression by Flow Cytometry on Day 1 of the $1^{st}$ and Subsequence Stimulation Cycles. Harvest the electroporated cells and perform a cell count using Trypan blue exclusion (Hemocytometer). Stain cells ($1-2 \times 10^6$) with antibody specific for CD3, CD4, CD8, and human IgG Fcγ as a measurement of CAR expression. Acquire cells on the FACS Calibur and analyze the data using FCS Express software to calculate expression of CAR. Calculate $CAR^+$ cells in culture by the formula: (No. of Total viable cells)×(% $CAR^+$ cells)=No. of $CAR^+$ cells.

Preparation of aAPC (Clone #4) on Day 1 of the $1^{st}$ and Subsequent Stimulation Cycles. aAPC (clone #4) was derived from K562 cells (parental line obtained from American Type Culture Collection) to co-express the desired T cell co-stimulatory molecule. Thaw an aliquot of frozen 100 Gy irradiated aAPC in a 37° C. water bath. Cells are washed twice by centrifugation at 400×g, 10 min in CCM and counted using Cellometer (Trypan blue exclusion). Calculate number of viable aAPC required for stimulation: (No. of $CAR^+$ cells)×2=No. of irradiated aAPC required aAPC-Mediated Stimulation of $CAR^+$ T Cells on Day 1 Beginning of $1^{st}$ and Subsequent Stimulation Cycles. Mix the electroporated cells (expressing CAR) and γ-irradiated aAPC (clone #4) in a sterile container at a ratio of 1:2 ($CAR^+$ cell: viable aAPC) in CCM. Note that the aAPC ratio is adjusted for the expression of CAR based on flow cytometry the day after electroporation. Add IL-21 (30 ng/mL) to the cell suspension. Aliquot in T-75 cm² flask(s) and/or VueLife Culture bags at a concentration of $10^6$ cells/mL and return to the incubator.

Continued Culture of $CAR^+$ T Cells on Days 3 and 5. Perform a half-media change, replenish IL-21, and maintain T cells at a concentration of $10^6$ cells/mL.

End of First aAPC-Mediated Stimulation Cycle on Day 7. Harvest cells, count, and stain for CD3, CD4, CD8, and Fcγ (CAR).

Depletion of $CD56^+$ Cells between 7 and 14 Days after electroporation. Perform a CD56 depletion using paramagnetic beads if $CD56^+CD3^{neg}$ lymphocytes ≥10%.

Recursive Addition of aAPC to Propagate T Cells to Clinically-sufficient Numbers During Stimulation Cycles #2, #3, & #4 Corresponding to Days 8→14, Days 15→21, & Days 22→28. Repeat the stimulation process up to 4 times. Add IL-2 (50 U/mL) to the cultures beginning on Days 7, 14 and 21, and then at each media change (three times a week, on a Monday-Wednesday-Friday schedule). Cryopreserve (archive) excess T cells as needed using a controlled rate freezer for release testing and infusion.

Example 2

Figure 2A:
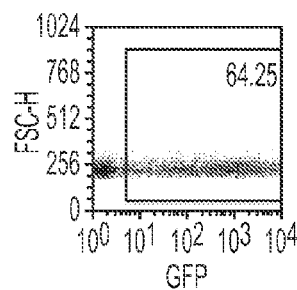
FIG. 2: Characterization of genetically modified T cells from PB. (A) Expression of EGFP at Day 0 of first stimulation cycle to assess the efficiency of gene transfer. Expression of CD19-specific CAR (CD19RCD28) as assessed by flow cytometry on CD3$^+$, CD8$^+$ and CD4$^+$ T cells at (B) approximately 24 hours after electroporation and (C) 28 days after co-culture on aAPC. Similar expression of CAR was observed with UCB-derived T cells. (D) Kinetics of CAR expression.
Figure 2B:
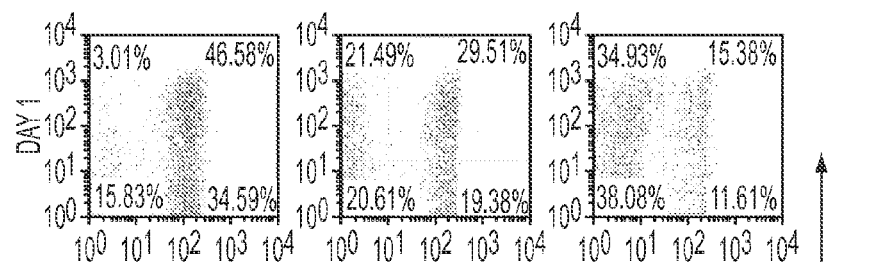
Figure 2C:
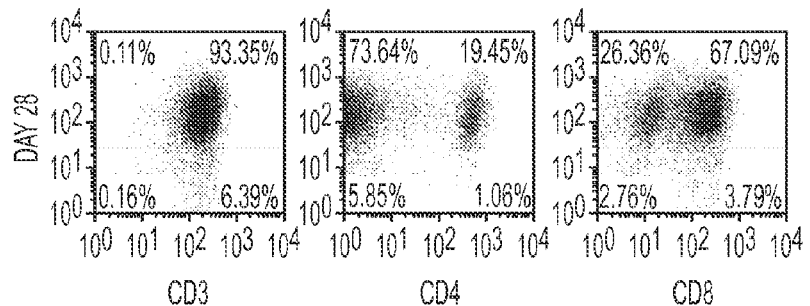
Figure 2D:
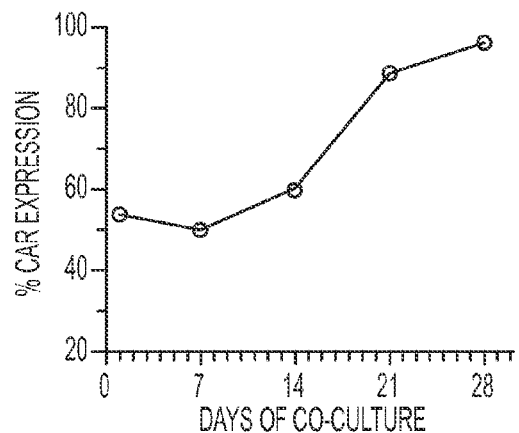
Figure 3:
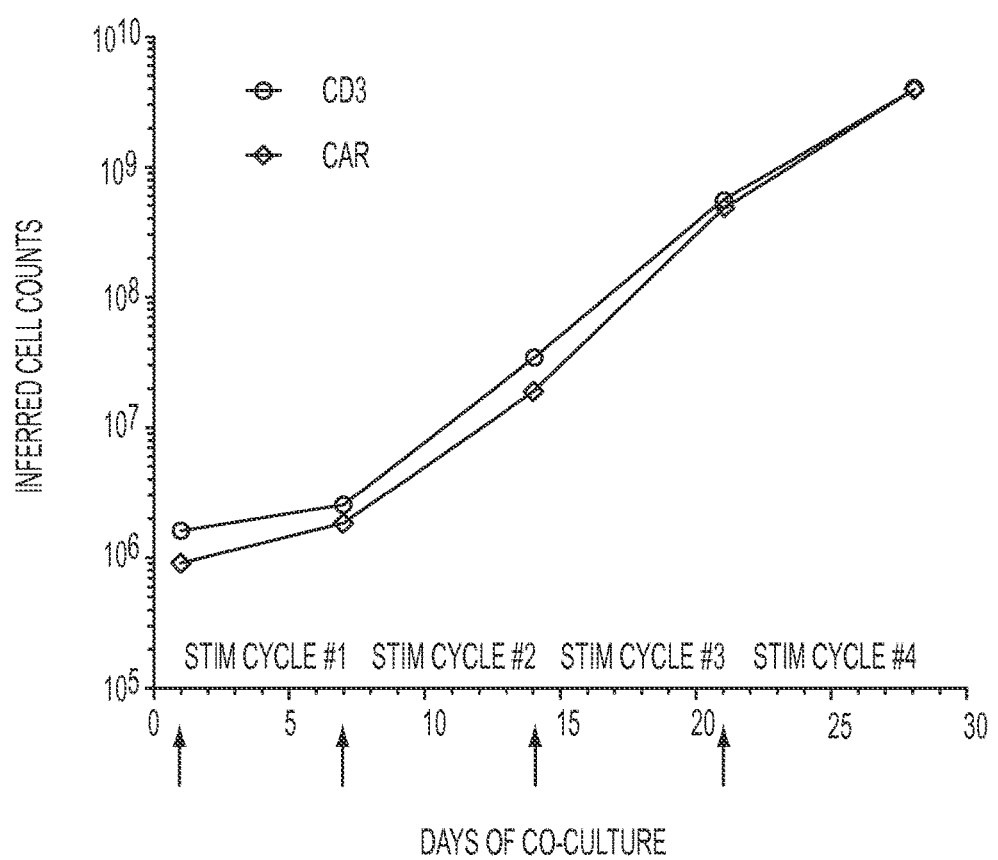
FIG. 3: Propagation of PB-derived CAR$^+$ T cells. Rate of numeric expansion of CD3$^+$ and CAR$^+$ T cells derived from PB by repeated co-culture on γ-irradiated aAPC in presence of recombinant human soluble IL-2 and IL-21. Upward arrows indicate the additions of γ-irradiated aAPC that mark the beginning of each stimulation cycle. UCB-derived CAR$^+$ T cells exhibit similar rates of numeric expansion.
Figure 4:
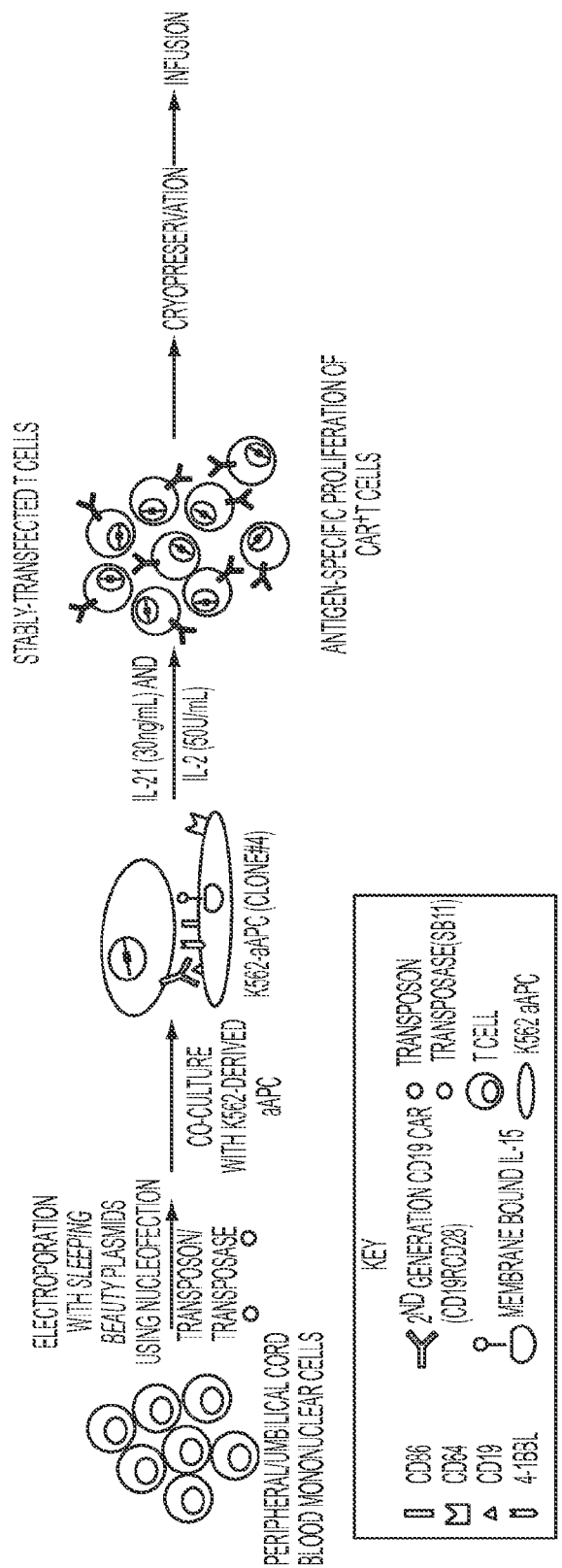
FIG. 4: Schematic of the manufacturing process using SB and aAPC systems to genetically modify and propagate CAR$^+$ T cells derived from PB and UCB. CD19-specific CAR$^+$ T cells were generated by electro-transfer of SB-derived supercoiled DNA plasmids and subsequent co-culture on K562-derived aAPC (clone #4) in the presence of recombinant human soluble IL-2 and IL-21.

Clinical Application of Sleeping Beauty and Artificial Antigen Presenting Cells to Genetically Modify T Cells from Peripheral and Umbilical Cord Blood Results Electro-transfer of DNA plasmids and propagation of T cells on γ-irradiated aAPC can be used to generate clinically-appealing numbers of T cells derived from PB and UCB for human applications. These genetically modified T cells express an introduced CAR that recognizes the TAA CD19, independent of major histocompatibility complex. The SB-derived DNA plasmids to express the (i) transposon, a $2^{nd}$ generation CAR (CD19RCD28) that signals through CD28 and CD3-$\epsilon^{14}$, and (ii) transposase, SB11 (Jin et al., 2011), have been previously described (Singh et al., 2011; Davies et al., 2010; Kebriaei et al., 2012). The plasmids used in the current study were produced commercially by Waisman Clinical Biomanufacturing Facility (Madison, Wis.). The aAPC (clone #4), derived from K562 cells (parental line obtained from American Type Culture Collection), co-express desired T cell co-stimulatory molecules (each introduced molecule at 90% on cell surface of aAPC), as previously described (Manuri et al., 2010). Here, CD19-specific T cells could be generated from mononuclear cells (MNC) derived from PB or UCB using SB transposition to introduce the CAR followed by addition of aAPC to numerically expand the T cells in a CAR-dependent manner (FIGS. 1 and 4) (Singh et al., 2011; Singh et al., 2008). Ten cuvettes ($2 \times 10^7$ MNC/cuvette) were electroporated for each recipient using 15 µg of DNA plasmid (CD19RCD28/pSBSO) coding for transposon (CAR) and 5 µg of DNA plasmid (pCMV-SB11) coding for transposase (SB11). The number of cuvettes can be reduced if MNC are limiting or scaled back for laboratory work. The day of electroporation is defined as "Day 0" of Stimulation cycle #1. As controls for flow cytometry and culture conditions, autologous T cells are mock electroporated (without DNA plasmid) and numerically expanded on γ-irradiated aAPC (clone #4) that had been pre-loaded with OKT3 to cross-link CD3 to sustain T cell proliferation. The efficiency of electrotransfer and viability of the T cells the day after electroporation was routinely assessed (FIG. 2B). The expression of EGFP from control DNA plasmid (designated pmaxGFP) and CAR at this initial time point reflects protein expression from the integrated and episomal plasmid. Typically, EGFP expression was measured at 60% the day after electroporation and CAR expression at ~40% (FIG. 2A) with T cell viability between 40%-50%. Recursive additions of γ-irradiated aAPC in the presence of soluble recombinant human IL-2 and IL-21 retrieve T cells stably expressing CAR (CD19RCD28). $CD3^{neg}CD56^+$ NK cells are depleted from the culture using CD56-specific paramagnetic beads if the percentage of these NK cells is ≥10% and especially if the percentage of CAR expressed on the T cells is low. This depletion prevents the rapid overgrowth of NK cells which interferes with the ability of aAPC to sustain the proliferation of $CAR^+$ T cells. On occasion, depletion of NK cells from $CAR^+$ T cells is undertaken during the last two stimulation cycles, but this introduces a loss of desired cells due to co-expression of CD56 on some $CAR^+$ T cells. The T cells were grown in a functionally closed system using VueLife culture bags past Day 14. A subset of the genetically modified and propagated T cells are typically cryopreserved at Day 14 or Day 21 (end of Stimulation cycles #2 or #3) of co-culture on aAPC to serve as a source of archived material for future analyses and to be thawed if unanticipated problems subsequently occur during the manufacturing process. T cells are typically harvested on or about Day 28 of culture (FIG. 3) that routinely express >90% CAR and are >80% viable (FIGS. 2C, D). After four weeks of co-culture on aAPC, the average fold-expansion of $CD3^+$ T cells is 19,800±11,313 with $CAR^+$ expression being 90%±7.5% (Singh et al., 2011). These T cells are cryopreserved and undergo in-process and release testing that informs on the safety and therapeutic potential of the manufactured product. Release testing is undertaken in compliance with clinical laboratory improvement amendments (CLIA) to generate a certificate of analysis prior to infusion into recipients on clinical trials.

Example 3

Figure 10:
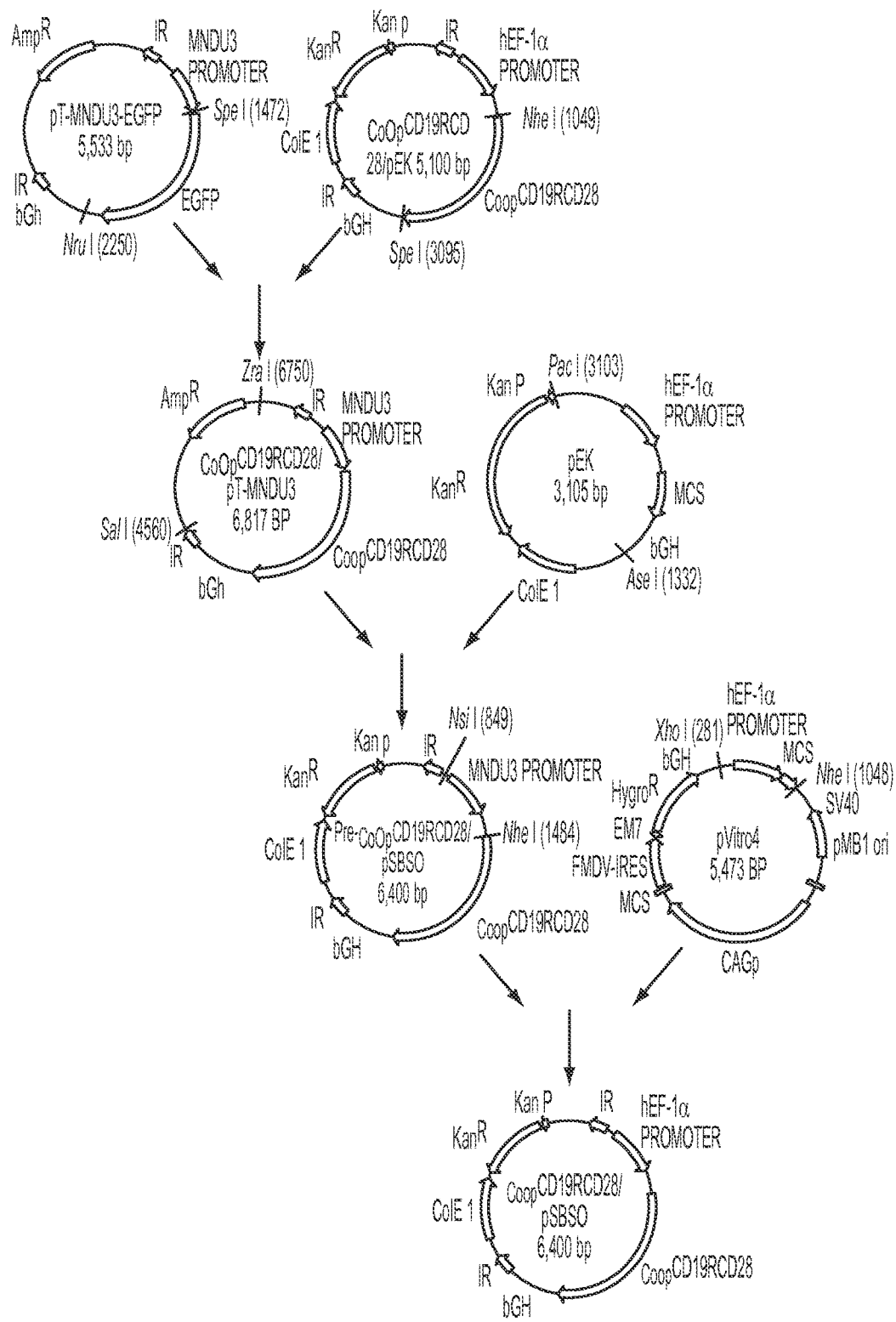
FIG. 10: Generation of CD19RCD28 CAR transposon. The CD19RCD28mz (CoOp)/pEK vector containing a codon optimized chimeric antigen receptor (CAR) and SB DNA plasmid pT-MNDU3-EGFP (Singh et al., 2008; Hollis et al., 2006) were digested with SpeI & NheI and SpeI & NruI to release CAR and EGFP fragments respectively. The EGFP-deleted pT-MNDU3 vector was then ligated with CAR fragment to generate CD19RCD28mz (CoOp)/pT-MNDU3 vector. Further the Kanamycin resistance gene and the ColE1 origin of replication obtained by AseI & PacI digestion of pEK vector was ligated into SalI & ZraI digested CD19RCD28mz (CoOp)pT-MNDU3 vector to create Pre-CD19RCD28mz (CoOp)/pSBSO. In the last step, MNDU3 promoter from Pre-CD19RCD28mz(CoOp)/pSBSO was released using digestion with NheI & NsiI and replaced with hEF-1a promoter fragment obtained from pVitro4 vector using XhoI & NheI, to generate the final vector CD19RCD29mz(CoOp)/pSBSO.
Figure 11:
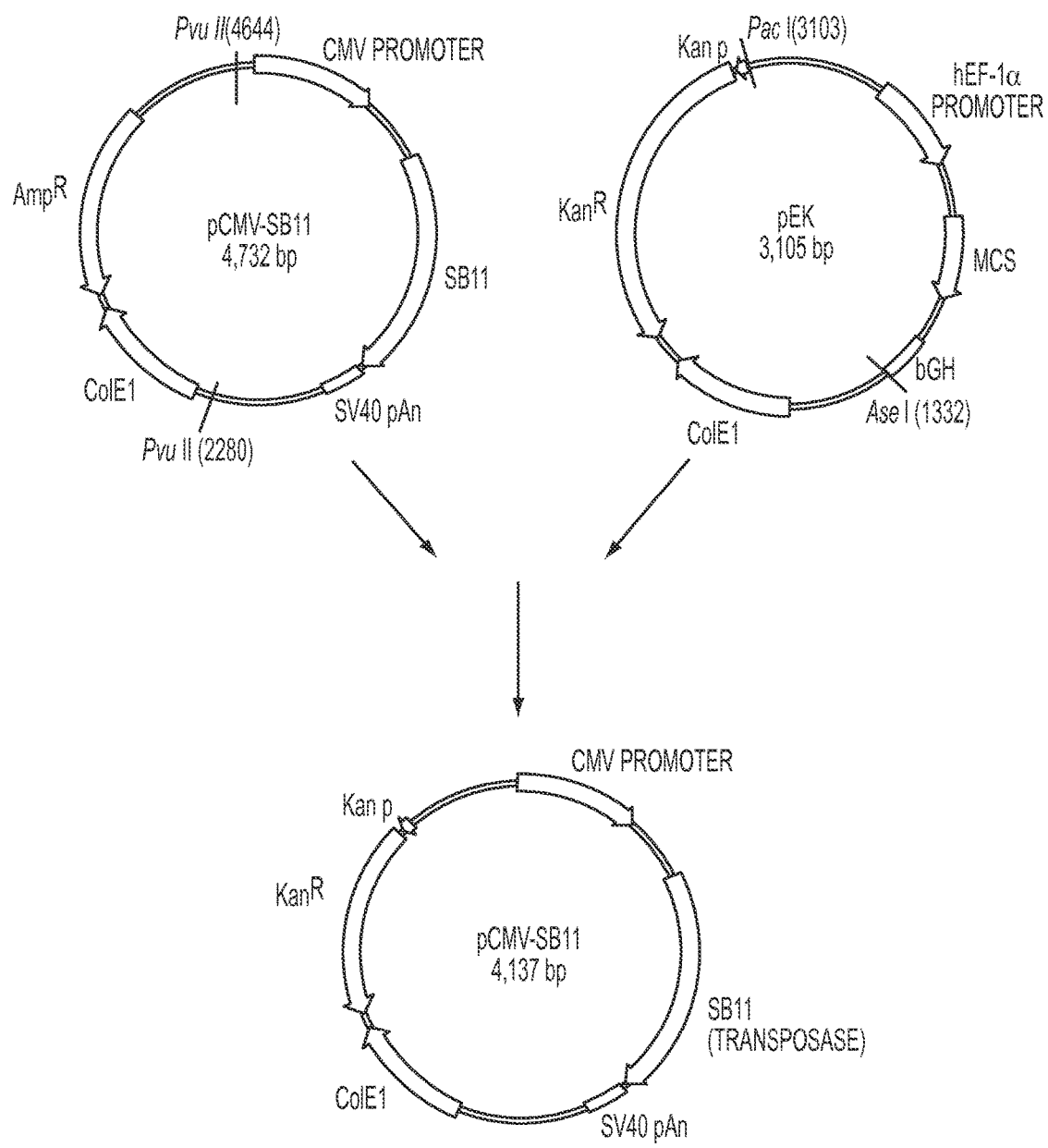
FIG. 11: Generation of SB11 transposase. SB transposase vector pCMV-SB11 was digested with PvuII to release the fragment containing CMV promoter/enhancer and SB transposase encoding gene, which was ligated to fragment containing Kanamycin resistance gene and ColE1 origin of replication from pEK vector to generate pKan-CMV-SB11 vector.
Figure 12:
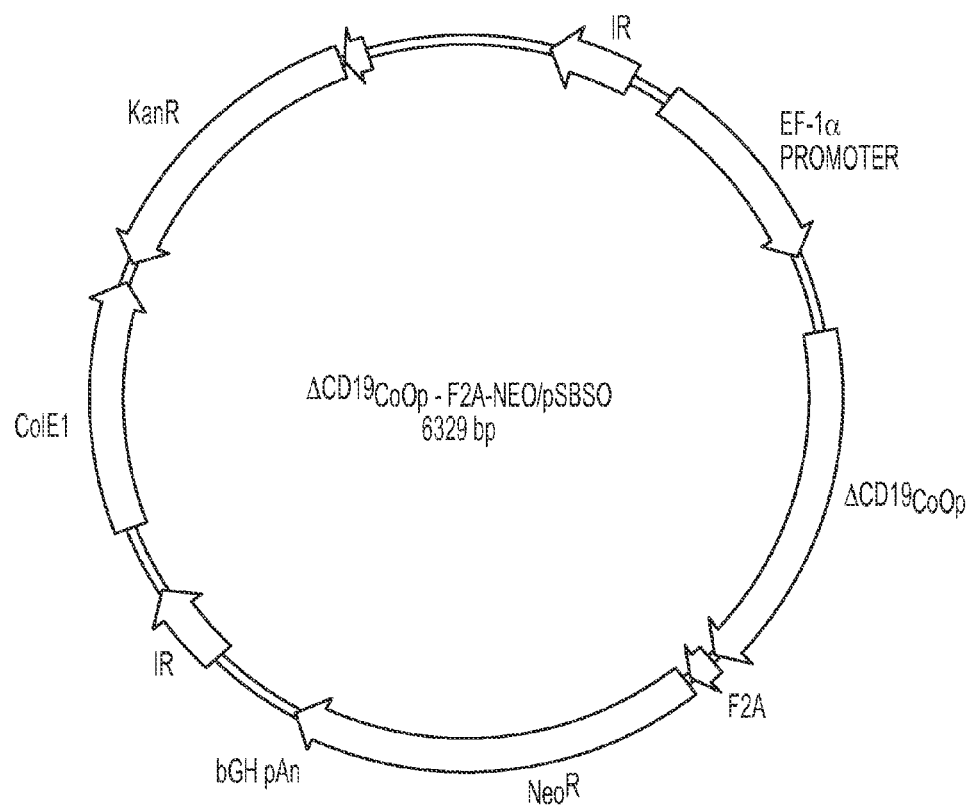
FIG. 12: Schematic of CD19 expression plasmid, ΔCD19CoOp-F2A-Neo/pSBSO. The DNA fragment encoding CD19RCD28 CAR from the plasmid CoOpCD19RCD28/pSBSO was swapped with DNA fragment encoding neomycin resistance gene (NeoR) [PCR cloned from pSelect-Neo (InvivoGen)] fused to codon-optimized (GENEART) truncated CD19 (ΔCD19, [Serrano et al., 2006; Mahmoud et al., 1999]) via a F2A linker (amino acid, VKQTLNFDLLKLAGDVESNPGP; [Szymczak et al., 2004; Yang et al., 2008; Kim et al., 2011]) to generate ΔCD19CoOp-F2A-Neo/pSBSO. EFloi promoter, Elongation factor-1α promoter; NeoR, Neomycin resistance gene; bGHpAn, polyadenylation signal from bovine growth hormone; ColE1, ori; KanR, Kanamycin resistance gene; IR, SB-inverted/direct repeats.

Manufacture of Clinical-Grade CD19-Specific T Cells Stably Expressing Chimeric Antigen Receptor Using Sleeping Beauty and Artificial Antigen Presenting Cells Materials and Methods Generation of Clinical-Grade DNA Plasmids. The SB transposon, $_{CoOp}$CD19RCD28/pSBSO, expresses the human codon optimized (CoOp) $2^{nd}$ generation $_{CoOp}$CD19RCD28 CAR (SEQ ID NO: 1) under EF-1/HTLV hybrid composite promoter (InvivoGen) comprised of Elongation Factor-1α (EF-1α) (Kim et al., 1990) and 5' untranslated region of the Human T-Cell Leukemia Virus (HTLV) (Singh et al., 2011; Davies et al., 2010). The derivation of this DNA plasmid is described in FIG. 10. The SB transposase, SB11, under the cytomegalovirus (CMV) promoter was expressed in cis from the DNA plasmid pCMV-SB11 (Singh et al., 2011). The derivation of this DNA plasmid is described in FIG. 11. Both plasmids were sequenced in their entirety and manufactured by Waisman Clinical Biomanufacturing Facility (Madison, Wis.) using kanamycin for selection of the bacterial strain E. coli DH5α. The release criteria for the DNA plasmids is shown in Table 1. CD19 was expressed using the DNA plasmid $\Delta CD19_{CoOp}$-F2A-Neo/pSBSO (FIG. 12).

TABLE 1

Release criteria for DNA plasmids coding for SB transposon and transposase.

| Test | Specification |
|---|---|
| Appearance | Clear colorless liquid |
| Restriction Mapping & Agarose Gel | Digest with Nde I; AflIII & NheI; HindIII & AvrII; Xba & NcoI for transposon. Digest with NdeI; XhoI & PvuII; AflIII; NcoI for transposase |

TABLE 1-continued

Release criteria for DNA plasmids coding for SB transposon and transposase.

| Test | Specification |
|---|---|
| Sequencing | Sequence conforms to original coding |
| Concentration via absorbance | 2.0 ± 0.2 mg/mL |
| A260/A280 absorbance ratio | 1.8-2.0 |
| Kinetic LAL test for Bacterial Endotoxin | <50 EU/mg |
| Plasmid Form (% supercoiled via HPLC) | >90% supercoiled |
| Sterility Test | No growth observed |
| E. coli host protein via ELISA | <0.3% |
| E. coli RNA via HPLC | <10% |

Cell counting. Trypan-blue exclusion was used to distinguish live from dead cells and counted using Cellometer (Nexecelom Bioscience) (Singh et al., 2011).

Isolation of PBMC. Leukapheresis products from two male volunteer healthy donors were purchased from Key Biologics LLC (Memphis, Tenn.). The peripheral blood mononuclear cells (PBMC) were isolated by adapting the Biosafe Sepax system (Eysins, Switzerland) for work in compliance with cGMP. Briefly, after closing all the clamps on the CS-900 kit, 100 mL Ficoll (GE Healthcare) was aseptically transferred via 60 mL syringes to a density gradient media bag ("ficoll bag") via Luer-lock connector and the tubing was heat sealed using a hand held sealer (Sebra, Model#2380). The kit was spike-connected to a 1,000 mL bag containing CliniMACS buffer (PBS/EDTA, Miltenyi, Cat#70026) with 20 mL 25% Human Serum Albumin (HSA) (Baxter) (2% v/v, wash buffer) for washes, a final product bag [300 mL Transfer Pack with Coupler (Baxter/Fenwal 4R2014)] and a reagent/blood bag. Using the density gradient-based separation protocol (v126), the syringe piston was loaded into the centrifuge chamber and the cover of the Sepax unit closed. The reagent/blood bag and product bags were hung and all stopcocks were seated on the rotary pins in the 'T' position. After connecting the pressure-sensor line, the kit was validated by automatic single-use test and then manually primed using gravity flow. After completion of the cycle, the final product was aseptically transferred into a centrifuge tube and washed once each with wash buffer and phosphate buffered saline (PBS) at 400 g for 10 minutes. After counting, cells were cryopreserved using cryopreservation media (50% HSA, 40% Plasmalyte, 10% DMSO) in CryoMACS Freeze bags (Miltenyi) and vials (Nunc) using BM5 program (4° C. to −4° C. at rate −2° C./min, −4° C. to −60° C. at rate −35° C./min, −60° C. to −20° C. at rate 8° C./min, −20° C. to −45° C. at rate −2.5° C./min, −45° C. to −80° C. at rate −10° C./min) in a controlled-rate freezer (Planer Kryo 750).

Manufacture of aAPC (clone #4) master and working cell banks. K562 were transduced by lentivirus at the University of Pennsylvania to generate aAPC (clone #4, designated CJK64.86.41BBL.GFP.IL-15.CD19) that co-express (i) CD19, (ii) CD64, (iii) CD86, (iv) CD137L, and (v) membrane bound IL-15 (mIL15) as a bi-cistronic vector with EGFP. The aAPC were numerically expanded in HyQ RPMI 1640 (Hyclone) containing 10% heat-inactivated defined FBS (Hyclone) and 2 mM Glutamax-1 (Life Technologies-Invitrogen) culture media (CM) maintaining the cells at $5\times10^5$ cells/mL. A master cell bank (MCB) of 320 vials was produced through Production Assistance of Cellular Therapies (PACT) (Table 2). A 200 vial working cell bank (WCB)

of Clone 4 aAPC derived from the MCB was then generated at MDACC and tested (Table 3).

TABLE 2

Release criteria for K562-derived aAPC (clone #4) master cell bank.

| Test | Specification |
| --- | --- |
| Replication-competent Lentivirus | Negative |
| Product Enhanced Reverse Transcriptase for Detection of Retrovirus | Negative |
| Endotoxin LAL | Negative |
| Agar Cultivable and Non-Agar Cultivable Mycoplasma | Negative |
| HIV-1/2 Proviral DNA by PCR | Negative |
| HBV DNA by PCR | Negative |
| HCV RNA by RT-PCR | Negative |
| CMV DNA by PCR | Negative |
| Parvovirus B19 | Negative |
| HTLV-I/II Proviral DNA by PCR | Negative |
| EBV DNA by PCR | Negative |
| HHV-6 DNA by PCR | Negative |
| HHV-7 DNA by PCR | Negative |
| HHV-8 DNA by PCR | Negative |
| Adeno-associated Virus | Negative |
| In vivo Inapparent Virus | Negative Negative |
| Bovine Virus by 9CFR | Negative |
| Porcine Virus by modified 9CFR PT-1 | Negative |
| Adeno-associated Virus | Negative |
| Isoenzyme analysis | Human Origin |
| Morphology by Transmission Electron Microscopy | No identifiable virus-like particles nor any other microbial agents |
| Immunophenotyping: | |
| CD19 | 90% |
| CD64 | 90% |
| CD86 | 90% |
| CD137L | 90% |
| EGFP-mIL15 | 90% |
| Bacteriostasis & Fungistasis | Negative |
| Sterility by 21CFR610.2 | Negative |

TABLE 3

Release criteria for K562-derived aAPC (clone #4) working cell bank.

| TEST | LABORATORY | SPECIFICATION |
| --- | --- | --- |
| Bacteriostasis and Fungistasis | AppTec Laboratory Services | Negative |
| Sterility by 21CFR610.12 | AppTec Laboratory Services | Negative |
| Agar Cultivable and Non-Agar Cultivable Mycoplasma | BioReliance | Negative |
| In vitro Adventitious Virus testing | BioReliance | Negative |
| Identity Isoenzyme analysis | BioReliance | Human Origin |
| Phenotype | MDACC GMP Flow Cytometry Laboratory | ≥80% GFP+ ≥80% CD19+ ≥80% CD86+ ≥80% CD137L+ ≥80% CD64+ ≥80% CD32+ |
| Endotoxin (LAL) EndoSafe | MDACC GMP Quality Control Laboratory | ≤5 EU/mL |
| Viability by Trypan Blue | MDACC GMP Quality Control Laboratory | ≥60% | aAPC (Clone #4) to Selectively Propagate CAR+ T Cells. The γ-irradiated aAPC were used to numerically expand the genetically modified T cells. Thawed aAPC from WCB were propagated in CM for up to 60 days in VueLife cell culture bags and harvested using Biosafe Sepax II harvest procedure. Briefly, a CS-490.1 kit was connected to a 300 mL output bag (transfer pack) via Luer lock connection. The separation chamber was installed in the pit and the tubing was inserted into the optical sensor and stopcocks aligned in the T position. After connecting the pressure sensor line, the product bag and supernatant/plasma bags were hung on the holder. The modified protocol PBSCv302 was selected from the Sepax menu and the volume of input product to be processed (initial volume) was set to ≤840 mL. After validation and kit test, the procedure was started. Following completion, the bags were removed, clamps closed and the kit was removed. The cells from the final product bag were aseptically removed, washed twice with wash media (10% HSA in Plasmalyte) and counted. aAPC were irradiated (100 Gy) using a CIS BIO International radiator (IBL-437 C#09433) and cryopreserved for later use in cryopreservation media using a controlled-rate freezer (Planer Kryo 750).

OKT3-loading of aAPC. The OKT3-loaded (via CD64) aAPC (clone#4) were used to propagate control (CAR$^{neg}$) autologous control T cells that had not undergone genetic modification. The aAPC, obtained from culture, were incubated overnight in serum-free X-Vivo 15 (cat #04-744Q, Lonza) containing 0.2% acetyl cysteine (Acetadote, Cumberland Pharmaceuticals) termed Loading Medium (LM). The next day cells were washed, irradiated (100 Gy) using a Gamma Cell 1000 Elite Cs-137 radiator (MDS Nordion), resuspended in LM at a concentration of $10^6$ cells/mL along with 1 μg/$10^6$ cells of functional grade purified anti-human CD3 (clone-OKT3, 16-0037-85, eBioscience) and incubated with gentle agitation on a 3-D rotator (Lab-Line) at 4° C. for 30 minutes. Following three washes with LM the cells were used in experiments or frozen in aliquots in liquid nitrogen in the vapor layer for later use.

Manufacture of CAR$^P$ T Cells. Thawed PBMC were resuspended in (i) Human T-cell kit (cat# VPA-1002, Lonza; 100 μL for $2 \times 10^7$ cells in one cuvette), with (ii) the DNA plasmid ($_{CoOp}$CD19RCD28/pSBSO) coding for CD19RCD28 CAR transposon (15 μg supercoiled DNA per $2 \times 10^7$ PBMC per cuvette), and (iii) the DNA plasmid (pCMV-SB11) coding for SB11 transposase (5 μg supercoiled DNA per $2 \times 10^7$ PBMC per cuvette). This mixture was immediately transferred to a cuvette (Lonza), electroporated (defining culture day 0) using Nucleofector II (Amaxa/Lonza), rested in 10% RPMI complete media for 2 to 3 hours, and after a half-media change, incubated overnight at 37° C., 5% $CO_2$. The following day, cells were harvested, counted, phenotyped by flow cytometry, and co-cultured with γ-irradiated aAPC at a ratio of 1:2 (CAR+ T cell:aAPC), which marked culture day 1 and the beginning of a 7-day stimulation cycle. IL-21 (cat # AF-200-21, PeproTech) and IL-2 (cat # NDC 65483-116-07, Novartis) were added on a Monday-Wednesday-Friday schedule onwards of day 1 and day 7, respectively. NK cells can prevent the numeric expansion of CAR+ T cells, especially if their overgrowth occurs early in the tissue culturing process. Therefore, CD56-depletion was performed if CD3$^{neg}$CD56+ cells ≥10% using CD56 beads (cat #70206, Miltenyi Biotech, 20 μL beads/$10^7$ cells) on LS columns (cat #130-042-401, Miltenyi Biotech) in CliniMACS buffer containing 25% HSA (80 μL/$10^7$ cells). T cells were cryopreserved as backup on culture day 21 after electroporation and the end of the 3$^{rd}$ stimulation cycle using a controlled-rate freezer (Planer Kryo 750) as described above, and stored in liquid nitrogen (vapor-layer). The cell counts for total, CD3+, and CAR+ T cells were plotted over time and slopes determined using linear regression. The fold-expansion results were compared using a Student's t-test. CD4/CD8 ratios were calculated for each time point and validation runs and averaged.

Generation of CAR$^{neg}$ control T cells. As a control, 5×10$^6$ mock transfected PBMC were co-cultured with irradiated and anti-CD3 (OKT3) loaded K562-derived aAPC clone #4 at a ratio of 1:1 in a 7-day stimulation cycle. All the cultures were supplemented with IL-21 (30 ng/mL) from culture day 1 onwards, and IL-2 (50 U/mL) starting 7 days after the start of the culture. All cytokines were subsequently added on a Monday-Wednesday-Friday schedule.

Cell lines. CD19$^+$ Daudiβ$_2$m [Burkitt lymphoma, co-expressing β2 microglobulin, (Rabinovich et al., 2008)] and CD19$^+$ NALM-6 (pre-B cell) were cultured as described previously (Singh et al., 2011). EL-4 cells (mouse T-cell lymphoma line) from ATCC were modified to express CD19 using the construct ΔCD19$_{CoOp}$-F2A-Neo/pSBSO. Briefly, 5×10$^6$ EL-4 cells were resuspended in 100 µL, of Amaxa Mouse T cell Nucleofector kit (Catalogue #VPA-1006) with SB transposon (ΔCD19$_{CoOp}$-F2A-Neo/pSBSO, 3 µg) and SB transposase (pCMV-SB11, 1 µg) and electroporated (program X-001) using Nucleofector II (Lonza). The transfectants were cultured in a cytocidal concentration of G418 (0.8 mg/mL) and underwent fluorescent activated cell sorting (FACS) for homogeneous expression of CD19 to obtain a clone (clone #17). Jurkat cell were obtained from ATCC and electroporated (Program T-14, Nucleofector II, Lonza) with $_{CoOp}$CD19RCD28mz (CoOp)/pSBSO using the Amaxa/Lonza Nucleofector solution (Kit V). Two weeks after electroporation, Jurkat cells stably expressing CAR underwent FACS for homogeneous expression of CAR to obtain a clone (clone #12) (Maiti et al., 2013). Cell lines were maintained in HyQ RPMI 1640 (Hyclone) supplemented with 2 mM Glutamax-1 (Invitrogen) and 10% heat-inactivated Fetal Calf Serum (FCS) (Hyclone; 10% RPMI). All cell lines were validated using STR profiling or karyotyping according to institutional cell line authentication policy.

Immunophenotype of cells. Cells were stained using antibodies (Table 4) in 100 µL FACS Buffer (2% FBS, 0.1% Sodium Azide) for 30 minutes at 4° C. For intracellular staining, after fixing/permeabilization for 20 minutes, cells were stained in perm wash buffer with appropriate antibodies for 30 minutes at 4° C. Acquisition was performed using FACSCalibur (BD Bioscience) and analyzed using Cell Quest BD Bioscience) or FCS Express 3.00.0612 (De Novo Software, Thornhill, Ontario, Canada).

TABLE 4

Antibodies used for flow cytometry.

| Cells | Antibody/Fluorochrome | Vendor | Catalogue No. |
|---|---|---|---|
| T cells | CD3-PE | BD Biosciences | 347347 |
|  | CD4-APC | BD Biosciences | 340443 |
|  | CD8-PerCPCy5.5 | BD Biosciences | 341051 |
|  | CD16-PE | BD Biosciences | 347616 |
|  | CD25-APC | BD Biosciences | 555434 |
|  | CD28-PerCPCy5.5 | BD Biosciences | 337181 |
|  | CD32-FITC | BD Biosciences | 555448 |
|  | CD39-FITC | eBioscience | 11-0399-42 |
|  | CD45TA-APC | BD Biosciences | 550855 |
|  | CD45RO-PE | BD Biosciences | 555489 |
|  | CD57-FITC | BD Biosciences | 555619 |
|  | CD56-APC | BD Biosciences | 555518 |
|  | CD62L-PE | BD Biosciences | 555544 |
|  | CD69-PE | BD Biosciences | 555531 |
|  | CD127 (IL-7Ra)-Alexa Fluor 647 | BD Biosciences | 558598 |
|  | CD150-PE | BD Biosciences | 559592 |
|  | CD279 (PD-1)-PE | BD Biosciences | 557946 |
|  | CCR7-PerCPCy5.5 | BioLegend | 335605 |
|  | Granzyme B-Alexa Fluor 647 | BD Biosciences | 560212 |
|  | HLA-DR-PerCPCy5.5 | BD Biosciences | 339205 |
|  | Perforin-FITC | BD Biosciences | 556577 |
|  | Anti-human Fcγ-PE | Invitrogen | H10104 |
| K562 aAPC (Clone #4) | CD19-PE | BD Biosciences | 555413 |
|  | CD19-APC | BD Biosciences | 555415 |
|  | CD64-PE | BD Biosciences | 558592 |
|  | CD86-PE | BD Biosciences | 555658 |
|  | CD137L-PE | BD Biosciences | 559446 |
|  | F(ab')2 fragment of Goat anti-Mouse IgG, F(ab')2 fragment specific-PE (For OKT3 loading) | Jackson Immunoresearch | 115-116-072 |

Western Blot. Protein expression of the chimeric CD3-ζ (73-kDa) derived from CD19RCD28 was assessed as described previously (Singh et al., 2008). Briefly, protein lysates were transferred using iBlot Dry Blotting System (Invitrogen) onto nitrocellulose membrane, incubated with mouse antihuman CD3-ζ monoclonal antibody (cat #551033, 0.5 µg/mL, BD Biosciences, CA) followed by horseradish peroxidase (HRP)-conjugated goat anti-mouse IgG (cat #1858413, 1:10,000; Pierce, Ill.), developed using SuperSignal West Femto Maximum Sensitivity substrate (Pierce, Ill.) and chemiluminescence captured using Versa-Doc™ 4000 gel documentation system (BioRad, CA).

Telomere Length Analysis by Fluorescence In situ Hybridization and Flow Cytometry (Flow-FISH). Telomere length of the T cells was measured by using the Telomere PNA Kit/FITC for Flow Cytometry (DAKO) according to the manufacturer's instructions. Briefly, isolated cells (CD4 or CD8) and control cells (cat #85112105, CEM-1301 cell line; ECACC) were mixed in equal measure in hybridization solution with or without FITC-labeled telomere PNA probe for 10 minutes at 82° C.; hybridized overnight in the dark at room temperature; washed twice with a wash solution at 40° C.; resuspended in PBS containing 2% FCS and propidium iodide (1 µg/mL); and analyzed on a FACSCalibur (BD Biosciences). FITC-labeled fluorescent calibration beads (cat #824A, Quantum™ FITC MESF, Bangs Laboratories) were used for calibration of the flow cytometry machine. Relative telomere length (RTL) was determined by comparing T cells with a CEM-1301 cell line per:

$$RTL = \frac{(\text{Mean } FL1 \text{ sample cells with probe} - \text{Mean } FL1 \text{ sample cells without probe}) \times 2 \times 100}{\text{Mean } FL1 \text{ reference cells with probe} - \text{Mean } FL1 \text{ reference cells without probe}}$$

Chromium Release Assay. T cells were evaluated for their cytotoxicity in a standard 4-hour chromium release assay using $^{51}$Cr-labeled target cells. T cells were plated in triplicate at 1×10$^5$, 0.5×10$^5$, 0.25×10$^5$, 0.125×10$^5$ and 0.0625× 10$^5$ cells/well with 5×10$^3$ target cells in a 96-well V-bottom plate (Costar). After incubation, 50 µL, of supernatant was harvested onto a LumaPlate (Perkin Elmer), read in Top-Count NXT (Perkin Elmer), and percent specific lysis was calculated per:

$$\frac{\text{Experimental 51Cr released} - \text{Spontaneous 51Cr released}}{\text{Maximum 51Cr released} - \text{Spontaneous 51Cr released}} \times 100$$

Spontaneous and maximum release was determined by measuring chromium in the conditioned supernatant from target cells incubated with CM or 0.1% Triton X-100 (Sigma), respectively.

Endotoxin Testing. Endotoxin level in final products was determined using Endosafe®-PTS Portable Test System (Charles River Laboratories) as per the manufacturer's guidelines. The test has a detection limit of 0.01-10 EU/mL, which can be converted to EU/patient weight.

*Mycoplasma* testing. *Mycoplasma* detection by PCR was performed using the TaKaRa *Mycoplasma* Detection Kit (Clontech) according to manufacturer's instructions.

T-cell receptor Vβ repertoire. T-cell receptor (TCR)-Vβ usage of culture day 28 and day 35 CAR$^+$ T cells was determined using a panel of 24 TCR Vβ-specific mAbs (cat # IM3497, IO TEST Beta Mark TCR-Vβ repertoire kit, Beckman Coulter) used in association with CD3-specific mAb (cat #340949, BD Biosciences, 10 μL) and isotype-matched control mAbs (cat #552834, BD Biosciences).

Real-time PCR to determine copy number of integrated CAR. To determine the copy number of integrated CD19RCD28 CAR in genetically modified T cells, 50-100 ng genomic DNA (cat #80204, AllPrep DNA/RNA Mini Kit, Qiagen) was amplified using Steponeplus real-time PCR system (Applied Biosystems) in a PCR reaction (2 min at 50° C., 10 min at 95° C., followed by 40 cycles of 15 sec at 95° C. and 1 min at 60° C.) using the following primers: forward (5'-CAGCGACGGCAGCTTCTT-3'; SEQ ID NO: 8), reverse (5'-TGCATCACGGAGCTAAA-3'; SEQ ID NO: 9) and probe (5'-AGAGCCGGTGGCAGG-3'; SEQ ID NO: 10). Primers (Cat #4316844, Applied Biosystems) for RNAse P gene was used as an internal control. Serially-diluted genomic DNA from a genetically modified Jurkat-cell (clone #12) containing 1 copy of CAR from CD19RCD28mz (CoOp)/pSBSO DNA plasmid was used to generate a standard curve (Maiti et al., 2013). All the primers, probes and TaqMan Gene Expression Master Mix were purchased from Applied Biosystems.

PCR for SB11 transposase. DNA (20 ng) (AllPrep DNA/RNA Mini Kit, Qiagen) isolated from CAR$^+$ T cells was amplified using a thermal cycler (PTC-200, DNA Engine, BioRad) using forward (5'-ATGGGAAAAT-CAAAAGAAATC-3'; SEQ ID NO: 11) and reverse (5'-CTAGTATTTGGTAGCATTGC-3'; SEQ ID NO: 12) primers in a PCR reaction (95° C. for 5 min; 25 cycles of 95° C. for 15 sec, 58° C. for 40 sec, 72° C. for 60 sec; followed by a final extension at 72° C. for 7 min) GAPDH was used as the housekeeping gene and was amplified in the same PCR reaction using the primers, forward (5'-TCTCCAGAACAT-CATCCCTGCCAC-3'; SEQ ID NO: 13) and reverse (5'-TGGGCCATGAGGTCCACCACCCTG-3'; SEQ ID NO: 14). Linearized pCMV-SB11 plasmid DNA (1 ng) and genomic DNA (20 ng) from genetically modified Jurkat cells stably expressing SB11 and EGFP (expressed from DNA plasmid SB11-IRES2-EGFP) (Maiti et al., 2013) were used as a positive control. Mock electroporated (no DNA) and OKT3-aAPC-propagated T cells were used as a negative control.

Assay to assess for unwanted autonomous T-cell growth. To monitor aberrant T-cell growth, 2×10$^5$ CAR$^+$ T cells, harvested after 4 aAPC-mediated stimulation cycles (28 days after electroporation) were cultured in triplicate in a 24-well tissue culture plate for an additional 18 days. (i) Positive control: the presence of aAPC and cytokines (50 U/mL IL-2 and 30 ng/mL IL-21). (ii) Test: the absence of aAPC and cytokines. The genetically modified T cells passed the assay when total viable cells at day 18 were (i) >2×10$^5$ cells for CAR$^+$ T cells cultured with aAPC and cytokines and (ii) <2×10$^4$ cells for CAR$^+$ T cells cultured without aAPC and cytokines.

G-band karyotyping. CAR$^+$ T cells at the end of co-culture were harvested and the slides were stained using Giemsa stain using standard procedure. A total of 20 G-banded metaphases were analyzed.

Example 4

Figure 5A:
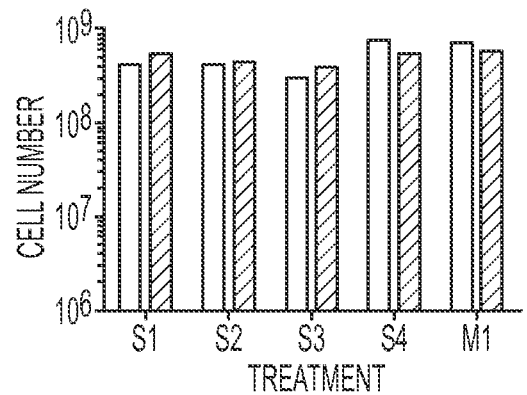
FIG. 5: Harvest and characterization of aAPC. (A, B) Sepax volume reduction. aAPC clone #4 grown in VueLife bags were harvested using CS-490.1 kit in Sepax II. The Sepax harvest (S, n=4) was compared to manual (M, n=1) procedure. The mean pre/post-processing cell-counts (4.9× $10^8$ vs. 5×$10^8$) were similar using the Sepax system. (C) Phenotype of aAPC (clone #4). Flow cytometry analysis showing expression of CD19, CD64, CD86, CD137L and a membrane-bound version of IL-15 (peptide fused to modified IgG4 Fc region) co-expressed with EGFP (mIL-15-EGFP) on K562 aAPC and K562 parental controls.
Figure 5B:
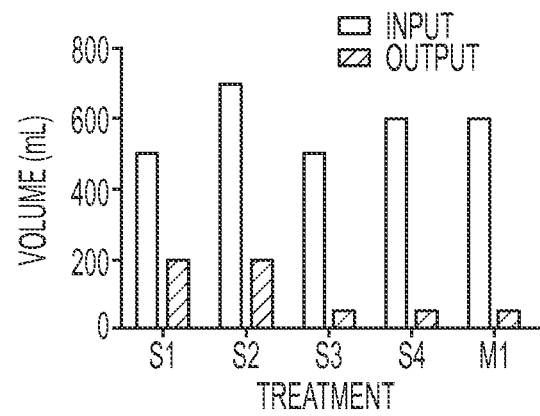
Figure 5C:
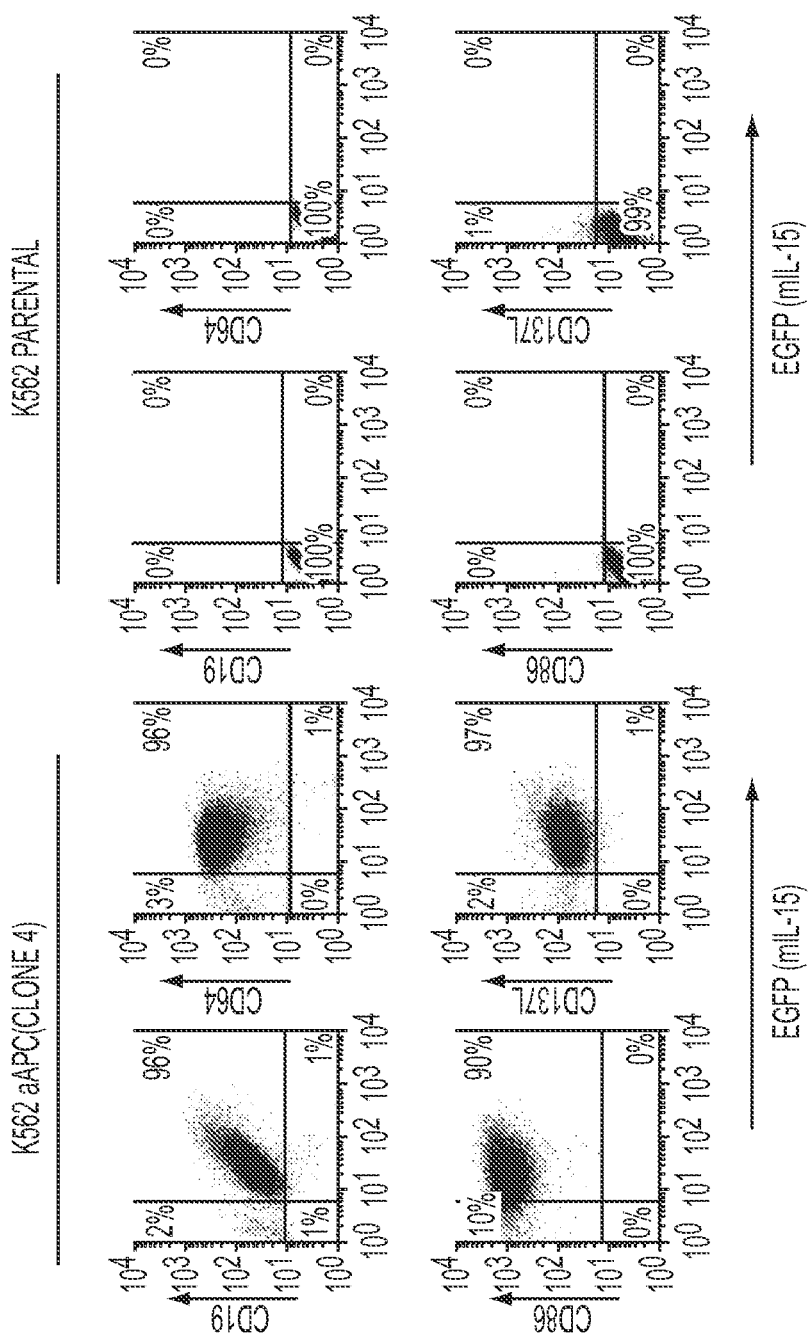

Manufacture Of Clinical-grade CD19-Specific T Cells Stably Expressing Chimeric Antigen Receptor Using Sleeping Beauty and Artificial Antigen Presenting Cells Results aAPC (Clone #4). K562 functioning as aAPC (clone #4) were employed to selectively propagate CAR$^+$ T cells. The cultured aAPC were harvested from VueLife bags by a Sepax II device using the volume reduction procedure, which took 40 minutes. The mean preprocessing volume and aAPC counts were 575 mL (range 500-700 mL) and 4.9×10$^8$ (range 3.2×10$^8$ to 7.7×10$^8$), respectively. After processing with Sepax II, mean recovery of cells was 108% (range 75% to 136%), with an output volume of 125 mL (range 50-200 mL) resulting in mean volume reduction of 78.3% (range 60% to 91.6%, FIGS. 5A, B). The automated cell recovery was similar to a manual volume reduction procedure (82%), which took 45 minutes of sustained operator time and resulted in 91% volume reduction. aAPC were regularly monitored by flow cytometry for >80% expression of the introduced transgenes coding for CD19, CD64, CD86, CD137L, and EGFP (as a marker for expression of mIL15). The immunophenotyping was undertaken upon generating the MCB and WCB and upon each addition of γ-irradiated aAPC to T-cell cultures (that marked the beginning of each stimulation cycle, FIG. 5C). MCB and WCB for Clone 4 aAPC tested negative for sterility and mycoplasma on cells and cell supernatant. In the biosafety testing, no virus was detected by adventitious virus testing, replication competent retrovirus testing, and screening for a range of human pathogenic viruses. Testing validated that the aAPC (clone #4) was derived from K562 based on finger printing (Table 5).

TABLE 5

| STR fingerprinting of K562 aAPC (Clone #4). | |
|---|---|
| STR | K562 aAPC (Clone 4) |
| AMEL | X |
| CSF1PO | 9, 10 |
| D13S317 | 8 |
| D16S539 | 11, 12 |
| D18S51 | 15, 16 |
| D19S433 | 14, 14.2 |
| D21S11 | 29, 30, 31 |
| D2S1338 | 17 |
| D3S1358 | 16 |
| D5S818 | 11 |
| D7S820 | 9, 11 |
| D8S1179 | 12 |
| FGA | 21 |
| TH01 | 9.3 |
| TPOX | 8, 9 |
| vWA | 16 |

Figure 6:
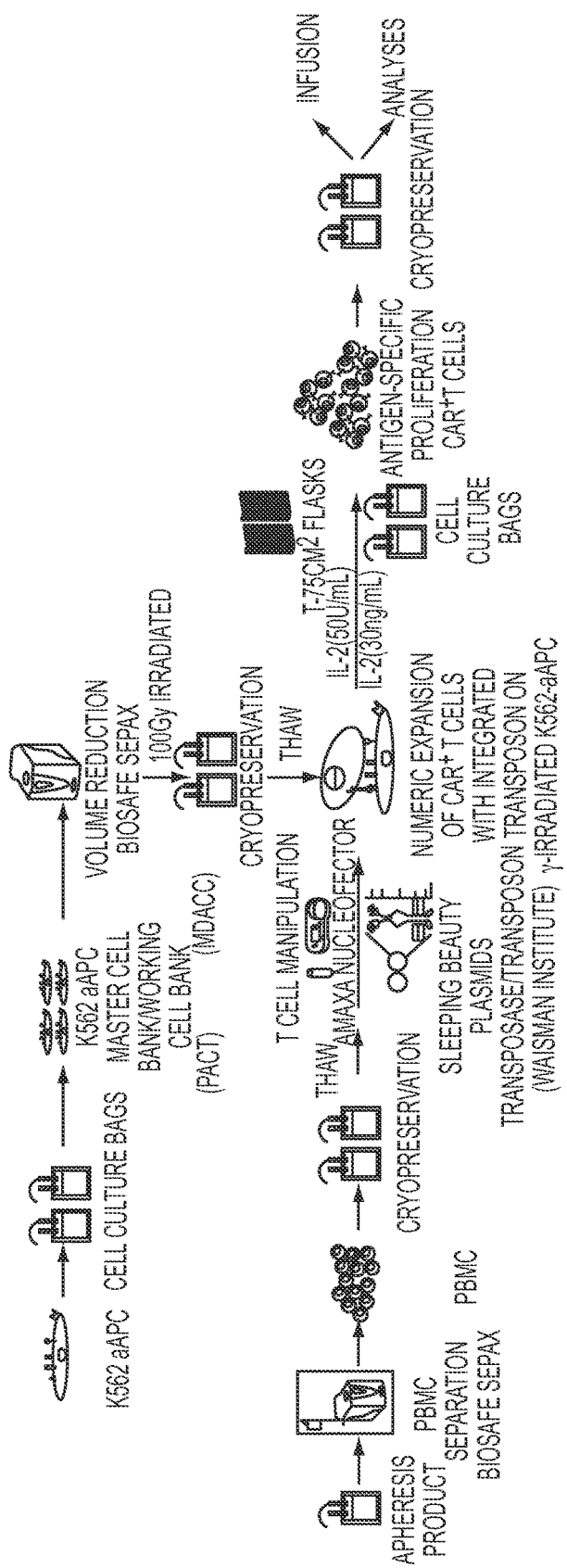
FIG. 6: Schematic of the process of generating clinical grade CD19-specific T cells. A MCB (PACT) and WCB (MDACC) were generated for K562-derived aAPC (clone #4). For the generation of CAR$^+$ T cells, aAPC were numerically expanded in bags, harvested using the Sepax II system, irradiated (100 Gy), and cryopreserved for later use. CD19-specific T cells were manufactured as follows; PBMC were isolated from normal donor apheresis products using the Sepax II system and cryopreserved. The PBMC were later thawed, electroporated with the SB DNA plasmids (CD19RCD28 CAR transposon, SB11 transposase) using the Nucleofector System, co-cultured with thawed irradiated aAPC along with cytokines (IL-2 and IL-21) for a culture period of 28 days and cryopreserved.
Figure 7A:
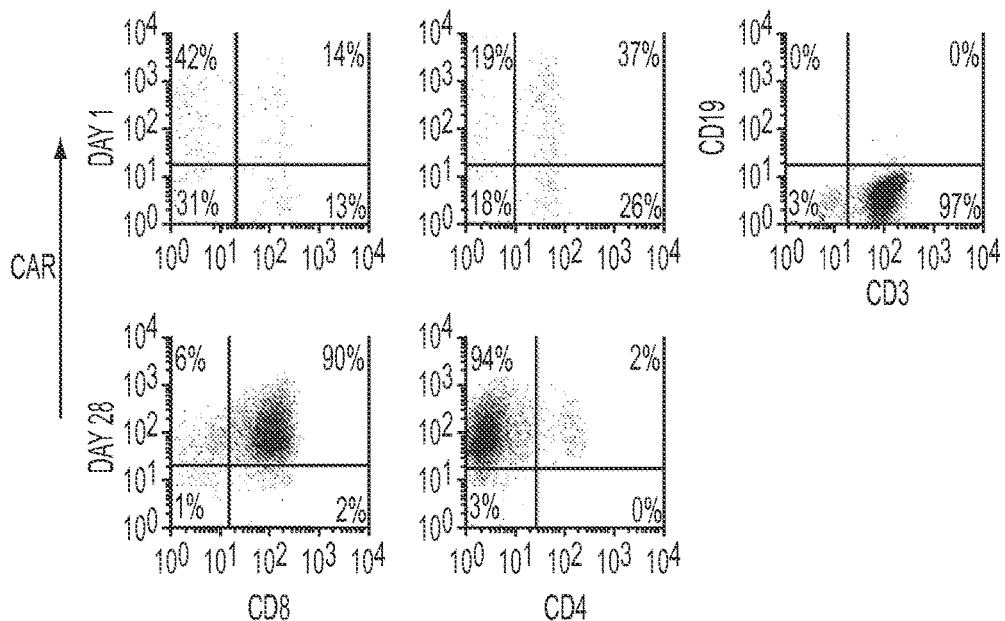
FIG. 7: Phenotype of CAR$^+$ T cell. (A) Expression of CD19RCD28 CAR on T cells day after electroporation (culture day 1) and after 28 days of co-culture on aAPC clone #4 along with lack of CD19$^+$ aAPC. (B) CAR expression by western blot analysis using CD3-ζ specific antibody. Whole cell lysates were run on SDS-PAGE under reducing conditions. Molecular weight marker (M), Parental Jurkat cells (Lane 1), CD19RCD28$^+$ Jurkat cells (Lane 2), CAR$^{neg}$ control primary T cells (Lane 3) and CD19RCD28$^+$ T cells (Lane 4). (C) Percent expression of CD3+, CD4$^+$CAR$^+$ and CD8$^+$CAR$^+$ T cells with in a lymphocyte gate in cultures over time. Each symbol represents a separate experiment; the solid lines are mean of the three validation experiments. (D) Immunophenotype of memory/naïve, adhesion, activation, cytolytic and exhaustion markers on CAR$^+$ T cells at the end (d28) of co-culture.
Figure 7B:
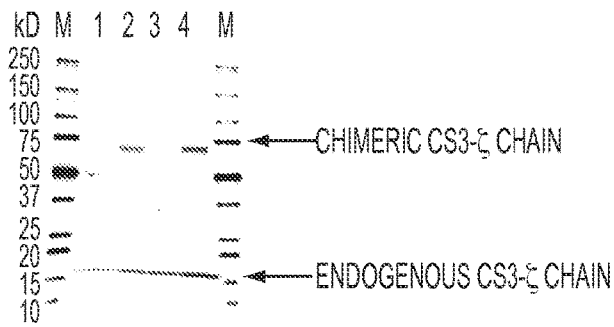
Figure 13:
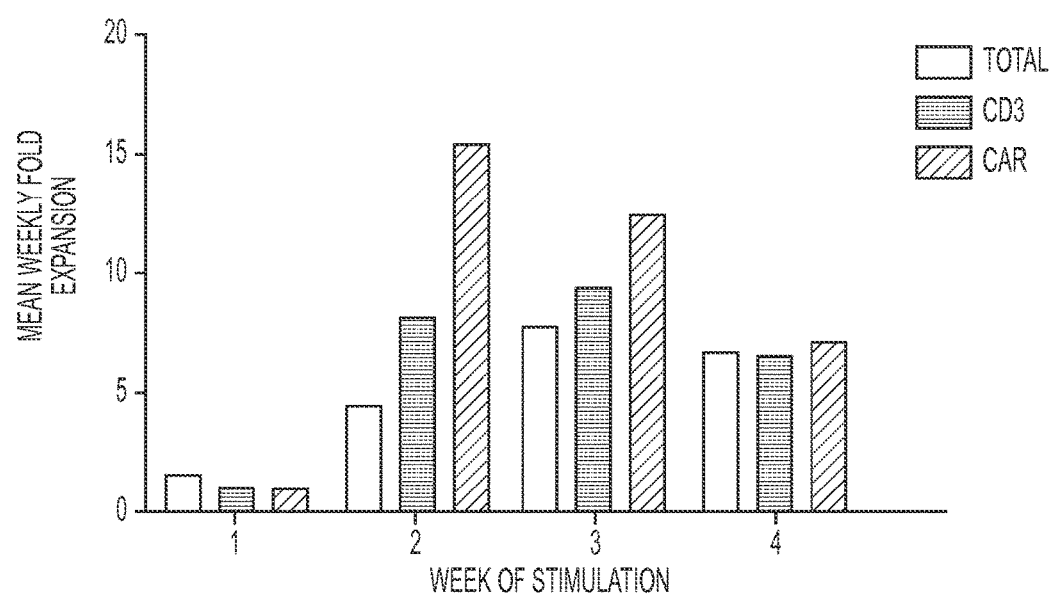
FIG. 13: Rate of numeric expansion of CD19-specific CAR$^+$ T cells. Genetically modified T cells were co-cultured with aAPC in a 7-day stimulation cycle, and weekly fold-expansion rate from each validation run at the end of each stimulation cycle for total, CD3$^+$ and CAR$^+$ T cells was calculated. Mean fold-expansion is shown (n=3).

Manufacture of CAR+ T cells. Validation studies were undertaken for large scale production of CD19-specific CAR+ T cells to establish that PBMC can be electroporated and propagated to clinically meaningful numbers (Huls et al., 2013) (FIG. 6) and meet pre-established release criteria (Table 6). Two normal donor apheresis products were processed to isolate mononuclear cells (MNC) using the Sepax cell-processing system. The apheresis products 201 mL (donor 1) and 202 mL (donor 2) were processed in two batches (~100 mL/batch) generating a 50 mL output product. The preprocessing counts were similar to post-processing counts of the apheresis products. A total of $5.3 \times 10^9$ and $7.1 \times 10^9$ cells were isolated containing 40.5% and 51% CD3+ T cells respectively from donor 1 and donor 2. Cells were then cryopreserved in aliquots ($4 \times 10^7$ cells/mL) in CryoMACS freeze bags (10 mL) and reference cryovials (1 mL) for later use. Three separate validation experiments were performed and are summarized in Table 6. For validation run 1 and 2 (V1, V2) cells from donor 1 and for validation 3 (V3) cells from donor 2 were used. For each run freshly-thawed PBMC were electroporated and ex vivo numerically expanded in separate culturing procedures (Table 7). On culture day 0, $3 \times 10^8$ (V1) and $8 \times 10^8$ (V2, V3) cells were thawed (viability, 88.9% to 97.6%) and rested for 2 hours prior to electroporation. 2 to $3 \times 10^8$ cells (V1=$2 \times 10^8$; V2 and V3=$3 \times 10^8$) were electroporated at $2 \times 10^7$ cells per cuvette with CD19RCD28mz(CoOp)/pSBSO transposon and pCMV-SB11 transposase DNA plasmids and the following day (culture day 1) co-cultured with aAPC clone #4 based on CAR expression. The electroporation efficiency for the three validation runs was assessed on culture day 1 as measured by expression of CAR (33.7%, 25.5% and 47.1%). CAR expression at the end of co-culture (culture day 28) was 92%, 99.2%, and 96.7%, and the cultures contained mean 95%±5.3% CD3+ T cells with negligible amounts of contaminating CD19+ cells (mean=0.7%±0.15%) and CD32+ aAPC (mean=0.6%±0.6%, FIG. 7A, Table 6). The inventors further confirmed CAR expression by Western blot of whole-cell lysates of electroporated/propagated T cells using CD3-ζ chain-specific mAb revealing an expected 73-kDa chimeric ζ chain (Singh et al., 2008) (FIG. 7B). Upon inspection of the kinetics of T-cell growth on aAPC, the inventors observed an accelerated rate of T-cell propagation at the end of the second week of culture (end of stimulation cycle 2), which is consistent with increased fold-expansion of total (p=0.01) and CD3+ (p=0.01) T cells as compared to the fold-expansion in the first week of stimulation. The weekly fold-expansion at the end of the third and fourth week for total (p=0.01, p<0.001), CD3+ (p=0.03, p<0.001), CAR+ (p=0.02, p<0.001) T cells was consistently higher than that of week-one, respectively (FIG. 13).

TABLE 6

Acceptance criteria for releasing electroporated and propagated T cells

| | | Results | | |
|---|---|---|---|---|
| Test | Specification | Validation Run #1 | Validation Run #2 | Validation Run#3 |
| Sterility-Bacteria and Fungi | Negative (No growth at 14 days) | No growth at 14 days | No growth at 14 days | No growth at 14 days |
| Mycoplasma | Negative by PCR | Negative | Negative | Negative |
| Visual Inspection | No evidence of contamination | No evidence of contamination | No evidence of contamination | No evidence of contamination |
| Viability (Trypan Blue or 7AAD) | ≥70% | 99% | 99% | 98% |
| Gated Immunophenotyping | ≥80% CD3+ | 89% CD3+ | 97% CD3+ | 99% CD3+ |
| | ≥10% CAR+ | 92% CAR+ | 99% CAR+ | 96% CAR+ |
| | <5% CD32+ | 1.3% CD32+ | 0.04% CD32+ | 0.51% CD32+ |
| | <5% CD19+ | 0.75% CD19+ | 0.49% CD19+ | 0.78% CD19+ |
| Endotoxin LAL | Endotoxin lebel <5 EU/recipient weight (for validation, per mL) | <0.004 EU/mL | <0.667 EU/mL | <0.089 EU/mL |
| Screen for Unwanted Autonomous Growth | <$2 \times 10^4$ cells/mL for the cells without cytokines or aAPC at Day 18 | <$2 \times 10^4$ cells/mL | <$2 \times 10^4$ cells/mL | <$2 \times 10^4$ cells/mL |

TABLE 7

Characterization of T cells before and after co-culture on γ-irradiated aAPC.

| | Aphersis | | | | Day 1 after electroporation | | | | | | Day 28 of co-culture | | | | | | | |
|---|---|---|---|---|---|---|---|---|---|---|---|---|---|---|---|---|---|---|
| Expt. | CD3 | CD4:CD8 | CD3+CD4+ | CD3+CD8+ | CD3 | CD4:CD8 | CAR | CD3+CAR+ | CD4+CAR+ | CD8+CAR+ | CD3 | CD4:CD8 | CAR | CD3+CAR+ | CD4+CAR+ | CD8+CAR+ | Viability | Fold exp* |
| V1 | 40.5 | 1.65 | 18.5 | 11.2 | 64.7 | 2.4 | 33.7 | 41.0 | 28.0 | 11.1 | 88.9 | 0.02 | 92.0 | 97.7 | 2.46 | 87.2 | 99% | 82.6 |
| V2 | | | | | 59.8 | 4.1 | 25.5 | 17.1 | 25.9 | 3.8 | 97.1 | 0.01 | 99.2 | 97.4 | 1.77 | 91.2 | 99% | 536.7 |
| V3 | 51.2 | 1.59 | 29.1 | 18.3 | 87.7 | 2.3 | 47.1 | 45.0 | 20.1 | 31.5 | 99.2 | 0.8 | 96.0 | 96.0 | 43.4 | 51.4 | 98% | 561.2 |

*Total (inferred) viable cells

The inventors observed similar weekly fold-expansion for CD3+ and CAR+ T cells past week one of stimulation. After 4 weeks of co-culture on γ-irradiated aAPC there was an average 545-fold numeric expansion of CD3+ T cells with a 1,111-fold expansion of CAR+ T cells. The ex vivo expansion (culture day 28) resulted in an average $2.86 \times 10^{10}$ CD3+ T cells, almost all of which were CAR+ ($2.65 \times 10^{10}$). The propagation kinetics of total (p=0.18), CD3+ (p=0.17) and CAR+ (p=0.2) T cells for the three validation runs were similar (FIGS. 8A, B, C). These data support the recursive addition of aAPC for the selective outgrowth of CD19-specific T cells.

Figure 7C:
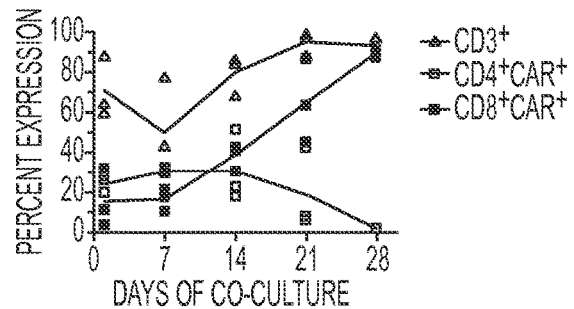

Immunophenotype of electroporated and propagated CAR+ T Cells. Two of the three validation runs resulted in a preferential growth of CD8+CAR+ T cells (mean 76%±22%) as compared to CD4+CAR+ T cells (mean 16%±24%) (FIG. 7C) which was predicted by inclusion of IL-21 (Singh et al., 2011). Mean CD4/CD8 ratios for CAR+ T cells modulated during the course of the co-culture as there was a predominance of CD4+CAR+ T cells at the start of the co-culture on aAPC (culture day 1, ratio=3.3) leading to equal amounts of CD4+CAR+ and CD8+CAR+ T cells at culture day 14 (ratio=0.9), after which the ratio declined (culture day 21, ratio=0.4; culture day 28, ratio=0.3). The total CD4/CD8 ratio followed a similar trend and declined over time (Table 7). The CAR+ T cells at the end of the propagation period (culture day 28) were activated (CD69 expression, mean 43.6%; HLA-DR expression, mean 61.2%), capable of cytolysis (Granzyme B expression, mean 92.3%) and expressed markers of memory/naïve T cells (CD62L expression, mean 45.6%; CD28 expression, mean 66.4%; CD27 expression, mean 77.5%, CD45RA expression, mean 99.7%). The inventors were not able to detect cell-surface markers of exhaustion/senescence (PD-1 expression, mean 2.7%; CD57 expression, mean 3.3%) (FIG. 7D). These data are consistent with the aAPC supporting the outgrowth of a heterogeneous population of CAR+ T cells.

Figure 14:
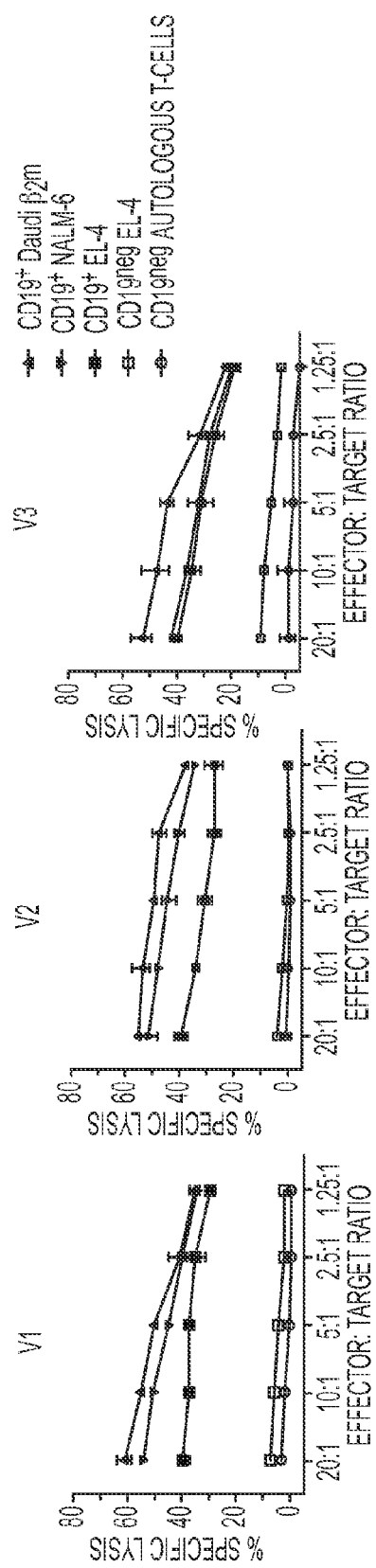
FIG. 14: Redirected specificity of CD19-specific CAR$^+$ T cells. CD19-specific lysis of CD19$^+$ tumor targets (Daudiβ$_2$m, NALM-6, CD19$^+$ EL-4) by CAR+ T cells generated in three validation runs (V1, V2, V3) in a standard 4-hr chromium assay. Background autologous lysis against the CAR$^{neg}$ control was 1.5%.

Redirected specificity of CAR+ T cells. T cells generated from all three validation runs were able to specifically lyse CD19+ tumor targets. An average of 57%±4% (mean±SD, range, 61.2% to 53.8%) Daudiβ$_2$m and 49%±7% (mean±SD, range, 41% to 54%) NALM-6 was lysed at an effector to target ratio of 20:1. CD19-specific killing was demonstrated by average 6.2±2.6 (mean±SD)-fold higher killing of CD19+ EL-4 (range, 4.2 to 9.2 fold) as compared to the CD19$^{neg}$ parental EL-4 cells at effector/target ratio of 20:1 with a 1.4±1 (mean±SD)-fold background CD19-specific lysis by CAR$^{neg}$ (mock electroporated) controls (FIGS. 8D, 14). This implies that the CAR in the electroporated and propagated T cells redirected killing to CD19.

Lack of unwanted autonomous proliferation by genetically modified and propagated T Cells. The inventors evaluated growth of CAR+ T cells in the presence/absence of K562 aAPC and cytokines (IL-2 and IL-21) to rule out aberrant T-cell growth due to potential genotoxicity caused by SB transposition. At the end of 18 days of culture the inventors observed <$2 \times 10^4$ cells (average 2,800, range 0.0-$5.6 \times 10^3$) in the genetically modified T cells receiving no cytokines and aAPC, while the control group receiving cytokines and aAPC numerically expanded to an average of $7.6 \times 10^7$ cells, range $4.12 \times 10^7$ to $12.8 \times 10^7$ (Table 8). These data indicate CAR+ T cells cannot sustain proliferation upon withdrawal of growth factors and antigenic stimulation.

TABLE 8

Lack of autonomous cell growth by genetically modified T cells.

| | | | No. of T cells (day 18) | | |
|---|---|---|---|---|---|
| Experiment | Day of culture$^a$ | No. of T cells seeded$^b$ | Without cytokines and aAPC$^c$ | With cytokines and aAPC$^d$ | % fold-change of T cells$^e$ |
| V1 | 28 | $2 \times 10^5$ | 0 | $12.80 \times 10^7$ | 0.000% |
| V2 | 28 | $2 \times 10^5$ | $5.6 \times 10^3$ | $5.88 \times 10^7$ | 0.009% |
| V3 | 28 | $2 \times 10^5$ | $2.8 \times 10^3$ | $4.12 \times 10^7$ | 0.007% |

$^a$Days of culture when T cells were seeded
$^b$Total number of T cells seeded in culture at the start of the experiments
$^c$Total number of T cells counted in the absence of cytokines and aAPC
$^d$Total (inferred) number of T cells counted in the presence of cytokines and aAPC (positive control)
$^e$Perfect fold-change = [(c/b) ÷ (d/b)] * 100

TABLE 9

In-process testing for electroporated and propagated T cells.

| Expression | |
|---|---|
| Cell Surface CAR Expression | Flow Cytometry |
| Total CAR Expression | Western Blot Analysis |
| Functionality | |
| Cytotoxicity | Chromium Release Assay |
| Persistence | |
| Memory/Naive Phenotype | Flow Cytometry |
| Telomere Length | Flow-FISH |
| Safety | |
| CAR Copy Number | Q-PCR |
| SB11 Detection | PCR |
| TCR Vβ Repertoire | Flow Cytometry |
| Karyotyping | G-banding |

Figure 9A:
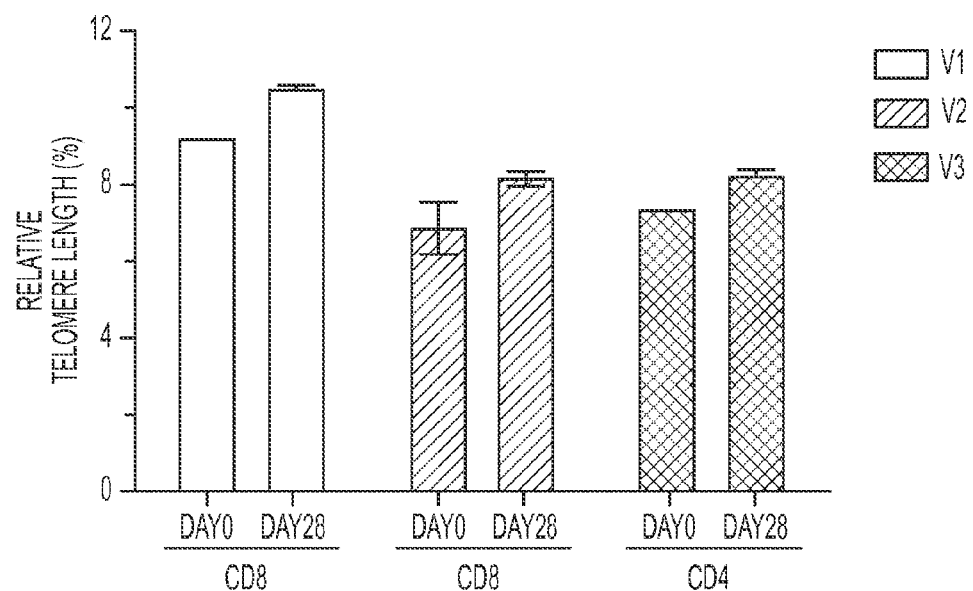
FIG. 9: Safety profile associated with the SB system. (A) Telomere length of cells was measured using fluorescence in situ hybridization and flow cytometry (Flow-FISH) assay. Predominant T cell population at day 28 (V1 and V2, CD8$^+$ T cells; V3, CD4$^+$ T cells) was compared to respective miltenyi column purified subset of T cells from day 0. (B) Genomic DNA from CAR$^+$ T cells at day 28 was amplified using primers and probes specific for CD19RCD28 CAR. Relative Quantity (RQ) analyses of the CD19RCD28 target copy number was determined using CD19RCD28 CAR-transduced Jurkat cells, which are known to have one integration of CD19RCD28 CAR per genome from FISH analysis, as a reference and endogenous RNaseP as a normalizer. (C) TCR Vβ analysis of day 28 and day 35 CAR$^+$ T cells. Data shows mean±SD of three validation run CAR$^+$ T cells as compared to day 0 unmanipulated controls. (D) Genomic PCR showing lack of SB11 transposase integration. Genomic DNA (20 ng) was amplified using SB11 or GAPDH primers. CAR$^{neg}$ control T cells (lane 5) and CAR$^+$ T cells (lane 7) amplified using SB11 primers; CAR$^{neg}$ control T cells (lane 6), CAR$^+$ T cells (lane 8) and Jurkat stably expressing SB11 (lane 4) amplified using GAPDH primers. Jurkat stably expressing SB11 (Jurkat/SB11-IRES2-EGFP) (lane 3) and the linearized plasmid, pKan-CMV-SB11 (lane 2) amplified using SB11 primers was used as positive control. (E) G-banded karyotypes of CAR$^+$ T cells from the three validation runs reveal no structural or numeric alteration. A representative spread from validation 2 is shown.

Telomere length in CAR+ T cells. Telomere length is an important measure of cellular differentiation and progression to senescence. Therefore to evaluate the effect of SB transposition and ex vivo numeric expansion of CAR+ T cells on telomere length, the inventors compared telomere lengths from CAR+ T cells (culture day 28) to their respective matched unmanipulated controls (prior to electroporation) using Flow-FISH assay. Due to the generation of predominately CD8+ CAR+ T cells in V1 and V2 and CD4+ CAR+ T cells in V3, the inventors compared telomere lengths of CD8+ T cells for V1 and V2 and CD4+ T cells for V3 to CD8+ and CD4+ T cells, respectively, from prior to propagation (FIG. 9A). The average telomere length of T cells after ex vivo numeric expansion (culture day 28, 8.93%±1.33%) was similar to that of unmanipulated control T cells (day 0, 7.77%±1.21%). These results indicate that electroporation and propagation of CAR+ T cells does not result in erosion of telomere lengths.

Figure 9B:
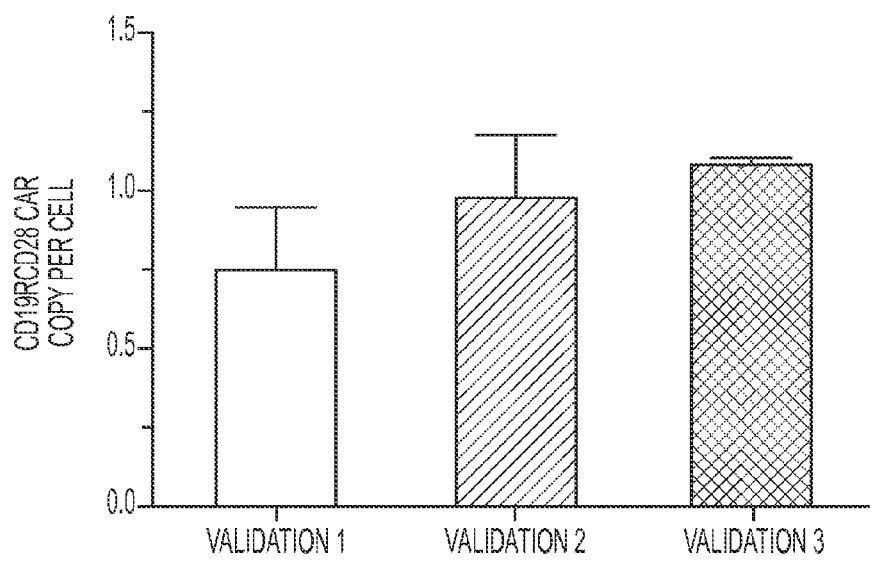

Copy number of CAR transgene. The copy number of integrated CD19RCD28 transgenes was determined using CD19RCD28+ Jurkat cell clone #12 as reference and endogenous RNase P as a normalizer (Maiti et al., 2013). The average transgene copy per T cells generated in the validation runs was 0.96±0.09 (range, 0.75 to 1.07, FIG. 9B). These data indicate that SB transposition resulted in approximately one integrated copy of CAR per T-cell genome.

Figure 9C:
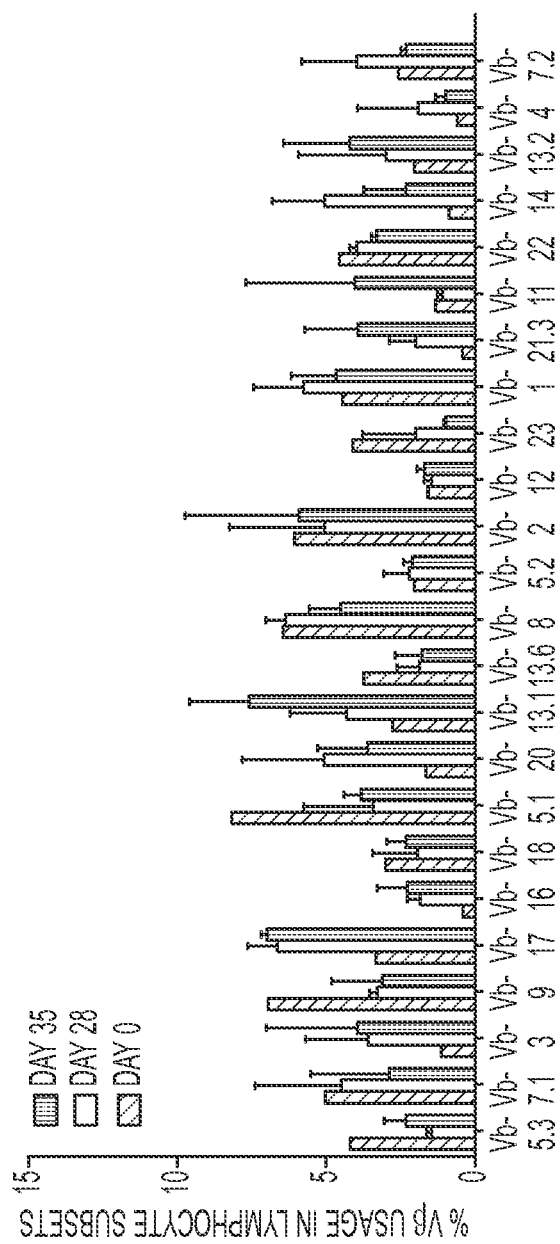

TCR Vβ usage. The electroporation and propagation of T cells may lead to emergence of oligoclonal or clonal population of T cells that could be indicative of preferential growth and thus an indicator of a genotoxic event. Therefore, the inventors evaluated TCR Vβ usage by flow cytometry as a means to assess repertoire diversity. All 24 TCR Vβ families tested were preserved in T cells after 28 days of co-culture on aAPC and similar to the pre-electroporation repertoire. Further, the TCR Vβ families were preserved upon prolong culture time (culture day 35, FIG. 9C). These data suggest maintenance of a broad TCR diversity in cultured CAR+ T cells and do not reveal an imbalance in the use of TCR sequences.

Figure 9E:
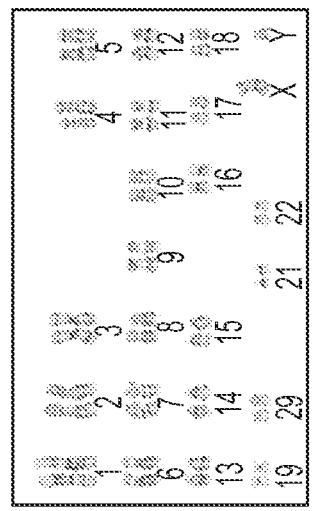
Figure 9D:
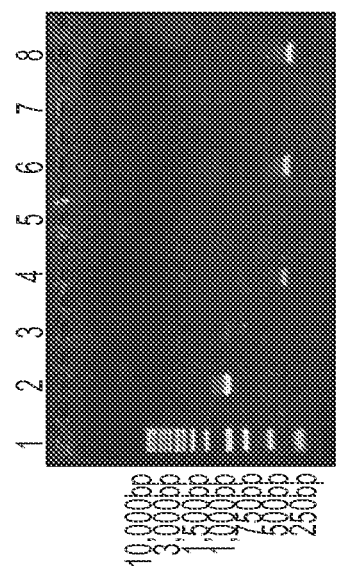

Lack of SB11 transposase in CAR+ T cells. Continued expression of SB11 transposase may lead to remobilization of the integrated CAR transgene. Therefore, the inventors performed a genomic PCR to rule out illegitimate homologous recombination of the DNA plasmid coding for SB11 in CAR+ T cells. Within the limits of the assay the inventors were unable to detect a band (~1 kb) in PCR reactions containing DNA from CAR+ T cells cultured for 28 days and amplified using SB11-specific primers (FIG. 9D). These data indicate a lack of integration of SB11 transposase in the electroporated and propagated T cells.

Figure 15:
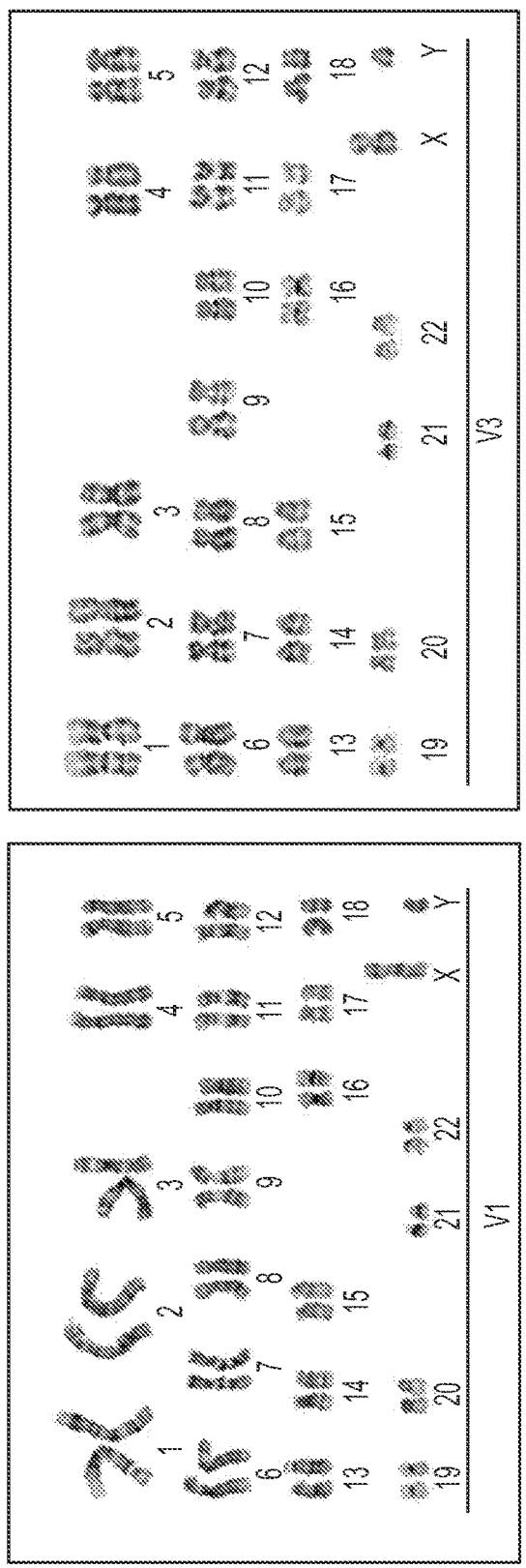
FIG. 15: Safety regarding chromosomal aberration. G-banded karyotypes of CAR$^+$ T cells generated from validation runs (V1 and V3) reveal no structural or numeric alteration.

Karyotype of CAR+ T cells. The integrity of chromosome structure was evaluated to rule out global genotoxicity associated with SB transposition. G-banding of CAR+ T cells (harvested 28 days after electroporation) from all the three validation runs revealed a normal (male) karyotype in all analyzed metaphase spreads (FIGS. 9E, 15).

Example 5

Targeting an Ancient Retrovirus Expressed in Cancers and Infections Using Adoptive T Cells Engineered to Express Chimeric Antigen Receptor Methods Immunohistochemistry. Tissue microarray (#ME1004a, ME2082b, FDA998t) obtained from U.S. Biomax (Rockville, Md.) was hydrated with $DiH_2O$. Antigen retrieval using citrate buffer pH 6 without EDTA was performed. Slides were blocked with 3% hydrogen peroxide (Biocare Medical, Concord, Calif.), avidin (Biocare Medical), biotin (Biocare Medical) and a polyvalent whole serum (Biocare Medical). Slides were incubated for 30 minute each with HERV-K mAb (0.6 mg/ml) at 1:20 dilution followed by biotinylated anti-mouse IgG (Biocare Medical) and strepavidin-HRP (Sigma-Aldrich, St Louis, Mo.) and visualized with a Mayer's Hematoxylin counterstain (Sigma-Aldrich). Similar staining procedures were performed on the slides with isotype control mouse IgG2a (0.25 mg/ml) antibody (BD Pharmingen, Franklin Lakes, N.J.).

Plasmids. The scFv sequence (from mAb clone 6H5) against HERV-K envelope protein was codon optimized (CoOp) (Invitrogen, Carlsbad, Calif.) and cloned into the SB transposon under control of the human elongation factor-1α (hEF-1α) promoter, flanked by SB inverted repeats forming $_{CoOp}$6H5CD28/pSBSO.

HERV-K antigen was expressed from SB plasmid containing bidirectional promoters hEF-1α and cytomegalovirus (CMV). The codon optimized full length antigen sequence with the viral transmembrane domain was cloned under the control of the hEF-1α promoter and the neomycin gene was transcribed under the control of the CMV promoter in a bi-directional vector. The transposase (SB11) was expressed in cis from the plasmid pCMV-SB11 (Davies et al., 2010).

To generate the in vivo imaging SB plasmid for T cells, codon optimized firefly luciferase was fused to a myc tag and was expressed under the control of the CMV promoter. A lentiviral vector encoding mKate-renilla luciferase under the control of the eEF1α promoter was used as an imaging vector for melanoma tumor cells in vivo.

Cells lines and their propagation. A375-mel and A888-mel were a kind gift from Dr. Lazio Radvanyi, The University of Texas MD Anderson Cancer Center (Houston, Tex.). A624-mel and EL4 parental were obtained from American Type Culture Collection (Rockville, Md.). A375-SM (super-metastatic melanoma cell line) was received from CCGS core facility at the University of Texas MD Anderson Cancer Center (Houston, Tex.). All cell lines were cultured in RPMI (Thermo Scientific, Rockford, Ill.) with 10% FBS (Thermo Scientific) and 5% glutamax (Gibco Life technologies, Grand Island, N.Y.). All cell lines were verified by morphology, cell finger printing and/or flow cytometry. They were tested for *Mycoplasma* and conserved in research cell banks.

Generation and expansion of HERV-K-Specific CAR expressing T Cells. PBMCs from healthy donors were isolated by Ficoll-Paque density gradient centrifugation (GE Healthcare Bio-Sciences, Piscataway, N.J.), and electroporated with the HERV-K SB transposon and SB11 transposase using the Amaxa electroporation system. Briefly, $2\times10^7$ PBMC cells were washed and incubated in complete RPMI supplemented with 10% fetal bovine serum (Thermo Scientific) and 1% glutamax (Gibco Life technologies) for 2 h. These cells were then resuspended in 100 µl of Amaxa Nucleofector solution (Human T-cell Kit), along with HERV-K CAR transposon (6H5CD28/pSBSO, 15 µg) and SB transposase (pCMV-SB11, 5 µg), transferred to a single cuvette, and electroporated using the U-14 program in the Amaxa electroporator (Lonza, USA). The electroporated T cells were incubated for 4 h at 37° C. in complete phenol-free RPMI (Thermo Scientific) after which a half-media change was performed.

K562 express endogenous HERV-K antigen and thus serve as aAPC to propagate HERV-K-specific CAR+ T cells. The electroporated T cells cultured in RPMI containing 10% FBS were supplemented with γ-irradiated (100 Gy) K562-aAPC at a 1:2 T cell:aAPC ratio. Irradiated aAPCs were added at the end of every week for T cell stimulation at the same ratio. Soluble IL-21 (eBioscience) and IL-2 (Chiron) cytokines were supplemented at a concentration of 30 ng/ml and 50 U/ml, respectively, to complete RPMI media every other day in the culture after electroporation. Mock transfected No DNA control T cells grown in the presence of OKT3 loaded K562 cells served as a negative control. CD19CAR+ T cells electroporated with $_{CoOp}$CD19CARCD28/pSBSO and SB11 transposase were grown under the same culture conditions as in CAR+ T cells and served as a non-specific CAR+ T cell control.

Every week the T cell cultures were monitored for the presence of $CD3^{neg}CD56^+$ cells and were depleted if the population exceeded 10% of the total population. This depletion usually occurred between 10 and 14 days of initial co-culture with aAPCs. The depletion was carried out using CD56 beads (Miltenyi Biotech Inc, Auburn, Calif.) on Automax (Miltenyi Biotech) using the positive selection "possel" according to manufacturer's instruction.

T-cell viability was assessed based on trypan blue exclusion using a Cellometer automated cell counter (Auto T4 Cell Counter, Nexcelom Bioscience, Lawrence, Mass.). The viability was analyzed using the program "PBMC_human_frozen" and "activated T cell," during electroporation and co-culture period. The fold expansion (compared to day 1) of total, $CD3^+$, $CD4^+$, $CD8^+$ and $CAR^+$ cells at the end of 7, 14, 28, 32 days of co-culture for individual donors was calculated and the average of 3 donors were compared between the CD19CAR+ T cells and No DNA control cells using a Student's t test.

Flow cytometry. All reagents were obtained from BD Biosciences (Franklin Lakes, N.J.) unless mentioned otherwise. One million cells were stained with antibody conjugated with fluorescein isothiocyanate (FITC), phycoerythrin (PE), peridinin chlorophyll protein conjugated to cyanine dye (PerCPCy5.5), or allophycocyanin (APC). The antibodies used include anti-CD3 FITC (5 µl), anti-CD3 PerCPCy5.5 (2.5 µl), anti-CD3 PE (2 µl) anti-CD4 APC (2.5 λl), anti-CD8 PerCPCy5.5 (4 µl), anti-CD56 APC (2.5 µl), AnnexinV (5 µl), anti-CD32 FITC (5 µl), anti-CD45RA FITC (5 µl), anti-CD45RO APC (2.5 µl), anti-Granzyme B FITC (5 µl), anti-CD62L APC (2.5 µl), anti-IFN-γ APC (2 µl), anti-CD27 PE (2 µl), anti-aPTCR FITC (5 µl), anti-γδTCR PE (2 µl), and anti-CCR7 PerCPCy5.5 (2.5 µl, Biolegend). FITC-conjugated (3 µl, Invitrogen) and PE-conjugated (2.5 µl, Invitrogen) F(ab')$_2$ fragment of goat anti-human Fcγ was used to detect cell surface expression of the HERV-K-specific CAR. Blocking of nonspecific antibody binding was achieved using FACS wash buffer (2% FBS and 0.1% sodium azide in PBS). Data acquisition was on a FACSCalibur (BD Biosciences) using CellQuest version 3.3 (BD Biosciences). Analyses and calculation of median fluorescence intensity (MFI) was undertaken using FlowJo version 7.5.5.

nCounter analysis digital gene expression system. Difference in gene expression between HERV-K-specific CAR+ T cells and No DNA control T cells were evaluated using the nCounter Analysis System (model no. NCT-SYST-120, NanoString Technologies; Geiss et al., 2008). Briefly, $10^4$ HERV-K-specific CAR+ T cells or No DNA T cells were lysed in RNeasy lysis buffer (RLT; 5 µl, Qiagen, Gaithersburg, Md.) and the mRNA were hybridized with a reported code set and a capture code set custom designed using the nCounter Gene Expression Assay Kit for 12 h at 65° C. An nCounter prep station was used for the post-hybridiztion processes. Nanomir software was used to normalize the mRNA levels with an internal control. R-program, tree-view and clustal view were used to output the data with statistical analysis. The normalized results were expressed as the relative mRNA level. Ingenuity Pathway Analysis (IPA) (Ingenuity Systems, www.ingenuity.com) was performed on statistically significant genes to understand their biological interaction based on a database derived from literature sources.

Integration analysis. Genomic DNA from HERV-K-specific CAR+ T cells was isolated using a QIAamp DNA mini kit (Qiagen) and real-time PCR was performed as previously described (Maiti et al., 2013). Genomic DNA from Jurkat cells (Clone #14) bearing a single integration of the CAR copy previously described was used as a positive control (Maiti et al., 2013). The experiment was done in triplicate with 100 ng of genomic DNA mixed with 10 µl of TaqMan Gene Expression Master Mix (Applied Biosystems, Foster City, Calif.), 1 µl (1× probe at 250 nM andlx primer at 900 nM) of 20× FAM-labeled CAR-specific TaqMan probe primer set specific for IgG4Fc [forward (5'-GAGGGCAACGTCTTTAGCTG-3'; SEQ ID NO: 15) and reverse (5'-GATGATGAAGGCCACTGTCA-3'; SEQ ID NO: 16) primers and carboxyfluorescein (FAM)-labeled probe (5"-AGATGTTCTGGGTGCTGGTC-3'; SEQ ID NO: 17)] and 1 µl (1× primer at 900 nM and 1× probe at 250 nM) of 20× VIC labeled TaqMan RNaseP Probe Primer set (Applied Biosystems) in a total reaction volume of 20 µl. The primer hybridization occurred at the IgGFc4 portion of the CAR. The amplification cycle included 2 minutes at 50° C., 10 minutes at 95° C., and forty cycles of 15 seconds at 95° C. and 1 minute at 60° C. Detection was performed with a StepOnePlus Real-Time PCR System (Applied Biosystems). The autosomal RNaseP gene, present at 2 copies per diploid cell, was used as an endogenous reference for normalization (Jin et al., 2011). The ΔΔCT method (Applied Biosystems, CA) was used to calculate the number of integrations with reference to RNaseP and Jurkat Clone as normalization controls.

Chromium release assay (CRA). The CRA was performed as previously described (Maiti et al., 2013; Jin et al., 2011). Briefly, HERV-K$^{+ve}$ targets were treated with $^{51}$Cr for 2 h and incubated with day 35 HERV-K-specific CAR+ T-cells or No DNA control T cells and the percentage of $^{51}$Cr release was calculated using the following formula:

$$\% \,^{51}Cr \, release = \frac{\text{Experimental release} - \text{Background release}}{\text{Maximum release} - \text{Background release}} \times 100$$

Time-lapse Bio-imaging. (A) To visualize CAR engagement with the antigen on the tumor cells, time lapse imaging was performed using a BioStation IM Cell-S1/Cell-S1-P system (Nikon, Melville, N.Y.). K562 parental cells were stained with anti-HERV-K APC antibody (1 µg) and the HERV-K-specific CAR+ T cells were stained for CAR surface expression using FITC labeled F(ab')2 fragment of goat anti-human Fcγ antibody (5 µl, BD Biosciences). The T cells and target cells were mixed at a ratio of 5:1 and plated in complete RPMI culture medium on a T-35 mm glass bottom plate (Fisher Scientific, Hampton, N.H.). The cells were immediately imaged every 2 minute at 37° C. for up to 8 h. Each image was recorded at 1600×1200 pixels with a 20× objective, using phase-contrast, fluorescence channel 2 to observe green HERV-K-specific CAR+ T cells, and fluorescence channel 3 to observe red K562 cells with an exposure time of 1/125 and 1/5 sec, respectively. CAR engagement with antigen was seen when the APC-labeled antigen overlapped with the green-labeled CAR.

(B) To visualize and quantify the time taken for HERV-K specific CAR+ T cells to kill a tumor cell, the tumor cells were plated with HERV-K-specific CAR+ T cells in a T-35 mm glass bottom plate with complete RPMI containing 1 ng/mg Sytox® (Invitrogen). Tumor cell death was recorded as the time when the tumor cell wall was punctured and the cells turned green using BiostationIM cell-S1-P system (Nikon). The intensity of green fluorescence in each tumor cell was recorded using live cell imaging software (Nikon) over a period of 15 h.

Intracellular IFN-γ release assay. HERV-K-specific CAR+ T cells were co-cultured with tumor cells at a 1:10 ratio in a round-bottom 96-well plate with 200 µl of complete RPMI culture medium. Protein transport inhibitor (BD Golgi Plug containing Brefeldin A) was added in all wells to trap the IFN-γ inside the cell. The co-culture was incubated for 4 h at 37° C. and then stained for HERV-K-specific CAR expression for 20 min at 4° C. The cells were then washed, fixed, and permeabilized with 100 µl of Cytofix/Cytoperm buffer (catalogue no. 555028) for 20 min at 4° C. The permeabilized cells were then stained for the cytokine with anti-IFN-γ APC conjugated antibody. The cells were washed and analyzed by FACSCalibur. PMA (phorbol 12 myristate 13 acetate)- and ionomycin-(BD Biosciences) treated T cells were used as positive controls for this assay. Similar assays were performed with No DNA control T cells.

Development of HERV-K$^{+ve}$ EL4 cell line. Two million EL4 cells were suspended in AMAXA mouse T cell nuclofector solution (Amaxa, USA) with HERV-K antigen-expressing SB transposon and SB11 transposase (2 μg of total DNA) to a final volume of 100 ml. This suspension was transferred to a single cuvette and electroporated using the C-09 program in Amexa electroporator. The cells were incubated for 4 h at 37° C. in electroporation media supplied with the kit supplemented with 10% FBS (Thermo Scientific Pierce). The cells were then transferred to DMEM, 10% FBS (Thermo Scientific Pierce) and 5% glutamax (Gibco Life Technologies). These cells were then grown in the presence of 0.8 mg/ml of G418 and neomycin-resistant HERVK$^{+ve}$ EL4 cells were sorted using HERV-K antibody and grown to obtain a pure population of cells.

shRNA-mediated HERV-K knockdown in A888-mel cells. A888-mel cells were grown to 90% confluence in a 6-well plate. The media was later replaced using 100 μl of either HERV-K-specific shRNA or scrambled shRNA lentivirus and polybrene (5 μg/ml) and transduced for 4 h at 37° C. and then replaced with regular RPMI media. The cells were then sorted based on GFP expression and grown. Scrambled shRNA-transduced A888-mel cells were used as control. An immunoblot assay of the cell line lysates was performed to determine the extent of HERV-K knockdown. The 6H5 HERV-K antibody was used to detect the HERV-K antigen expression on A888-mel cells with HERV-K shRNA or scrambled shRNA or parental cells. Ten million cells were lysed with RIPA buffer containing protease inhibitor (Roche Applied Science, San Francisco, Calif.). BCA assay was performed to detect protein concentration (Thermo Scientific Pierce). A 4%-20% gradient gel (Biorad, Hercules, Calif.) was used to run 10 μg of protein boiled in SDS loading buffer. The protein was then transferred to a nitrocellulose membrane and blocked with 5% milk in PBST and incubated with 6H5 HERV-K antibody (mg/ml). Binding was detected by goat anti-mouse Fc-HRP (Sigma-Aldrich) and developed using ECL Westfemto™ substrate (Thermo Scientific Pierce). The blot was imaged using Versa doc Quantityone™ software (Biorad) and blot quantified using Image J software.

In vivo Analysis. Metastatic melanoma model: 5-week-old female NOD.Cg-Prkdc$_{scid}$Il2rg$_{tmIwjt}$/SzJ (NSG) mice (Jackson Laboratories, Bar Harbor, Me.) were intravenously injected with $10^6$ A375-SM cells on Day 0. A375-SM cells were previously stably transduced with mKate-rRLuc and cell sorted for homogenous population. Mice in the treatment cohorts (n=7) started receiving $2 \times 10^6$ HERV-K-specific CAR-FfLuc T cells starting on Days 7, 14 and 21. IL-2 (600 U; eBioscience) was injected intraperitoneally (i.p.) three times a week during the treatment period. One cohort of mice (n=6) bearing the tumor received no treatment while a control group of mice (n=3) without tumor received a similar number of CAR$^+$ T cells as in treatment group.

Flux quantification: Bioluminescence imaging (BLI) was performed every week to image the tumor and T cell activity in vivo. Mice were anesthetized and placed in anterior-posterior position for BLI using a Xeno IVIS 100 series system (Caliper Life Sciences) as previously descreibed (Singh et al., 2007). To image the HERV-K-specific CAR-ffLuc T cell activity, 150 μl (200 μg/mouse) of D-Luciferin potassium salt (Caliper Life Sciences) was injected intraperitoneal (i.p.). Ten minutes after injection emitted photons were quantified using the Living Image 2.50.1 (Caliper Life Sciences) program. To image the tumor cell activity, 100 μl of Endurin (Promega, Fitchburg, Wash.) was injected i.p. Twenty minutes after injection the tumor activity was quantified similar to ffLuc. Unpaired student's t-tests were performed to establish statistical significance of the flux.

Statistical Analysis. For analyzing statistical differences in antigen expression between various grades and stages of melanoma and normal tissue, student's t-tests and ANOVA were used. For analyzing the differences between control versus HERV-K-specific CAR$^+$ T cell expansion, phenotype analysis, and functional assays, student's t-tests, means, standard deviations, and 95% confidence intervals (CIs) were calculated. For the metastatic melanoma model, in vivo, student's t-tests were used to analyze the significance in the flux data between the tumor and treatment group. All statistical tests were two-sided and performed using Graph Pad Prism software (GraphPad Software Inc, San Diego, Calif.). All P values less than 0.05 were considered statistically significant.

Example 6

Figure 16A:
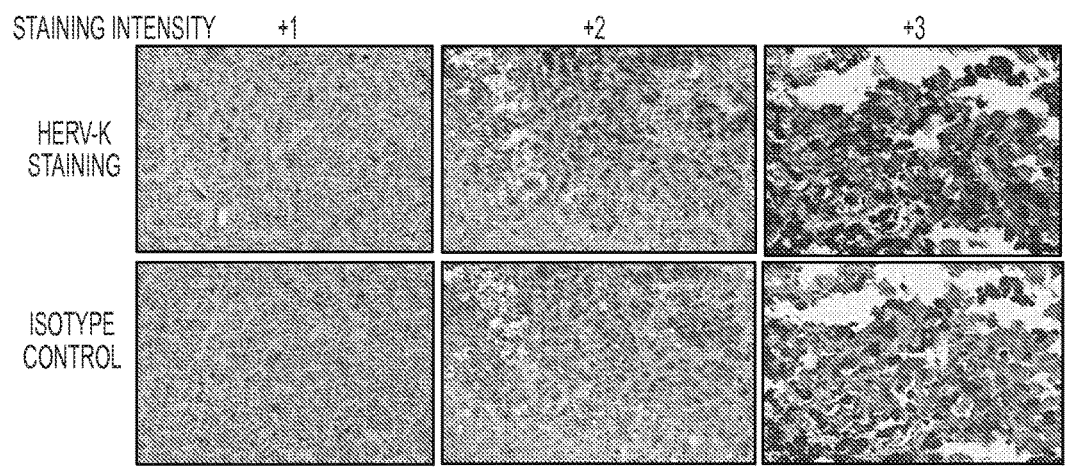
FIG. 16: (A) A representative picture of tumor cells (200×) with varying intensity (Scored 0-3) of HERV-K expression (top panel) when compared to isotype IgG2a control staining (bottom panel). (B) A picture of tumor cells (400×) showing HERV-K staining that is punctate and bordering the cell membrane (solid arrow) or more diffuse cytoplasmic staining (dotted arrow). (C) A dot plot representing H-index of each patient showed a significant difference (p<0.0267) between the benign and tumor tissues. (D) No significant difference was seen between malignant and metastatic tumor. And significant difference was seen between the benign tumor and malignant or metastatic tumor.
Figure 16B:
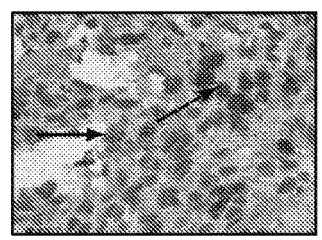
Figure 22A:
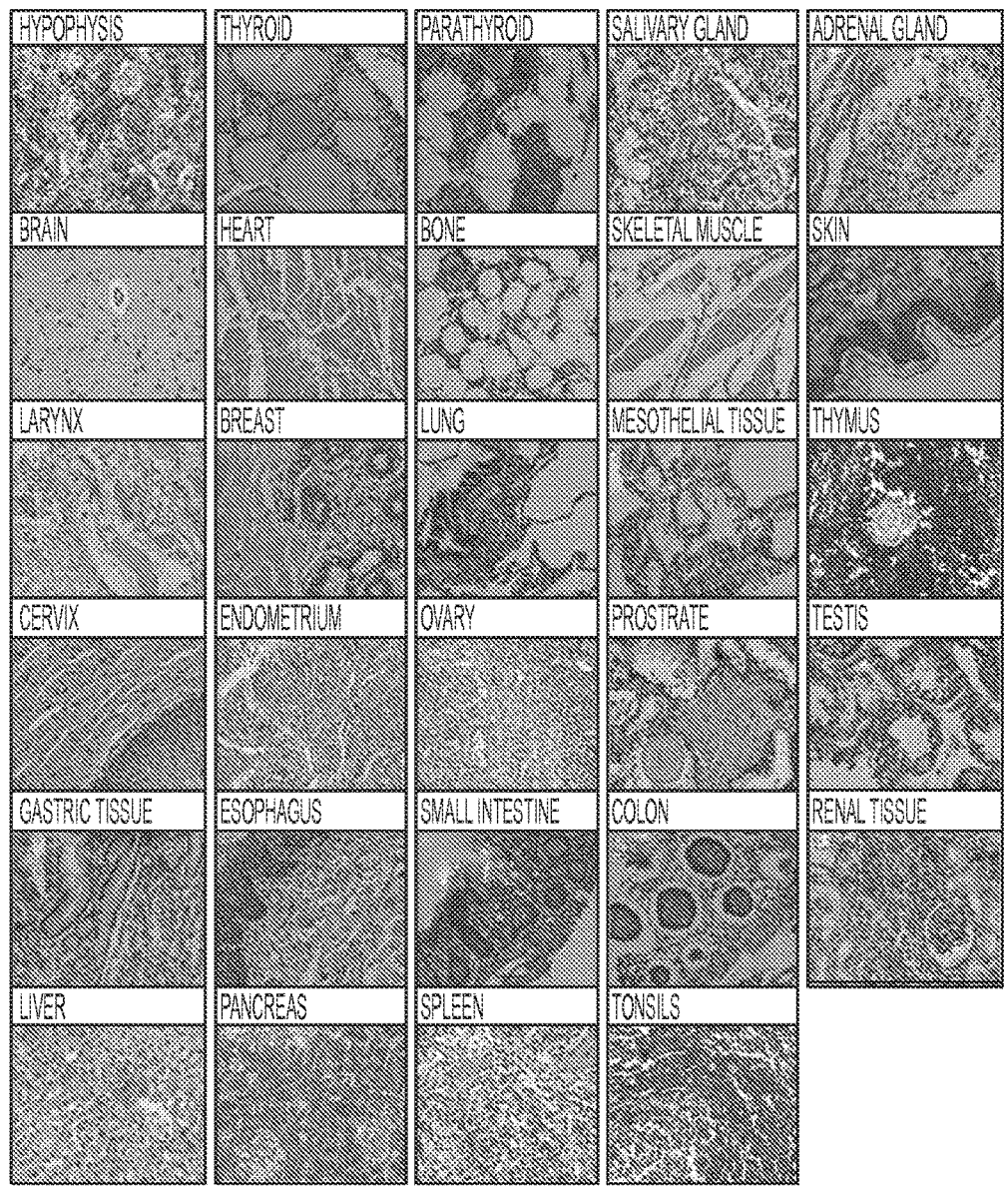
FIG. 22: (A) Representative pictures (200×) of HERV-K antigen expression on tissues sections from 29 normal organs are shown. The H-index was calculated as zero since no staining was observed in any of these tissues. (B) H-index of malignant tissue from various organs and different patient are shown in a dot plot.
Figure 22B:
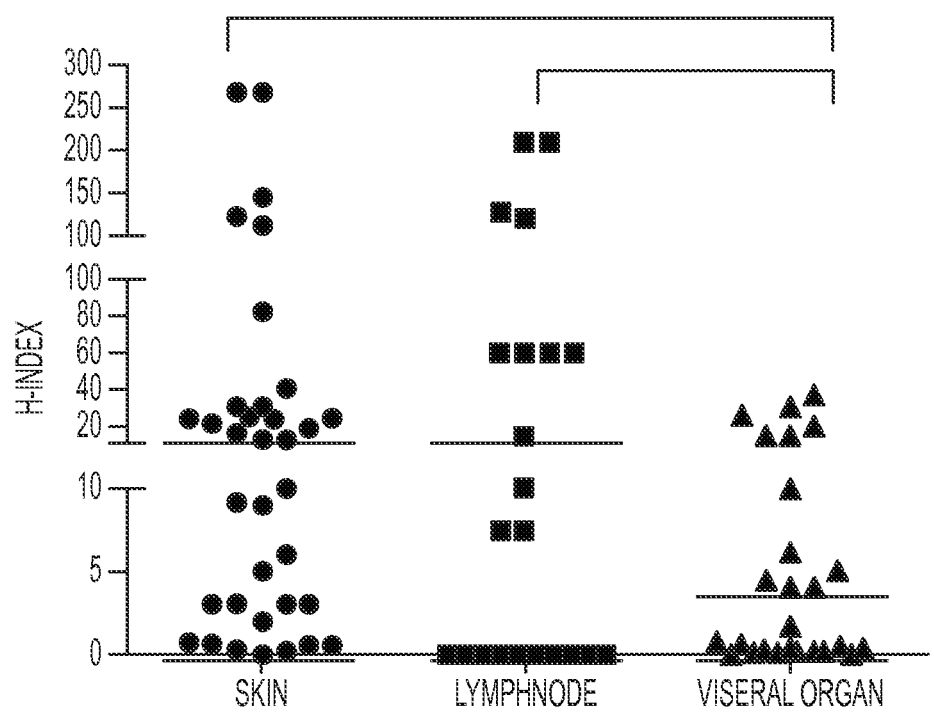

Targeting an Ancient Retrovirus Expressed in Cancers and Infections Using Adoptive T Cells Engineered to Express Chimeric Antigen Receptor Results Expression of HERV-K in melanoma patient samples. To elucidate the physiological relevance of HERV-K during melanoma invasion and metastasis in vivo, the inventors sought to assess the expression of the tumor antigen HERV-K envelope protein in biopsies obtained from patients with various stages of melanoma. Malignant tumor tissues from two hundred sixty-eight patients and benign skin and breast tissue from forty patients were analyzed using IHC. The tumor tissue staining was graded based on the percentage of tumor cells positive for HERV-K and the intensity of staining and their product was calculated to obtain the H-index. Tumor tissues showed varied level of staining intensity and were scored 0, 1, 2 or 3 (FIG. 16A) when compared to the isotype control staining on the same tissue. The antigen was expressed on the cells either in a punctuate form along the cell surface as shown with a solid arrow or as diffuse cytoplasmic staining as shown with dotted arrow (FIG. 16B). This may suggest the circulation and accumulation of the antigen onto the cell surface for the purpose of shedding the viral protein (REF). Tumor cells express significantly higher H-index of HERV-K antigen compared to benign tumor (FIG. 16C). Though there is no difference in H-index between the malignant and metastatic tumor, a significant difference can be seen between the tumors in stage I and II compared to tumors in stage III and IV (FIGS. 16D, E). In order to further show the specificity of HERV-K expression on tumor cells and not on normal cells, tissue from thirty-three types of normal organ each obtained from three normal donors were analyzed. No significant expression of HERV-K was observed in any of the normal organ tissues (FIG. 22). These findings suggest that HERV-K up-regulation specifically in tumor cells can serve as a unique target marker for immunotherapy.

Figure 17A:
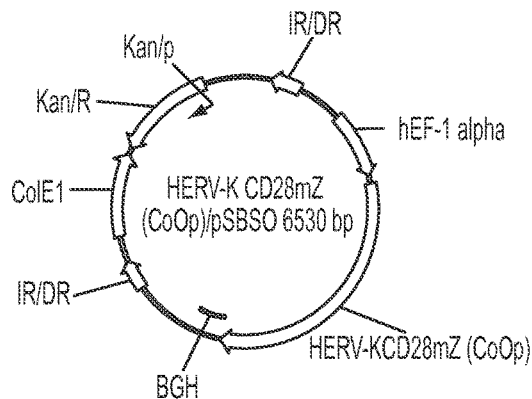
FIG. 17: (A) HERV-K-specific CAR encoding SB plasmid. (B) Flow plot representing CAR (Fc) expression on Day 1 and Day 35 of CD3$^+$ HERV-K-specific CAR$^+$ T cells. Quadrant percentages of flow plots are in upper right corner. CAR, chimeric antigen receptor. (C) No significant difference in total cell growth between the HERV-K-specific CAR+ T cells and non-specific CD-19 CAR+ T cells. (D) By Day 21 all HERV-K-specific CAR cells are CD3+ T cells. (E) The CAR integration analysis shows that the HERV-K-specific CAR+ T cells have less than 2 integrations per cell. Data represents mean of two independent experiments with 3 different donors performed in triplicate. (F) The phenotype of HERV-K-specific CAR+ T cells are CD3+CD56+ CD45RO$^{hi}$ CD45RA$^{lo}$CD27+CD62L+ T cells that produce high levels of granzyme B. All data represent average of four donors.

Propagation and Characterization of HERV-K-specific CAR$^+$ T cells. The HERV-K env-specific monoclonal antibody (mAb) was developed in mouse and the 6H5 mAb clone was found most sensitive in detecting antigen in vitro (Wang-Johanning et al., 2003). The scFv sequence of the 6H5 mAb clone was used to construct the CAR. The scFv cassette was fused to IgG4Fc region by a flexible linker, followed by the CD28 transmembrane and CD28 and CD3z intracellular domains. This was then cloned into the SB transposon vector (FIG. 17A).

To generate CAR⁺ T cells specific to HERV-K env antigen, the inventors electroporated peripheral blood mononuclear cells (PBMCs) with SB transposon along with SB11 transposase and propagated the cells on endogenously-derived HERV-K$^{+ve}$ K562 aAPC. To selectively propagate T cells with stable expression of CAR, these aAPC, which endogenously express the HERV-K antigen, were genetically modified to co-express desired T-cell co-stimulatory molecules CD86, 4-1BBL, and membrane bound IL-15 (co-expressed with enhanced green fluorescent protein, EGFP) (Singh et al., 2008). PBMCs without any transposon electroporated, grown on OKT3-loaded aAPCs under the same culture conditions served as a negative No DNA control.

Figure 17B:
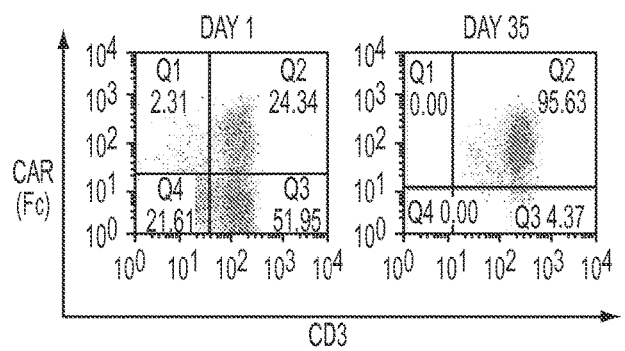
Figure 17C:
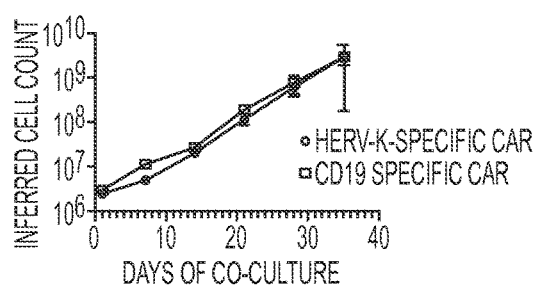
Figure 17D:
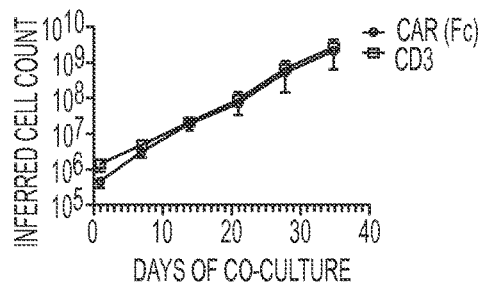
Figure 17E:
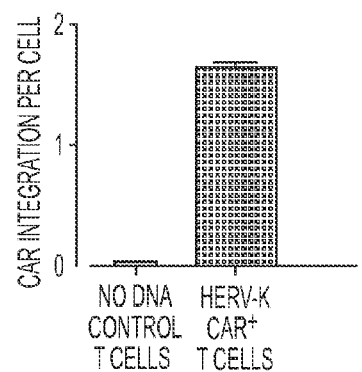
Figure 17F:
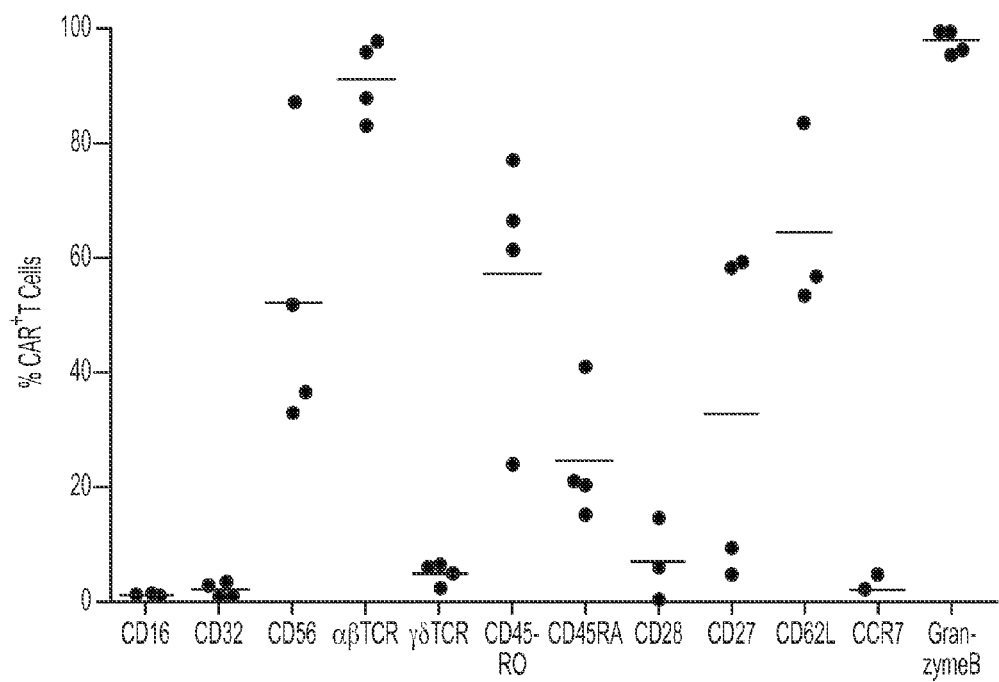
Figure 23A:
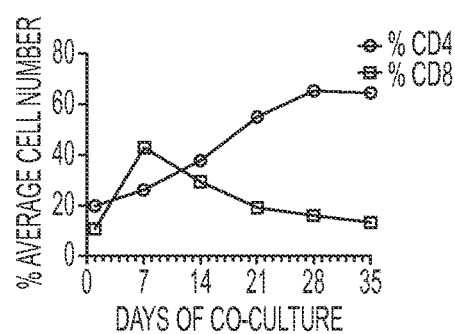
FIG. 23: (A) Growth of CD4+ versus CD8+ HERV-K-specific CAR+ T cells is shown. (B) nCounter analysis representing expression of various genes in HERV-K-specific CAR+ T cells versus No DNA control cells. Red indicates high expression while green indicates low mRNA levels. (C) Ingenuity pathway analysis of genes highly expressed in HERV-K-specific CAR+ T cells.

The expression of CAR was detected using a polyclonal Fc antibody specific for the IgG4Fc region. The CAR⁺ T cells were stained with Fc antibody every seventh day before supplementing the culture with irradiated aAPCs. The flow data revealed that 95% of T cells express CAR on its surface, which could be detected for up to 35 days of culture (FIG. 17B). No significant difference was seen in the growth kinetics of HERV-K-specific CAR⁺ T cells when compared to No DNA control cells, and all the HERV-K-specific CAR⁺ T cells were CD3⁺ T cells by day 14 of culture (FIGS. 17C, D). The percent average number of CAR⁺ CD4 increases while CAR⁺ CD8 cells decreases along the culture period (FIG. 23A). Real-time PCR analysis on the genomic DNA of HERV-K-specific CAR⁺ T cells compared to No DNA control cells showed that there are less than two integration of the CAR in the CAR⁺ T cell genome (FIG. 17D). The cultured CAR⁺ T cells have an effector memory phenotype, which includes CD3⁺ CD56⁺CD45RO⁺ TCRαβ⁺ CD27$^{neg}$CCR7$^{neg}$ cells with substantial lytic potential observed by Granzyme B levels (FIG. 17F).

Figure 23B:
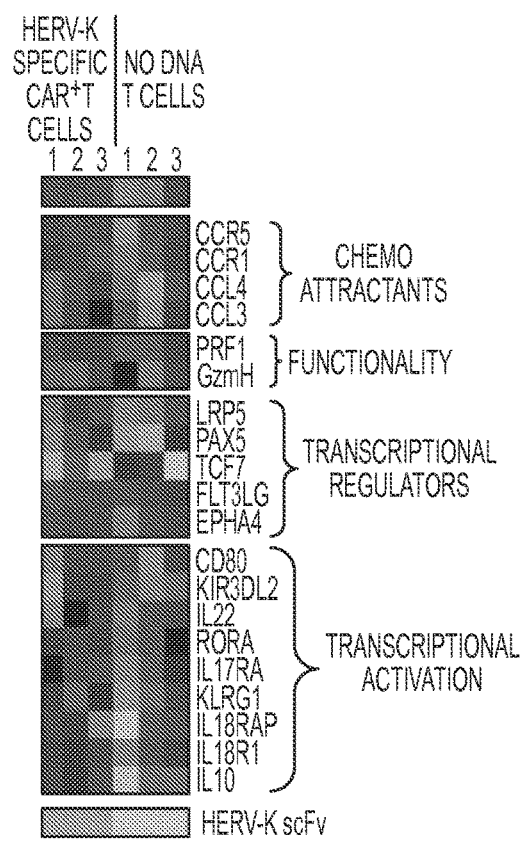
Figure 23C:
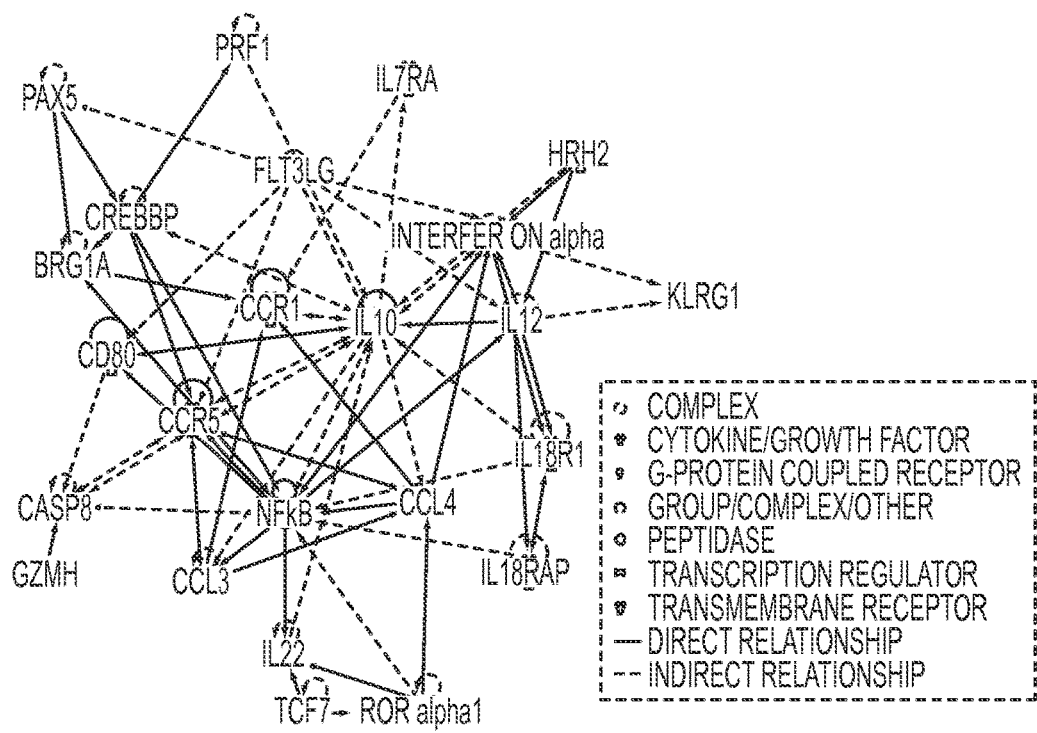

The mRNA levels of HERV-K-specific CAR⁺ T cells from three normal donors were measured and compared to mRNA levels from No DNA control T cells on Day 28 of culture using nCounter analysis. HERV-K-specific CAR⁺ T cells had significantly higher levels of chemoattractants, transcriptional regulators and activators. Increased levels of Perforin1 and Granzyme H in CAR⁺ T cells shows the higher lytic potential of these cells (FIG. 23B). Ingenuity Pathway Analysis (IPA) ($p<0.05$) suggested several of these upregulated genes in HERV-K-specific CAR⁺ T cells were involved in NF-κB activation. The chemoattractant and the cytokines were involved in IL-10, IFN-γ and IL-12 regulation (FIG. 23C). These data strengthen the previous observation that HERV-K-specific CAR⁺ T cells have a central effector phenotype.

Figure 18A:
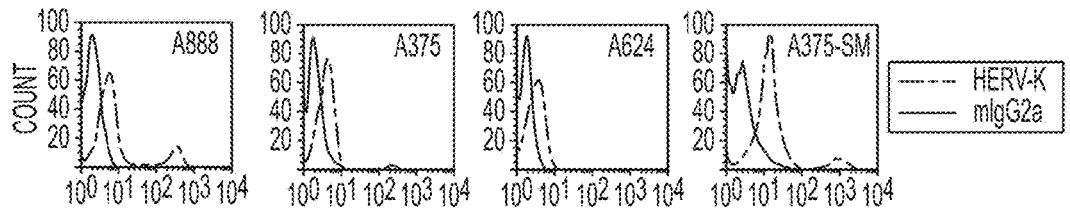
FIG. 18: (A) A histogram representation on HERV-K antigen expression (in red) on tumor cell surface compared to isotype control (in blue). (B) A standard 4-h CRA of melanoma tumor targets with varying dilution of HERV-K-specific CAR+ T cells (in solid line) compared to No DNA control T cells (in dotted lines). Data are mean±SD from four healthy donors (average of triplicate measurements for each donor) that were pooled from two independent experiments. Two-way ANOVA with Bonferroni post-test was performed on (B) and (C) between the HERV-K-specific CAR+ T cells and No DNA control cells. CAR, chimeric antigen receptor; CRA, chromium release assay; E:T, effector to target ratio. (D) IFN-γ production by CAR+ T cells upon incubation with targets. PMA-ionomycin is used as a positive control.
Figure 18B:
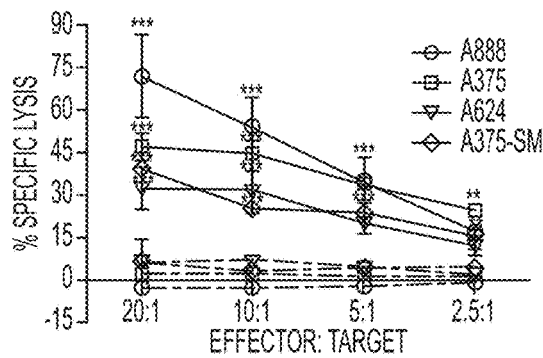
Figure 24:
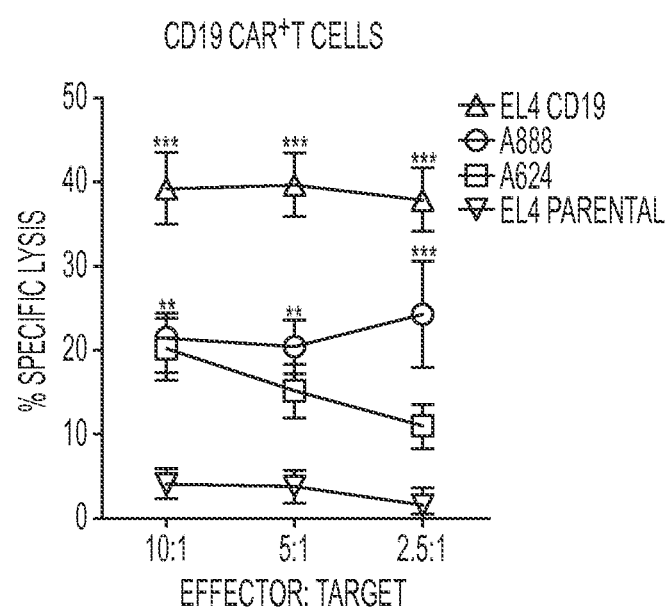
FIG. 24: A 4 h standard CRA was performed with melanoma and CD19-specific tumor targets and CD19 CAR+ T cells. All data represent two independent experiments performed with an average of 6 donors and analyzed using 2-way ANOVA with Bonferroni post-test.

Characterization of HERV-K CAR⁺ T cell functionality. The antigen expression on melanoma cell lines, such as A888, A375, A375-SM, A624 were analyzed using the monoclonal 6H5 antibody directed against the HERV-K env protein (FIG. 18A). The HERV-K antigen expression on melanoma cells were compared with the isotype control (mouse IgG2a). In order to analyze the functionality of HERV-K-specific CAR⁺ T cells, HERV-K⁺ tumor cells were pulsed with radioactive chromium and cultured with varying ratios of HERV-K-specific CAR⁺ T cells. CRA was performed with no DNA control as a negative control. Significantly higher levels of HERV-K⁺ tumor cell lysis were observed with HERV-K-specific CAR⁺ T cells when compared to no DNA control T cells (FIG. 18B). An unrelated CAR, such as CD19-specific CAR⁺ T cells were also used to perform CRA and basal levels of non-specific killing were observed with HERV-K antigen positive tumor cells when compared to CD19 antigen positive tumor cells, such as EL-4 cells bearing CD19 antigen (FIG. 24A).

Figure 18C:
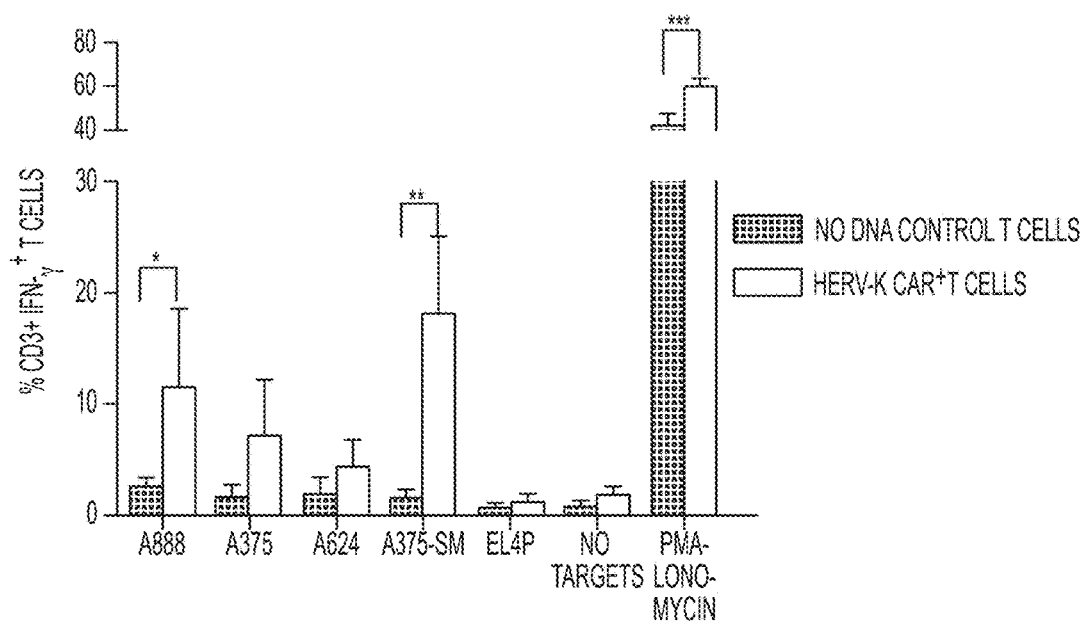

In order to further prove the functionality of these HERV-K-specific CAR⁺ T cells, a four-hour IFN-γ release was performed. Melanoma tumor targets were co-cultured with HERV-K-specific CAR⁺ T cells or No DNA control T cells at a 1:10 ratio and intracellular cytokine levels were analyzed using flow cytometry. T cells cultured with PMA-Ionomycin served as a positive control. The HERV-K-specific CAR⁺ T cells showed higher levels of IFN-γ release compared to the no DNA control T cells (FIG. 18C) and this result correlates with the CRA.

Figure 19A:
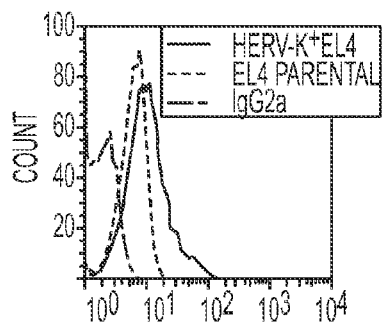
FIG. 19: Specificity of HERV-K-specific CAR+ T cells. (A) Histogram of EL4 cells artificially expressing HERV-K antigen (in black) was plotted along with HERV-K$^{neg}$ EL4 parental (blue) and isotype control staining (orange). (B) A four hour CRA showed a significant increase (p<0.001) in killing EL4 cells expressing the antigen compared to the parental by the HERV-K-specific CAR+ T cells at varying E:T ratios. (C) Immunoblot assay was performed to show HERV-K env-specific shRNA-mediated knockdown in A888 cells when compared to A888 parent or A888 treated with scrambled shRNA. Lower panel shows actin protein expression as control. (D) CRA of HERV-K-specific CAR+ T cells with the A888 HERV-K KD cells, A888 parental (A888P) and A888 scrambled control (A888 sera) showed significant antigen-specific killing by the T cells. All data represent the mean of two independent experiments by three donors preformed in triplicate. Two-way ANOVA with Bonferroni post-test was used for (B) to compare EL4 parental to HERV-K+ EL4 and one-way ANOVA with Newman-Keuls multiple comparison test for (C) to compare A888KD to A888 P and A888 sera.
Figure 19B:
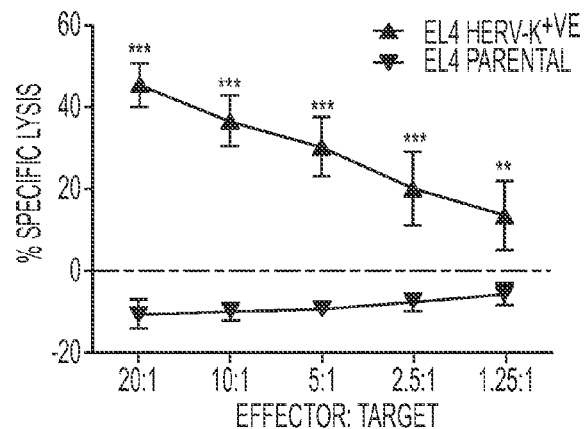
Figure 25:
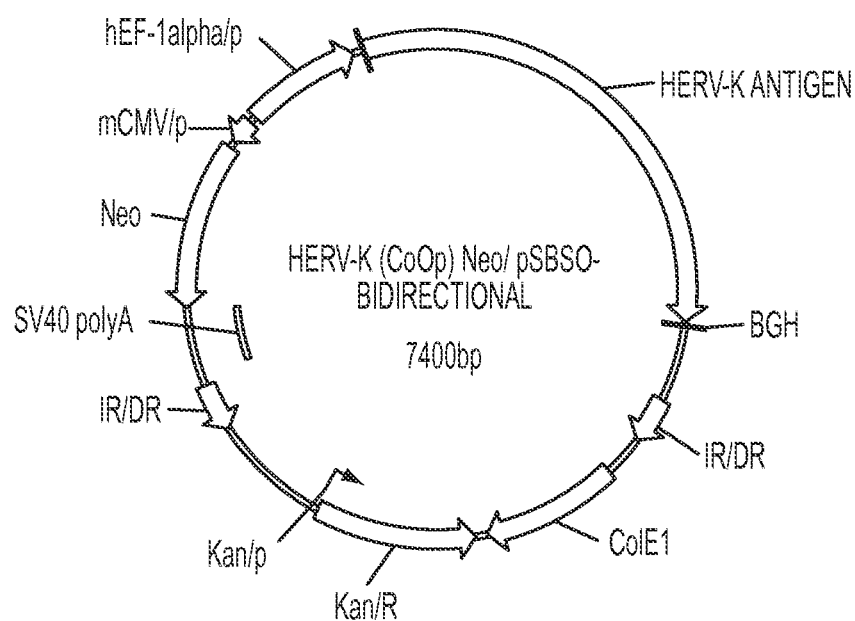
FIG. 25: Bi-directional SB plasmid encoding HERV-K antigen under hEF-1α promoter and neomycin resistance gene under CMV promoter.

Specificity of HERV-K-Specific CAR⁺ T cells. To show the specificity of the HER-K-specific CAR, HERV-K$^{neg}$ EL-4 cells were electroporated with bi-directional SB vector encoding HERV-K antigen under the hEF-1α promoter and neomycin resistance under the CMV promoter (FIG. 25A). The EL-4 HERV-K$^{+ve}$ cells were then single cell sorted and grown in the presence of mammalian selection marker, neomycin, to obtain a pure HERV-K env-expressing population. Interestingly, these cells lost the HERV-K antigen expression within ten days of culture due post-translational modification and proteolytic cleavage. A four-hour CRA was performed on these EL-4 HERV-K$^{+ve}$ cells within ten days of sorting. Chromium pulsed EL-4 HERV-K$^{+ve}$ cells and HERV-K$^{neg}$ EL4 parental cells were co-cultured with varying concentrations of HERV-K-specific CAR⁺ T cells and graded tumor-specific lysis was observed in an antigen-specific manner (FIG. 19B).

Figure 19C:
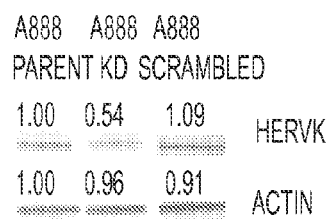
Figure 19D:
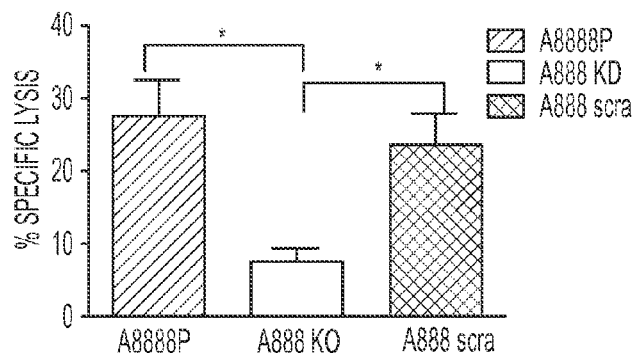
Figure 20A:
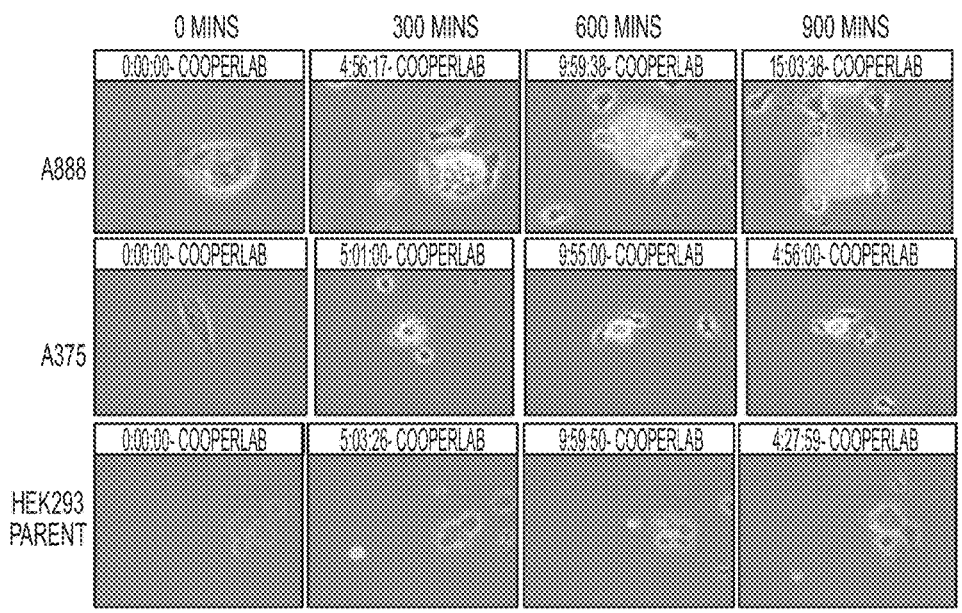
FIG. 20: To determine the activity of HERV-K-specific CAR+ T cells over 15 h period target and effector cells were plated in 1:5 ratio with Sytox® (Invitrogen, dead cell stain) in the media. Fifty images of each target with effector cells were recorded every 7 min for this period. (A) Picture representing HERV-K+ melanoma cells (A888 and A375) and HERV-Kneg control (HEK293 parent) cells with CAR+ T cells are various time points. Cells that turned green were recorded as dead cells and the intensity of the fluorescence was measured. (B, C, D) Represents the mean fluorescent intensity of the target cell. Upper lines represent the dead cells while the lower lines represent the basal intensity of live cells. (E) A plot representing a significant difference (*p<0.05) in the mean fluorescent intensity at 15 h time point compared to HEK293 parental cells. Data represents average of 2 independent experiments with 50 images each. A one-way ANOVA with Tukey's post-test was performed.
Figure 20B:
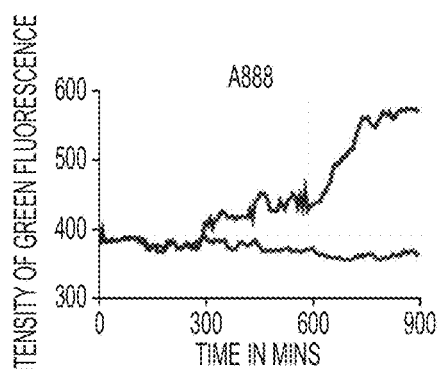
Figure 20C:
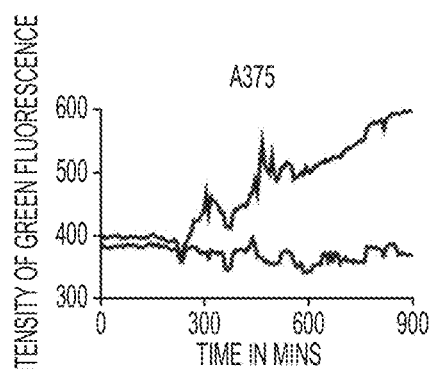
Figure 20D:
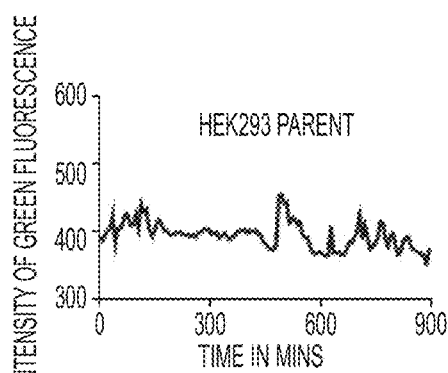
Figure 20E:
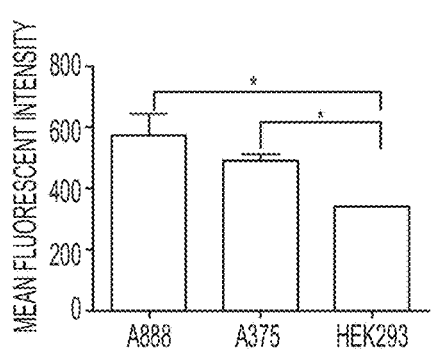

To further prove the specificity, HERV-K env antigen was knocked down in A888 melanoma cells using shRNA lentivirus. An immunoblot analysis showed about 50% knockdown in the HERV-K protein level compared to the A888 parent and control scrambled shRNA (FIG. 19C). A CRA of HERV-K-specific CAR⁺ T cells with the HERV-K knockdown cells, A888 parental, and A888-with scrambled shRNA showed significant reduction in killing with HERV-K knockdown compared to the parent and control tumor cells (FIG. 19D).

Figure 26:
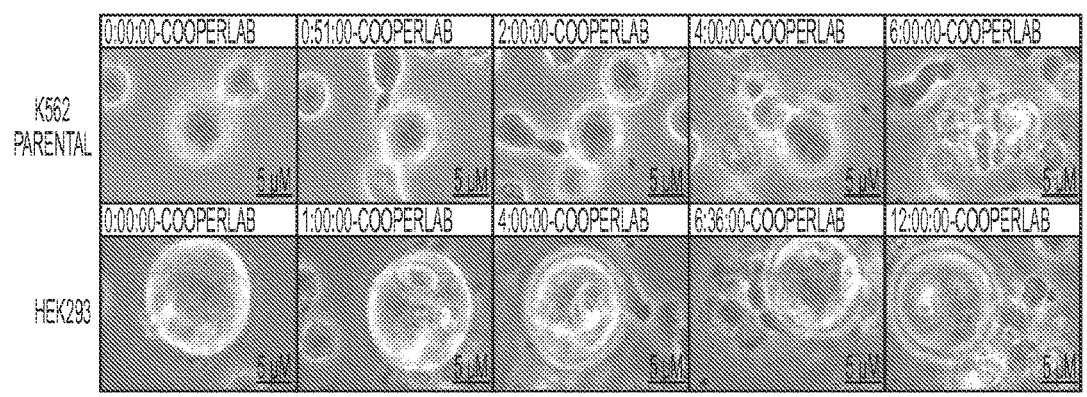
FIG. 26: Figure representing HERV-K-specific CAR (in green) engagement with HERV-K antigen (in red) on tumor cell surface.

Time lapse imaging was performed to visualize and quantify the time taken for CAR⁺ T cells to kill the tumor target and the number of tumor cells killed over a period of 15 h. The tumor cells and T cells were cultured at a ratio of 1:5 in the presence of Sytox®, which turns cells green when the cell membrane is damaged. As the melanoma target A888 and A375 cells were killed by the HERV-K-specific CAR⁺ T cells, a spike in green florescence was reported around 5 h, which gradually increased over a 15 h time period. No killing was observed with HERVK-K$^{neg}$ HEK293 parental targets. About 30% of A888 cells and 35% of A375 cells were killed by CAR⁺ T cells over a period of 15 h. To visualize the antigen-specific CAR engagement, K562 cells were stained positive for HERV-K antigen in red and HERV-K-specific CAR was stained for Fc in green. The overlap of CAR and antigen was seen over a period of 5 h after which the antibody-bound antigen and CAR were internalized by the cells (FIG. 26A).

Tumor killing ability of HERV-K-Specific CAR⁺ T cells in vivo. PBMCs were double electroporated with SB vectors encoding HERV-K-specific CAR and myc-FFLuc with SB11 transpsosase. The SB vector with the myc-ffLuc gene has a neomycin resistance gene attached through a linker (FIG. 27A). These HERV-K-specific CAR-ffLuc⁺ T cells had similar growth kinetics as the HERV-K-specific-CAR⁺ T cells and their tumor killing ability and specificity was comparable (FIGS. 27B, C).

Figure 21A:
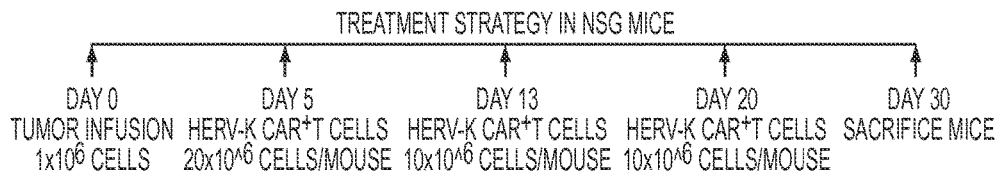
FIG. 21: In vivo antitumor activity of HERV-K-specific CAR+ T cells. (A) Schematic of experiment. (B) Representative images of mice from day 3 to day 25. (C) BLI derived from mKate+rRLuc+HERV-K+ A375-SM tumor and (D) postmortem analysis of liver tissues with the red dots representing mKate+tumor metastatic foci. Data are mean±SD (n=5-6 mice per group). Statistics performed with (in D) two-way ANOVA with Bonferroni's post-tests between treated and untreated mice. P<0.01 and *P<0.001. ANOVA, analysis of variance; BLI, bioluminescent imaging; CAR, chimeric antigen receptor; IL, interleukin.
Figure 21B:
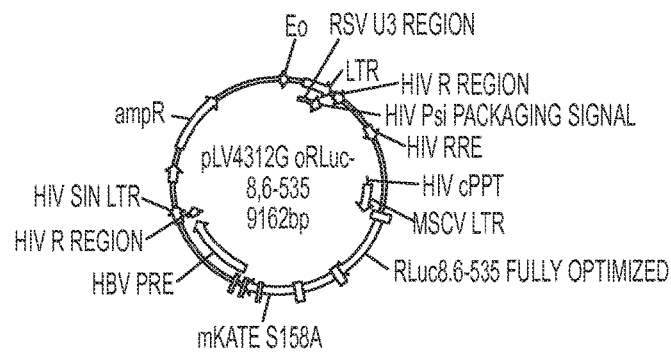
Figure 21C:
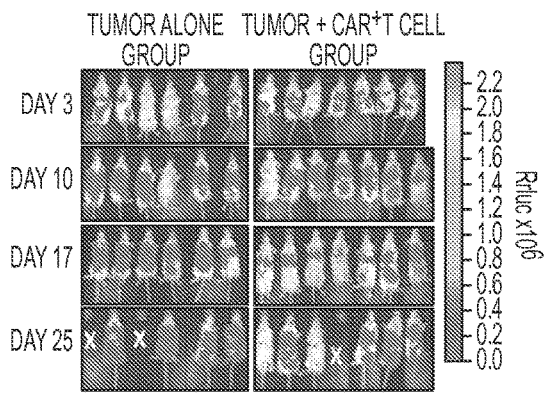
Figure 21D:
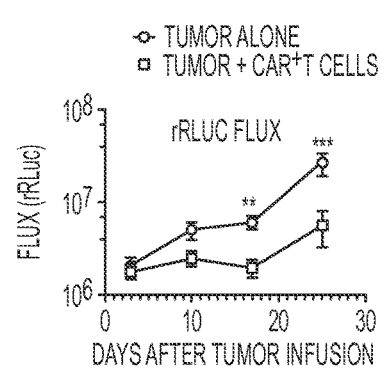
Figure 21E:
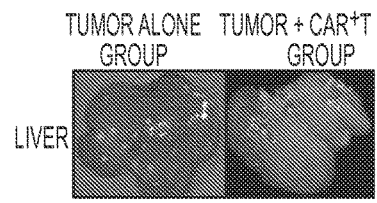

A metastatic melanoma model in which the A375-super metastatic (A375-SM) cell line was infused though the tail vein of NSG mice was developed. These cells engrafted in the lungs and metastasized to the liver. In order to visualize the reduction in tumor mass non-invasively, the tumor cells were transduced with a lentiviral vector bearing the mKate-rRLuc gene and sorted using mKate marker to obtain a pure population of the cells (FIG. 21A). After a week of tumor cell engraftment, 20 million CAR+ T cells were infused intravenously on days 8, 15, and 22 days along with IL-2 (i.p.) twice a week for three weeks. Bioluminescence imaging (BLI) was used to assess the rRLuc activity in each group of mice. The mouse group with tumor cells alone had significantly higher luciferase activity by day 25 compared to the mouse group with tumor cells that received the HERV-K CAR+ T cells (FIGS. 21A, B). Also mice with tumor alone became moribund by day 28 due to the high metastasis of the tumor to the liver while the mouse group receiving the CAR+ T cells exhibited a healthy appetite and activity. Ex vivo imaging of mKate on tumor cells showed that the tumor alone mice had substantially more tumor colonies on the liver than the treatment group (FIG. 21C). Pathological examination proved this observation where the tumor group had significantly higher metastatic colonies in the liver compared to the treatment group suggesting the role of HERV-K CAR+ T cells in reducing tumor growth and metastasis (FIG. 21D).

Discussion. These results show that HERV-K-specific CAR+ T cells were able to successfully target a viral glycoprotein and kill HERV-K+ tumor cells in an antigen-specific manner in vitro and reduce the melanoma tumor growth and metastasis in vivo.

HERV-K env is markedly up-regulated during melanoma metastasis and exclusively present on tumor cells and not on adjacent normal melanocytes. In melanoma, HERV-K env protein is associated with MEK-ERK and p16INK4A-CDK4 pathway activation relating to tumor progression (Li et al., 2010). HERV-K molecular mimicry also results in reduced glutathione peroxidase levels resulting in increased reactive oxygen species in tissue leading to melanomogenesis (Krone et al., 2005). Abnormal levels of HERV-K env expression appear to be a trigger factor involved in melanoma onset resulting in morphological and cellular modifications resulting in tumor progression (Serafino et al., 2009). Modulation of viral transcription of HERV-K resulted in increased inflammation and morphological differentiation in melanoma cells (Sciamanna et al., 2005). The tissue microarray represents increased levels of antigen expression correlating with melanoma progression while the normal human tissue has a basal level or an absence of HERV-K expression.

The immunogenic nature of melanoma makes it an attractive model and target to develop potent T cell-based therapy. One of the major limitations on T cell-based therapy is the HLA-based restriction on TCR, which limits antigen recognition (Garrido et al., 1997. Genetically modifying T cells to express tumor antigen specific receptor circumvents this restriction and confers non-HLA-based antigen recognition (Gross et al., 1989). The T cell modifications can be brought about by using either viral or non-viral vectors. The Sleeping Beauty vector is a non-viral approach to introduce genes into T cells. One of the main advantages of the Sleeping Beauty system over other viral transduction methods is that it is genetically safe, efficient, and less expensive than retroviral transduction (Maiti et al., 2013). Culturing these CAR+ T cells with IL-2 and IL-21 yields enough cells for infusion purposes. This has led to preliminary clinical trials using CD19 CAR+ T cells against B-lineage malignancies. HERV-K-specific CAR+ T cells were grown in a similar manner to the clinical-grade CD19 CAR+ T cells. These HERV-K-specific CAR+ T cells were mainly of an effector memory phenotype, which are well adapted to target and kill tumor cells.

Multiple factors, such as cytokines, hormones and chemicals, are known to regulate HERV-K levels during cancer (Taruscio and Mantovani, 2004). The HERV-K env antigen is known to circulate between the cell membrane and cytoplasm and also bud off from the cell surface in certain tumor conditions. Hence, using adoptive T cell therapy can be a favorable treatment strategy that only requires transient antigen expression on the cell surface.

HERV-K env antigen is also found associated with breast cancer, ovarian cancer, prostate cancer, lymphoma, teratocarcinoma, autoimmune diseases, such as multiple sclerosis, and infectious diseases, such as HIV (Wang-Johanning et al., 2003; Contreras-Galindo et al., 2008; Jones et al., 2012; Ono, 1986; Wang-Johanning et al., 2007). Thus, targeting the env antigen using adoptive T cell therapy can be a treatment option for multiple disease conditions. Consistent with this hypothesis, HERV-K env can be successfully and selectively targeted by HERV-K CAR+ T cells. Infusing these genetically modified CAR+ T cells in vivo was associated with tumor regression and reduced metastasis showing the antitumor activity of these cells.

Example 7

Figure 28A:
FIG. 28A-B: Schematics of mIL15. A) The mIL15 construct flanked by inverted repeats which are components of the Sleeping Beauty expression plasmid. The mIL15 mutein is a fusion of IL-15 with the full-length IL-15Rα by a flexible serine-glycine linker. B) A schematic representing the expressed protein structure of mIL15.
Figure 28B:
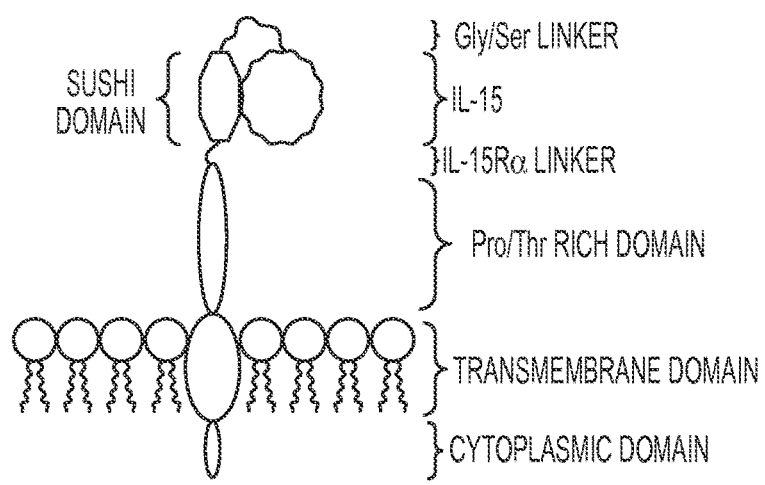
Figure 29A:
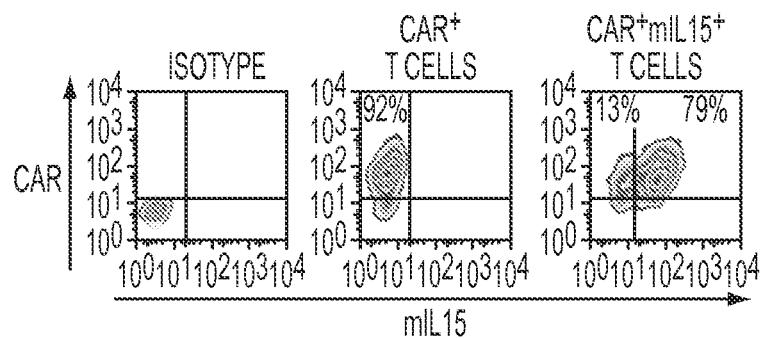
FIGS. 29A-B: CAR and mIL15 expression in genetically modified T cells after ex vivo expansion on aAPC after five stimulation cycles. A) Expression of a representative sample of five donors. B) Expression of the denoted marker (CAR and/or mIL15) in genetically modified T cells.
Figure 29B:
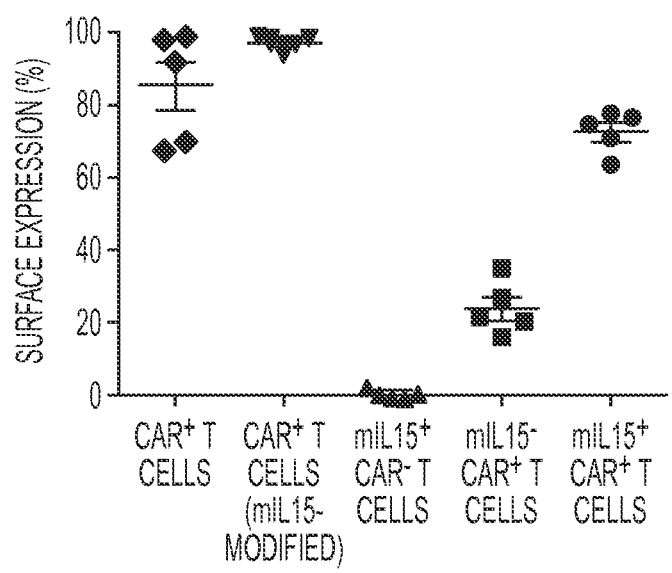

Using Membrane-Bound Cytokine(s) to Generate T Cells with Long-Lived In Vivo Potential for Use in Immunotherapy of Minimal Residual Disease Generation and Expression of mIL15. The mIL15 construct (FIG. 28) fuses the IL-15 cDNA sequence (NM_000585.4) to the full length IL-15Rα (NM_002189.3) with a serine-glycine linker. The signal peptides for IL-15 and IL-15Rα were omitted and the IgE signal peptide (gb|AAB59424.1) was used for the mIL15 construct. This construct will produce an IL-15 that is membrane-bound, but also presented in the context of IL-15Rα which is akin to the trans-presentation model described above. The DNA plasmids were synthesized by GeneArt (Regensburg, Germany) and subsequently subcloned into a Sleeping Beauty plasmid (a non-viral gene transfer method). Primary human T cells were co-electroporated with a CAR plasmid (specific for CD19), with or without the mIL15 plasmid, and the SB-11 transposon. Propagation and expansion of the genetically modified T cells was achieved by weekly stimulation a CD19+ K562 artificial antigen presenting cell (aAPC) variant expressing 41BBL and CD86 co-stimulatory molecules. The CAR used is a 2nd generation CAR containing CD3ζ and CD28 signaling cytoplasmic domains. The presence of CD19 on the aAPC allows for the selective outgrowth of antigen-specific T cells while the costimulatory molecules improve in vitro expansion. The mIL15 molecule can be stably co-expressed with the CAR by the modified T cells and the co-expressing T cells represent the bulk of population (FIG. 29). Additionally, total CAR-expression in the modified T cells reaches greater than 90% for the mIL15-CAR-modified T cells (FIG. 29).

Figure 30:
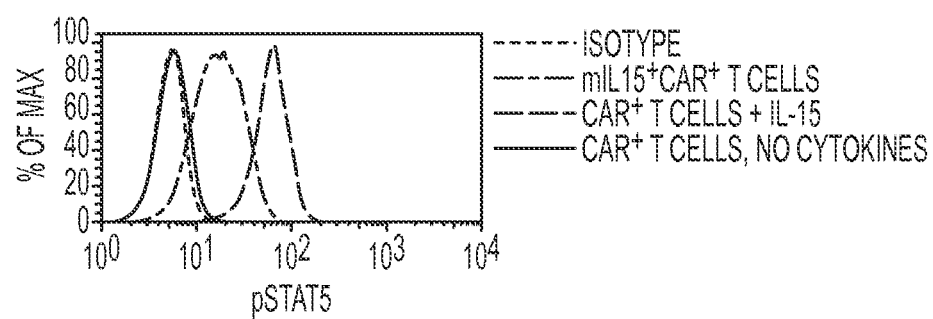
FIG. 30: Validation of the functionality of mIL15 via phosflow of pSTAT5. A five hour incubation of cells in serum and cytokine-free conditions, unless otherwise noted, to obtain basal and IL-15-mediated phosphorylation. Representative plot (n=6).

Functionality of mIL15. IL-15 receptor complex signaling primarily induces phosphorylation of signal transducer and activator of transcription 5. By looking at phosphorylated STAT5 (pSTAT5) using phosflow, it can be determined whether mIL15 is capable of inducing the cytokine signaling pathway. The pSTAT5 levels were elevated in CAR$^+$ T cells having had cytokine supplementation with these levels abrogated under serum and cytokine starvation. Under starvation conditions, pSTAT5 levels in mIL15$^+$CAR$^+$ T cells were maintained (FIG. 30). These data demonstrate that mIL15 is functional and activates the pSTAT5 portion of the cytokine signaling pathway.

Figure 31:
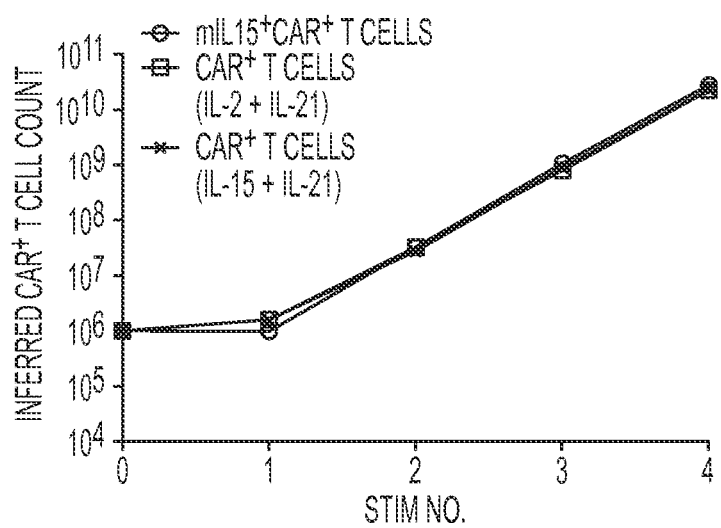
FIG. 31: Inferred counts of CAR+ T cells with or without co-expression of mIL15 after four stimulation cycles on aAPC. CAR+ T cells were cultured with soluble IL-2 and IL-21 (the standard culture condition) or IL-15 and IL-21 (the soluble cytokine control), and mIL15+CAR+ T cells with IL-21. Data are mean±SD, n=4.

Propagation of clinically significant numbers of mIL15$^+$ CAR$^+$ T Cells. In redirecting T cell specificity with the CAR, the focus in ex vivo expansion is on driving the CAR$^+$ T cell population, in this case CAR with or without mIL15. The standard CAR$^+$ T cells are grown with soluble IL-2 and IL-21 while mIL15$^+$CAR$^+$ T cells were given soluble IL-21 to capitalize on a reported synergy between IL-15 and IL-21. The mIL15$^+$CAR$^+$ T cells supplemented with IL-21 demonstrated comparable expansion to the standard CAR$^+$ T cells, as well as the control CAR$^+$ T cells given IL-15 and IL-21 (P=0.53, 2-way ANOVA; FIG. 31). The ex vivo expansion of mIL15$^+$CAR$^+$ T cells produces clinically significant numbers of cells.

Figure 32A:
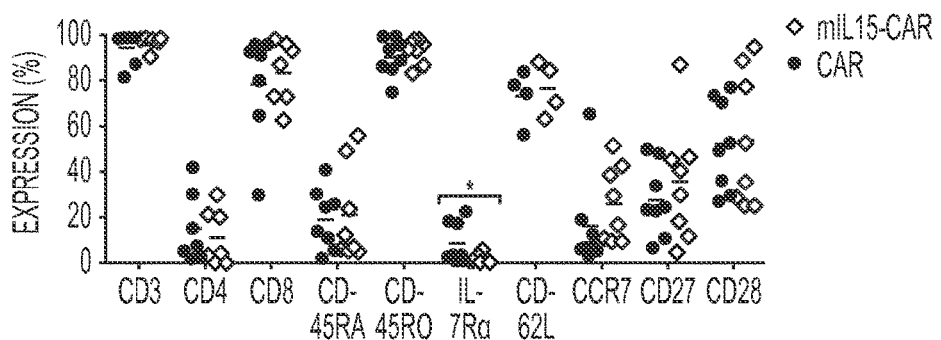
FIGS. 32A-B: Phenotype and specific lysis capacity of ex vivo expanded mIL15+CAR+ T cells. A) Percent surface expression of certain T cell, activation, and differentiation-associated markers after 4 stimulations on aAPC. Horizontal line indicates the mean value. *P=0.047, paired t test, n>4. B) CAR+ T cell (left panel) and mIL15+CAR+ T cell (right panel) specific lysis after 5 stimulations on aAPC of CD19+ or CD19$^{neg}$ targets from a four-hour chromium release assay. Data are represented as mean±SD, n=3.
Figure 32B:
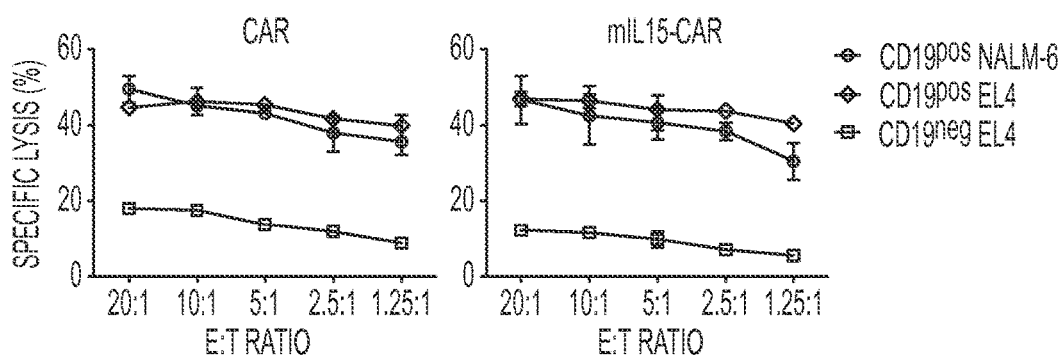

Assessing the phenotype and functionality of mIL15$^+$ CAR$^+$ T cells. The phenotype of the ex vivo expanded mIL15$^+$CAR$^+$ T cells are largely similar to the CAR$^+$ T cells except for IL-7Ra expression. The general phenotype of the cells, which at this time point represents the infusion product, are predominantly CD8$^+$ (cytotoxic) T cells with moderate to high expression of the activation markers CD45RO and CD25. There were variable low to moderate levels of the expression of T cell memory-associated markers (CD62L, CCR7, CD27, and CD28) (FIG. 32A) for both T cell groups. After ex vivo expansion of the modified T cells, it is necessary for the T cells to retain their redirected T cell specificity and lytic function. A chromium release assay was conducted to assess the function of the T cells in the expansion product. CD19$^+$ and CD19$^-$ EL4 targets were plated with the modified T cells at varying effector to target ratios. Specific lysis of CD19$^+$ tumor targets was demonstrated across all effector to target ratios by both mIL15$^+$ CAR$^+$ T cells and CAR$^+$ T cells (P<0.001, 2-way ANOVA, n=3) and did not differ from one another (P >0.05, 2-way ANOVA). CD19$^+$ target lysis by mIL15$^+$CAR$^+$ T cells was specific and significantly different from background lysis of CD19$^-$ targets (P<0.001, 2-way ANOVA) (FIG. 32B). The mIL15$^+$CAR$^+$ T cells retained their redirected specificity and lytic capacity.

Figure 33A:
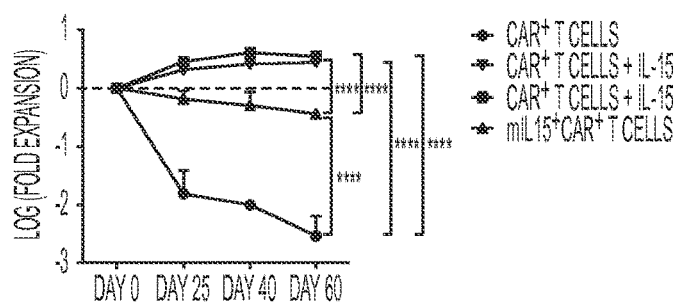
FIG. 33: In vitro long-term persistence of mIL15+CAR+ T cells that remain functionally competent and resistant to AICD. A) Ex vivo expanded mIL15+/−CAR+ T cells after four aAPC stimulations underwent withdrawal from antigen re-stimulation to assess long-term in vitro persistence and observe expansion kinetics over 60+ days. The mIL15+CAR+ T cells did not receive any exogenous cytokine support, whereas CAR+ T cells received no cytokines, IL-2, or IL-15. Data are log of mean±SD, ****P<0.0001, RM ANOVA, n=3. B) The surviving T cells at greater than 75 days post-antigen exposure were tested for antigen responsiveness by incubation with: no target, CD19+/− EL4, CD19+ Nalm-6, or LAC for 6 hours. Analysis was by flow cytometry of IFNγ intracellular staining. Representative flow plots shown, n=3. C) The surviving T cells after 75 days post-withdrawal were tested stimulated 1:1 with aAPC as previously described and media was supplemented with the cytokine (if any) used during the withdrawal culture maintenance plus the addition of IL-21. After eight days, T cells were stained with Annexin V to determine the proportion of live versus apoptotic/necrotic cells in the stimulated culture. Representative flow plot shown, n=3.
Figures 33B, 33C:
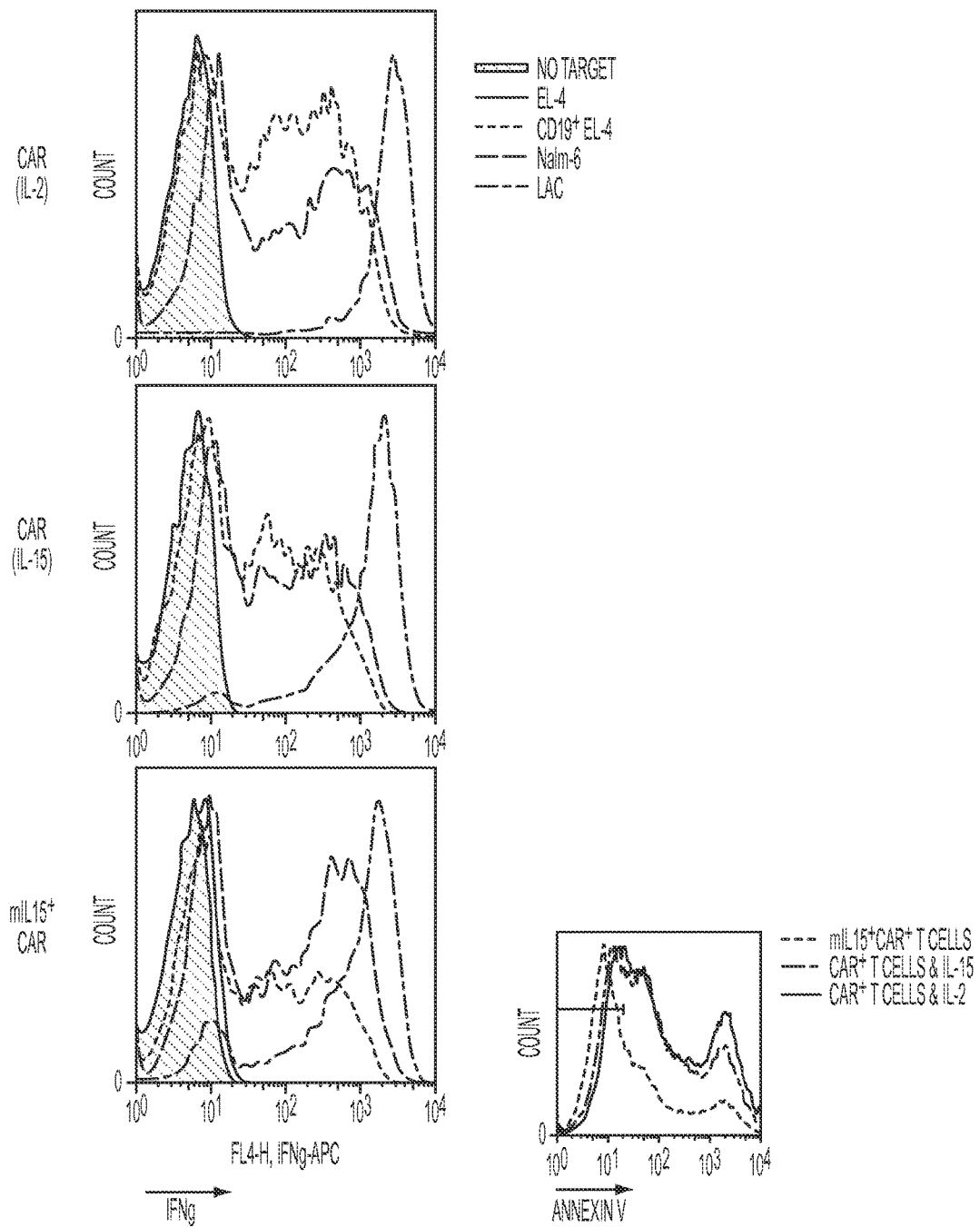

Specific mIL15$^+$CAR$^+$ T cell subsets persist long-term in vitro and Remain Functional. To assess long-term in vitro persistence, four aAPC stimulation expanded mIL15$^{+/-}$ CAR$^+$ T cells were cultured long-term without further antigen re-stimulation. CAR$^+$ T cells received IL-2, IL-15, or no cytokine supplementation while mIL15$^+$CAR$^+$ T cells did not receive exogenous cytokines. As anticipated, CAR$^+$ T cells receiving no cytokine supplementation did not persist. The mIL15$^+$CAR$^+$ T cells as well as CAR$^+$ T cells receiving IL-2 or IL-15 had significantly greater relative fold expansion than the unsupplemented CAR$^+$ T cells (P<0.0001, repeated measures ANOVA, n=3; FIG. 33A). The maintenance of mIL15$^+$CAR$^+$ T cell relative expansion near zero also suggests that these modified cells are not growing in an unrestricted manner. To be a benefit for the clinical application, CAR$^+$ T cells must remain responsive to antigen. Hence, these T cells at 75+ days from antigen encounter were challenged with: no target, CD19$^-$ EL-4, CD19$^+$ EL-4, CD19$^+$ Nalm-6 (a human leukemia cell line), or lymphocyte activating cocktail (LAC) and interferon γ (IFNg) production was assessed by intracellular cytokine staining after 6 hours incubation with the targets. Similarly to the CAR$^+$ T cells receiving either IL-2 or IL-15, the mIL15$^+$CAR$^+$ T cells also produced IFNg in response to CD19$^+$ targets and the LAC (FIG. 33B). In another assay, these 75-day withdrawal T cells were stimulated with aAPC and supplemented with IL-21. Thus, CAR$^+$ T cells cultured with IL-2 now had IL-2 and IL-21 provided, the IL-15 culture T cells then received IL-15 and IL-21, and the mIL15$^+$CAR$^+$ T cells were supplemented with IL-21 only. T cell viability was assessed via Annexin V staining eight days after the aAPC stimulation. The mIL15$^+$CAR$^+$ T cells were shown to have the greatest live cell population (Annexin V$^{neg}$) (FIG. 33C) and indicates a resistance to activation induced cell death.

Persisting mIL15$^+$CAR$^+$ T cells possess traits of less differentiated T cells. In characterizing the long-term persisting mIL15$^+$CAR$^+$ T cells, the inventors hypothesized that persisting mIL15$^+$CAR$^+$ T cells would exhibit characteristics associated with less differentiated T cell subsets as these cell subsets are known for their long-lived potential. With the constitutive presence, and thus possible constitutive signaling, during the ex vivo culture of the mIL15$^+$ CAR$^+$ T cells, the inventors assessed if these T cells had a molecular programming for a less differentiated state that would yield cells with a persistence advantage. Analysis of multiplexed digital gene profiling using the nCounter Analysis System was performed on CAR$^+$ and the mIL15$^+$CAR$^+$ T cells from stimulation 4 (withdrawal assay T cell input). Analysis of normalized mRNA counts used a negative binomial distribution-based statistical program (Lohse et al., Nucleic Acids Res. (2012) 40, W622-7). Genes were considered significantly differentially expressed if greater than two-fold differential mRNA counts, P<0.05, FDR q<0.05. Only five genes were considered differentially expressed using these criteria, thus indicating there is no culture or molecular programming advantage afforded by mIL15.

Figure 34A:
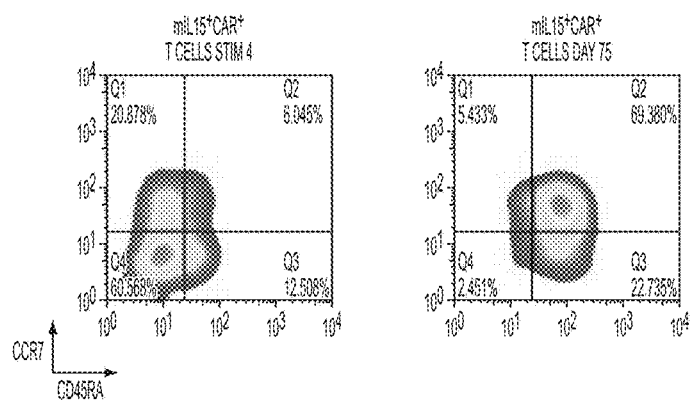
FIGS. 34A-C: Long-term persisting mIL15+CAR+ T cells take on dichotomous CD45RA+CCR7+/− phenotypes. A) Representative flow plots of CD45RA and CCR7 populations of mIL15+CAR+ T cells from stimulation 4 and those persisting 75 days after last antigen stimulation, n=7. B) Frequencies of populations subsets from (A). *P<0.001 and **P<0.0001, RM ANOVA, n=7. C) A representative histogram showing Annexin V levels in CCR7$^{neg}$ and CCR7+ mIL15+CAR+ T cells from stimulation 4 and those persisting 75 days after last antigen stimulation, n=3. Histograms are gated on the lymphocyte population to avoid non-specific CCR7 staining
Figure 34B:
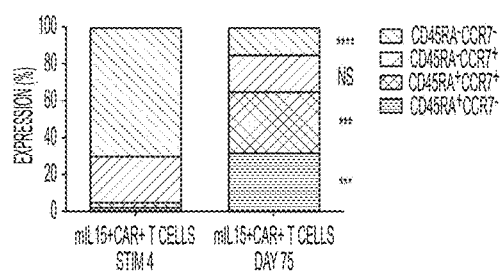
Figure 34C:
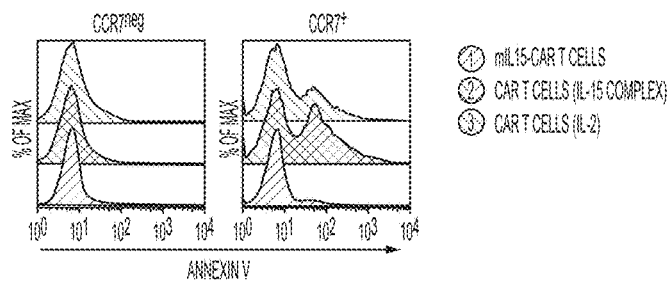

The inventors then characterized the long-term persisting mIL15$^+$CAR$^+$ T cells. First, their phenotype was assessed using CD45RA and CCR7 markers to phenotypically describe their differentiation state. These markers characterize the differentiation state of T cells as CD45RA$^+$CCR7$^+$ <CD45RA$^-$CCR7$^+$<CD45RA$^-$CCR7$^-$<CD45RA$^+$CCR7$^-$ representing cells from the least to most differentiated state. In comparing the 75-day withdrawal mIL15$^+$CAR$^+$ T cells to their counterparts at the initiation of the experiment (the Stim 4 mIL15$^+$CAR$^+$ T cells), it is observed that the persisting mIL15$^+$CAR$^+$ T cell culture has an increased proportions of CD45RA$^+$CCR7$^+$ and CD45RA$^+$CCR7$^-$ T cell subsets (***P<0.001, 2-way repeated measures ANOVA, n=7; FIG. 34). CCR7 expression was significantly enhanced in the withdrawal mIL15$^+$CAR$^+$ T cells relative to CAR T cells. Viability of CCR7$^{neg}$ and CCR7$^+$ subsets was assessed by Annexin V staining of mIL15$^+$CAR$^+$ T cells, CAR$^+$ T cells receiving IL-2 (50 U/ml), and CAR$^+$ T cells receiving soluble IL-15 (5 ng/ml) after antigen withdrawal. It was found that irrespective of the type of cytokine stimulation (IL-2, IL-15 complex, or mIL15), CCR7$^{neg}$ T cells showed equal frequencies of live cells. In contrast, CCR7$^+$ T cells exposed to mIL15 had significantly higher viability than the CAR T cells receiving IL-2 or IL-15 complex (both P<0.05; FIG. 34). These data suggest that mIL15 is sufficient to support the CCR7$^+$ phenotype which thus contributes to maintaining the less differentiated CD45RA$^+$CCR7$^+$ T cell subset. The capacity for the mIL15$^+$CAR$^+$ T cells to promote the persistence of less differentiated T cells is a desired phenotype for adoptive therapy and appears to corroborate other studies reporting that long-lived T cells subsets possess a less differentiated phenotype. Additionally, the survival of a highly differentiated subset was also observed, possibly supported by constitutive IL-15 signaling.

Figure 36:
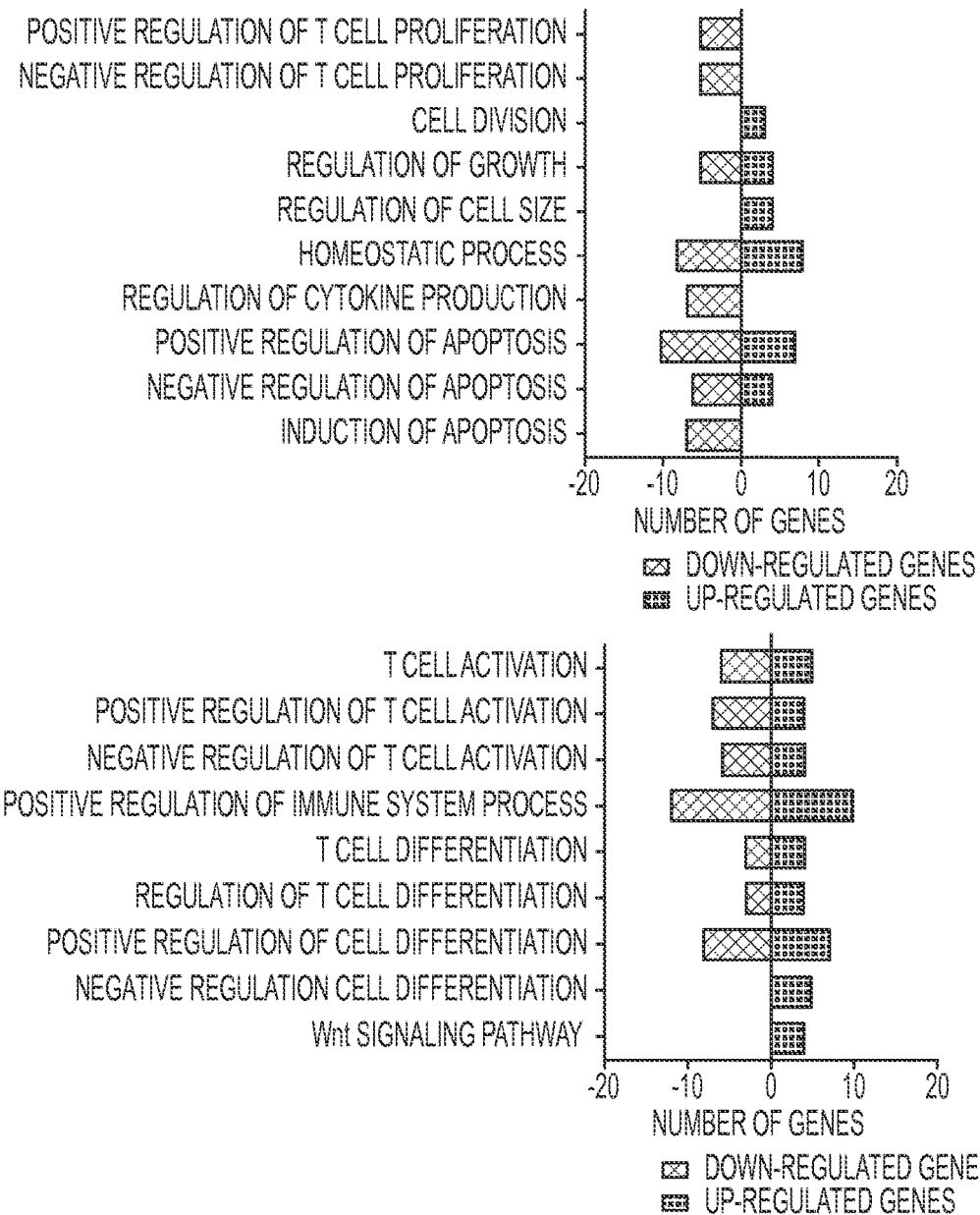
FIG. 36: Molecular profiling indicates long-term persisting mIL15+CAR+ T cells exhibit characteristics associated with less differentiated T cell subsets. All genes significantly differentially expressed between mIL15+CAR+ T cells from stimulation four and those persisting through withdrawal conditions are functionally classified under broad categories based on gene ontology information. Genes within categories are partitioned based on up- or down-regulation in the persisting withdrawal mIL15+CAR+ T cells.

Long-term persisting mIL15$^+$CAR$^+$ T cells display some molecular markers associated with less differentiated T cell subsets. The T cells were analyzed for their gene expression patterns using the nCounter Analysis System and a heirarchically clustered heat map of differentially expressed genes between mIL15$^+$CAR$^+$ T cells from stimulation 4 and those surviving to day 75 of withdrawal was produced (>2-fold cutoff, P<0.05, FDR q<0.05). These studies identified 108 significantly differentially expressed genes (>2-fold cutoff, P<0.05, FDR q<0.05). Gene Ontology classification was assessed using DAVID functional annotation. The functional classification of the differentially expressed genes can be grouped into broad categories: T cell activation, differentiation, proliferation, and apoptosis. Namely, there were greater numbers of genes in mIL15$^+$CAR$^+$ T cells that were down-regulated in the positive regulation of differentiation, regulation of apoptosis, and induction of apoptosis. Greater numbers of genes in mIL15$^+$CAR$^+$ T cells were up-regulated in the negative regulation of differentiation and the Wnt signaling pathway (FIG. 36). This suggests that the molecular signature of persisting mIL15$^+$CAR$^+$ T cells is less differentiated than mIL15$^+$CAR$^+$ T cells at stimulation 4 (T cells at experiment initiation).

Figure 37:
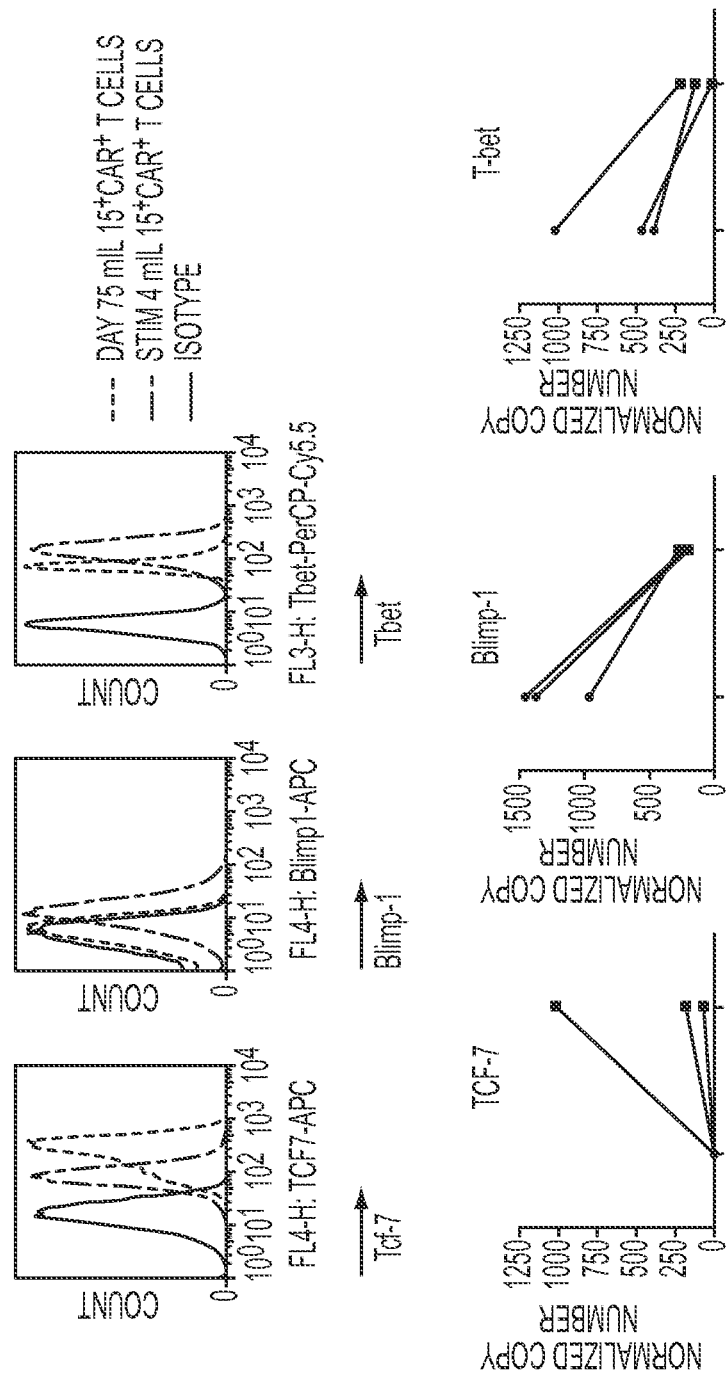
FIG. 37: Validation of transcription factors associated with T cell differentiation states indicates long-term persisting mIL15+CAR+ T cells exhibit a low differentiation state. Top panel: Selected differentially expressed genes (Tcf-7, Blimp-1, and T-bet) were validated by intracellular staining and analyzed by flow cytometry. Representative flow plots shown, n=5. Bottom panel: Normalized mRNA copy number from the nCounter Analysis System output.
Figure 38A:
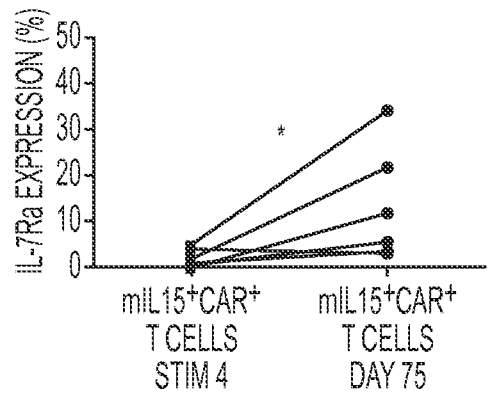
FIG. 38: Validation of surface markers associated with T cell differentiation states indicates long-term persisting mIL15+CAR+ T cells exhibit less differentiation. Top panel: Selected differentially expressed genes, IL-7Ra and CCR7, were validated by staining and analyzed by flow cytometry. *P=0.0156 and ***P<0.001, 1-tailed Wilcoxon matched-pairs signed rank test and paired 1-tailed T test, respectively. Representative flow plots shown, n=5-7. Bottom panel: Normalized mRNA copy number from the nCounter Analysis System output, n=3.
Figure 38B:
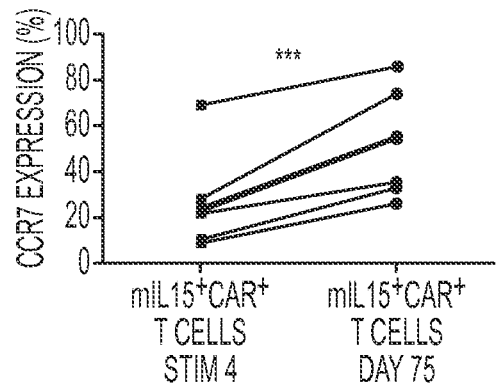
Figure 38C:
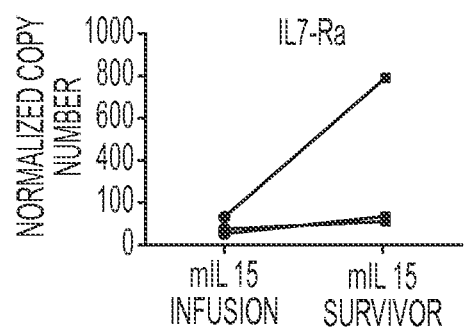
Figure 38D:
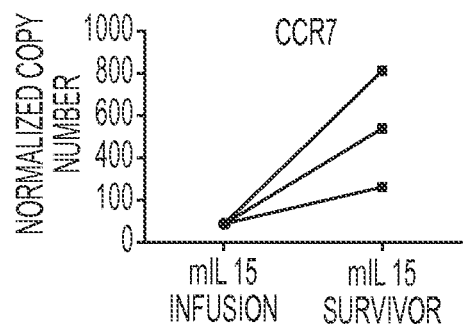
Figure 39A:
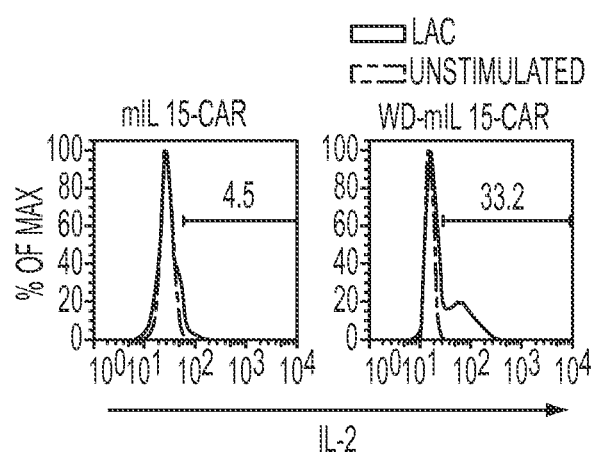
FIG. 39: Acquisition of IL-2 production capability by mIL15+CAR+ T cells. A) Representative histograms of IL-2 intracellular staining of stimulation 4 and persisting antigen withdrawal mIL15+CAR+ T cells (WD-mIL15-CAR) that were either unstimulated or activated with lymphocyte activation cocktail (LAC) for 6 hours, followed by intracellular IL-2 staining and analysis by flow cytometry. B) Frequency of LAC-stimulated T cells producing IL-2 from (A). ****P<0.0001, n=6, paired t test.
Figure 39B:
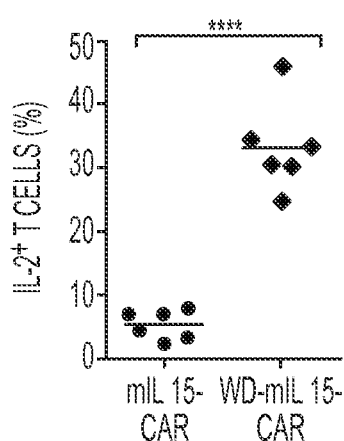

Expression of selected genes was validated by flow cytometry. Expression of transcription factors associated with a less differentiated state (Tcf-7) and acquisition of effector function/differentiated state (Blimp-1 and Tbet) indicate that persisting mIL15$^+$CAR$^+$ T cells exhibit a transcription factor balance associated with less differentiated cells. This is characterized by greater expression of Tcf-7 and lower expression of Blimp-1 and Tbet (FIG. 37). Assessment of the cell surface markers IL-7Ra and CCR7 was done as they are characteristically expressed by less differentiated T cell subsets. The persisting mIL15$^+$CAR$^+$ T cells have increased expression of these markers associated with long-lived T cell subsets (FIG. 38). One additional measure for distinguishing the level of T cell differentiation is by the capacity of less differentiated T cells to produce IL-2. The mIL15$^+$CAR$^+$ T cells from either stimulation 4 or the 75-day withdrawal cultures were mock-treated or treated with LAC for 6 hours and then assessed for IL-2 production by intracellular cytokine staining. The stimulation 4 T cells were unable to produce IL-2 whereas the persisting 75-day withdrawal T cells acquired the capability to produce IL-2 (FIG. 39). These results collectively suggest that while there is no identifiable difference between ex vivo expanded CAR$^+$ T cells or mIL15$^+$CAR$^+$ T cells, the resulting long-term persisting mIL15$^+$CAR$^+$ T cells exhibit characteristics associated with less-differentiated T cells subsets which demonstrate long-term survival in vivo.

Figure 40A:
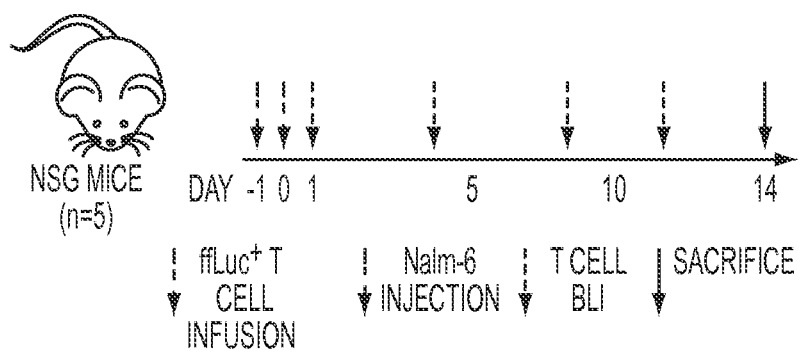
FIGS. 40A-D: In vivo persistence and anti-tumor activity of mIL15+CAR+ T cells in an environment with abundant tumor antigen. A) Schematic of experiment. B) BLI derived from mIL15+/−CAR+ffluc+ T cells adoptively transferred into mice after Nalm-6 tumor introduction (n=5). C) Analysis of spleen (top panel) and bone marrow (bottom panel) at day 14 for the presence of human T cells by staining with human CD3 and detection by flow cytometry. Representative flow plot (n=5). D) Analysis of peripheral blood by flow cytometry for the presence of CD3+ and CD19+ cells. Frequencies obtained after gating out murine CD45+ cells. Data depicts individual mice and mean±SD. ***P<0.001, 1-way ANOVA, n=3-5.
Figure 40B:
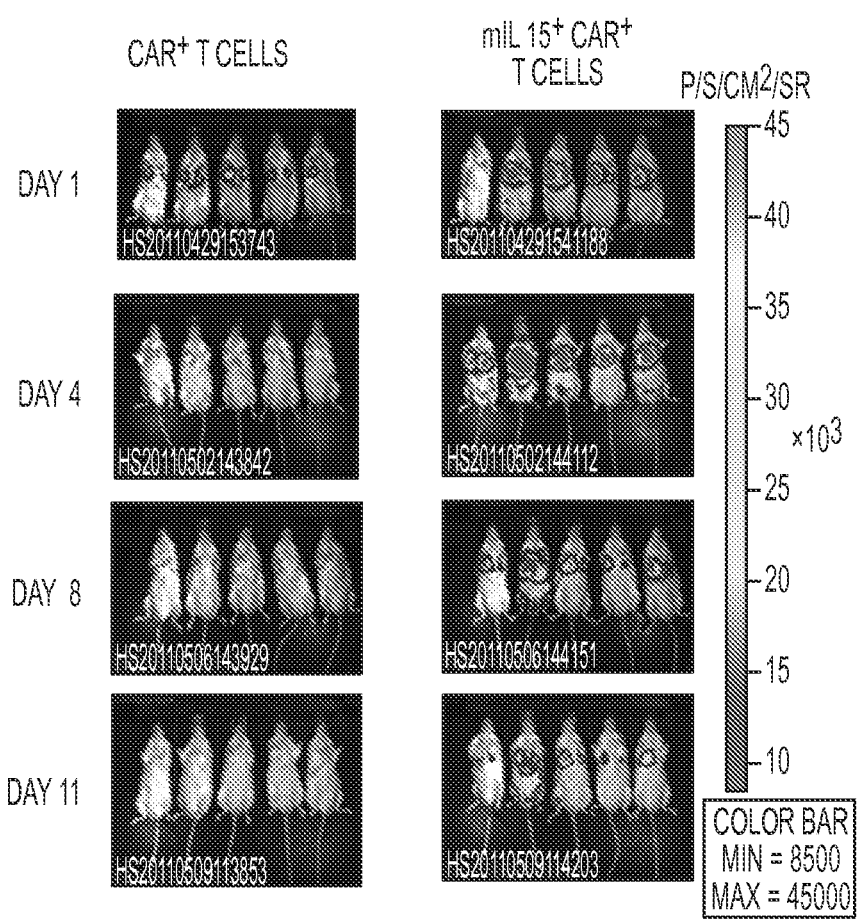
Figure 40C:
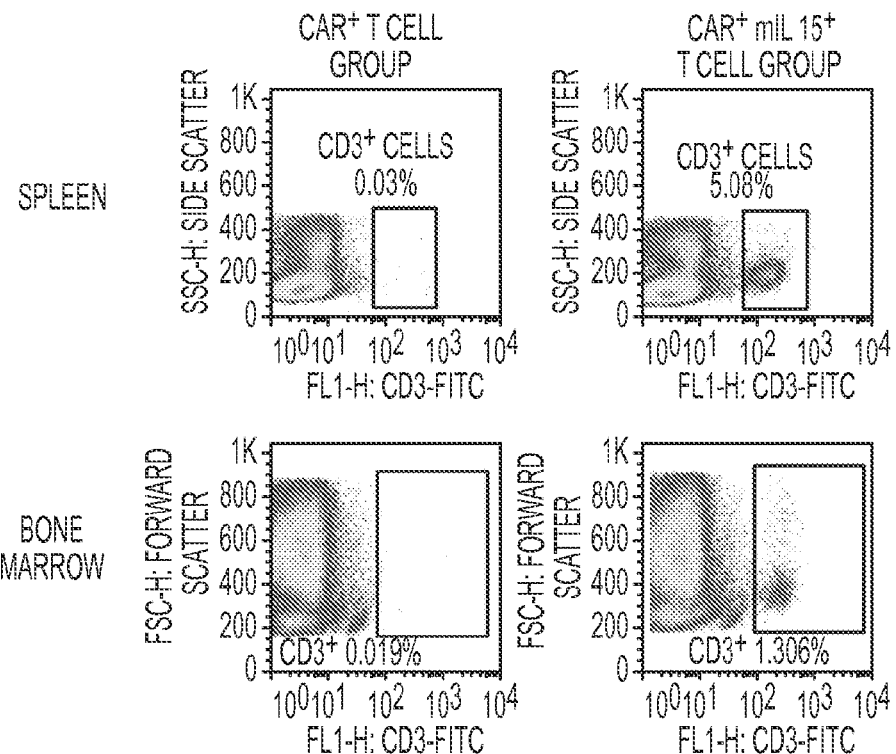
Figure 40D:
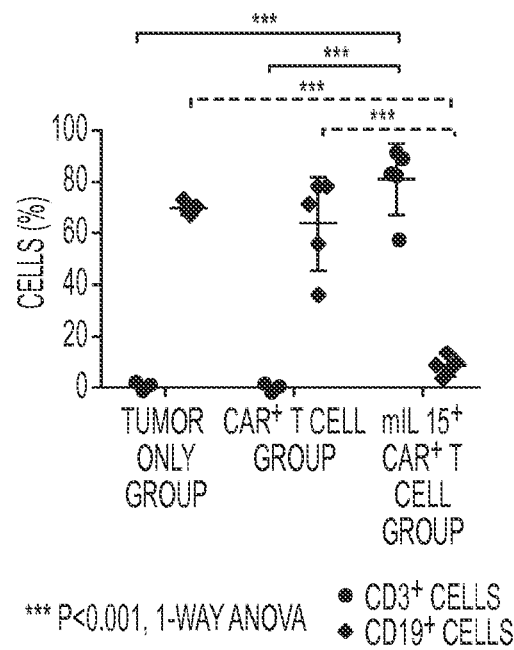

In vivo persistence and anti-tamor tfficacy of mIL15$^+$ CAR$^+$ T cells in a high tumor burden model. To assess in vivo persistence, mIL15$^+$CAR$^+$ T cells and CAR$^+$ T cells were co-modified to express firefly luciferase (ffLuc) to enable longitudinal monitoring of T cells in vivo using bioluminescence imaging (BLI). These modified T cells were adoptively transferred, using one T cell infusion of 20×10$^6$ CAR$^+$ T cells, into NSG mice bearing disseminated Nalm-6 (CD19) malignancy with a no treatment control group. After 14 days the mice were sacrificed. While CAR$^+$ T cells were not found to persist, the mIL15$^+$CAR$^+$ T cells were observed by BLI to persist throughout the 11 day imaging period (FIG. 40B). Bone marrow, spleen, and peripheral blood, were harvested and assessed by flow cytometry for the presence of human T cells using human CD3 as a marker and gating out murine lymphocytes. Mice infused with the mIL15$^+$CAR$^+$ T cells had significant CD3$^+$ T cells detected in the bone marrow (0.49-2.17%, P=0.0001, unpaired t-test, n=5), spleen (1.15-12.38%, P<0.0001, unpaired t-test, n=5) and peripheral blood (58.39-92.60%, P<0.0001, unpaired t-test, n=5) (FIG. 40C). There were no CD3$^+$ cells detected in samples from the CAR$^+$ T cell treated group (FIG. 40C) and the no treatment group (tumor only) in any of the assessed tissues. In this model, mIL15$^+$CAR$^+$ T cells demonstrated tumor control in the peripheral blood (FIG. 40D), but complete tumor clearance was not observed. These data indicate that despite the prevalence of tumor antigen, CAR$^+$ T cells had insufficient in vivo persistence whereas mIL15$^+$CAR$^+$ T cells were present at significant levels throughout the body.

Figure 41A:
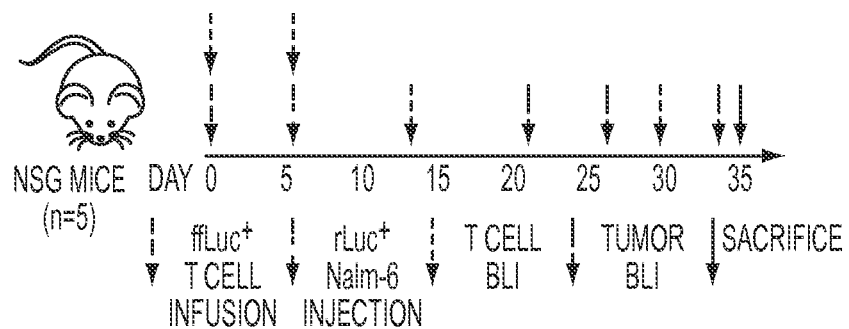
FIGS. 41A-F: In vivo model assessing mIL15+CAR+ T cell persistence and anti-tumor efficacy in a low antigen environment. A) Schematic of experiment. B) T cell (ffLuc+) BLI of mice receiving adoptive transfer of either CAR+ T cells or mIL15+CAR+ T cells followed by CD19+ Nalm-6 tumor injection after 6 days of T cell engraftment. C) Longitudinal BLI monitoring Nalm-6 burden. Images represent photon flux from Nalm-6 cell-derived rLuc activity. D) Tumor flux (rLuc) over time of mice treated with either CAR+ T cells, mIL15+CAR+ T cells, or no T cells. Data are mean±SD. ****P<0.0001, one-way ANOVA, n=4-5. E) Analysis of harvested tissues and blood where human T cells (human CD3+) and Nalm-6 tumor cells (human CD19+) were detected by flow cytometry. F) Using the low tumor model, long-term survival of mice was evaluated out to day 98. Experimental conditions were carried out similarly as previously described for the low tumor model where mice were engrafted with mIL15-CAR T cells (n=7), CAR T cells (n=8), or no T cells (n=8) followed by NALM-6 tumor challenge. Fractions in parentheses represent the proportion of mice surviving to day 98. *P=0.045 (mIL15-CAR versus CAR T cell treatment), log-rank (Mantel-Cox).
Figure 41B:
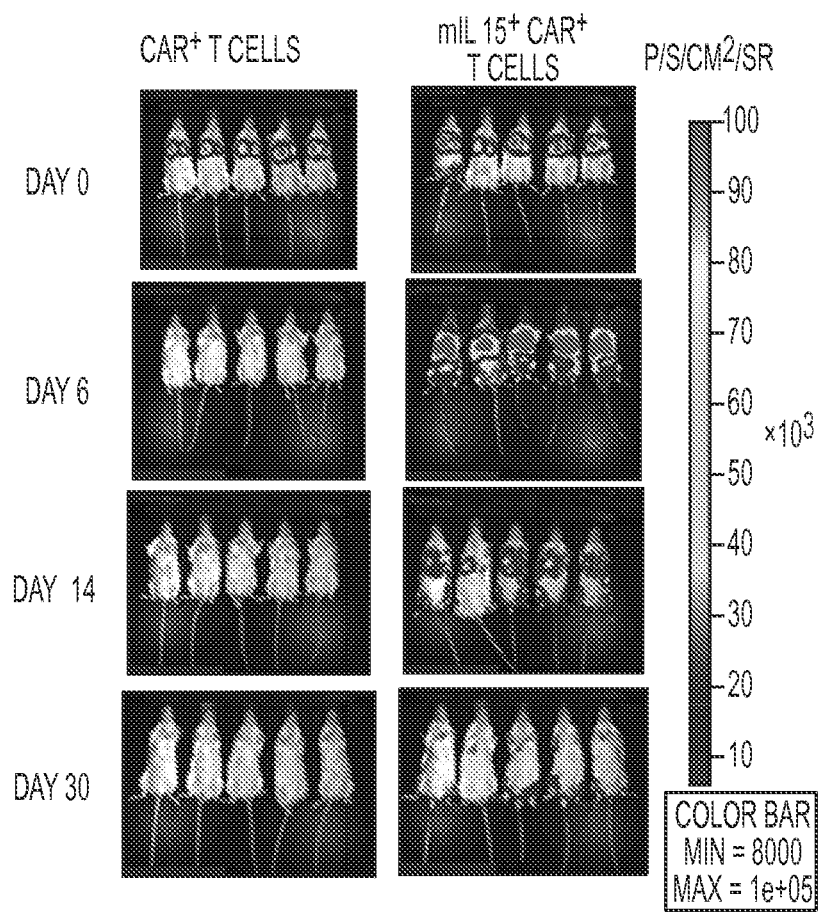
Figure 41C:
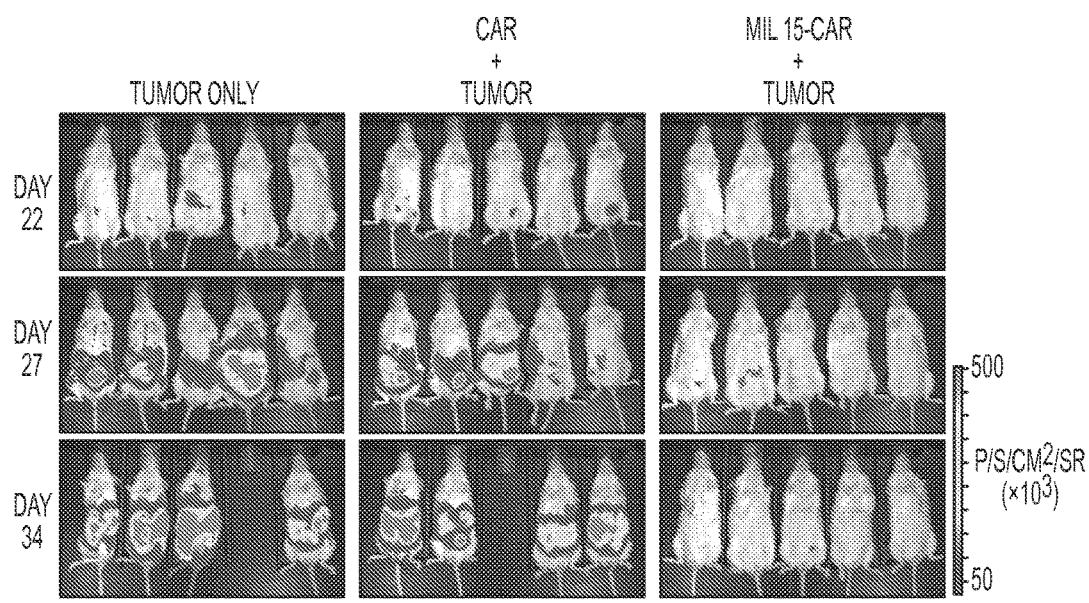
Figure 41D:
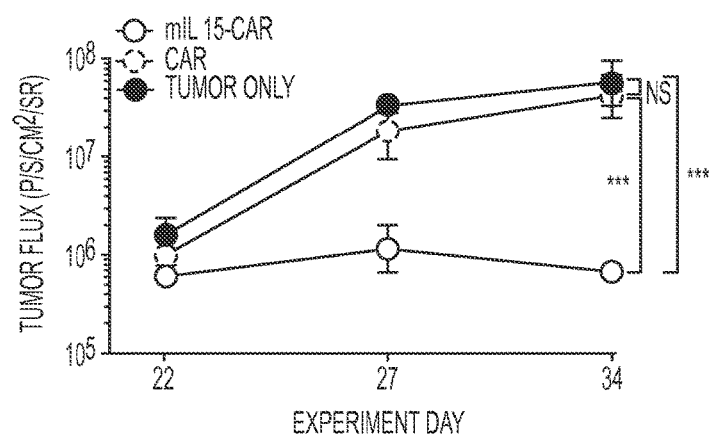
Figure 41E:
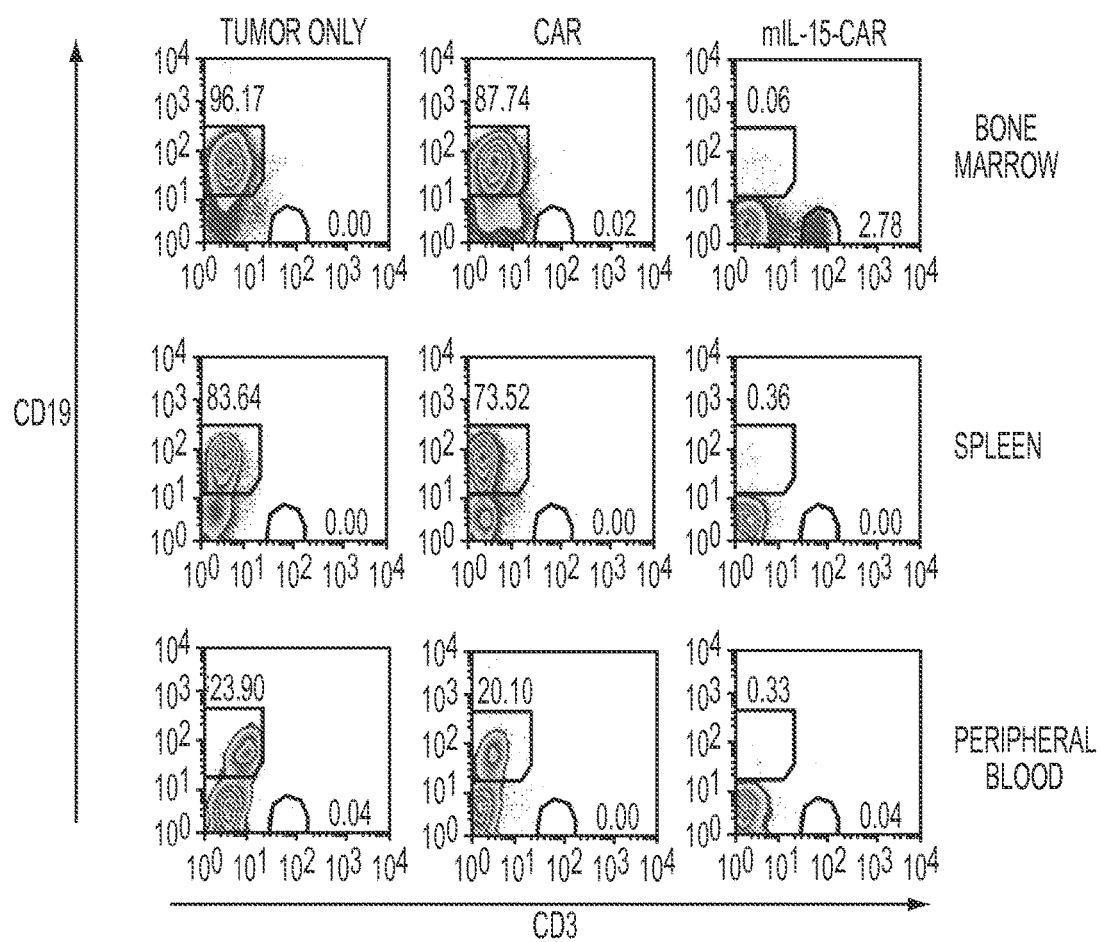
Figure 41F:
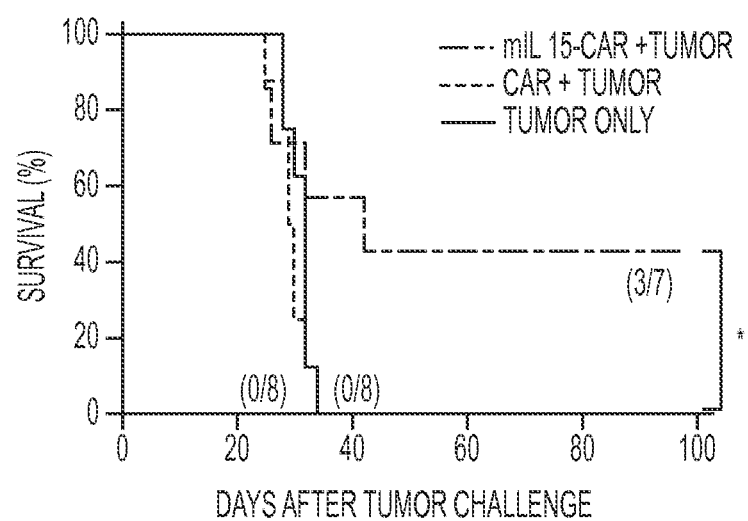

In vivo persistence and anti-tumor efficacy of mIL15$^+$CAR$^+$ T cells in a low tumor burden model. The inventors next assessed T cell engraftment and anti-tumor activity in a preventative model with a low tumor burden. The modified T cells (mIL15$^{+/-}$CAR$^+$ffLuc$^+$) were infused into the NSG mice with no exogenous cytokines and allowed to engraft for six days before an infusion of renilla luciferase (rLuc)-modified Nalm-6. The mice underwent BLI over the course of 30 days. In this preventative model, the mIL15$^+$CAR$^+$ T cells were observed to persist throughout the duration of the experiment and prevented tumor engraftment, which was a significant anti-tumor effect compared to the CAR$^+$ T cell and no T cell treatment groups (P<0.0001, one-way ANOVA, n=4-5) (FIG. 41C-D). Analysis of the organs and peripheral blood by flow cytometry detected human CD3$^+$ T cells in the mIL15$^+$CAR$^+$ T cell treatment group, but interestingly the T cells were only found in the bone marrow (FIG. 41E) and may indicate preferential homing or survival after tumor encounter. In a similar experiment, survival was tested and mIL15$^+$CAR$^+$ T cell-treated mice exhibited significantly improved survival compared to the no T cell treatment or CAR$^+$ T cell-treated mice [P=0.045 (mIL15$^+$ CAR$^+$ T cells versus CAR$^+$ T cells, Log-rank Mantel-Cox test, n=7-8; FIG. 41).

Figure 42A:
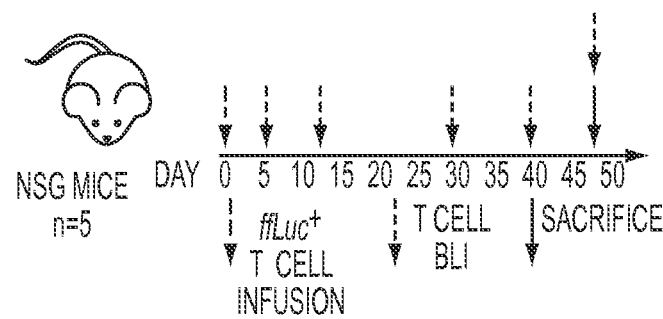
FIGS. 42A-E: Persistence and retained function of mIL15+CAR+ T cells independent of antigen. A) Schematic of experiment. B) BLI of ffLuc+ T cells in mice treated with CAR+ and mIL15+CAR+ T cells in the absence of tumor antigen. C) Analysis of bone marrow, spleen, and peripheral blood for human CD3+ T cells and CD19+ tumor cells, as detected by flow cytometry. Representative flow plots are shown (left panels) and plotted frequencies of human CD3+ T cells (right panel). Data are represented as mean±SD, n=5. P=0.0027 (bone marrow), P=0.0081 (spleen), ns=not significant, unpaired t test. D) Longitudinal plotting of T cell flux (ffluc). Background luminescence (gray shaded) was defined by flux obtained from mice not receiving ffluc+ T cells. Data are represented as mean±SD, n=5. *P=0.0128, **P+0.00231, unpaired t test. E) Cells isolated from spleen, liver, or bone marrow were ex vivo expanded on aAPC to generate sufficient cell numbers for assessing intracellular IFNγ production in response to CD19− and CD19+ targets (as previously described), n=7 from three tissue sources and four mice. Histograms were gated on CD3.
Figure 42B:
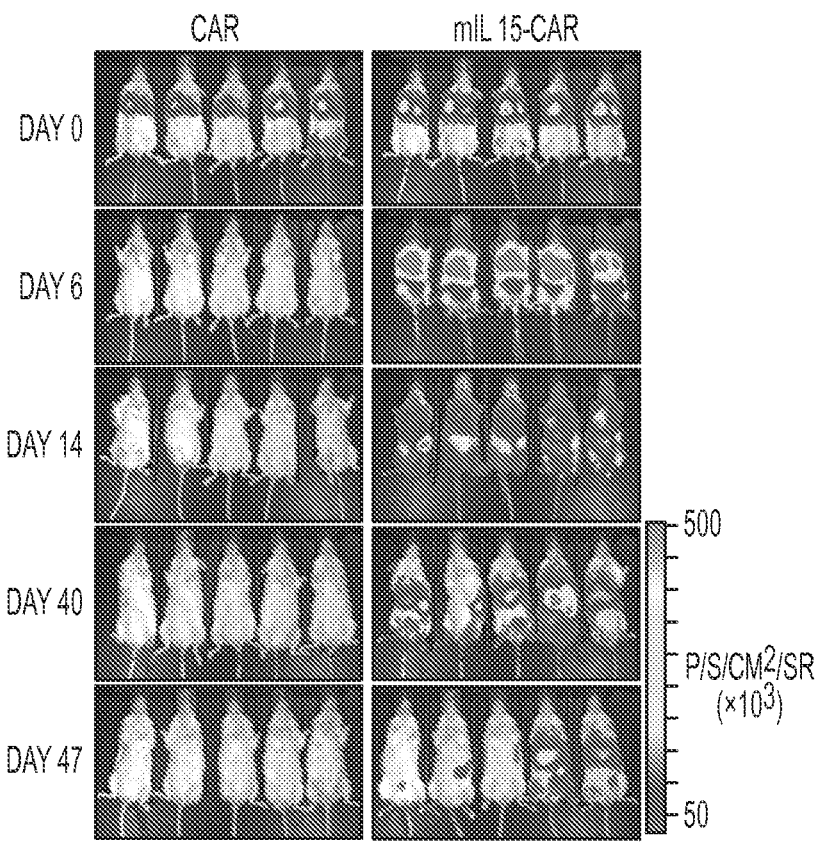
Figure 42C:
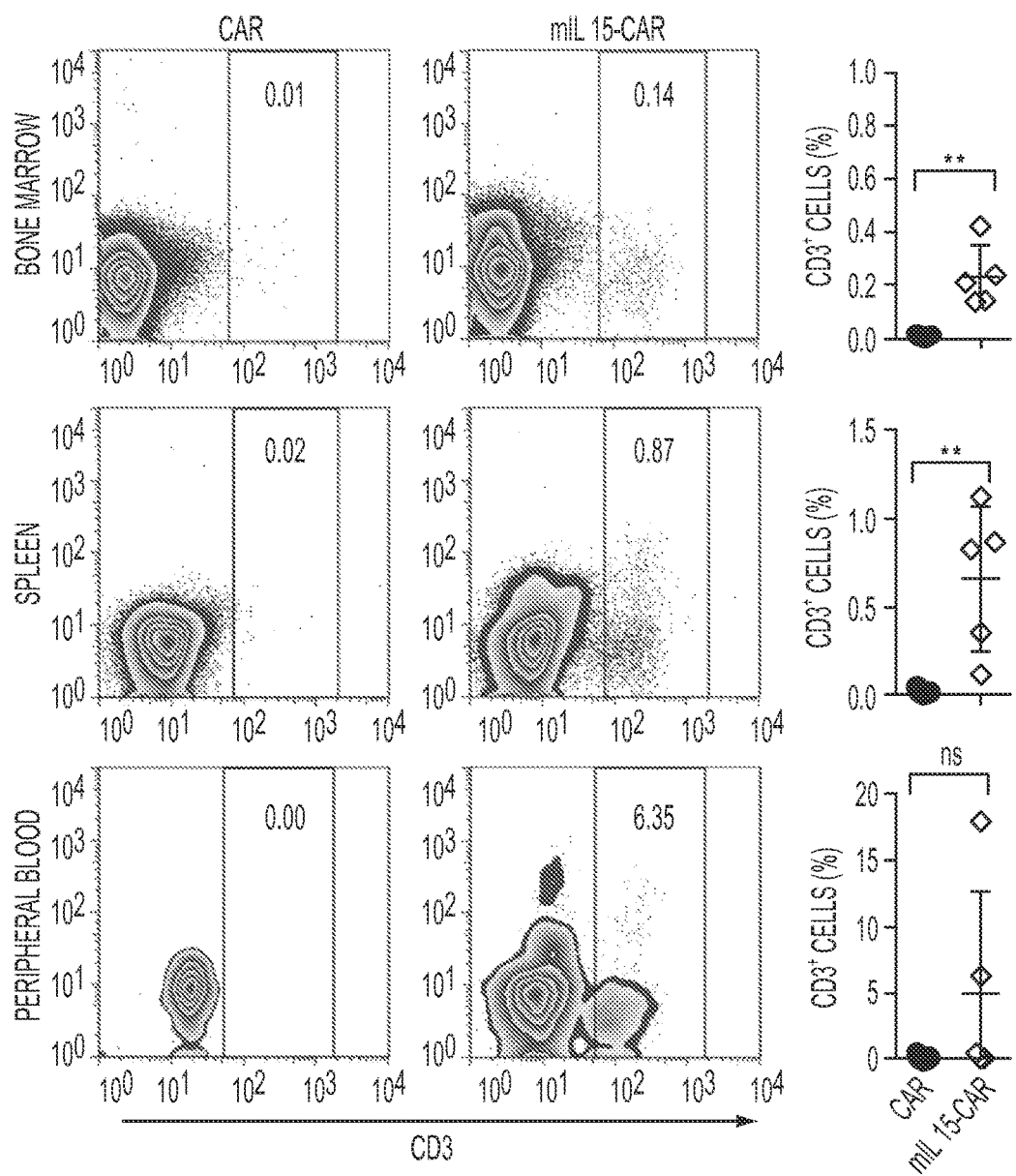
Figure 42D:
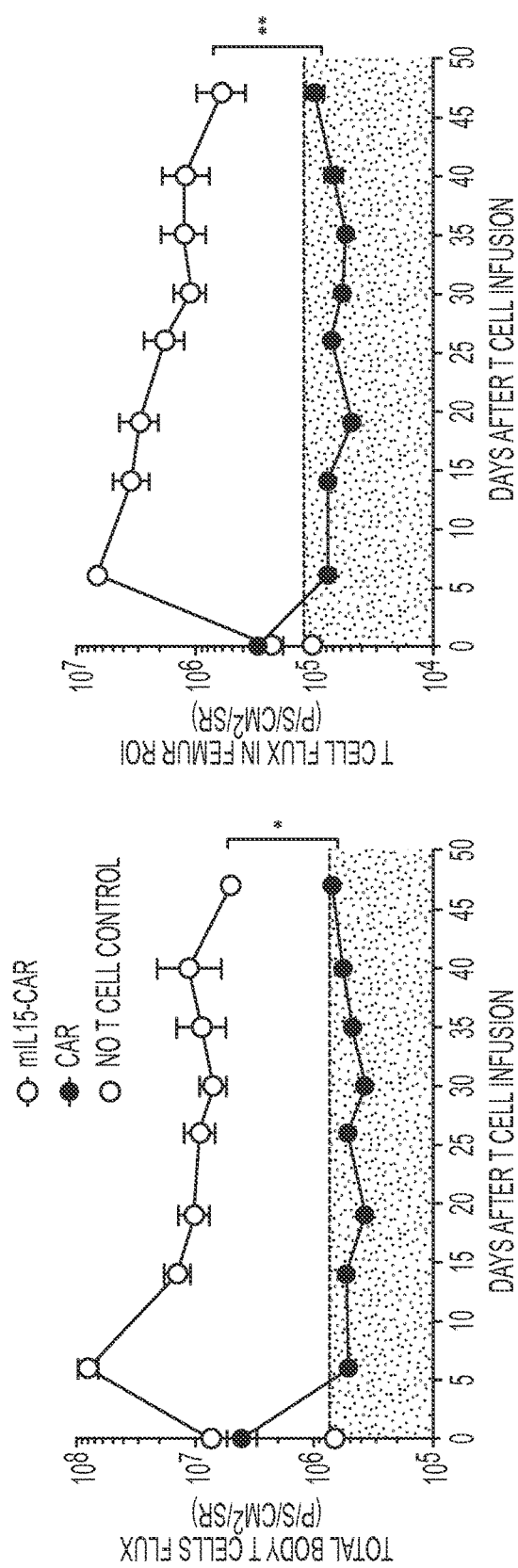
Figure 42E:
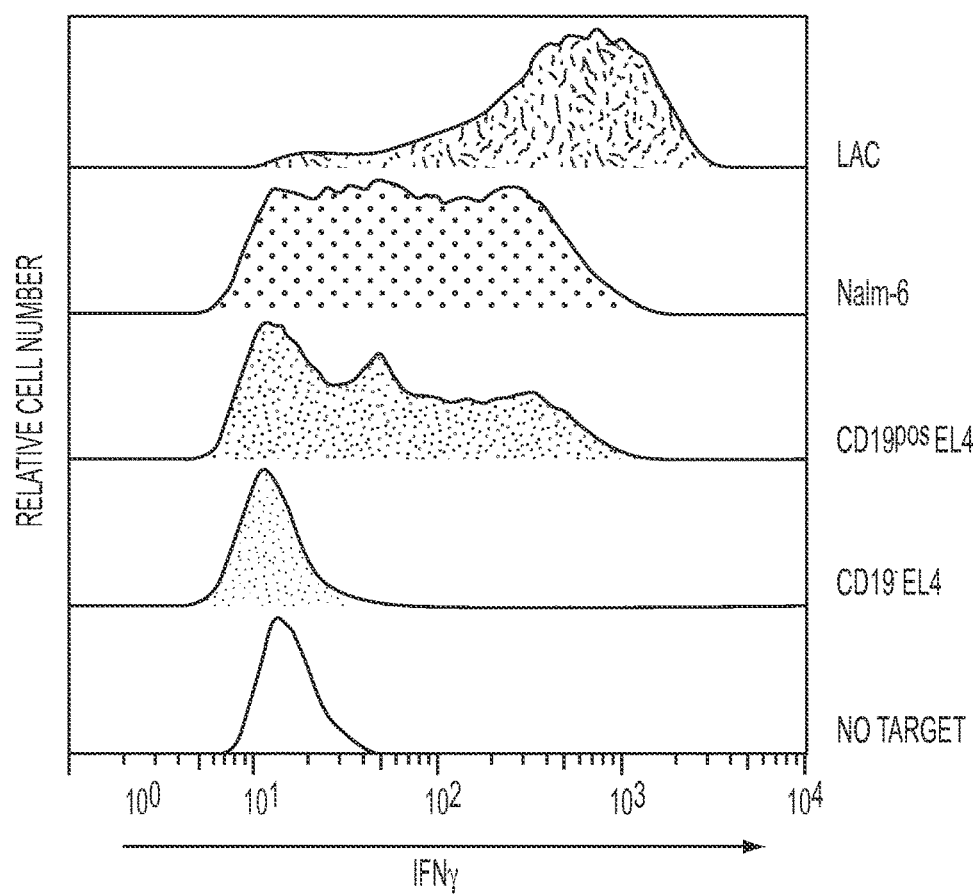

In vivo persistence of mIL15$^+$CAR$^+$ T cells in the absence of CAR activation. To assess if mIL15$^+$CAR$^+$ T cells can persist long-term in vivo without the need for CAR signaling, modified T cells (mIL15$^{+/-}$CAR$^+$ffLuc$^+$) were infused into mice (with no tumor or exogenous cytokines) and monitored for up to 47 days. Testing the T cells in this manner will also elucidate whether the persisting T cells demonstrate unrestricted growth or if they maintain their population in a homeostatic-like manner No CAR$^+$ T cells were observed to persist, whereas the presence of mIL15$^+$ CAR$^+$ T cells exhibited sustained persistence in the absence of exogenous cytokines and antigen (FIG. 42B). This was further confirmed by flow cytometry of CD3 stained cells isolated from the bone marrow, spleen, and peripheral blood (FIG. 43C). Assessing longitudinal T cell persistence, flux values indicate that mIL15$^+$CAR$^+$ T cell levels appeared to level off over time or slowly decline, but did not indicate the occurrence of uncontrolled expansion (FIG. 42D). These persisting T cells were harvested and ex vivo expanded in the same manner as previously described for ex vivo expansion of genetically modified T cells. These cells were capable of antigen-specific activation as assayed by interferon-γ production (FIG. 42E). This in vivo data demonstrates enhanced persistence of mIL15$^+$CAR$^+$ T cells in a CAR-independent and homeostatic-like manner whilst retaining their antigen-specific responsiveness.

Figure 35B:
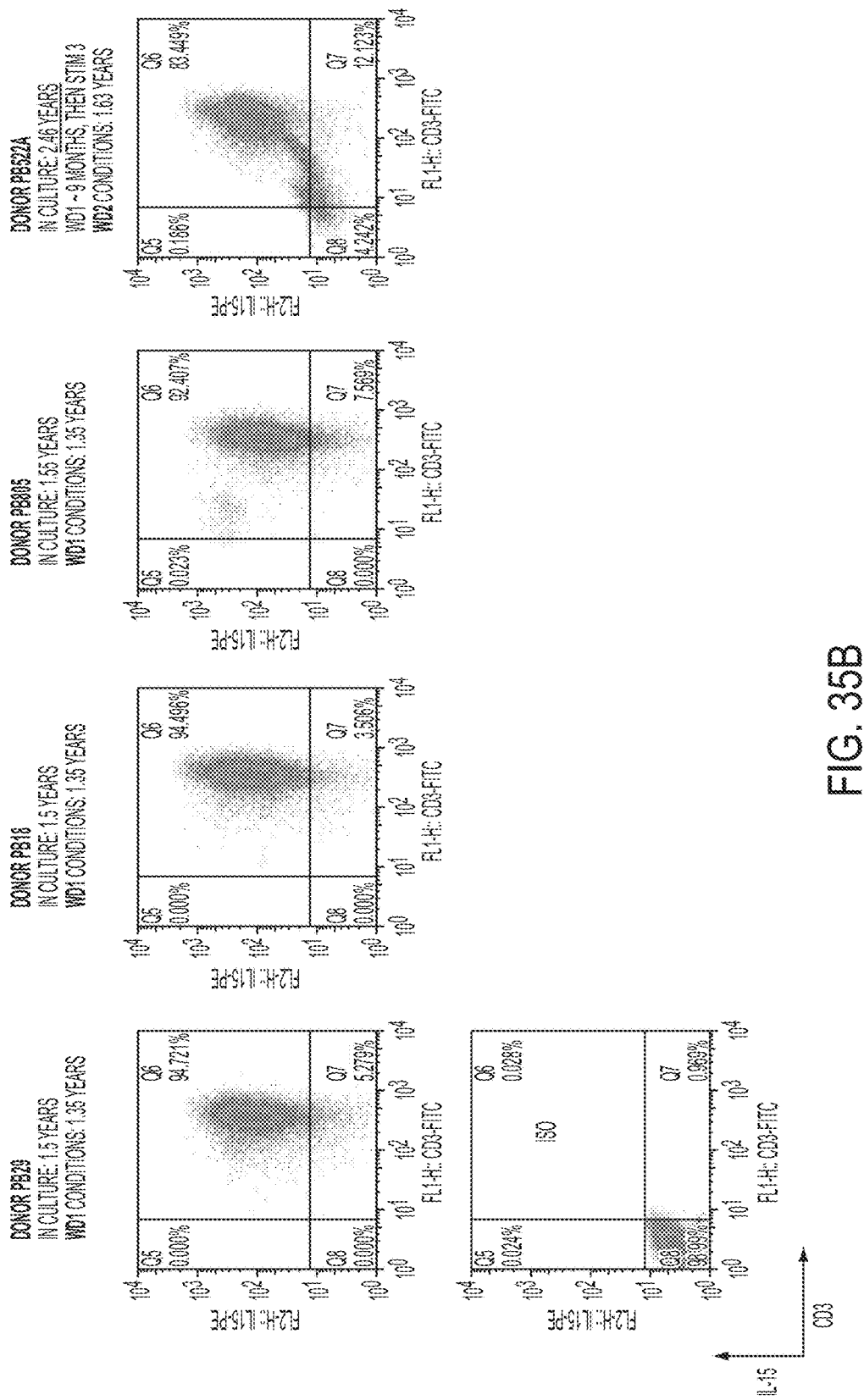
Figure 35C:
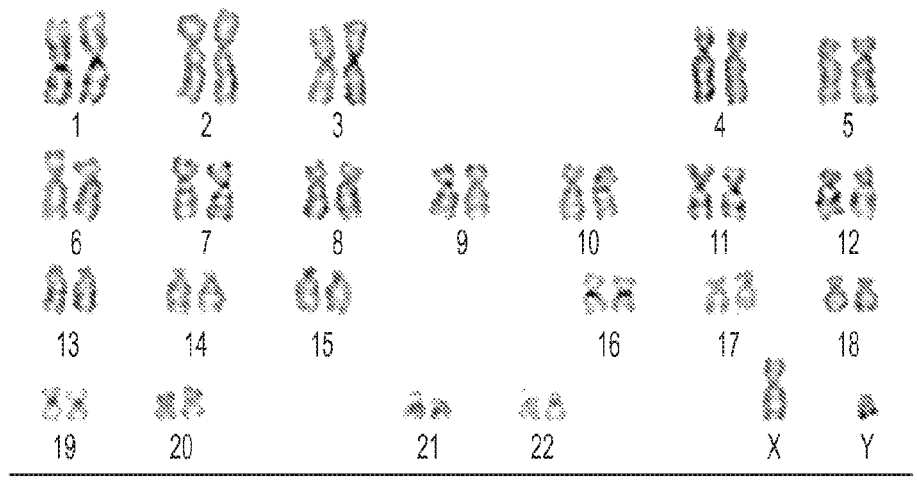
Figure 35D:
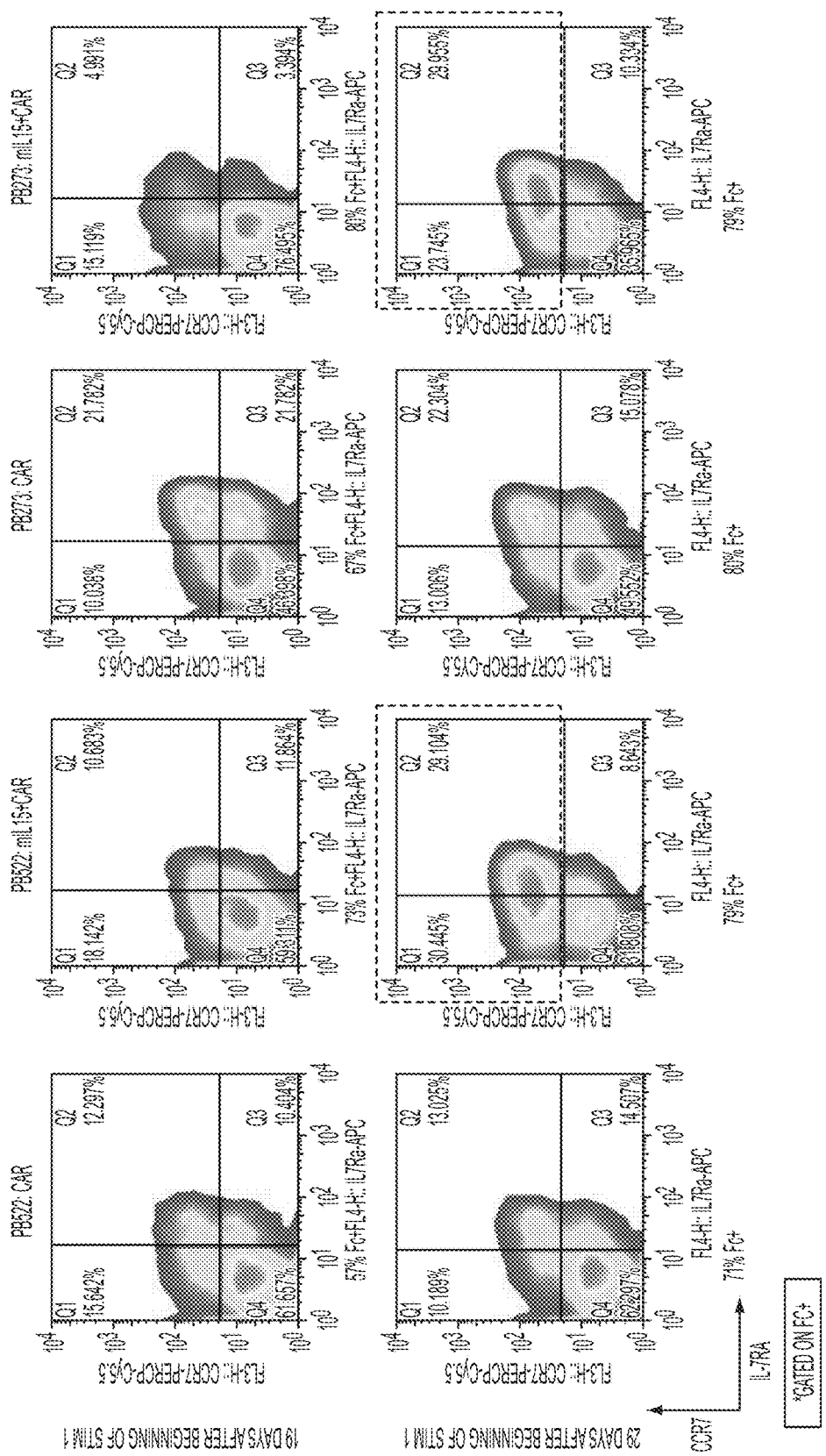
Figure 35E:
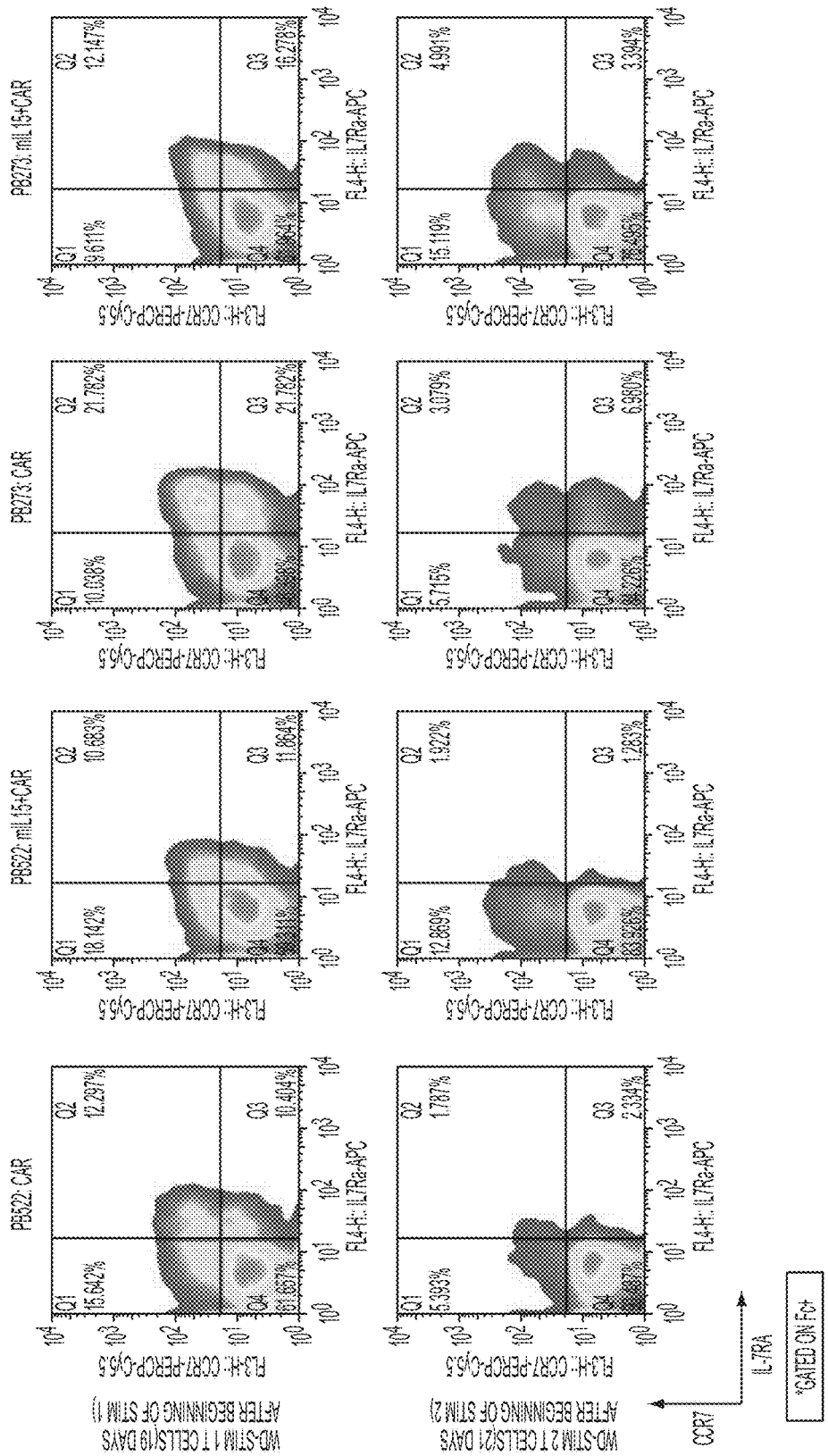

Cell proliferation and memory kinetics in mIL15$^+$CAR$^+$ T cells. Flow cytometry analyses were used to further characterize mIL15+CAR+ T cells (results shown in FIG. 35). Long-term persisting mIL15+CAR+ T cells maintain in culture with low turnover rates as indicated by minimal PKH dilution over 10 days in samples that have been in constant culture for greater than one year. Moreover, dividing cells appeared to be predominantly CCR7−. Such data indicates that the T cells are maintained homeostatically as opposed to unrestricted autonomous proliferation or growth (FIG. 35A). The mIL15+CAR+ T cells in continuous long-term culture (1.5 to 2.45 years) were activated with aAPCs, phenotyped and submitted for karyotyping. Phenotyping showed that these T cells expressed mIL15 and karyoptyping results for all submitted donors showed normal metaphase-spreads (FIG. 35B-C). FIG. 35D shows the memory kinetics after stimulation of cells using K562 aAPCs: Stim 1-CAR versus mIL15+ CAR conditions during withdrawal: For these studies CAR T cells got only IL-21 during the first 9 days of the stimulation and then only IL2 during Ag withdrawal conditions; mIL5+ CAR T cells got IL-21 during the first 9 days and then no exogenous cytokines during withdrawal conditions. Results indicate that there is no difference in CCR7 and IL-7Ra expression at Day 19 post-Stim1 between CAR and mIL15+ CAR T cells. CCR7 and IL-7Ra expression increases with time away from antigen exposure (Day 29 vs Day 19) for mIL15-modified T cells only. CAR expression increases to ~80% without exposure to antigen (PB522 was 51% and PB273 was 53% at 9 days post-Stim1. FIG. 35E, shows memory kinetics 1 versus 2 stimulations of CAR and mIL15+ CAR T cells. Conditions during withdrawal: CAR T cells got only IL2 during Ag withdrawal which was instituted 10 days after the stimulation; mIL15+CAR T cells got no exogenous cytokines during withdrawal. Comparing CCR7 and IL-7Ra expression at similar time points after 1 Stim and 2 Stims indicated no memory difference between CAR vs mIL15+ CAR with the 1 Stim at 19 days. In Stim 2, at equivalent time point to Stim 1 CAR T cells having 2 Stims have far less CCR7 and almost no IL-7Ra compared to Stim 1 counterparts mIL15+ CAR T cells having 2 Stims also have less memory, but retain more "memory" than CAR only T cells with mIL15+ CAR T cells having some CCR7 left (but IL-7Ra is almost completely gone).

Example 8

Generation of Minimally Manipulated T-Cells Using mRNA Coding SB Transposase

Figure 43:
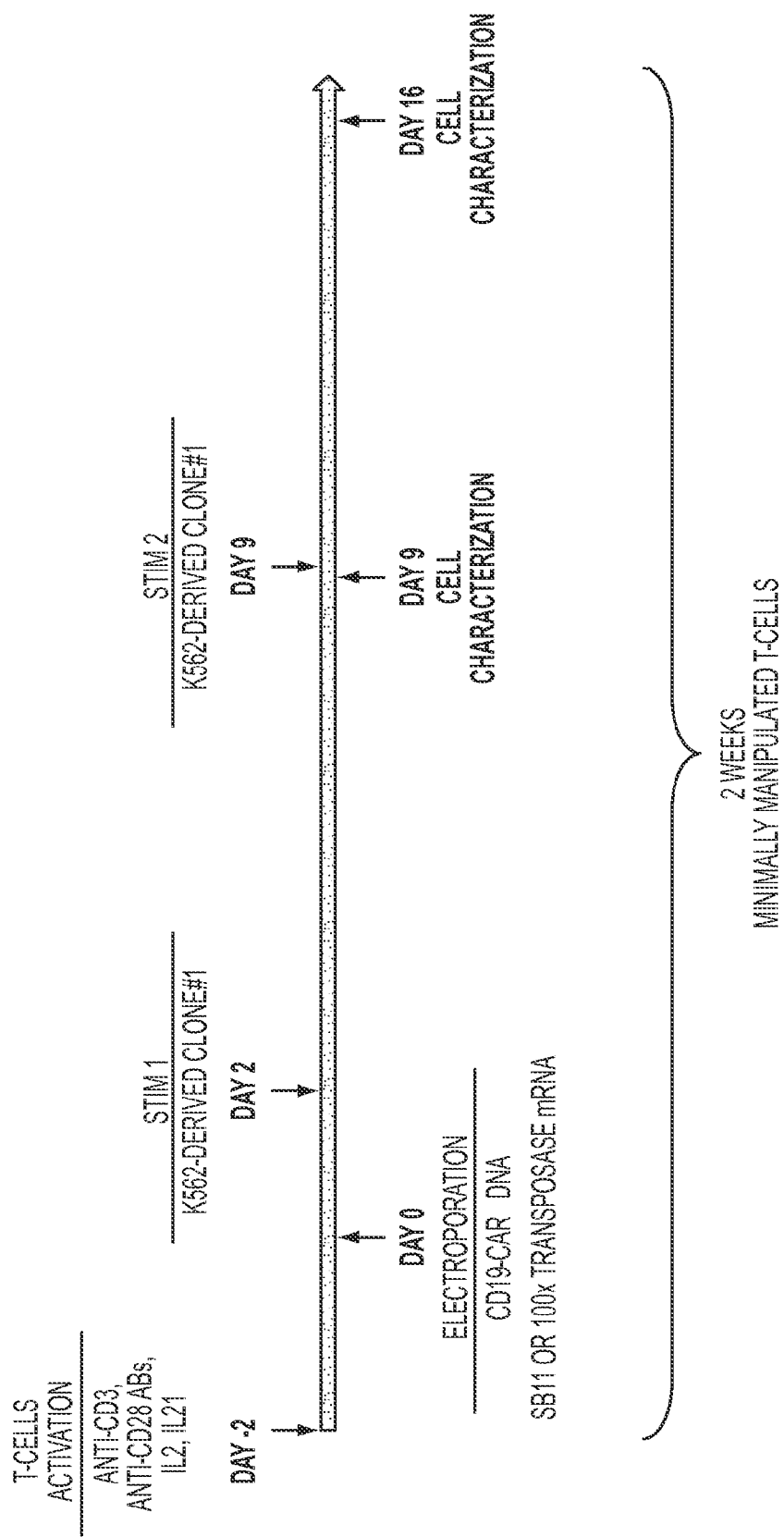
FIG. 43: A schematic showing an example protocol for CAR T cell production using SB transposase provided as a mRNA. Effective quantities of active CAR T cells could be produced in two weeks or less (e.g., 16 days).

Studies were undertaken to determine if use of a SB transposase provided as an mRNA for electroporation could further enhance CAR T cell production using a SB transposase system. For these studies cells were electroporated as detailed above using both a plasmid encoding a CAR flanked by transposon repeats and a mRNA encoding the transposase (e.g., SB11 or 100×). mRNA for the studies were m7GTP capped and included a poly-A tail. A schematic showing a protocol for CAR T cell production using a mRNA SB transposase provided as a mRNA is shown in FIG. 43. For these studies cells from donor #0 were electroporated with the SB11 mRNA, while studies cells from donor #1 were electroporated with the 100× mRNA.

Figure 44A:
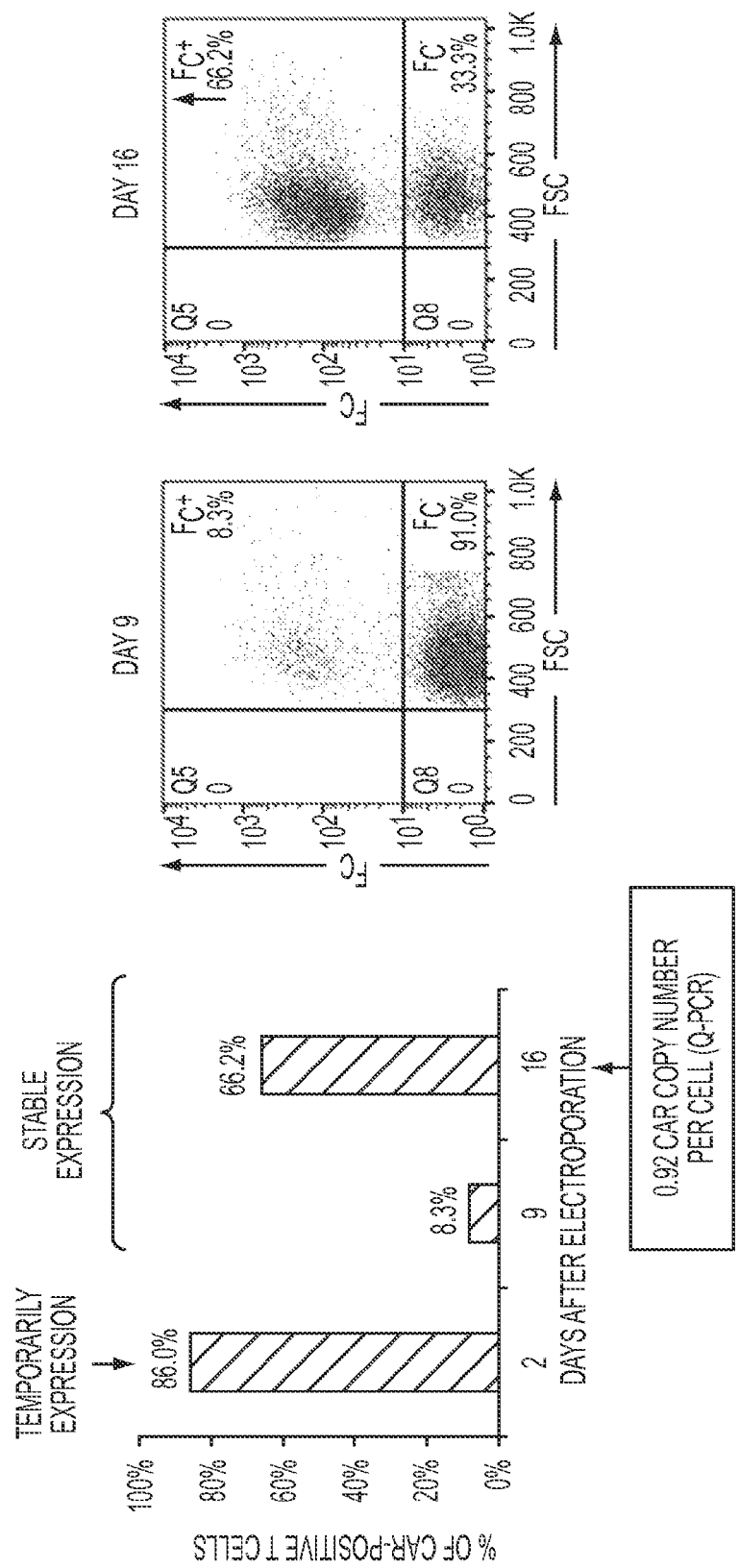
FIG. 44A-D.
Figure 44B:
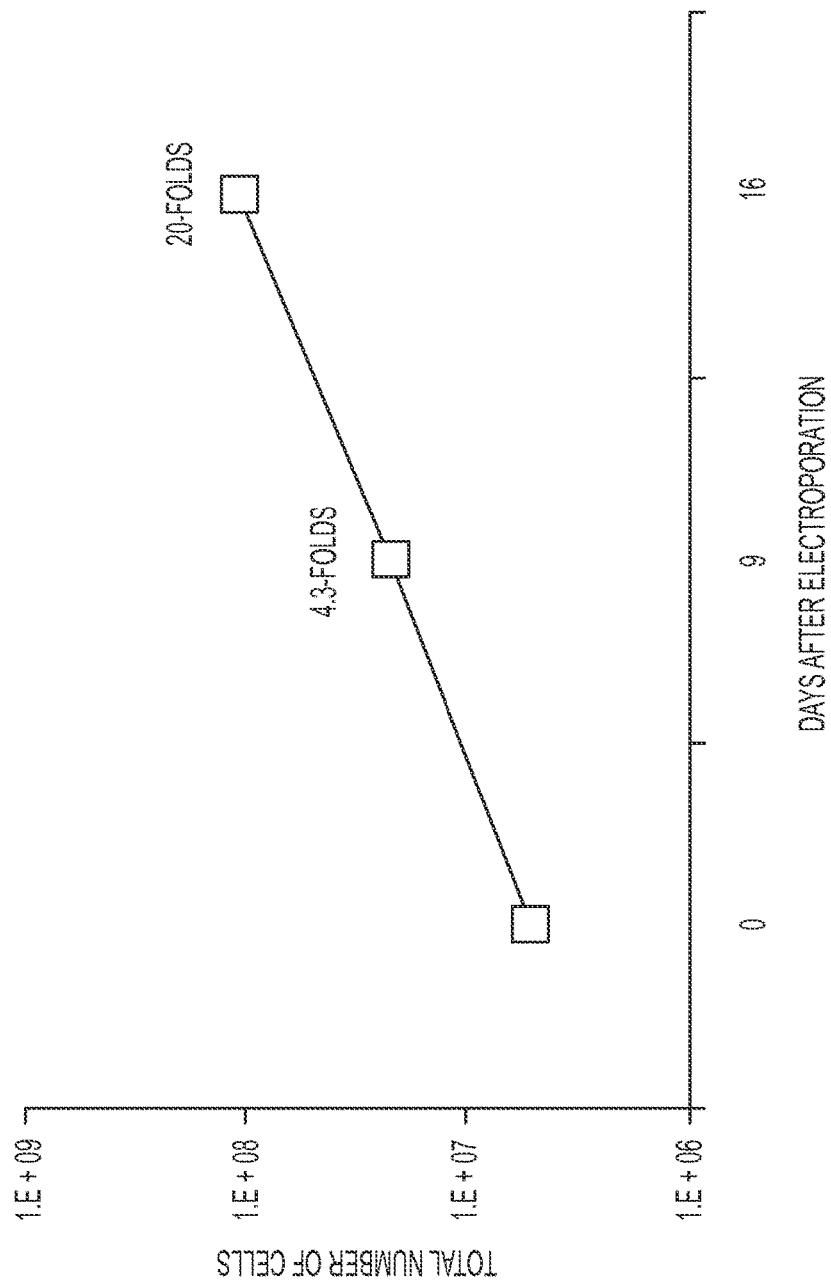
Figure 44C:
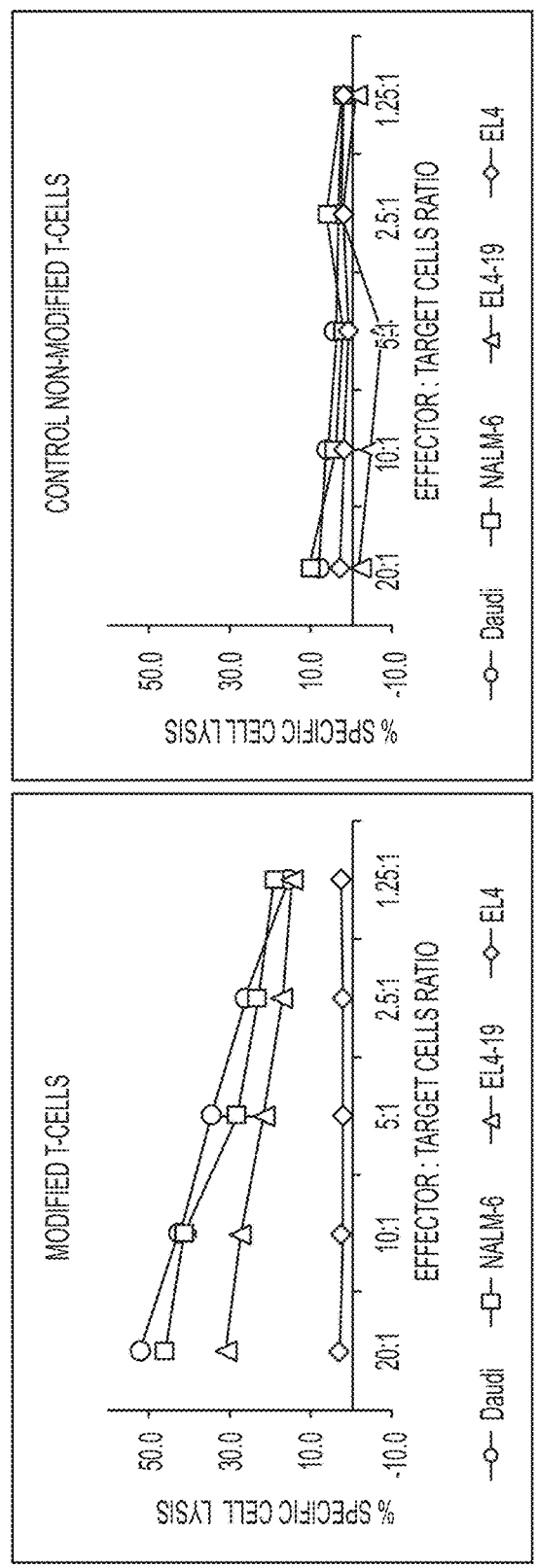
Figure 44D:
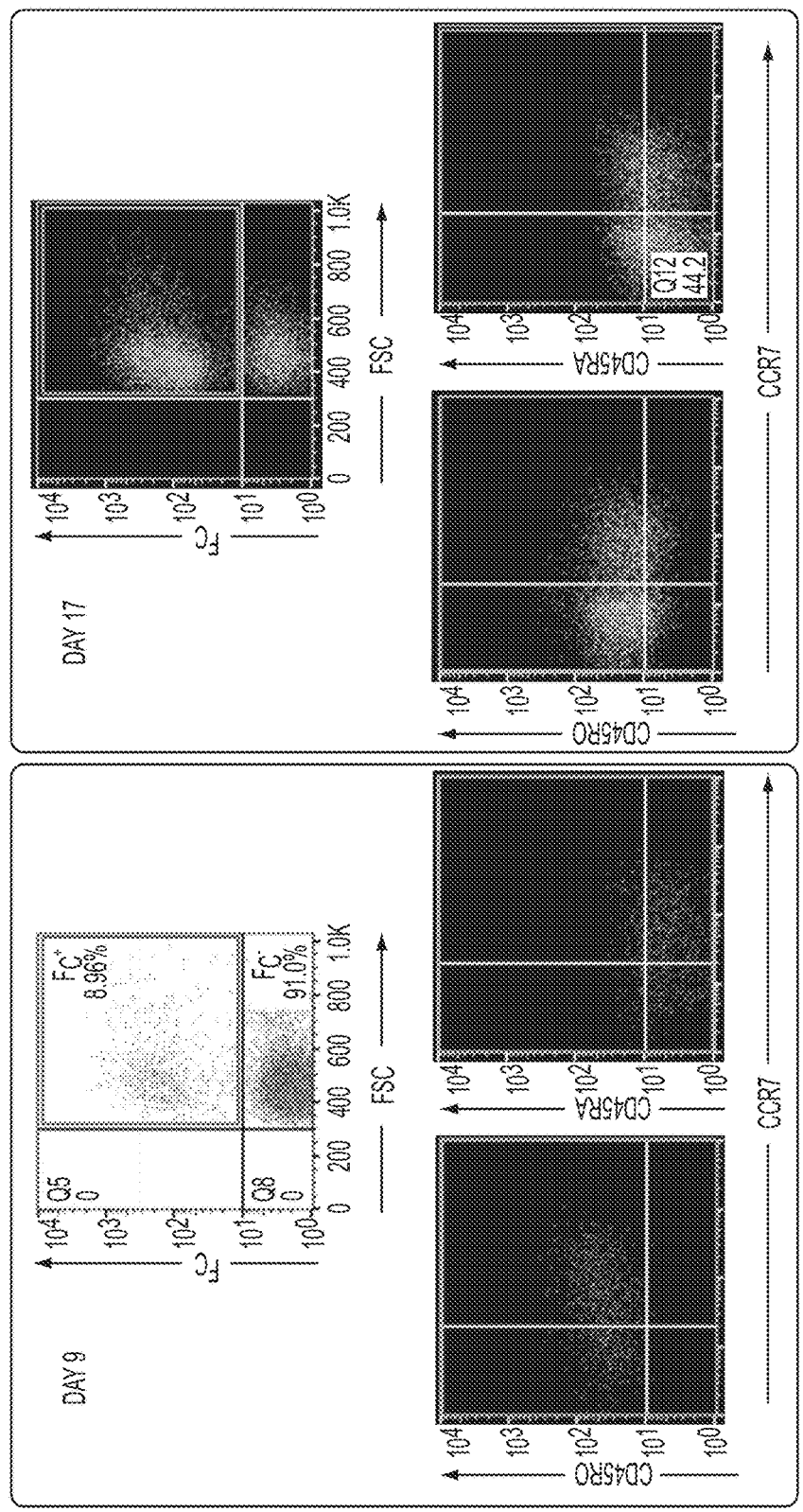

Cell produced from donor #0 were characterized by flow cytometry analysis for CAR expression and cell proliferation. As shown in FIG. 44A the percentage of T-cells stably expressing CAR increases significantly from day 9 (8.3%) to day 16 (66.2%). The T-cells grow quickly and amplify by 20-folds to day 16 after electroporation (FIG. 44B). Further studies shown in FIG. 44D were used to assess the number of central memory T-cells (Tcm) at day 9 (left panel) and day 17 (right panel) post electroporation. These results show that though the number of less differentiated central memory T-cells (Tcm) declines between day 9 and day 17, it still remains relatively high (27%). Next, chromium release assays were used to determine the cytotoxic activity of the cells. As shown in FIG. 44C the CAR T-cell produced provided CD-19-specific cytotoxicity against target cells, while essentially no cytotoxic activity was seen for unmodified T-cells.

Figure 45A:
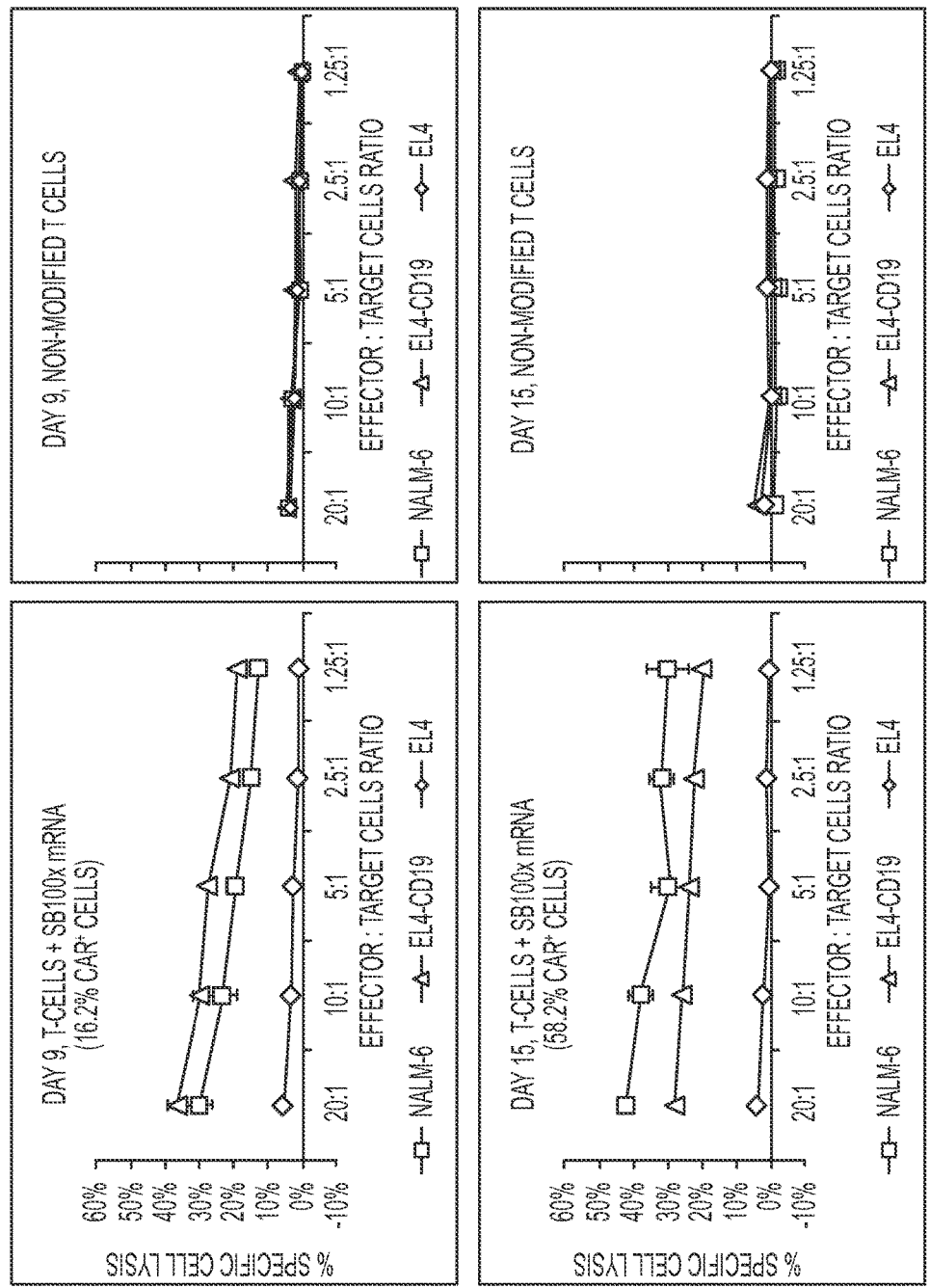
FIG. 45A-B.
Figure 45B:
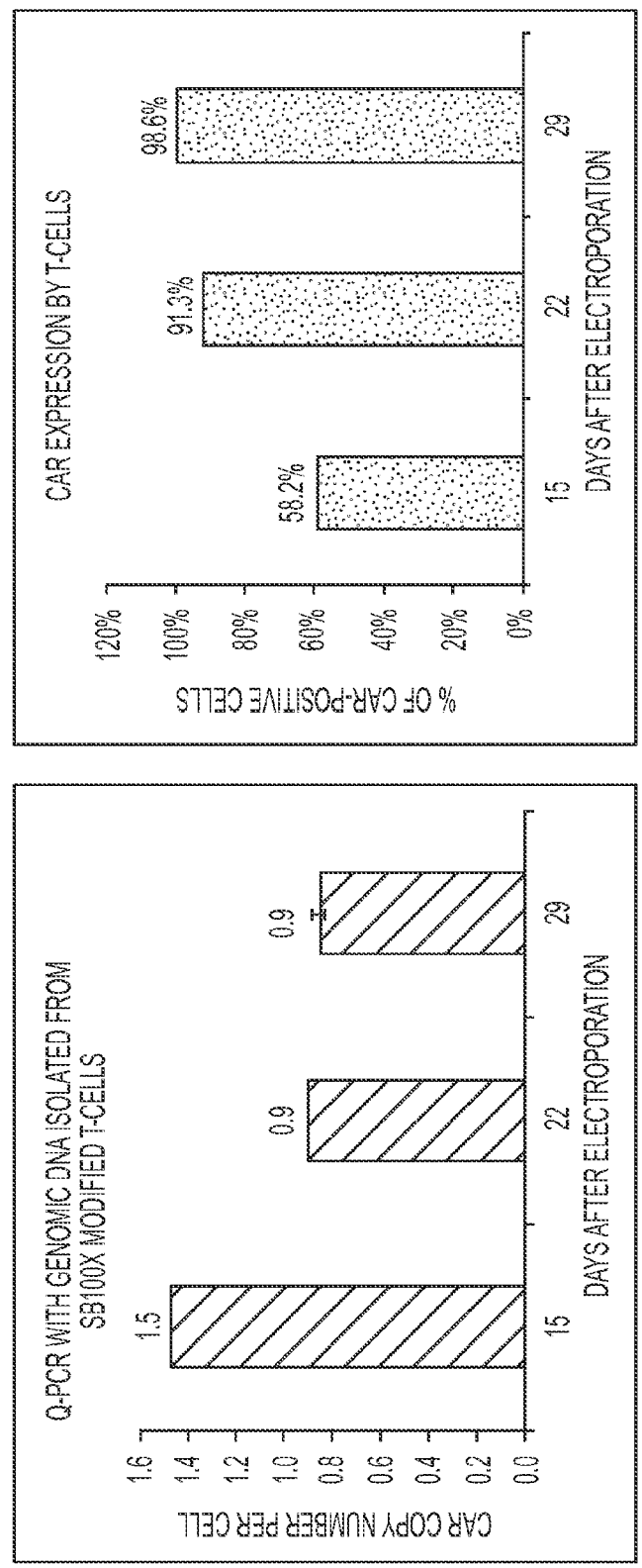

Cell produced from donor #1 were also studied. As shown in FIG. 45A the CAR T-cell produced from this donor also provided CD-19-specific cytotoxicity against target cells and essentially no cytotoxic activity was seen for unmodified T-cells (right panels). Moreover, the modified T-cells kill CD19-positive target cells on day 9 and day 15 with similar efficiency despite the different number of CAR-positive cells. In FIG. 45B the results of studies to assess CAR copy number and expression as shown. These results indicate that CAR DNA copy number decreases from 1.5 to 0.9 from day 15 to day 22 and stays stable after that time point.

Figure 46:
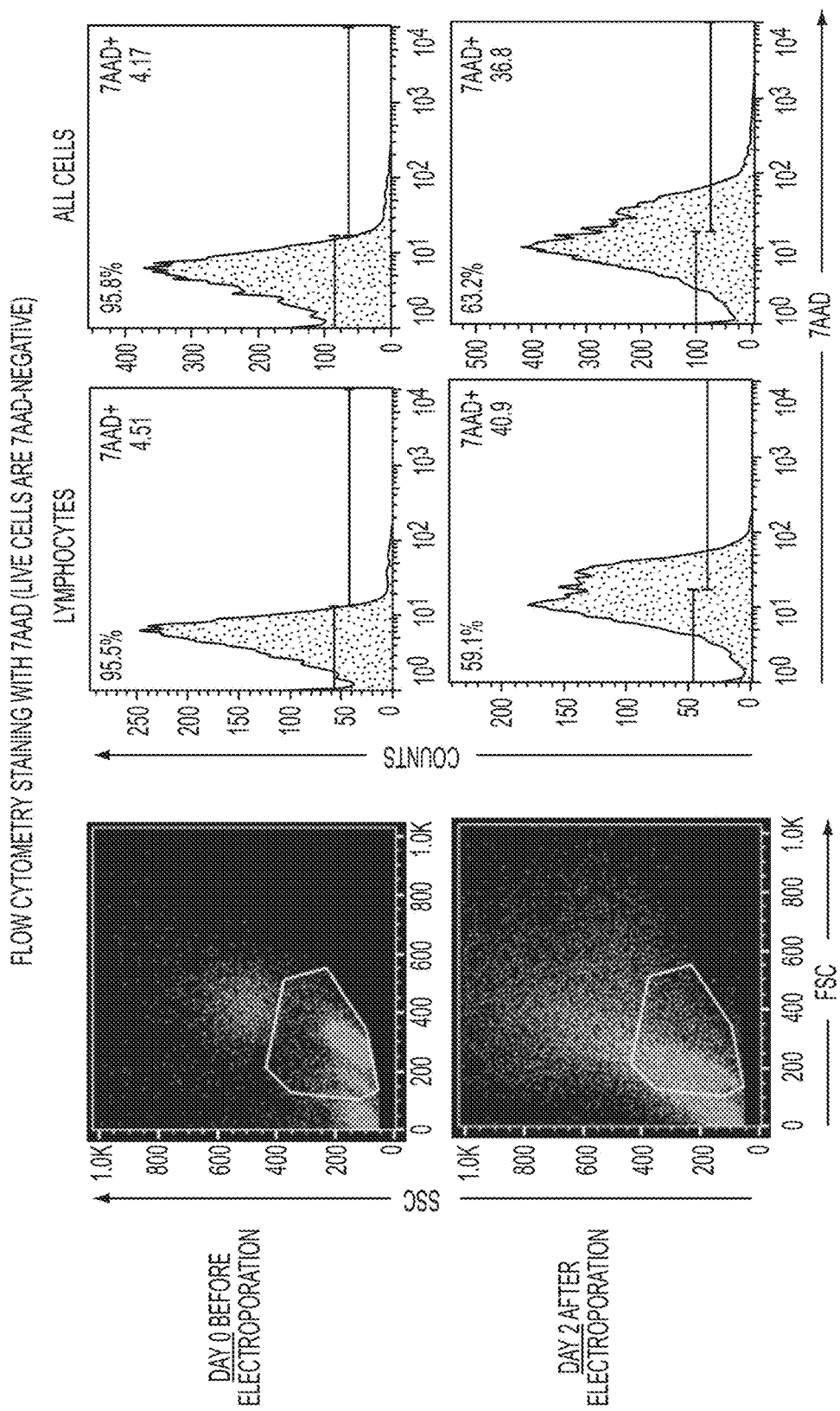
FIG. 46: Flow cytometry data showing cell viability following electroporation. After electroporation with DNA/mRNA the total number of cells decreases first (day 1 and 2) and then cells start to grow. According to the cellometer counts the cell number decrease by 59%-76% on day 2 after electroporation (viability 24-41%).

Finally, flow cytometry was used to assess cell viability following electroporation. As shown in FIG. 46, after electroporation with DNA/mRNA the total number of cells decreases first (day 1 and 2) and then cells start to grow. According to the cellometer counts the cell number decrease by 59%-76% on day 2 after electroporation (viability 24-41%).

Thus, the foregoing data demonstrated that by use of a CAR production techniques that employs mRNA encoding a transposase an effective number of target-specific cytotoxic T cells can be produced in an extremely show period of time and with minimal manipulation. Although the efficiency of mRNA electroporation is donor-dependent, it appears that the SB100× transposase may be more efficient in CAR production. Interestingly, even though earlier after electroporation (day 9) the lower percentage of cells express CAR, the total population of cells kills targeted tumor cells almost as efficiently as one from the later stage (day 15-16) and contains more central memory (less differentiated) cells. It was also confirmed that SB11 and SB100× coding mRNA provide integration of about one copy CAR-coding gene per cell genome under tested conditions.

* * *

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Aronovich et al., The Sleeping Beauty transposon system: a non-viral vector for gene therapy. *Hum. Mol Genet.,* 20:R14-20, 2011.

Bhatia et al., Treatment of metastatic melanoma: an overview. *Oncology,* 23:488-496, 2009.

Bieda et al., Phenotypic heterogeneity of human endogenous retrovirus particles produced by teratocarcinoma cell lines. *J. Gen. Virol.,* 82:591-596, 2001.

Brentjens et al., Safety and persistence of adoptively transferred autologous CD19-targeted T cells in patients with relapsed or chemotherapy refractory B-cell leukemias. *Blood,* 118:4817-4828, 2011.

Brentjens et al., CD19-Targeted T Cells Rapidly Induce Molecular Remissions in Adults with Chemotherapy-Refractory Acute Lymphoblastic Leukemia. *Sci. Transl. Med.,* 5:177ra138, 2013.

Buscher et al., Expression of human endogenous retrovirus K in melanomas and melanoma cell lines. *Cancer Res.,* 65:4172-4180, 2005.

Contreras-Galindo et al., Human endogenous retrovirus K (HML-2) elements in the plasma of people with lymphoma and breast cancer. *J. Virol.,* 82:9329-9336, 2008.

Cooper and Bollard, Good T cells for bad B cells. *Blood,* 119:2700-2702, 2012.

Davies et al., Combining CD19 redirection and alloanergization to generate tumor-specific human T cells for allogeneic cell therapy of B-cell malignancies. *Cancer Res.,* 70: 3915-3924, 2010.

Dreyfus, Autoimmune disease: A role for new anti-viral therapies? *Autoimmunity Reviews,* 11:88-97, 2011.

Ertl et al., Considerations for the clinical application of chimeric antigen receptor T cells: observations from a recombinant DNA Advisory Committee Symposium held Jun. 15, 2010. *Cancer Res.,* 71:3175-3181, 2011.

Garrido et al., Implications for immunosurveillance of altered HLA class I phenotypes in human tumours. *Immunol. Today,* 18:89-95, 1997.

Geiss et al., Direct multiplexed measurement of gene expression with color-coded probe pairs. *Nat Biotechnol.,* 26:317-325, 2008.

Geurts et al., Structure-based prediction of insertion-site preferences of transposons into chromosomes. *Nucleic Acids Res.,* 34:2803-2811, 2006.

Gross et al., Expression of immunoglobulin-T-cell receptor chimeric molecules as functional receptors with antibody-type specificity. *Proc. Natl. Acad. Sci. USA,* 86:10024-10028, 1989.

Hackett et al., A transposon and transposase system for human application. *Mol. Ther.,* 18:674-683, 2010.

Hackett et al., Efficacy and safety of Sleeping Beauty transposon-mediated gene transfer in preclinical animal studies. *Curr. Gene Ther.,* 11:341-349, 2011.

Hahn et al., Serological response to human endogenous retrovirus K in melanoma patients correlates with survival probability. *AIDS Research and Human Retroviruses,* 24:717-723, 2008.

Hollis et al., Stable gene transfer to human CD34(+) hematopoietic cells using the Sleeping Beauty transposon. *Exp. Hematol.,* 34:1333-1343, 2006.

Huang et al., Genetically modified T cells targeting interleukin-11 receptor alpha-chain kill human osteosarcoma cells and induce the regression of established osteosarcoma lung metastases. *Cancer Res.,* 72:271-281, 2012.

Huang et al., Sleeping Beauty transposon-mediated engineering of human primary T cells for therapy of CD19+ lymphoid malignancies. *Mol. Ther.,* 16:580-589, 2008.

Huang et al., DNA transposons for modification of human primary T lymphocytes. *Methods Mol. Biol.,* 506:115-126, 2009.

Huls et al., Clinical application of sleeping beauty and artificial antigen presenting cells to genetically modify T cells from peripheral and umbilical cord blood. *J. Vis. Exp.,* e50070, 2013.

Ivics et al., Molecular reconstruction of Sleeping Beauty, a Tc1-like transposon from fish, and its transposition in human cells. *Cell,* 91:501-510, 1997.

Izsvak and Ivics, Sleeping beauty transposition: biology and applications for molecular therapy. *Mol. Ther.,* 9:147-156, 2004.

Izsvak et al., Translating Sleeping Beauty transposition into cellular therapies: victories and challenges. *Bioessays,* 32:756-767, 2010.

Jena et al., Redirecting T-cell specificity by introducing a tumor-specific chimeric antigen receptor. *Blood,* 116: 1035-1044, 2010.

Jena et al., Chimeric Antigen Receptor (CAR)-Specific Monoclonal Antibody to Detect CD19-Specific T Cells in Clinical Trials. *PLoS ONE,* 8:e57838, 2013.

Jin et al., The hyperactive Sleeping Beauty transposase SB100x improves the genetic modification of T cells to express a chimeric antigen receptor. *Gene Ther.,* 18:849-856, 2011.

Jones et al., HERV-K-specific T cells eliminate diverse HIV-1/2 and SIV primary isolates. *J. Clin. Invest.,* 122: 4473-4489, 2012.

Kalos et al., T cells with chimeric antigen receptors have potent antitumor effects and can establish memory in patients with advanced leukemia. *Sci. Transl. Med.,* 3:95ra73, 2011.

Kebriaei et al., Infusing CD19-directed T cells to augment disease control in patients undergoing autologous hematopoietic stem-cell transplantation for advanced B-lymphoid malignancies. *Hum. Gene Ther.,* 23:444-450, 2012.

Kebriaei et al., CARs: driving T-cell specificity to enhance anti-tumor immunity *Front. Biosci. (Schol. Ed.),* 4:520-531, 2012.

Kim et al., Use of the human elongation factor 1 alpha promoter as a versatile and efficient expression system. *Gene,* 91:217-223, 1990.

Kim et al., High Cleavage Efficiency of a 2A Peptide Derived from Porcine Teschovirus-1 in Human Cell Lines, Zebrafish and Mice. *PLoS ONE,* 6:e18556, 2011.

Kochenderfer et al., Eradication of B-lineage cells and regression of lymphoma in a patient treated with autologous T cells genetically engineered to recognize CD19. *Blood,* 116:4099-4102, 2010.

Kochenderfer et al., B-cell depletion and remissions of malignancy along with cytokine-associated toxicity in a clinical trial of anti-CD19 chimeric-antigen-receptor-transduced T cells. *Blood,* 119:2709-2720, 2012.

Kohn et al., CARs on track in the clinic. *Mol. Ther.,* 19:432-438, 2011.

Kowolik et al., CD28 costimulation provided through a CD19-specific chimeric antigen receptor enhances in vivo persistence and antitumor efficacy of adoptively transferred T cells. *Cancer Res.,* 66:10995-11004, 2006.

Krone et al., Protection against melanoma by vaccination with Bacille Calmette-Guerin (BCG) and/or vaccinia: an epidemiology-based hypothesis on the nature of a melanoma risk factor and its immunological control. *Eur. J. Cancer,* 41:104-117, 2005.

Li et al., Expression of HERV-K correlates with status of MEK-ERK and p16INK4A-CDK4 pathways in melanoma cells. *Cancer Invest.*, 28:1031-1037, 2010.

Lower et al., A general method for the identification of transcribed retrovirus sequences (R-U5 PCR) reveals the expression of the human endogenous retrovirus loci HERV-H and HERV-K in teratocarcinoma cell. *Virology*, 192:501-511, 1993.

Mahmoud et al., Enforced CD19 expression leads to growth inhibition and reduced tumorigenicity. *Blood*, 94:3551-3558, 1999.

Maiti et al., Sleeping beauty system to redirect T-cell specificity for human applications. *J. Immunother.*, 36:112-123, 2013.

Manuri et al., piggyBac transposon/transposase system to generate CD19-specific T cells for the treatment of B-lineage malignancies. *Hum. Gene Ther.*, 21:427-437, 2010.

Mates et al., Molecular evolution of a novel hyperactive Sleeping Beauty transposase enables robust stable gene transfer in vertebrates. *Nat. Genetics.* 41(6):753-61, 2009.

Muster et al., An endogenous retrovirus derived from human melanoma cells. *Cancer Res.*, 63:8735-8741, 2003.

Nakazawa et al., PiggyBac-mediated cancer immunotherapy using EBV-specific cytotoxic T-cells expressing HER2-specific chimeric antigen receptor. *Mol. Ther.*, 19:2133-2143, 2011.

Ono, Molecular cloning and long terminal repeat sequences of human endogenous retrovirus genes related to types A and B retrovirus genes. *J. Virol.*, 58:937-944, 1986.

Patience et al., Human endogenous retrovirus expression and reverse transcriptase activity in the T47D mammary carcinoma cell line. *J. Virol.*, 70:2654-2657, 1996.

Porter et al., Chimeric antigen receptor-modified T cells in chronic lymphoid leukemia. *N. Engl. J. Med.*, 365:725-733, 2011.

Rabinovich et al., A role for the MHC class I-like Mill molecules in nutrient metabolism and wound healing. *Immunol. Cell. Biol.*, 86:489-496, 2008.

Reiche et al., Differential expression of human endogenous retrovirus K transcripts in primary human melanocytes and melanoma cell lines after UV irradiation. *Melanoma Res.*, 20:435-440, 2010.

Sciamanna et al., Inhibition of endogenous reverse transcriptase antagonizes human tumor growth. *Oncogene*, 24:3923-3931, 2005.

Seifarth et al., Retrovirus-like particles released from the human breast cancer cell line T47-D display type B- and C-related endogenous retroviral sequences. *J. Virol.*, 69:6408-6416, 1995.

Serafino et al., The activation of human endogenous retrovirus K (HERV-K) is implicated in melanoma cell malignant transformation. *Exp. Cell Res.*, 315:849-862, 2009.

Serrano et al., Differentiation of naive cord-blood T cells into CD19-specific cytolytic effectors for posttransplantation adoptive immunotherapy. *Blood*, 107:2643-2652, 2006.

Singh et al., Combining adoptive cellular and immunocytokine therapies to improve treatment of B-lineage malignancy. *Cancer Res.*, 67:2872-2880, 2007.

Singh et al., Redirecting specificity of T-cell populations for CD19 using the Sleeping Beauty system. *Cancer Res.*, 68:2961-2971, 2008.

Singh et al., Reprogramming CD19-specific T cells with IL-21 signaling can improve adoptive immunotherapy of B-lineage malignancies. *Cancer Res.*, 71:3516-3527, 2011.

Szymczak et al., Correction of multi-gene deficiency in vivo using a single 'self-cleaving' 2A peptide-based retroviral vector. *Nat. Biotechnol.*, 22:589-594, 2004.

Taruscio and Mantovani, Factors regulating endogenous retroviral sequences in human and mouse. *Cytogenet. Genome Res.*, 105:351-362, 2004.

Till et al., Adoptive immunotherapy for indolent non-Hodgkin lymphoma and mantle cell lymphoma using genetically modified autologous CD20-specific T cells. *Blood*, 112:2261-2271, 2008.

Wang-Johanning et al., Quantitation of HERV-K env gene expression and splicing in human breast cancer. *Oncogene*, 22:1528-1535, 2003.

Wang-Johanning et al., Expression of multiple human endogenous retrovirus surface envelope proteins in ovarian cancer. *Int. J. Cancer*, 120:81-90, 2007.

Williams, Sleeping beauty vector system moves toward human trials in the United States. *Mol. Ther.*, 16:1515-1516, 2008.

Yang et al., Development of optimal bicistronic lentiviral vectors facilitates high-level TCR gene expression and robust tumor cell recognition. *Gene Ther.*, 15:1411-1423, 2008.

---

The invention claimed is:

1. An engineered cell comprising:
   (a) a chimeric antigen receptor (CAR); and
   (b) a fusion protein comprising IL-15 and IL-15Rα.

2. The cell of claim 1, wherein said fusion protein further comprises a linker connecting said IL-15 and IL-15Rα.

3. The cell of claim 2, wherein the fusion protein comprises an amino acid sequence which is at least 90% identical to SEQ ID NO:6.

4. The cell of claim 3, wherein the fusion protein comprises the amino acid sequence of SEQ ID NO:6.

5. The cell of claim 1, wherein the fusion protein is encoded by a DNA comprising a sequence which is at least 90% identical to SEQ ID NO: 7.

6. The cell of claim 5, wherein the fusion protein is encoded by a DNA comprising the sequence of SEQ ID NO: 7.

7. The cell of claim 1, wherein DNA encoding the CAR is integrated into the genome of the cell.

8. The cell of claim 1, wherein DNA encoding the fusion protein is comprised in an extra chromosomal vector.

9. The cell of claim 1, wherein DNA encoding the fusion protein is integrated into the genome of the cell.

10. A method of treating cancer in a human subject in need thereof comprising administering to the subject an effective amount of one or more cells in accordance with claim 1.

11. The method of claim 10, wherein said cell comprises a CAR that targets a cancer-cell antigen.

12. The method of claim 11, wherein the subject has undergone a previous anti-cancer therapy.

13. The method of claim 12, wherein the subject is in remission.

14. The method of claim 12, wherein the subject is free of symptoms of the cancer but comprises detectable cancer cells.

15. An IL-15, IL-15Rαfusion protein comprising an amino acid sequence which is at least 90% identical to SEQ ID NO: 6.

16. The fusion protein of claim 15, comprising the amino acid sequence of SEQ ID NO: 6.

17. A polynucleotide comprising a DNA sequence encoding an IL-15, IL-15Rαfusion protein which is at least 90% identical to SEQ ID NO: 6.

18. The polynucleotide of claim 17 comprising a sequence which is at least 90% identical to SEQ ID NO: 7.

19. An engineered cell comprising a polynucleotide in accordance with claim 17.

20. The cell of claim 19 wherein the cell is a T-cell, a T-cell precursor, a NK cell or an aAPC.

21. The method of claim 11, wherein the cancer-cell antigen is CD19, ROR1, CD56, EGFR, CD123, c-met, GD2, HER2, CD20, MUC-1, CD23, or CD30.

22. The method of claim 11, wherein the cancer is leukemia or a solid tumor.

23. The cell of claim 2, wherein said linker further comprises a serine-glycine linker.

24. The cell of claim 1, wherein said fusion protein further comprises a IgE signal peptide.

25. An engineered cell comprising DNA encoding:
   (a) a chimeric antigen receptor (CAR); and
   (b) a fusion protein comprising IL-15 and IL-15Rα.

26. The cell of claim 25, further comprising a transposase.

27. The cell of claim 26, wherein the transposase is a Sleeping Beauty transposase.

28. The cell of claim 26, wherein the transposase is provided as a DNA expression vector.

29. The cell of claim 26, wherein the transposase is a mRNA encoding a Sleeping Beauty transposase.

30. The cell of claim 29, wherein the mRNA comprises a cap, a poly-A tail or both.

31. The cell of claim 2, wherein the fusion protein comprises an amino acid sequence which is at least 85% identical to SEQ ID NO:6.

* * * * *

UNITED STATES PATENT AND TRADEMARK OFFICE
CERTIFICATE OF CORRECTION

PATENT NO. : 9,629,877 B2  
APPLICATION NO. : 14/890977  
DATED : April 25, 2017  
INVENTOR(S) : Cooper et al.

Page 1 of 1

It is certified that error appears in the above-identified patent and that said Letters Patent is hereby corrected as shown below:

In the Claims

In Claim 15, Column 100, Line 34, delete "IL-15αfusion" and replace with --IL-15α fusion-- therefor.

In Claim 17, Column 100, Line 40, delete "IL-15αfusion" and replace with --IL-15α fusion-- therefor.

Signed and Sealed this  
Eleventh Day of July, 2017

Joseph Matal  
*Performing the Functions and Duties of the*  
*Under Secretary of Commerce for Intellectual Property and*  
*Director of the United States Patent and Trademark Office*